United States Patent
Mullane et al.

(10) Patent No.: US 12,144,711 B2
(45) Date of Patent: *Nov. 19, 2024

(54) PATTERNED APERTURED WEBS

(71) Applicant: The Procter & Gamble Company, Cincinnati, OH (US)

(72) Inventors: Timothy Ian Mullane, Union, KY (US); Kelyn Anne Arora, Cincinnati, OH (US); Jill Marlene Orr, Liberty Township, OH (US); Donald Carroll Roe, West Chester, OH (US); Jennifer Schutte, Cincinnati, OH (US); John Brian Strube, Okeana, OH (US); Ann Cecilia Tapp, West Chester, OH (US); Rachael Eden Walther, Union, KY (US); Amanda Margaret Bicking, Cincinnati, OH (US); Jennifer Lynn Dusold, Cincinnati, OH (US); Margaret Elizabeth Porter, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,868

(22) Filed: Apr. 27, 2023

(65) Prior Publication Data
US 2024/0074922 A1 Mar. 7, 2024

Related U.S. Application Data

(63) Continuation of application No. 17/668,469, filed on Feb. 10, 2022, now Pat. No. 11,766,367, which is a (Continued)

(51) Int. Cl.
*A61F 13/15* (2006.01)
*A61F 13/511* (2006.01)
(Continued)

(52) U.S. Cl.
CPC .......... *A61F 13/512* (2013.01); *A61F 13/511* (2013.01); *A61F 13/5116* (2013.01);
(Continued)

(58) Field of Classification Search
CPC .. A61F 13/512; A61F 13/511; A61F 13/5116; A61F 13/513; A61F 13/5126;
(Continued)

(56) References Cited

U.S. PATENT DOCUMENTS

| D116,633 S | 9/1939 | Rubner |
|---|---|---|
| 3,137,893 A | 6/1964 | Gelpke |

(Continued)

FOREIGN PATENT DOCUMENTS

| CA | 2182304 A1 | 1/1997 |
|---|---|---|
| CA | 2183776 A1 | 3/1997 |

(Continued)

OTHER PUBLICATIONS

14061 PCT Search Report and Written Opinion for PCT/US2015/059190 dated Feb. 15, 2016, 11 pages.
(Continued)

*Primary Examiner* — Jacqueline F Stephens
(74) *Attorney, Agent, or Firm* — Christian M. Best

(57) ABSTRACT

A patterned apertured web is disclosed. The patterned apertured web includes a plurality of land areas in the patterned apertured web and a plurality of apertures defined in the patterned apertured web. At least some land areas of the plurality of land areas surround at least some apertures of the plurality of apertures. The patterned apertured web has an Effective Open Area in the range of about 3% to about 30%, according to the Aperture Test herein. The patterned apertured web has a plurality of Interaperture Distances, according to the Aperture Test herein. The Interaperture Distances have a distribution having a median and a mean. The
(Continued)

plurality of apertures include a first set of apertures defining a first shape and a second set of apertures defining a second shape.

20 Claims, 83 Drawing Sheets

Related U.S. Application Data continuation of application No. 17/361,681, filed on Jun. 29, 2021, now Pat. No. 11,813,150, which is a continuation of application No. 16/854,073, filed on Apr. 21, 2020, now Pat. No. 11,633,311, which is a continuation of application No. 16/432,084, filed on Jun. 5, 2019, now Pat. No. 10,667,962, which is a continuation of application No. 14/933,030, filed on Nov. 5, 2015, now Pat. No. 10,350,119.

(60) Provisional application No. 62/177,405, filed on Mar. 13, 2015, provisional application No. 62/076,043, filed on Nov. 6, 2014.

(51) Int. Cl.

| | |
|---|---|
| *A61F 13/512* | (2006.01) |
| *A61F 13/513* | (2006.01) |
| *A61F 13/514* | (2006.01) |
| *B32B 3/06* | (2006.01) |
| *B32B 3/26* | (2006.01) |
| *B32B 3/30* | (2006.01) |
| *B32B 5/02* | (2006.01) |
| *B32B 5/14* | (2006.01) |
| *B32B 7/05* | (2019.01) |
| *A61F 13/51* | (2006.01) |
| *A61F 13/515* | (2006.01) |
| *A61F 13/551* | (2006.01) |
| *A61F 13/84* | (2006.01) |
| *B32B 5/26* | (2006.01) |
| *B44F 99/00* | (2013.01) |
| *D04H 3/14* | (2012.01) |

(52) U.S. Cl.
CPC ...... *A61F 13/5123* (2013.01); *A61F 13/5126* (2013.01); *A61F 13/51394* (2013.01); *A61F 13/51484* (2013.01); *B32B 3/06* (2013.01); *B32B 3/26* (2013.01); *B32B 3/266* (2013.01); *B32B 3/30* (2013.01); *B32B 5/022* (2013.01); *B32B 5/142* (2013.01); *B32B 7/05* (2019.01); *A61F 13/15699* (2013.01); *A61F 2013/15715* (2013.01); *A61F 2013/51078* (2013.01); *A61F 2013/51092* (2013.01); *A61F 13/51104* (2013.01); *A61F 13/51121* (2013.01); *A61F 2013/51147* (2013.01); *A61F 2013/51165* (2013.01); *A61F 2013/51178* (2013.01); *A61F 2013/51182* (2013.01); *A61F 2013/51186* (2013.01); *A61F 2013/5127* (2013.01); *A61F 2013/5128* (2013.01); *A61F 13/51305* (2013.01); *A61F 2013/51322* (2013.01); *A61F 2013/51377* (2013.01); *A61F 13/51476* (2013.01); *A61F 13/51478* (2013.01); *A61F 2013/51486* (2013.01); *A61F 13/515* (2013.01); *A61F 13/551* (2013.01); *A61F 2013/8497* (2013.01); *B32B 5/26* (2013.01); *B32B 2250/03* (2013.01); *B32B 2250/04* (2013.01); *B32B 2250/20* (2013.01); *B32B 2250/242* (2013.01); *B32B 2307/726* (2013.01); *B32B 2555/00* (2013.01); *B32B 2555/02* (2013.01); *B44F 99/00* (2013.01); *D04H 3/14* (2013.01); *D10B 2509/026* (2013.01); *Y10T 428/24314* (2015.01); *Y10T 428/24322* (2015.01); *Y10T 428/24331* (2015.01); *Y10T 428/24612* (2015.01); *Y10T 428/24793* (2015.01); *Y10T 428/24826* (2015.01); *Y10T 442/60* (2015.04); *Y10T 442/66* (2015.04)

(58) Field of Classification Search
CPC .......... A61F 13/51394; A61F 13/51484; A61F 13/51104; A61F 13/51699; A61F 13/51121; A61F 13/51305; A61F 13/51476; A61F 13/51478; A61F 13/515; A61F 13/551; A61F 2013/15715; A61F 2013/51078; A61F 2013/51092; A61F 2013/51147; A61F 2013/51165; A61F 2013/51178; A61F 2013/51182; A61F 2013/51186; A61F 2013/5127; A61F 2013/5128; A61F 2013/51322; A61F 2013/51377; A61F 2013/51486; A61F 2013/8497; B32B 7/05; B32B 3/06; B32B 3/266; B32B 3/30; B32B 5/022; B32B 5/142; B32B 5/26; B32B 2250/04; B32B 2250/20; B32B 2250/242; B32B 2250/00; B32B 2250/02

See application file for complete search history.

(56) References Cited

U.S. PATENT DOCUMENTS

| | | |
|---|---|---|
| 3,559,648 A | 2/1971 | Mason, Jr. |
| 3,655,501 A | 4/1972 | Tesch |
| 3,673,026 A | 6/1972 | Brown |
| 3,814,101 A | 6/1974 | Kozak |
| 3,849,845 A | 11/1974 | Obenaus |
| 3,860,003 A | 1/1975 | Buell |
| 3,886,941 A | 6/1975 | Duane et al. |
| 3,890,974 A | 6/1975 | Kozak |
| D237,114 S | 10/1975 | Widlund |
| 3,911,173 A | 10/1975 | Sprague, Jr. |
| 3,929,135 A | 12/1975 | Thompson |
| D238,449 S | 1/1976 | Matsumoto |
| D239,137 S | 3/1976 | Appleman |
| D240,563 S | 7/1976 | Whitehead |
| D240,564 S | 7/1976 | Whitehead |
| D247,368 S | 2/1978 | Whitehead |
| D247,371 S | 2/1978 | Whitehead |
| 4,137,180 A | 1/1979 | Naik |
| 4,199,464 A | 4/1980 | Cambre |
| D259,219 S | 5/1981 | Bates et al. |
| 4,306,559 A | 12/1981 | Nishizawa et al. |
| 4,323,069 A | 4/1982 | Ahr et al. |
| 4,324,246 A | 4/1982 | Mullane et al. |
| 4,327,730 A | 5/1982 | Sorensen |
| D276,184 S | 10/1984 | Whitehead |
| D276,368 S | 11/1984 | Whitehead |
| 4,573,986 A | 3/1986 | Minetola |
| 4,588,630 A | 5/1986 | Shimalla |
| 4,609,518 A | 9/1986 | Curro et al. |
| 4,610,678 A | 9/1986 | Weisman |
| 4,623,340 A | 11/1986 | Luceri |
| 4,629,643 A | 12/1986 | Curro |
| D287,637 S | 1/1987 | Grasso |
| 4,637,819 A | 1/1987 | Ouellette et al. |
| 4,673,402 A | 6/1987 | Weisman et al. |
| 4,676,784 A | 6/1987 | Erdman |
| 4,704,112 A | 11/1987 | Suzuki et al. |
| 4,741,941 A | 5/1988 | Englebert |
| 4,780,352 A | 10/1988 | Palumbo |
| 4,781,710 A | 11/1988 | Megison et al. |
| 4,785,996 A | 11/1988 | Ziecker |
| 4,798,604 A | 1/1989 | Carter |

(56) References Cited

U.S. PATENT DOCUMENTS

| | | |
|---|---|---|
| 4,818,587 A | 4/1989 | Ejima et al. |
| 4,834,735 A | 5/1989 | Alemany |
| 4,840,829 A | 6/1989 | Suzuki et al. |
| 4,842,666 A | 6/1989 | Werenicz |
| 4,844,965 A | 7/1989 | Foxman |
| 4,888,231 A | 12/1989 | Angstadt |
| 4,908,026 A | 3/1990 | Becker et al. |
| 4,950,264 A | 8/1990 | Osborn, III |
| 5,108,820 A | 4/1992 | Kaneko et al. |
| 5,122,407 A | 6/1992 | Yeo et al. |
| 5,147,345 A | 9/1992 | Lavon |
| 5,151,092 A | 9/1992 | Buell |
| 5,226,992 A | 7/1993 | Morman |
| 5,234,423 A | 8/1993 | Alemany et al. |
| 5,296,622 A | 3/1994 | Uphues |
| D349,159 S | 7/1994 | Huffman |
| D350,196 S | 8/1994 | Huffman |
| D350,197 S | 8/1994 | Huffman |
| H1377 H | 11/1994 | Perry |
| 5,369,858 A | 12/1994 | Gilmore et al. |
| 5,370,764 A | 12/1994 | Alikhan |
| D354,856 S | 1/1995 | Schulz |
| 5,382,773 A | 1/1995 | Kurihara et al. |
| 5,415,640 A | 5/1995 | Kirby et al. |
| 5,418,045 A | 5/1995 | Pike et al. |
| 5,433,715 A | 7/1995 | Tanzer |
| 5,437,653 A | 8/1995 | Gilman et al. |
| D362,120 S | 9/1995 | Suskind et al. |
| D363,610 S | 10/1995 | Saffran et al. |
| 5,456,982 A | 10/1995 | Hansen et al. |
| 5,485,662 A | 1/1996 | Hodges, Jr. et al. |
| D367,764 S | 3/1996 | Makoui et al. |
| D368,587 S | 4/1996 | Schulz |
| 5,503,076 A | 4/1996 | Yeo |
| 5,518,801 A | 5/1996 | Chappell |
| 5,520,673 A | 5/1996 | Yarbrough et al. |
| 5,536,555 A | 7/1996 | Zelazoski et al. |
| 5,571,096 A | 11/1996 | Dobrin |
| 5,573,830 A | 11/1996 | Schulz |
| D377,419 S | 1/1997 | Schulz |
| 5,597,645 A | 1/1997 | Pike et al. |
| 5,599,335 A | 2/1997 | Goldman |
| 5,605,749 A | 2/1997 | Pike et al. |
| 5,607,760 A | 3/1997 | Roe |
| 5,609,587 A | 3/1997 | Roe |
| 5,628,097 A | 5/1997 | Benson |
| 5,628,737 A | 5/1997 | Dobrin et al. |
| 5,635,191 A | 6/1997 | Roe |
| 5,643,588 A | 7/1997 | Roe |
| D382,162 S | 8/1997 | Saffran et al. |
| D382,713 S | 8/1997 | Giesler |
| 5,660,788 A | 8/1997 | Gray et al. |
| D384,210 S | 9/1997 | Du |
| 5,665,083 A | 9/1997 | Igaue et al. |
| 5,667,562 A | 9/1997 | Midkiff |
| 5,667,619 A | 9/1997 | Alikhan |
| 5,704,101 A | 1/1998 | Majors |
| 5,709,735 A | 1/1998 | Midkiff et al. |
| 5,714,107 A | 2/1998 | Levy et al. |
| 5,718,698 A | 2/1998 | Dobrin et al. |
| 5,731,061 A | 3/1998 | Bezier |
| 5,735,984 A | 4/1998 | Hoff et al. |
| H1732 H | 6/1998 | Jhonson |
| 5,759,990 A | 6/1998 | Wahl |
| 5,770,144 A | 6/1998 | James et al. |
| D395,955 S | 7/1998 | Du |
| 5,780,155 A | 7/1998 | Ishizawa et al. |
| 5,797,894 A | 8/1998 | Cadieux et al. |
| 5,804,021 A | 9/1998 | Abuto et al. |
| 5,824,352 A | 10/1998 | Yang et al. |
| D402,475 S | 12/1998 | Kelly et al. |
| 5,846,230 A | 12/1998 | Osborn et al. |
| 5,873,968 A | 2/1999 | Pike et al. |
| 5,874,160 A | 2/1999 | Keck |
| D406,791 S | 3/1999 | Dwiggins et al. |
| 5,885,267 A | 3/1999 | Mishima et al. |
| D407,902 S | 4/1999 | Dwiggins et al. |
| D408,152 S | 4/1999 | Veith et al. |
| 5,895,380 A | 4/1999 | Turi et al. |
| 5,897,541 A | 4/1999 | Uitenbroek et al. |
| 5,897,543 A | 4/1999 | Francis |
| 5,914,084 A | 6/1999 | Benson et al. |
| 5,916,661 A | 6/1999 | Benson |
| 5,919,177 A | 7/1999 | Georger et al. |
| D412,574 S | 8/1999 | Trombetta et al. |
| D412,575 S | 8/1999 | Trombetta |
| D412,980 S | 8/1999 | Trombetta et al. |
| D412,981 S | 8/1999 | Trombetta et al. |
| 5,941,864 A | 8/1999 | Roe |
| 5,965,468 A | 10/1999 | Marmon et al. |
| 5,968,025 A | 10/1999 | Roe |
| 5,990,376 A | 11/1999 | Inoue et al. |
| 5,998,696 A | 12/1999 | Schone |
| 6,015,936 A | 1/2000 | Takai et al. |
| 6,025,535 A | 2/2000 | Octavio et al. |
| 6,030,372 A | 2/2000 | Buell et al. |
| D421,341 S | 3/2000 | Schulz et al. |
| D426,303 S | 6/2000 | Weyenberg |
| D426,709 S | 6/2000 | Latchoo et al. |
| D426,887 S | 6/2000 | Rubio |
| D426,889 S | 6/2000 | Bissah et al. |
| 6,093,871 A | 7/2000 | Takai et al. |
| D429,893 S | 8/2000 | Jahner et al. |
| D430,406 S | 9/2000 | Ingalls |
| D430,407 S | 9/2000 | Ingalls |
| D430,665 S | 9/2000 | Daniels |
| 6,114,595 A | 9/2000 | Moore et al. |
| 6,117,523 A | 9/2000 | Sugahara |
| 6,117,524 A | 9/2000 | Hisanaka et al. |
| 6,120,488 A | 9/2000 | Vanrijswijck et al. |
| 6,129,972 A | 10/2000 | Mcneil et al. |
| D433,572 S | 11/2000 | Bissah et al. |
| D434,568 S | 12/2000 | Bissah et al. |
| D434,849 S | 12/2000 | Daniels |
| 6,159,881 A | 12/2000 | Datta et al. |
| 6,168,849 B1 | 1/2001 | Braverman et al. |
| D439,057 S | 3/2001 | Bissah |
| D439,660 S | 3/2001 | Velazquez et al. |
| D439,661 S | 3/2001 | Velazquez et al. |
| 6,203,905 B1 | 3/2001 | Pike |
| 6,206,865 B1 | 3/2001 | Chen et al. |
| 6,228,462 B1 | 5/2001 | Lee |
| 6,231,555 B1 | 5/2001 | Lynard |
| 6,261,666 B1 | 7/2001 | Enderby et al. |
| 6,262,331 B1 | 7/2001 | Nakahata |
| 6,270,623 B1 | 8/2001 | Goda et al. |
| 6,271,192 B1 | 8/2001 | Verstrat |
| 6,274,218 B1 | 8/2001 | Shimizu |
| 6,274,237 B1 | 8/2001 | Nakajima et al. |
| D448,078 S | 9/2001 | Deoliveira et al. |
| D448,478 S | 9/2001 | Deoliveira et al. |
| 6,303,208 B1 | 10/2001 | Pelkie |
| D451,682 S | 12/2001 | Jahner et al. |
| 6,326,430 B1 | 12/2001 | Berte |
| 6,344,111 B1 | 2/2002 | Wilhelm |
| 6,348,541 B1 | 2/2002 | Kanda |
| 6,361,781 B2 | 3/2002 | Lorant |
| 6,376,456 B1 | 4/2002 | Murphy |
| 6,410,823 B1 | 6/2002 | Daley et al. |
| 6,413,920 B1 | 7/2002 | Bettiol |
| 6,452,064 B1 | 9/2002 | Thoren et al. |
| 6,454,747 B1 | 9/2002 | Shimada et al. |
| 6,454,989 B1 | 9/2002 | Neely et al. |
| 6,464,831 B1 | 10/2002 | Trokhan et al. |
| 6,468,626 B1 | 10/2002 | Takai et al. |
| 6,475,600 B1 | 11/2002 | Morman et al. |
| 6,479,130 B1 | 11/2002 | Takai et al. |
| 6,494,920 B1 | 12/2002 | Weuthen |
| 6,498,284 B1 | 12/2002 | Roe |
| 6,506,473 B1 | 1/2003 | Hisanaka et al. |
| 6,528,439 B1 | 3/2003 | Stokes et al. |
| 6,534,149 B1 | 3/2003 | Daley et al. |
| 6,610,391 B2 | 8/2003 | Molee |
| 6,620,777 B2 | 9/2003 | Heibel |

(56) References Cited

U.S. PATENT DOCUMENTS

| | | |
|---|---|---|
| 6,632,504 B1 | 10/2003 | Gillespie |
| 6,649,547 B1 | 11/2003 | Arnold et al. |
| 6,676,646 B2 | 1/2004 | Bast et al. |
| 6,713,159 B1 | 3/2004 | Blenke et al. |
| 6,716,441 B1 | 4/2004 | Osborne et al. |
| 6,846,561 B1 | 1/2005 | Gownder et al. |
| 6,849,065 B2 | 2/2005 | Schmidt et al. |
| 6,849,319 B2 | 2/2005 | Cree |
| D506,317 S | 6/2005 | Hallberg |
| D506,618 S | 6/2005 | Seguinot |
| D507,413 S | 7/2005 | Farahat |
| 6,916,969 B1 | 7/2005 | Helmfridsson et al. |
| 6,924,261 B2 | 8/2005 | Grandmaire |
| D512,505 S | 12/2005 | Vinson |
| 6,992,058 B2 | 1/2006 | Grandmaire |
| 6,996,851 B2 | 2/2006 | Nordness et al. |
| 7,005,558 B1 | 2/2006 | Johansson et al. |
| D517,816 S | 3/2006 | Dwiggins et al. |
| 7,033,340 B1 | 4/2006 | Muscat et al. |
| 7,056,404 B2 | 6/2006 | Mcfall et al. |
| 7,063,895 B2 | 6/2006 | Rodrigues |
| 7,067,711 B2 | 6/2006 | Kuroda et al. |
| D529,607 S | 10/2006 | Lindner et al. |
| 7,118,639 B2 | 10/2006 | Delucia et al. |
| D545,572 S | 7/2007 | Barkey et al. |
| D546,068 S | 7/2007 | Vidal et al. |
| D551,343 S | 9/2007 | Haersjoe |
| D561,481 S | 2/2008 | Mecchi et al. |
| 7,371,919 B1 | 5/2008 | Busam |
| 7,378,033 B2 | 5/2008 | Harrison |
| 7,381,417 B2 | 6/2008 | Gamez-Garcia |
| D581,170 S | 11/2008 | Delaney |
| D581,524 S | 11/2008 | Macaulay et al. |
| D583,464 S | 12/2008 | Francoeur |
| D584,401 S | 1/2009 | Francoeur |
| D585,649 S | 2/2009 | Bachmann |
| D586,564 S | 2/2009 | Enderby et al. |
| D612,491 S | 3/2010 | Sullivan |
| 7,803,244 B2 | 9/2010 | Siqueira et al. |
| 7,806,880 B2 | 10/2010 | Roe et al. |
| D632,496 S | 2/2011 | Nugent |
| D632,896 S | 2/2011 | Sanders et al. |
| 7,887,522 B2 | 2/2011 | Roe et al. |
| 7,967,801 B2 | 6/2011 | Hammons |
| 7,981,850 B2 | 7/2011 | Doi |
| 8,022,267 B2 | 9/2011 | Hellstroem et al. |
| D651,410 S | 1/2012 | Nugent |
| D656,740 S | 4/2012 | Nugent |
| 8,186,296 B2 | 5/2012 | Brown |
| 8,188,022 B2 | 5/2012 | Sengupta |
| 8,211,414 B2 | 7/2012 | Chen |
| 8,226,625 B2 | 7/2012 | Turner |
| 8,226,626 B2 | 7/2012 | Turner et al. |
| 8,227,660 B2 | 7/2012 | Hara et al. |
| 8,231,595 B2 | 7/2012 | Turner et al. |
| 8,251,965 B2 | 8/2012 | Costea |
| D668,332 S | 10/2012 | Hough et al. |
| D673,780 S | 1/2013 | Van Straten |
| 8,388,594 B2 | 3/2013 | Turner |
| D682,420 S | 5/2013 | Abram et al. |
| 8,454,571 B2 | 6/2013 | Rezai et al. |
| 8,524,649 B2 | 9/2013 | Leyrer |
| 8,981,178 B2 | 3/2015 | Ng et al. |
| 9,018,154 B2 | 4/2015 | Blondel |
| 9,034,230 B2 | 5/2015 | Qureshi et al. |
| 9,044,353 B2 | 6/2015 | Stone et al. |
| 9,149,968 B2 | 10/2015 | Wilhelm et al. |
| 9,237,973 B2 | 1/2016 | Abuto et al. |
| 9,441,188 B2 | 9/2016 | Schramm, Jr |
| 9,468,092 B2 | 10/2016 | Sawada et al. |
| 9,550,309 B2 | 1/2017 | Gibson et al. |
| D778,436 S | 2/2017 | Coslett et al. |
| 10,076,451 B2 | 9/2018 | Giovanni |
| 10,270,000 B2 | 4/2019 | Derkacs |
| 10,350,119 B2 | 7/2019 | Mullane et al. |
| 10,357,410 B2 | 7/2019 | Mullane et al. |
| 10,667,962 B2 | 6/2020 | Mullane et al. |
| 10,786,401 B2 | 9/2020 | Mullane et al. |
| 11,766,367 B2 | 9/2023 | Mullane |
| 2001/0005540 A1 | 6/2001 | Hisanaka et al. |
| 2001/0008683 A1 | 7/2001 | Takai et al. |
| 2001/0053901 A1 | 12/2001 | Mizutani et al. |
| 2002/0013563 A1 | 1/2002 | Lassen et al. |
| 2002/0016122 A1 | 2/2002 | Curro |
| 2002/0022817 A1 | 2/2002 | Ishikawa |
| 2002/0028624 A1 | 3/2002 | Mizutani et al. |
| 2002/0034912 A1 | 3/2002 | Curro et al. |
| 2002/0062113 A1 | 5/2002 | Thomas et al. |
| 2002/0062115 A1 | 5/2002 | Wada et al. |
| 2002/0081927 A1 | 6/2002 | Maldonado et al. |
| 2002/0089079 A1 | 7/2002 | Shelley et al. |
| 2002/0098762 A1 | 7/2002 | Shelley et al. |
| 2002/0098764 A1 | 7/2002 | Mleziva et al. |
| 2002/0132749 A1 | 9/2002 | Smith |
| 2002/0147435 A1 | 10/2002 | Coles et al. |
| 2002/0172371 A1 | 11/2002 | Baker et al. |
| 2002/0182371 A1 | 12/2002 | Soon et al. |
| 2002/0182396 A1 | 12/2002 | Delucia et al. |
| 2002/0193032 A1 | 12/2002 | Newkirk et al. |
| 2003/0003269 A1 | 1/2003 | Lee et al. |
| 2003/0004481 A1 | 1/2003 | Matsuoka et al. |
| 2003/0011099 A1 | 1/2003 | Maldonado et al. |
| 2003/0021951 A1 | 1/2003 | Desai et al. |
| 2003/0026945 A1 | 2/2003 | Lasko |
| 2003/0028165 A1 | 2/2003 | Curro et al. |
| 2003/0077430 A1 | 4/2003 | Grimm et al. |
| 2003/0082377 A1 | 5/2003 | Hartzog et al. |
| 2003/0082979 A1 | 5/2003 | Bean et al. |
| 2003/0104748 A1 | 6/2003 | Brown et al. |
| 2003/0109839 A1 | 6/2003 | Costea |
| 2003/0125687 A1 | 7/2003 | Gubernick et al. |
| 2003/0145517 A1 | 8/2003 | Miller |
| 2003/0149412 A1 | 8/2003 | Damaghi et al. |
| 2003/0187415 A1 | 10/2003 | Kudo |
| 2003/0217945 A1 | 11/2003 | Kiene et al. |
| 2003/0232558 A1 | 12/2003 | Moody, III et al. |
| 2004/0029479 A1 | 2/2004 | Snider et al. |
| 2004/0038851 A1 | 2/2004 | Aubay |
| 2004/0043189 A1 | 3/2004 | Huang |
| 2004/0065208 A1 | 4/2004 | Hart |
| 2004/0067709 A1 | 4/2004 | Kishine et al. |
| 2004/0071716 A1 | 4/2004 | Jansen |
| 2004/0081804 A1 | 4/2004 | Basler et al. |
| 2004/0087924 A1 | 5/2004 | Sroda |
| 2004/0092902 A1 | 5/2004 | Hoffman |
| 2004/0116027 A1 | 6/2004 | Termonia et al. |
| 2004/0116321 A1 | 6/2004 | Salesses |
| 2004/0116322 A1 | 6/2004 | Manakopoulos |
| 2004/0118811 A1 | 6/2004 | Stone et al. |
| 2004/0122396 A1 | 6/2004 | Maldonado et al. |
| 2004/0122404 A1 | 6/2004 | Meyer et al. |
| 2004/0127128 A1 | 7/2004 | Thomas |
| 2004/0127875 A1 | 7/2004 | Hammons et al. |
| 2004/0161586 A1 | 8/2004 | Cree |
| 2004/0162536 A1 | 8/2004 | Becker |
| 2004/0170813 A1 | 9/2004 | Digiacomantonio |
| 2004/0176734 A1 | 9/2004 | Rasmussen et al. |
| 2004/0181199 A1 | 9/2004 | Moberg-Alehammar et al. |
| 2004/0204337 A1 | 10/2004 | Corona |
| 2004/0209042 A1 | 10/2004 | Peacock |
| 2004/0229769 A1 | 11/2004 | Smith |
| 2004/0241399 A1 | 12/2004 | Marmon et al. |
| 2004/0265533 A1 | 12/2004 | Hoying et al. |
| 2005/0003980 A1 | 1/2005 | Baker |
| 2005/0025964 A1 | 2/2005 | Fairbanks et al. |
| 2005/0026527 A1 | 2/2005 | Schmidt et al. |
| 2005/0027270 A1 | 2/2005 | Cree et al. |
| 2005/0087292 A1 | 4/2005 | Mcfall et al. |
| 2005/0096614 A1 | 5/2005 | Perez et al. |
| 2005/0131366 A1 | 6/2005 | Shimada |
| 2005/0145523 A1 | 7/2005 | Zander et al. |
| 2005/0148971 A1 | 7/2005 | Kuroda et al. |
| 2005/0175385 A1 | 8/2005 | Cho et al. |
| 2005/0202208 A1 | 9/2005 | Kelly |

(56) References Cited

U.S. PATENT DOCUMENTS

| | | |
|---|---|---|
| 2005/0228353 A1 | 10/2005 | Thomas |
| 2005/0233140 A1 | 10/2005 | Oh et al. |
| 2005/0244619 A1 | 11/2005 | Kauschke et al. |
| 2005/0256027 A1 | 11/2005 | Heibel |
| 2005/0256475 A1 | 11/2005 | Komatsu et al. |
| 2005/0288647 A1 | 12/2005 | Ellingson et al. |
| 2006/0019063 A1 | 1/2006 | Kelly |
| 2006/0020251 A1 | 1/2006 | Kelly |
| 2006/0068176 A1 | 3/2006 | Zafiroglu et al. |
| 2006/0069361 A1 | 3/2006 | Olson |
| 2006/0087053 A1 | 4/2006 | Odonnell |
| 2006/0107505 A1 | 5/2006 | Desai et al. |
| 2006/0113049 A1 | 6/2006 | Knobloch et al. |
| 2006/0129114 A1 | 6/2006 | Mason et al. |
| 2006/0135026 A1 | 6/2006 | Arendt et al. |
| 2006/0135923 A1 | 6/2006 | Boggs et al. |
| 2006/0141885 A1 | 6/2006 | Cobbs et al. |
| 2006/0142710 A1 | 6/2006 | Kigata |
| 2006/0148358 A1 | 7/2006 | Hall et al. |
| 2006/0179539 A1 | 8/2006 | Harber |
| 2006/0252669 A1 | 11/2006 | Heibel |
| 2007/0015427 A1 | 1/2007 | Yanagawase et al. |
| 2007/0021022 A1 | 1/2007 | Kishine et al. |
| 2007/0032772 A1 | 2/2007 | Ehrnsperger |
| 2007/0036943 A1 | 2/2007 | Hirose et al. |
| 2007/0048498 A1 | 3/2007 | Cree |
| 2007/0073254 A1 | 3/2007 | Ponomarenko et al. |
| 2007/0088307 A1 | 4/2007 | Arizti et al. |
| 2007/0099817 A1 | 5/2007 | Smith |
| 2007/0135787 A1 | 6/2007 | Raidel et al. |
| 2007/0191802 A1 | 8/2007 | Gubernick |
| 2007/0256286 A1 | 11/2007 | Ngai |
| 2007/0275622 A1 | 11/2007 | Masuda et al. |
| 2007/0275866 A1 | 11/2007 | Dykstra |
| 2007/0293413 A1 | 12/2007 | Mcfarland |
| 2008/0076692 A1 | 3/2008 | Carvell |
| 2008/0138574 A1 | 6/2008 | Maschino et al. |
| 2008/0143009 A1 | 6/2008 | Kurian et al. |
| 2008/0249494 A1 | 10/2008 | Digiacomantonio et al. |
| 2008/0294135 A1 | 11/2008 | Hara |
| 2008/0294138 A1 | 11/2008 | Andersson et al. |
| 2008/0295256 A1 | 12/2008 | Broze |
| 2008/0300562 A1 | 12/2008 | Ahoniemi et al. |
| 2008/0312343 A1 | 12/2008 | Braun |
| 2008/0312622 A1 | 12/2008 | Hundorf |
| 2008/0317984 A1 | 12/2008 | Yamashita et al. |
| 2009/0030390 A1 | 1/2009 | Hammons |
| 2009/0030391 A1 | 1/2009 | Hammons et al. |
| 2009/0082746 A1 | 3/2009 | Thomas et al. |
| 2009/0104831 A1 | 4/2009 | Bornemann et al. |
| 2009/0124155 A1 | 5/2009 | Tiemeier et al. |
| 2009/0131896 A1 | 5/2009 | Ebitsuka et al. |
| 2009/0157021 A1 | 6/2009 | Sullivan |
| 2009/0191779 A1 | 7/2009 | Cree |
| 2009/0233046 A1 | 9/2009 | Iulianetti |
| 2009/0247978 A1 | 10/2009 | Boissier |
| 2009/0259208 A1 | 10/2009 | Hellstrom et al. |
| 2009/0299316 A1 | 12/2009 | Seyler |
| 2009/0318050 A1 | 12/2009 | Okaya |
| 2010/0004615 A1 | 1/2010 | Boissier |
| 2010/0019415 A1 | 1/2010 | Stone et al. |
| 2010/0035014 A1 | 2/2010 | Hammons |
| 2010/0036338 A1 | 2/2010 | Hammons |
| 2010/0036346 A1 | 2/2010 | Hammons |
| 2010/0100067 A1 | 4/2010 | Pugliese, III |
| 2010/0105273 A1 | 4/2010 | Motomura et al. |
| 2010/0107396 A1 | 5/2010 | Yagyu et al. |
| 2010/0130952 A1 | 5/2010 | Murai |
| 2010/0159770 A1 | 6/2010 | Walser et al. |
| 2010/0164733 A1 | 7/2010 | Ales et al. |
| 2010/0190679 A1 | 7/2010 | Vanpachtenbeke |
| 2010/0196653 A1 | 8/2010 | Curro et al. |
| 2010/0227130 A1 | 9/2010 | Takahashi |
| 2010/0233438 A1 | 9/2010 | Stone |
| 2010/0252138 A1 | 10/2010 | Tseng |
| 2010/0261399 A1 | 10/2010 | Katsuya et al. |
| 2010/0280471 A1 | 11/2010 | Shah |
| 2010/0330326 A1 | 12/2010 | Turner et al. |
| 2011/0004176 A1 | 1/2011 | Andersson et al. |
| 2011/0024940 A1 | 2/2011 | Qureshi et al. |
| 2011/0046592 A1* | 2/2011 | Nishikawa ............ A61F 13/511 156/219 |
| 2011/0073513 A1 | 3/2011 | Weisman et al. |
| 2011/0106036 A1 | 5/2011 | Staahl et al. |
| 2011/0117307 A1 | 5/2011 | Fraser |
| 2011/0184370 A1 | 7/2011 | Seyler et al. |
| 2011/0189915 A1 | 8/2011 | Morimoto et al. |
| 2011/0196330 A1 | 8/2011 | Hammons |
| 2011/0236683 A1 | 9/2011 | Takebe et al. |
| 2011/0245141 A1 | 10/2011 | Gizaw |
| 2011/0264064 A1 | 10/2011 | Arora |
| 2011/0269663 A1 | 11/2011 | Clowes |
| 2011/0301312 A1 | 12/2011 | Blondel |
| 2011/0305870 A1 | 12/2011 | Curro et al. |
| 2011/0313385 A1 | 12/2011 | Hammons et al. |
| 2011/0319853 A1 | 12/2011 | Yamashita et al. |
| 2012/0003423 A1 | 1/2012 | Cree |
| 2012/0035566 A1 | 2/2012 | Sagisaka et al. |
| 2012/0043036 A1 | 2/2012 | Polat et al. |
| 2012/0095426 A1 | 4/2012 | Visscher et al. |
| 2012/0121882 A1 | 5/2012 | Okaya |
| 2012/0171913 A1 | 7/2012 | Fox et al. |
| 2012/0177886 A1 | 7/2012 | Kanya |
| 2012/0273990 A1 | 11/2012 | O'Donnell et al. |
| 2012/0282436 A1 | 11/2012 | Coe |
| 2012/0289917 A1 | 11/2012 | Abuto et al. |
| 2012/0295060 A1 | 11/2012 | Mullane |
| 2012/0296304 A1 | 11/2012 | Choo et al. |
| 2012/0316532 A1 | 12/2012 | Mccormick |
| 2013/0012898 A1 | 1/2013 | Bergendahl et al. |
| 2013/0029555 A1 | 1/2013 | Morimoto |
| 2013/0097101 A1 | 4/2013 | Ortiz |
| 2013/0109612 A1 | 5/2013 | Corona, III |
| 2013/0121944 A1 | 5/2013 | Leyrer |
| 2013/0121945 A1 | 5/2013 | Leyrer |
| 2013/0129657 A1 | 5/2013 | Streuli |
| 2013/0139666 A1 | 6/2013 | Raidel et al. |
| 2013/0226122 A1 | 8/2013 | Roe et al. |
| 2013/0253461 A1 | 9/2013 | Xu et al. |
| 2013/0310300 A1 | 11/2013 | Leyrer |
| 2013/0310301 A1 | 11/2013 | Sivik |
| 2014/0029815 A1 | 1/2014 | Kadir et al. |
| 2014/0031779 A1 | 1/2014 | Hammons et al. |
| 2014/0033605 A1 | 2/2014 | Sondjaja et al. |
| 2014/0044934 A1 | 2/2014 | Bills |
| 2014/0047649 A1 | 2/2014 | Blondel |
| 2014/0066873 A1 | 3/2014 | Kawakami et al. |
| 2014/0087130 A1 | 3/2014 | Seyler et al. |
| 2014/0121624 A1* | 5/2014 | Kirby ................ A61F 13/51108 604/383 |
| 2014/0148773 A1 | 5/2014 | Brown |
| 2014/0148774 A1 | 5/2014 | Brown et al. |
| 2014/0151934 A1 | 6/2014 | Thomas et al. |
| 2014/0163500 A1 | 6/2014 | Roe et al. |
| 2014/0163506 A1 | 6/2014 | Roe |
| 2014/0163511 A1 | 6/2014 | Roe et al. |
| 2014/0228795 A1 | 8/2014 | Castanares |
| 2014/0296809 A1 | 10/2014 | Hammons et al. |
| 2014/0296815 A1 | 10/2014 | Takken |
| 2014/0303581 A1 | 10/2014 | Karlsson |
| 2014/0315779 A1 | 10/2014 | Zander |
| 2014/0324009 A1 | 10/2014 | Lee |
| 2014/0336605 A1 | 11/2014 | Hardie et al. |
| 2014/0378639 A1 | 12/2014 | Blondel |
| 2015/0099086 A1 | 4/2015 | Kim et al. |
| 2015/0191677 A1 | 7/2015 | Blondel |
| 2015/0197708 A1 | 7/2015 | Jin |
| 2015/0209189 A1 | 7/2015 | Mullane |
| 2015/0250663 A1 | 9/2015 | Wagner et al. |
| 2015/0283001 A1 | 10/2015 | Arizti et al. |
| 2015/0283003 A1 | 10/2015 | Rosati et al. |
| 2015/0329799 A1 | 11/2015 | Schramm,, Jr |
| 2015/0337239 A1 | 11/2015 | Gonzalez De Cossio |
| 2016/0024426 A1 | 1/2016 | Sivik |

(56) References Cited

U.S. PATENT DOCUMENTS

| | | |
|---|---|---|
| 2016/0024427 A1 | 1/2016 | Sivik |
| 2016/0024428 A1 | 1/2016 | Dykstra |
| 2016/0024429 A1 | 1/2016 | Dykstra |
| 2016/0024430 A1 | 1/2016 | Dykstra |
| 2016/0024431 A1 | 1/2016 | Dykstra |
| 2016/0024432 A1 | 1/2016 | Sivik |
| 2016/0024434 A1 | 1/2016 | Sivik |
| 2016/0032220 A1 | 2/2016 | Sivik |
| 2016/0113826 A1 | 4/2016 | Liu et al. |
| 2016/0129626 A1 | 5/2016 | Arora et al. |
| 2016/0136003 A1 | 5/2016 | Mullane et al. |
| 2016/0136010 A1 | 5/2016 | Roe et al. |
| 2016/0136014 A1 | 5/2016 | Arora |
| 2016/0136015 A1 | 5/2016 | Giovanni et al. |
| 2016/0136016 A1 | 5/2016 | Mullane et al. |
| 2016/0136919 A1 | 5/2016 | Roe et al. |
| 2017/0151103 A1 | 6/2017 | Bianchi |
| 2018/0000654 A1 | 1/2018 | Arora et al. |
| 2018/0000655 A1 | 1/2018 | Mullane et al. |
| 2018/0000656 A1 | 1/2018 | Roe et al. |
| 2018/0228660 A1 | 8/2018 | Mullane et al. |
| 2018/0229216 A1 | 8/2018 | Smith et al. |
| 2018/0235817 A1 | 8/2018 | Mullane et al. |
| 2018/0318144 A1 | 11/2018 | Giovanni et al. |
| 2019/0240082 A1 | 8/2019 | Mullane et al. |
| 2019/0290503 A1 | 9/2019 | Mullane et al. |
| 2020/0139346 A1 | 5/2020 | Smith et al. |
| 2020/0246199 A1 | 8/2020 | Mullane et al. |
| 2021/0322231 A1 | 10/2021 | Mullane et al. |
| 2022/0226168 A1 | 7/2022 | Giovanni et al. |
| 2022/0265486 A1 | 8/2022 | Mullane et al. |

FOREIGN PATENT DOCUMENTS

| | | |
|---|---|---|
| CA | 2449437 A1 | 1/2003 |
| CA | 2733472 A1 | 12/2009 |
| CA | 2482306 C | 10/2011 |
| CN | 1207662 A | 2/1999 |
| CN | 1222596 A | 7/1999 |
| CN | 2331362 Y | 8/1999 |
| CN | 1290156 A | 4/2001 |
| CN | 2567250 Y | 8/2003 |
| CN | 1547631 A | 11/2004 |
| CN | 1549770 A | 11/2004 |
| CN | 1575787 A | 2/2005 |
| CN | 1620533 A | 5/2005 |
| CN | 1678271 A | 10/2005 |
| CN | 1772984 A | 5/2006 |
| CN | 2897211 Y | 5/2007 |
| CN | 201505226 U | 6/2010 |
| CN | 101790606 A | 7/2010 |
| CN | 201618014 U | 11/2010 |
| CN | 101925459 A | 12/2010 |
| CN | 102112084 A | 6/2011 |
| CN | 201855363 U | 6/2011 |
| CN | 101724132 B | 11/2011 |
| CN | 102470542 A | 5/2012 |
| CN | 102673030 A | 9/2012 |
| CN | 102791234 A | 11/2012 |
| CN | 102844004 A | 12/2012 |
| CN | 202724134 U | 2/2013 |
| CN | 103356337 A | 10/2013 |
| CN | 101940514 B | 12/2013 |
| CN | 103491916 A | 1/2014 |
| CN | 103747955 A | 4/2014 |
| CN | 103842570 A | 6/2014 |
| DE | 2806401 A1 | 8/1979 |
| DE | 4106295 A1 | 9/1992 |
| DE | 19647459 A1 | 5/1998 |
| DE | 19846857 C1 | 3/2000 |
| EP | 0165807 A1 | 12/1985 |
| EP | 0172025 A2 | 2/1986 |
| EP | 0172723 A2 | 2/1986 |
| EP | 0172724 A2 | 2/1986 |
| EP | 0330212 A2 | 8/1989 |
| EP | 0343840 A2 | 11/1989 |
| EP | 0359501 A2 | 3/1990 |
| EP | 0495212 A1 | 7/1992 |
| EP | 0535579 A1 | 4/1993 |
| EP | 0545423 A1 | 6/1993 |
| EP | 0212284 B1 | 9/1993 |
| EP | 0589224 A1 | 3/1994 |
| EP | 0691427 A1 | 1/1996 |
| EP | 0696655 A1 | 2/1996 |
| EP | 0710472 A1 | 5/1996 |
| EP | 0749736 A1 | 12/1996 |
| EP | 0749737 A1 | 12/1996 |
| EP | 0749738 A1 | 12/1996 |
| EP | 0749739 A1 | 12/1996 |
| EP | 0749740 A1 | 12/1996 |
| EP | 0761846 A2 | 3/1997 |
| EP | 0934737 A1 | 8/1999 |
| EP | 1022007 A1 | 1/2000 |
| EP | 0983758 A1 | 3/2000 |
| EP | 1040807 A1 | 10/2000 |
| EP | 1084689 A2 | 3/2001 |
| EP | 1086676 A1 | 3/2001 |
| EP | 1290995 A2 | 3/2003 |
| EP | 1066006 B1 | 5/2003 |
| EP | 1352948 A1 | 10/2003 |
| EP | 1140228 A1 | 3/2004 |
| EP | 1550425 A1 | 7/2005 |
| EP | 1625195 B1 | 5/2007 |
| EP | 1818032 A1 | 8/2007 |
| EP | 1988793 A1 | 11/2008 |
| EP | 1740682 B1 | 6/2009 |
| EP | 1756168 B1 | 7/2009 |
| EP | 2110472 A1 | 10/2009 |
| EP | 2284250 A1 | 2/2011 |
| EP | 2347872 A2 | 7/2011 |
| EP | 1781717 B1 | 11/2012 |
| EP | 2570102 A1 | 3/2013 |
| FR | 2862975 B1 | 2/2006 |
| GB | 2002400 A | 2/1979 |
| GB | 2103933 A | 3/1983 |
| GB | 2225724 A | 6/1990 |
| GB | 2284786 A | 6/1995 |
| GB | 2296464 A | 7/1996 |
| GB | 2310606 A | 9/1997 |
| JP | H0524783 B2 | 6/1985 |
| JP | H03186261 A | 8/1991 |
| JP | H04327211 A | 11/1992 |
| JP | H04327256 A | 11/1992 |
| JP | H05502602 A | 5/1993 |
| JP | H05195406 A | 8/1993 |
| JP | H0638818 A | 2/1994 |
| JP | H06280150 A | 10/1994 |
| JP | H07216653 A | 8/1995 |
| JP | 2587116 B2 | 3/1997 |
| JP | H0959823 A | 3/1997 |
| JP | H09310226 A | 12/1997 |
| JP | H09512504 A | 12/1997 |
| JP | H10506586 A | 6/1998 |
| JP | 2790875 B2 | 8/1998 |
| JP | H10272152 A | 10/1998 |
| JP | H10272154 A | 10/1998 |
| JP | H11152624 A | 6/1999 |
| JP | 2001032139 A | 2/2001 |
| JP | 2002180331 A | 6/2002 |
| JP | 2003003334 A | 1/2003 |
| JP | 2003522043 A | 7/2003 |
| JP | 2003275238 A | 9/2003 |
| JP | 2003525640 A | 9/2003 |
| JP | 200408596 A | 1/2004 |
| JP | 2004041870 A | 2/2004 |
| JP | 2004141640 A | 5/2004 |
| JP | 2004154250 A | 6/2004 |
| JP | 2004187810 A | 7/2004 |
| JP | 2004532758 A | 10/2004 |
| JP | 2004536239 A | 12/2004 |
| JP | 2005502509 A | 1/2005 |
| JP | 2005040235 A | 2/2005 |
| JP | 2005200795 A | 7/2005 |
| JP | 2005245789 A | 9/2005 |

(56) References Cited

FOREIGN PATENT DOCUMENTS

| | | |
|---|---|---|
| JP | 2006511375 A | 4/2006 |
| JP | 2008006272 A | 1/2008 |
| JP | 2008127705 A | 6/2008 |
| JP | 2008174880 A | 7/2008 |
| JP | 2008179939 A | 8/2008 |
| JP | 2009050621 A | 3/2009 |
| JP | 4353767 B2 | 8/2009 |
| JP | 4357591 B1 | 8/2009 |
| JP | 2009172354 A | 8/2009 |
| JP | 2010051697 A | 3/2010 |
| JP | 2010200974 A | 9/2010 |
| JP | 2010269029 A | 12/2010 |
| JP | 2011078477 A | 4/2011 |
| JP | 2011135979 A | 7/2011 |
| JP | 2011239835 A | 12/2011 |
| JP | 2011529773 A | 12/2011 |
| JP | 2012050548 A | 3/2012 |
| JP | 5034078 B2 | 7/2012 |
| JP | 2012154010 A | 8/2012 |
| JP | 2012158547 A | 8/2012 |
| JP | 2012517536 A | 8/2012 |
| JP | 2013011051 A | 1/2013 |
| JP | 2013500175 A | 1/2013 |
| JP | 2013208320 A | 10/2013 |
| JP | 2014034741 A | 2/2014 |
| JP | 5528660 B2 | 4/2014 |
| JP | 2014097240 A | 5/2014 |
| JP | 2014511739 A | 5/2014 |
| JP | 2014519421 A | 8/2014 |
| JP | 3209591 B2 | 3/2017 |
| KR | 20010064584 A | 7/2001 |
| KR | 20030089593 A | 11/2003 |
| KR | 100648560 B1 | 11/2006 |
| KR | 20140006704 A | 1/2014 |
| KR | 20150100549 A | 9/2015 |
| RU | 2496460 C1 | 10/2013 |
| WO | 9003464 A2 | 4/1990 |
| WO | 9110415 A2 | 7/1991 |
| WO | 9311726 A1 | 6/1993 |
| WO | 9315701 A1 | 8/1993 |
| WO | 9513773 A1 | 5/1995 |
| WO | 9517867 A2 | 7/1995 |
| WO | 9607689 A1 | 3/1996 |
| WO | 9610380 A2 | 4/1996 |
| WO | 9610481 A1 | 4/1996 |
| WO | 9611107 A1 | 4/1996 |
| WO | 9619313 A1 | 6/1996 |
| WO | 9621759 A1 | 7/1996 |
| WO | 9702133 A2 | 1/1997 |
| WO | 9703818 A1 | 2/1997 |
| WO | 9709020 A1 | 3/1997 |
| WO | 9710788 A1 | 3/1997 |
| WO | 9711661 A1 | 4/1997 |
| WO | 9853896 A1 | 12/1998 |
| WO | 9920725 A1 | 4/1999 |
| WO | 9930660 A1 | 6/1999 |
| WO | 9939671 A1 | 8/1999 |
| WO | 9960975 A1 | 12/1999 |
| WO | 0001334 A1 | 1/2000 |
| WO | 0013636 A1 | 3/2000 |
| WO | 0024351 A1 | 5/2000 |
| WO | 0028929 A1 | 5/2000 |
| WO | 0037249 A1 | 6/2000 |
| WO | 0062826 A1 | 10/2000 |
| WO | 0172251 A1 | 10/2001 |
| WO | 02057400 A2 | 7/2002 |
| WO | 02098653 A1 | 12/2002 |
| WO | 02100632 A1 | 12/2002 |
| WO | 03002699 A1 | 1/2003 |
| WO | 03008688 A2 | 1/2003 |
| WO | 03015681 A1 | 2/2003 |
| WO | 03024706 A1 | 3/2003 |
| WO | 03071019 A1 | 8/2003 |
| WO | 03102043 A1 | 12/2003 |
| WO | 2004009009 A1 | 1/2004 |
| WO | 2004050812 A1 | 6/2004 |
| WO | 2004058497 A1 | 7/2004 |
| WO | 2004061065 A1 | 7/2004 |
| WO | 2004098474 A1 | 11/2004 |
| WO | 2005087907 A1 | 9/2005 |
| WO | 2005097834 A2 | 10/2005 |
| WO | 2005103215 A1 | 11/2005 |
| WO | 2005120411 A1 | 12/2005 |
| WO | 2007001320 A1 | 1/2007 |
| WO | 2007116346 A1 | 10/2007 |
| WO | 2008005693 A2 | 1/2008 |
| WO | 2009097498 A2 | 8/2009 |
| WO | 2010017351 A1 | 2/2010 |
| WO | 2010017362 A1 | 2/2010 |
| WO | 2010078959 A1 | 7/2010 |
| WO | 2010079100 A1 | 7/2010 |
| WO | 2010141309 A1 | 12/2010 |
| WO | 2011017285 A1 | 2/2011 |
| WO | 2011080643 A2 | 7/2011 |
| WO | 2012014957 A1 | 2/2012 |
| WO | 2012052172 A1 | 4/2012 |
| WO | 2012076432 A1 | 6/2012 |
| WO | 2013068388 A1 | 5/2013 |
| WO | 2013068394 A1 | 5/2013 |
| WO | 2013085447 A1 | 6/2013 |
| WO | 2013091150 A1 | 6/2013 |
| WO | 2013114231 A1 | 8/2013 |
| WO | 2013142486 A1 | 9/2013 |
| WO | 2013147222 A1 | 10/2013 |
| WO | 2013163360 A1 | 10/2013 |
| WO | 2013163360 A2 | 10/2013 |
| WO | 2013163388 A1 | 10/2013 |
| WO | 2013189010 A1 | 12/2013 |
| WO | 2014022652 A1 | 2/2014 |
| WO | 2014108106 A1 | 7/2014 |
| WO | 2015130088 A1 | 9/2015 |
| WO | 2015157248 A1 | 10/2015 |
| WO | 2015157254 A1 | 10/2015 |
| WO | 2017082834 A1 | 5/2017 |

OTHER PUBLICATIONS

All Office Actions; U.S. Appl. No. 17/709,757, filed Mar. 31, 2022.
All Office Actions; U.S. Appl. No. 14/933,021, filed Nov. 5, 2015.
All Office Actions; U.S. Appl. No. 14/933,024, filed Nov. 5, 2015.
All Office Actions; U.S. Appl. No. 14/933,030, filed Nov. 5, 2015.
All Office Actions; U.S. Appl. No. 14/933,034, filed Nov. 5, 2015.
All Office Actions; U.S. Appl. No. 14/933,039, filed Nov. 5, 2015.
All Office Actions; U.S. Appl. No. 15/704,027, filed Sep. 14, 2017.
All Office Actions; U.S. Appl. No. 15/704,035, filed Sep. 14, 2017.
All Office Actions; U.S. Appl. No. 15/953,586, filed Apr. 16, 2018.
All Office Actions; U.S. Appl. No. 15/953,742, filed Apr. 16, 2018.
All Office Actions; U.S. Appl. No. 16/032,117, filed Jul. 11, 2018.
All Office Actions; U.S. Appl. No. 16/386,632, filed Apr. 17, 2019.
All Office Actions; U.S. Appl. No. 16/432,084, filed Jun. 5, 2019.
All Office Actions; U.S. Appl. No. 16/733,554, filed Jan. 3, 2020.
All Office Actions; U.S. Appl. No. 16/854,073, filed Apr. 21, 2020.
All Office Actions; U.S. Appl. No. 17/361,681, filed Jun. 29, 2021.
All Office Actions; U.S. Appl. No. 17/668,469, filed Feb. 10, 2022.
All Office Actions; U.S. Appl. No. 18/302,322, filed Apr. 18, 2023.
All Office Actions; U.S. Appl. No. 18/307,895, filed Apr. 27, 2023.
All Office Actions; U.S. Appl. No. 15/704,030, filed Sep. 14, 2017.
Amimasr E., "Analysis of Basis Weight Uniformity of Microfiber Nonwovens and Its Impact on Permeability and Filtration Properties," North Carolina State University, 2012, retrieved from the Internet URL https://repositoryJib.ncsu.edu/handle/1840.16/9096, pp. 294.
Analyze Menu, retrieved from the Internet URL "https://imagej.nih.gov/ij/docs/menus/analyze.html", retrieved on Dec. 19, 2021, 12 pages.
ASTM D3954-94 (Reapproved 2010), Standard Test Method for Dropping Point of Waxes.
Auto Threshold—ImageJ, http://imagej.netlAuto_Threshold, last modified on Dec. 15, 2017, 7 pages.
Ferreira, T. and Rasband W., "ImageJ User Guide," IJ 1.46r, Retrieved from the Internet URL https://imagej.nih.gov/ij/docs/guide/user-guide.pdf, Last modified Sep./Oct. 2012, p. 79.

(56) References Cited

OTHER PUBLICATIONS

Morphological Image Processing, Retrieved from the Internet URL https://www.cs.auckland.ac.nz/courses/compsci773slc/lectures/ImageProcessing-html/topic4.htm#erosion, retrieved on Apr. 19, 2021, pp. 7.
Party in my Pants Cloth Pads, Pad Size Chart, Apr. 2015 (Year: 2015), 2 Pgs.
Process Menu, retrieved from the Internet URL "https://imagej.nih.gov/ij/docs/menus/process.html", retrieved on Dec. 19, 2021, 17 pages.
Schuck, Peter, Size-Distribution Analysis of Macromolecules by Sedimentation Velocity Ultracentrifugation and Lamm Equation Modeling, Biophysical Journal, Mar. 2000, pp. 1606-1619, vol. 78, No. 3.
Schuck, Peter, Size-Distribution Analysis of Macromolecules by Sedimentation Velocity Ultracentrifugation and Lamm Equation Modeling, Biophysical Journal, vol. 78, Mar. 2000, pp. 1606-1619.
U.S. Appl. No. 18/302,322, filed Apr. 18, 2023, to Timothy Ian Mullane et al.
U.S. Appl. No. 18/307,895, filed Apr. 27, 2023, to Timothy Ian Mullane et al.
All Office Actions: U.S. Appl. No. 18/529,196, filed Dec. 5, 2023.
All Office Actions: U.S. Appl. No. 18/529,232, filed Dec. 5, 2023.
All Office Actions: U.S. Appl. No. 18/529,256, filed Dec. 5, 2023.
U.S. Appl. No. 18/529,196, filed Dec. 5, 2023, Timothy Ian Mullane et al.
U.S. Appl. No. 18/529,232, filed Dec. 5, 2023, Timothy Ian Mullane et al.
U.S. Appl. No. 18/529,256, filed Dec. 5, 2023, Timothy Ian Mullane et al.

\* cited by examiner

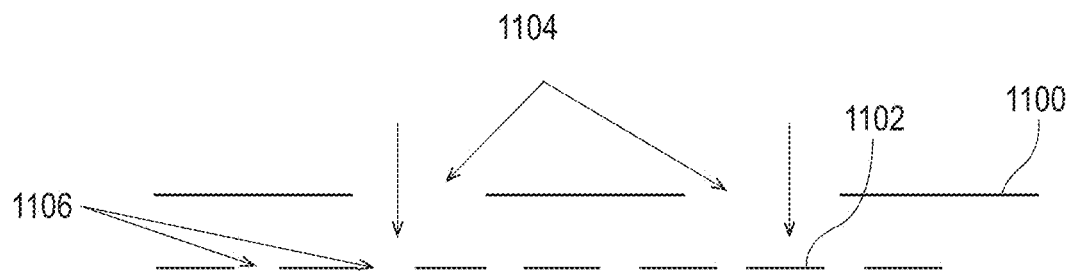
Fig. 100
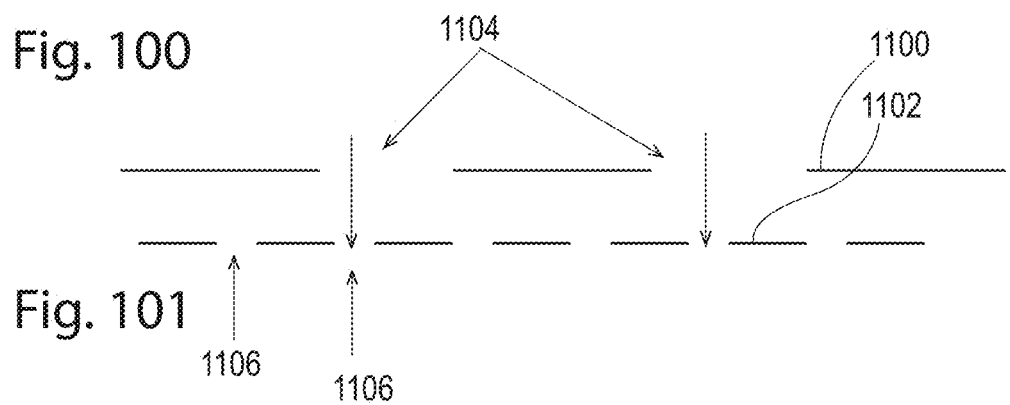
Fig. 101
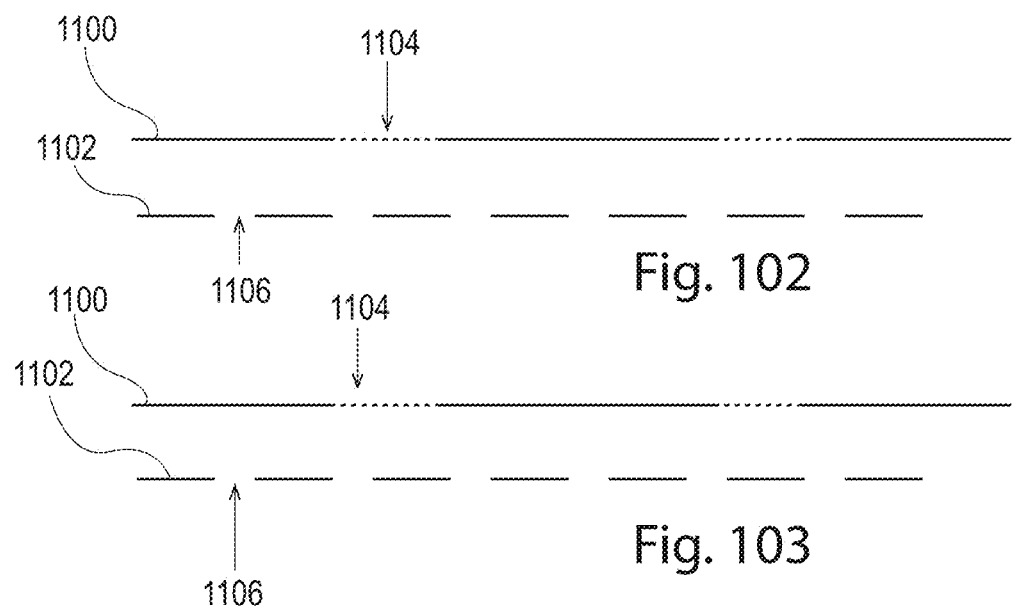
Fig. 102
Fig. 103

PATTERNED APERTURED WEBS

CROSS REFERENCE TO RELATED APPLICATIONS

This application is a continuation of, and claims priority under 35 U.S.C. § 120 to, U.S. patent application Ser. No. 17/668,469, filed on Feb. 10, 2022, which is a continuation of U.S. patent application Ser. No. 17/361,681, filed on Jun. 29, 2021, which is a continuation of U.S. patent application Ser. No. 16/854,073, filed on Apr. 21, 2020, now U.S. Pat. No. 11,633,311, granted on Apr. 5, 2023, which is a continuation of U.S. patent application Ser. No. 16/432,084, filed on Jun. 5, 2019, now U.S. Pat. No. 10,667,962, granted on Jun. 2, 2020, which is a continuation of U.S. patent application Ser. No. 14/933,030 filed on Nov. 5, 2015, now U.S. Pat. No. 10,350,119, granted on Jul. 16, 2019, which claims the benefit, under 35 U.S.C. § 119(e), of U.S. Provisional Patent Application Ser. No. 62/177,405, filed on Mar. 13, 2015, and U.S. Provisional Patent Application Ser. No. 62/076,043, filed on Nov. 6, 2014, the entire disclosures of all of which are fully incorporated by reference herein.

FIELD

The present disclosure generally relates to webs, apertured webs, patterned apertured webs, zonal patterned apertured webs, laminates, pre-strained laminates, moiré effect laminates, and methods for making the same. The webs, apertured webs, patterned apertured webs, zonal patterned apertured webs, laminates, pre-strained laminates, and moiré effect laminates are particularly suited for use in disposable absorbent articles, such as diapers, adult incontinence products, training pants, feminine hygiene products, wipes, dusting substrates, cleaning substrates, and any other suitable consumer products or other products.

BACKGROUND

Apertured webs are sometimes useful in disposable absorbent products and other consumer products. These apertured webs typically have uniformly sized and shaped circular or ovate apertures throughout their area. The circular or ovate apertures may be uniformly spaced in the cross-machine direction and in the machine direction with respect to each other. These uniform aperture patterns provide webs that have the same amount of fluid penetration and/or absorbency throughout their area owing to the uniform circular or ovate aperture designs. Furthermore, land areas (i.e., non-apertured portions) in these apertured webs typically have the same size, shape, orientation, and spacing with respect to each other. While such uniform apertured webs may be desirable in some applications, other applications would benefit from improved apertured webs. Furthermore, these apertured webs are typically planar, but some consumers may desire three-dimensional features and other features.

SUMMARY

The patterned apertured webs of the present disclosure provide patterns of nonhomogeneous apertures that have different sizes, shapes, and/or Absolute Feret Angles. This allows the webs to have better depth perception, improved fluid handling properties, and/or aesthetically pleasing appearances relative to apertured webs that have uniformly sized and shaped, homogeneous apertures. Laminates having at least one pre-strained layer of the present disclosure, whether comprising patterned apertured webs, apertured webs, or not, provide three-dimensional features in the laminates, thereby providing consumer preferred executions that, in one example, may keep bodily exudates away from the skin of a wearer or user. Moiré effect laminates may also be provided. Outer covers, and other components of absorbent articles also benefit from these patterned apertured webs, pre-strained laminates, moiré effect laminates, and other non-pre-strained laminates of the present disclosure. Methods of making the patterned apertured webs, moiré effect laminates, and pre-strained or non-pre-strained laminates are also provided.

In a form, the present disclosure is directed, in part, to a patterned apertured web. The patterned apertured web comprises a plurality of land areas in the patterned apertured web and a plurality of apertures defined in the patterned apertured web. At least some of the land areas surround at least some of the apertures. The patterned apertured web has an Effective Open Area in the range of about 5% to about 50%, according to the Aperture Test herein. The patterned apertured web has a plurality of Interaperture Distances, according to the Aperture Test herein. The Interaperture Distances have a distribution having a median and a mean, wherein the mean is greater than the median.

In a form, the present disclosure is directed, in part, to a patterned apertured web. The patterned apertured web comprises a plurality of land areas in the patterned apertured web. At least some of the land areas have a width of at least 5 mm. The patterned apertured web comprises a plurality of apertures defined in the patterned apertured web. At least some of the land areas surround at least some of the plurality of apertures. The plurality of apertures are non-homogeneous in a repeat unit such that at least three of the apertures have a different size, a different shape, or a different Absolute Feret Angle, according to the Aperture Test herein. The plurality of the apertures have an Effective Aperture Area in a range of about 0.3 mm$^2$ to about 15 mm$^2$, according to the Aperture Test herein. The patterned apertured web has an Effective Open Area in a range of about 5% to about 50%, according to the Aperture Test herein.

In a form, the present disclosure is directed, in part, to a patterned apertured web. The patterned apertured web comprises a plurality of land areas in the patterned apertured web and a plurality of apertures defined in the patterned apertured web, wherein at least some of land areas surround at least some of the apertures. The plurality of apertures are non-homogeneous in a repeat unit such that at least three of the apertures have a different size or a different shape. The patterned apertured web has an Effective Open Area in the range of about 5% to about 50%, according to the Aperture Test herein.

In a form, the present disclosure is directed, in part, to a patterned apertured web comprising a plurality of first arrays forming a first zone in the patterned apertured web. At least some of the first arrays comprise a first plurality of land areas and a first plurality of apertures. At least some of the first plurality of land areas surround at least some of the first plurality of apertures. The first plurality of apertures in the first zone have a plurality of Interaperture Distances, according to the Aperture Test herein. The Interaperture Distances of the first zone have a first distribution having a first mean and a first median. The first mean is greater than the first median by at least 4%. The first arrays comprise an Effective Open Area in the range of about 5% to about 50%, according to the Aperture Test herein. The patterned apertured web comprises a plurality of second, different arrays forming a second zone. At least some of the second arrays comprise a second plurality of land areas and a second plurality of apertures. At least some of the second land areas surround at least some of the second plurality of apertures. The second plurality of apertures in the second zone have a plurality of Interaperture Distances, according to the Aperture Test herein. The Interaperture Distances of the second zone have a second distribution having a second mean and a second median. The second mean is greater than the second median. The second arrays comprise an Effective Open Area of about 5% to about 50%, according to the Aperture Test herein.

In a form, the present disclosure is directed, in part, to a patterned apertured web. The patterned apertured web comprises a plurality of first arrays forming a first zone in the patterned apertured web. At least some of the first arrays comprise a first plurality of land areas and a first plurality of non-homogeneous apertures. At least some of the first plurality of land areas surround at least some of the first plurality of apertures. The first plurality of apertures have an Average Absolute Feret Angle of greater than about 20 degrees, according to the Aperture Test herein. The first arrays comprise an Effective Open Area in the range of about 5% to about 50%, according to the Aperture Test herein. The patterned apertured web comprises a plurality of second, different arrays forming a second zone in the patterned aperture web. At least some of the second arrays comprise a second plurality of land areas and a second plurality of non-homogeneous apertures. At least some of the second plurality of land areas surround at least some of the second plurality of apertures. The second arrays comprise an Effective Open Area of about 5% to about 50%, according to the Aperture Test herein.

In a form, the present disclosure is directed, in part, to a patterned apertured web. The patterned apertured web comprises a layer comprising a plurality of apertures and a plurality of land areas. The plurality of apertures comprise a first set of apertures in a first zone and a second set of apertures in a second zone. The first set of apertures in the first zone have Interaperture Distances, according to the Aperture Test herein. Interaperture Distances of the first set of apertures have a first distribution having a first mean and a first median. The first mean is different than the first median. The second set of apertures in the second zone have Interaperture Distances, according to the Aperture Test herein. The Interaperture Distances of the second set of apertures have a second distribution having a second mean and a second median. The second mean is different than the second median. The first and second sets of apertures have different patterns.

In a form, the present disclosure is directed, in part, to a laminate. The laminate comprises a first layer comprising a plurality of lower opacity zones positioned within a higher opacity zone. The plurality of lower opacity zones form a first pattern. The laminate comprises a second layer comprising a second pattern. The first layer is intermittently joined to the second layer to form the laminate. The laminate comprises a non-joined span of the first and second layers having a dimension of at least about 20 mm. A first portion of the second pattern is visible through at least some of the plurality of lower opacity zones when the first layer, within the non-joined span, is in a first position relative to the second layer, within the non-joined span. A second portion of the second pattern is visible through at least some of the plurality of lower opacity zones when the first layer, within the non-joined span, is in a second position relative to the first layer, within the non-joined span.

In a form, the present disclosure is directed, in part, to an absorbent article comprising a laminate. The laminate comprises a first nonwoven layer comprising a plurality of lower opacity zones positioned within a higher opacity zone. The plurality of lower opacity zones form a first pattern. The laminate comprises a second layer comprising a second pattern. The first layer is intermittently joined to the second layer to form the laminate. The laminate comprises a non-joined span of the first and second layers having a dimension of at least about 20 mm. A first portion of the second pattern is visible through at least some of the plurality of lower opacity zones when the first layer, within the non-joined span, is in a first position relative to the second layer, within the non-joined span. A second portion of the second pattern is visible through at least some of the plurality of lower opacity zones when the first layer, within the non-joined span, is in a second position relative to the first layer, within the non-joined span.

In a form, the present disclosure is directed, in part, to an absorbent article comprising a laminate. The laminate comprises a first nonwoven layer comprising a plurality of apertures in a first pattern and a second layer comprising a second, different pattern. The first layer is intermittently joined to the second layer to form the laminate. The laminate comprises a non-joined span of the first and second layers having a dimension of at least about 30 mm. A first portion of the second pattern is visible through at least some of the plurality of apertures when the first layer, within the non-joined span, is in a first position relative to the second layer, within the non-joined span. A second portion of the second pattern is visible through at least some of the plurality of apertures when the first layer, within the non-joined span, is in a second position relative to the first layer, within the non-joined span.

In a form, the present disclosure is directed, in part, to a method of producing a patterned apertured web. The method comprises providing a web having a central longitudinal axis. The web comprises a plurality of overbonds extending substantially parallel to the central longitudinal axis. The method comprises conveying the web in a machine direction that is substantially parallel to a direction of extension of the central longitudinal axis of the web. The method comprises stretching the web in a cross-machine direction that is substantially perpendicular to the machine direction to cause at least some of the overbonds to at least partially rupture and at least partially form patterned apertures in the web. At least some of the patterned apertures have Absolute Feret Angles, according to the Aperture Test herein, of at least about 20 degrees. At least some of the patterned apertures have an Aspect Ratio, according to the Aperture Test herein, in the range of about 2:1 to about 6:1.

In a form, the present disclosure is directed, in part, to a method of forming patterned apertures in a web. The method comprises providing a web having a central longitudinal axis, conveying the web in a machine direction that is substantially parallel to the central longitudinal axis, and creating a plurality of overbonds in the web. The overbonds have central longitudinal axes that are substantially parallel to the central longitudinal axis of the web. The method comprises stretching the web in a cross-machine direction that is substantially perpendicular to the machine direction to at least partially form patterned apertures in the web at, at least some of the overbonds. At least some of the patterned apertures have Absolute Feret Angles, according to the Aperture Test herein, of at least about degrees. The at least some of the patterned apertures have an Aspect Ratio, according to the Aperture Test herein, of greater than about 2:1.

In a form, the present disclosure is directed, in part, to a method of producing a patterned apertured web. The method comprises providing a web having a central longitudinal axis. The web comprises a plurality of overbonds extending substantially parallel to the central longitudinal axis. The method comprises conveying the web in a machine direction that is substantially parallel to a direction of extension of the central longitudinal axis of the web. The method comprises stretching the web in a cross-machine direction that is substantially perpendicular to the machine direction to cause at least some of the overbonds to at least partially rupture and at least partially form patterned apertures in the web. At least some of the patterned apertures have Absolute Feret Angles, according to the Aperture Test herein, that are at least about 25 degrees. At least some of the patterned apertures have an Aspect Ratio, according to the Aperture Test herein, in the range of about 2:1 to about 6:1. At least three of the apertures are nonhomogeneous.

In a form, the present disclosure is directed, in part, to a laminate comprising a first nonwoven layer comprising a plurality of apertures and a second nonwoven layer. One of the first and second nonwoven layers is a pre-strained layer and is joined to the other one of the first and second nonwoven layers. The other one of the first and second nonwoven layers is a non-pre-strained layer. The pre-strained layer and the non-pre-strained layer together form a three-dimensional laminate.

In a form, the present disclosure is directed, in part, to a laminate comprising a first nonwoven layer comprising a patterned apertured web comprising a plurality of apertures and a second nonwoven layer. One of the first and second nonwoven layers is a pre-strained layer and is joined to the other one of the first and second nonwoven layers. The other one of the first and second nonwoven layers is a non-pre-strained layer. The pre-strained layer and the non-pre-strained layer together form a three-dimensional laminate. The plurality of apertures have Interaperture Distances, according to the Aperture Test herein. The Interaperture Distances have a distribution having a mean and a median, wherein the mean is greater than the median.

In a form, the present disclosure is directed, in part, to a laminate comprising a first nonwoven layer comprising a patterned apertured web comprising plurality of apertures and a second nonwoven layer. One of the first and second nonwoven layers is a pre-strained layer and is joined to the other one of the first and second nonwoven layers. The other one of the first and second nonwoven layers is a non-pre-strained layer. The pre-strained layer and the non-pre-strained layer together form a three-dimensional laminate. The first nonwoven layer or the second nonwoven layer comprises an indicia or a patterned adhesive that has a different color than the first nonwoven layer or the second nonwoven layer. The plurality of apertures have Interaperture Distances, according to the Aperture Test herein. The Interaperture Distances have a distribution having a mean and a median. The mean is greater than the median. The laminate is free of any elastic strands or elastic films.

In a form, the present disclosure is directed, in part, to an absorbent article. The absorbent article comprises a liquid permeable topsheet on a wearer-facing side of the absorbent article, a garment-facing laminate on a garment-facing side of the absorbent article. The garment-facing laminate comprises a first nonwoven layer and a second layer joined to the first nonwoven layer. The first nonwoven layer comprises a plurality of apertures. At least 3 of the plurality of apertures in a repeat unit have a different size, a different shape, or a different Absolute Feret Angle, according to the Aperture Test herein. The absorbent article comprises an absorbent core disposed at least partially intermediate the liquid permeable topsheet and the garment-facing laminate.

In a form, the present disclosure is directed, in part, to an absorbent article. The absorbent article comprises a liquid permeable topsheet on a wearer-facing side of the absorbent article and a garment-facing laminate on a garment-facing side of the absorbent article. The garment-facing laminate comprises a first nonwoven layer and a second layer joined to the first nonwoven layer when the first nonwoven layer or the second layer is in a pre-strained condition and when the other of the first nonwoven layer or the second layer is in a non-pre-strained condition to form a three-dimensional material. The first nonwoven layer comprises a plurality of apertures. The absorbent article comprises an absorbent core disposed at least partially intermediate the liquid permeable topsheet and the garment-facing laminate.

In a form, the present disclosure is directed, in part, to an absorbent article. The absorbent article comprises a liquid permeable topsheet on a wearer-facing side of the absorbent article and a garment-facing layer on a garment-facing side of the absorbent article. The garment-facing layer comprises a first zone comprising a plurality of overbonds and a second zone comprising a plurality of apertures. At least 3 of the plurality of apertures in a repeat unit have a different size, a different shape, or a different Absolute Feret Angle, according to the Aperture Test herein. The absorbent article comprises a liquid impermeable backsheet and an absorbent core disposed at least partially intermediate the liquid permeable topsheet and the backsheet.

In a form, the present disclosure is directed, in part, to an absorbent article. The absorbent article comprises a liquid permeable topsheet on a wearer-facing side of the absorbent article and a garment-facing laminate on a garment-facing side of the absorbent article. The garment-facing laminate comprises a first nonwoven layer and a second nonwoven layer joined to the first nonwoven layer. The first nonwoven layer comprises a plurality of apertures. The absorbent article comprises an absorbent core disposed at least partially intermediate the liquid permeable topsheet and the garment-facing laminate.

In a form, the present disclosure is directed, in part, to a method of forming a three-dimensional laminate for an absorbent article. The method comprises providing a first nonwoven layer, providing a second nonwoven layer, and applying a pre-strain force to the first nonwoven layer or to the second nonwoven layer. The method comprises joining the first nonwoven layer to the second nonwoven layer while the first nonwoven layer or the second nonwoven layer is in a pre-strained condition, and releasing the pre-strain force to form the three-dimensional laminate.

In a form, the present disclosure is directed, in part, to a method of forming a three-dimensional laminate for an absorbent article. The method comprises providing a first layer, providing a separate, second layer, and applying a pre-strain force to the first layer or to the second layer. The method comprises overbonding the first layer and the second layer while the first layer or the second layer is in a pre-strained condition to join the first layer and the second layer, and releasing the pre-strain force to form the three-dimensional laminate.

In a form, the present disclosure is directed, in part, to a method of forming a three-dimensional laminate for an absorbent article. The method comprises providing a nonwoven first layer, providing a separate, nonwoven second layer, and applying a pre-strain force substantially in the machine direction to the first nonwoven layer or to the second nonwoven layer. The method comprises overbonding the first layer and the second layer while the first layer or the second layer is in a pre-strained condition to join the first layer and the second layer. The method comprises stretching the first and second nonwoven layers in a substantially cross-machine direction to cause at least some of the overbonds to at least partially rupture and at least partially form apertures in the first and second nonwoven layers, and releasing the pre-strain force to form the three-dimensional laminate. The three-dimensional laminate is free of elastic strands or elastic films.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

FIG. 100 is a cross-sectional illustration of a portion of a non-joined span of a moiré effect laminate, wherein a first layer is in a first position relative to a second layer, and wherein a first portion of a second pattern of the second layer is visible through a first pattern of the first layer, in accordance with the present disclosure;

FIG. 101 is a cross-sectional illustration of a portion of a non-joined span of the moiré effect laminate of FIG. 100, wherein the first layer has been moved into a second position relative to the second layer, and wherein a second portion of the second pattern is visible through the first pattern, in accordance with the present disclosure;

FIG. 102 is a cross-sectional illustrate of a portion of a non-joined span of a moiré effect laminate, wherein a first layer is in a first position relative to a second layer, and wherein a first portion of a second pattern of the second layer is visible through a first pattern of the first layer, in accordance with the present disclosure;

FIG. 103 is a cross-sectional illustration of the portion of the non-joined span of the moiré effect laminate of FIG. 102, wherein the first layer has been moved into a second position relative to the second layer, and wherein a second portion of the second pattern is visible through the first patter, in accordance with the present disclosure;

DETAILED DESCRIPTION

Figure 1:
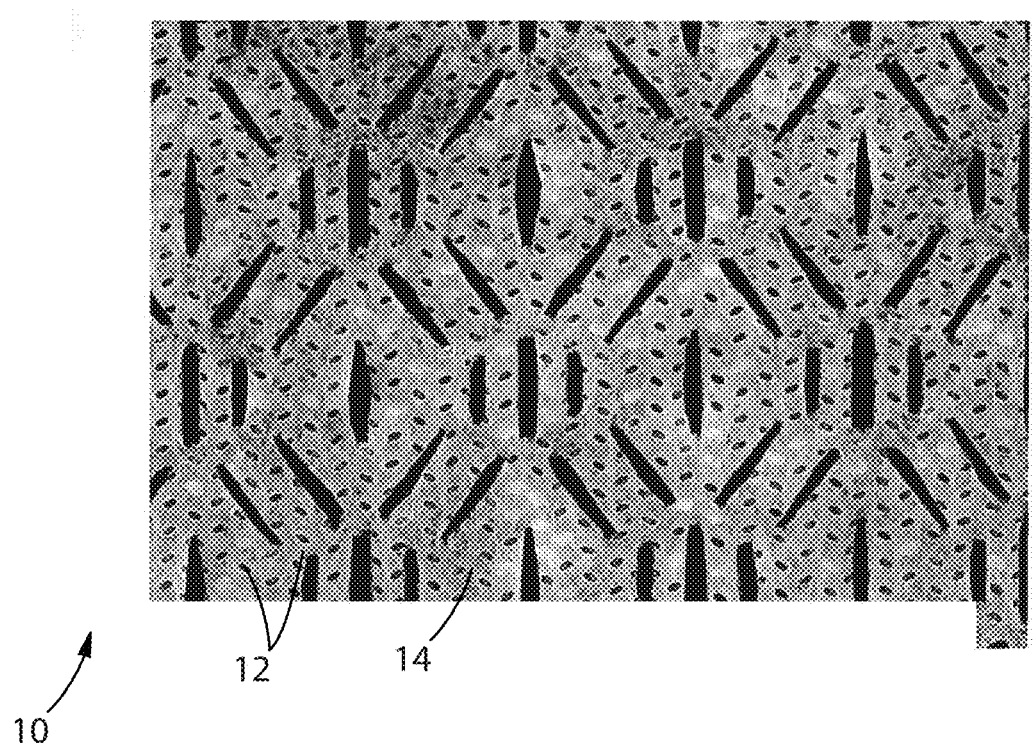
FIGS. 1-4 are photographs of portions of example patterned apertured webs in accordance with the present disclosure.

Various non-limiting forms of the present disclosure will now be described to provide an overall understanding of the principles of the structure, function, manufacture, and use of the patterned apertured webs disclosed herein. One or more examples of these non-limiting forms are illustrated in the accompanying drawings. Those of ordinary skill in the art will understand that the patterned apertured webs specifically described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

As used herein, the terms "nonwoven material", "nonwoven", or "nonwoven layer" are used in their normal sense and specifically, refers to a web that has a structure of individual fibers or threads which are interlaid, but not in any regular, repeating manner. Nonwoven materials, nonwovens, or nonwoven layers have been, in the past, formed by a variety of processes, such as, for example, meltblowing processes, spunbonding processes and bonded carded web processes.

As used herein, the term "microfibers", refers to small diameter fibers having an average diameter not greater than about 100 microns.

As used herein, the term "nanofibers", refers to very small diameter fibers having an average diameter less than about 1 micron.

As used herein, the term "meltblown", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carded by the high velocity gas stream and are deposited on a collecting surface to form a web of randomly dispersed meltblown fibers.

As used herein, the term "spunbond", refers to small diameter fibers which are formed by extruding a molten thermoplastic material as filaments from a plurality of fine, usually circular, capillaries of a spinneret with the diameter of the extruded filaments then being rapidly reduced as by, for example, educative drawing or other well-known spunbonding mechanisms.

As used herein, the term "polymer" generally includes, but is not limited to, homopolymers, copolymers, such as, for example, block, graft, random, and alternating copolymers, terpolymer, etc., and blends and modifications thereof. Furthermore, unless otherwise specifically limited, the term "polymer" shall include all possible geometrical configurations of the material. These configurations include, but are not limited to, isotactic, syndiaotactic and random symmetries.

As used herein, the terms "join", "joined", "joining", "bond", "bonded", "bonding", "attach", "attached", or "attaching" encompass configurations whereby an element is directly secured to another element by affixing the element directly to the other element, and configurations whereby an element is indirectly secured to another element by affixing the element to intermediate member(s) which in turn are affixed to the other element.

As used herein, the term "elastic" refers to any material that, upon application of a biasing force, can stretch to an elongated length of at least about 110% of its relaxed, original length (i.e., can stretch to 10 percent), without rupture or breakage, and upon release of the applied force, recovers at least about 40% of its elongation. For example, a material that has an initial length of 100 mm can extend at least to 110 mm, and upon removal of the force would retract to a length of 106 mm (40% recovery). "Elastic" may refer to a single material, or it may refer to a combination of materials making up a laminate in an article. An elastic material may be incorporated into a laminate which is not elastic, or which is less elastic than one or more of the elastic materials of the laminate.

As used herein, the term "nonelastic" refers to any material which does not fall within the definition of "elastic" above.

As used herein, the term "extensible" refers to any material which, upon application of a biasing force, is elongatable, at least about 10%, at least about 20%, at least about 30%, at least about 50%, without experiencing catastrophic failure. Recovery of the elongation is not required, but may at least partially occur.

As used herein, the term "melt-stabilized" refers to portions of a nonwoven material which have been subjected to localized heating and/or localized pressure to substantially consolidate the fibers of the nonwoven material into a stabilized film-like form.

As used herein, the term "absorbent article", refers to devices which absorb and contain bodily exudates (e.g., BM, urine, blood), and, more specifically, refers to devices which are placed against or in proximity to the body of the wearer to absorb and contain the various bodily exudates discharged from the body. The term absorbent article includes, but is not limited to, diapers, pants, training pants, adult incontinence products, sanitary napkins, tampons, wipes, and liners. The term "absorbent article" may also encompass cleaning or dusting pads or substrates that have some absorbency.

The term "machine direction" (MD) is used herein to refer to the primary direction of material, strip of substrate, or article flow through a process.

The term "cross direction" (CD) is used herein to refer to a direction that is generally perpendicular to the machine direction.

As used herein, the term "aperture aspect ratio" is the ratio of the major axis to the minor axis of a single aperture.

As used herein, the term "pre-strain" or "pre-strained" means a material that has been elongated to at least 105% of one of its original (i.e., before being strained) dimensions and then is capable of at least partial recovery after the elongating force is removed.

Patterned Apertured Webs

Figure 2:
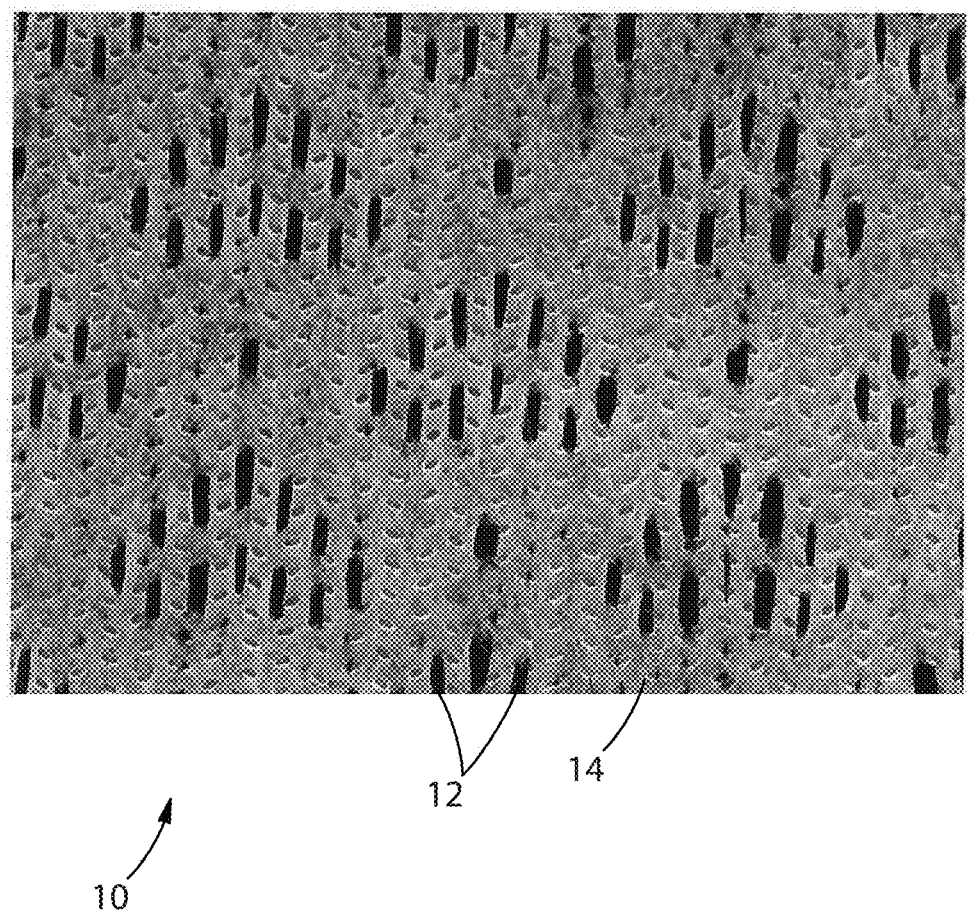
Figure 3:
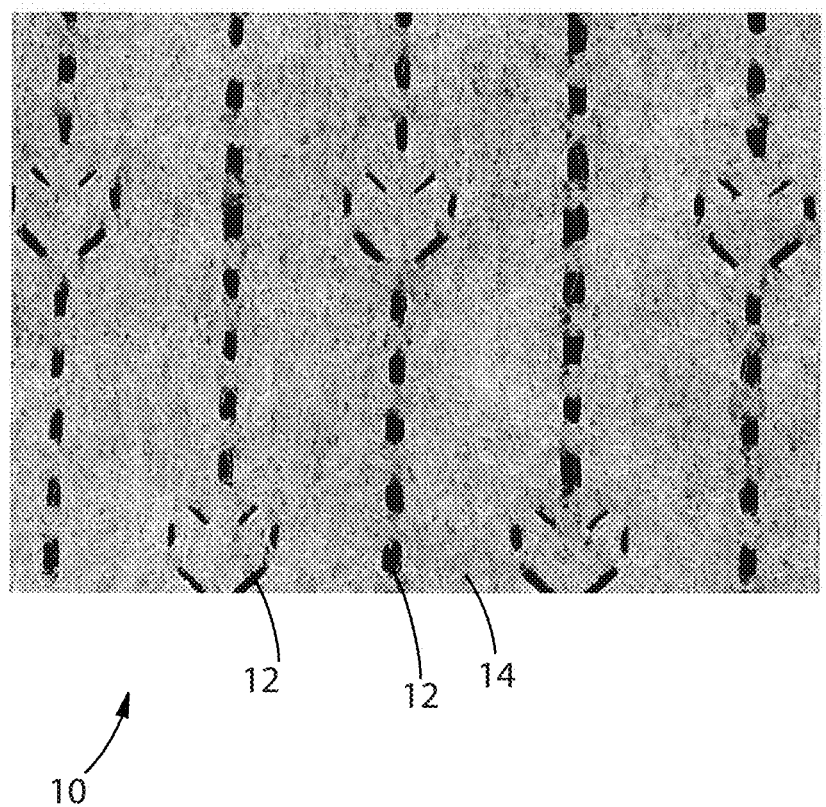
Figure 4:
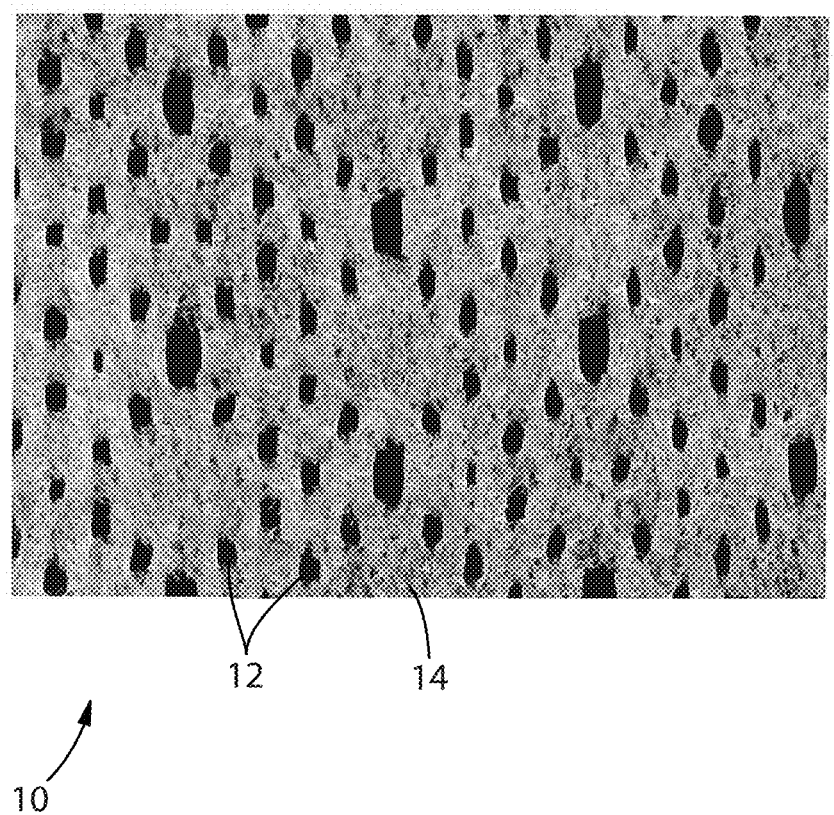

The patterned apertured webs of the present disclosure provide many benefits over conventional apertured topsheets, as will be described herein. Four examples of patterned apertured webs 10 are illustrated in FIGS. 1-4. As illustrated, the patterned apertured webs 10 may take on a number of configurations. The apertures are labeled 12 and the land areas (non-apertured areas) are labeled 14. Additional examples of patterned apertured webs are illustrated in subsequent figures. Some of the patterned apertured webs may have land area widths of at least about 4 mm, at least about 5 mm, at least about 6 mm, at least about 7 mm, at least about 8 mm, at least about 9 mm, at least about 10 mm, or in the range of about 4 mm to about 15 mm, specifically reciting all 0.1 mm increments within the specified range and all ranges formed therein. These land area widths may be measured using a NIST traceable/certified ruler from a perimeter of one aperture to a perimeter of another aperture in any direction. As an example, FIG. 2 illustrates discrete aperture patterns (e.g., set apart from other aperture patterns).

Layers

The patterned apertured webs of the present disclosure may comprise a single apertured layer (see FIGS. 1-4) or more than one layer (apertured or non-apertured), for example, two, three, or four layers. The term "layer" means a self-sustaining web (e.g., a nonwoven or a film) and not a non-self-sustaining web (e.g., a spunbond layer of an SMMS nonwoven). Thus, a Spunbond-Meltblown-Meltblown-Spunbond (SMMS) nonwoven material would be considered a single layer for purposes of this disclosure, much like a film would be considered a single layer. The patterned apertured webs may comprise one or more non-apertured layers that have not been put through an aperturing process, but merely have pores (that are not apertures for purposes of this disclosure) created in the formation of the material. If two apertured layers are provided in a patterned apertured web, each layer may have the same aperturing pattern or a different aperturing pattern.

Figure 5:
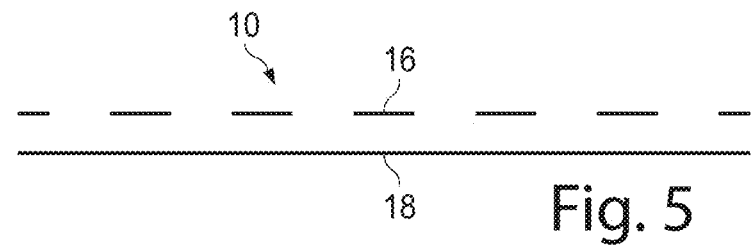
FIG. 5 is a schematic representation of a cross-sectional view of a patterned apertured web having two layers, with one layer having patterned apertures and the other layer being non-apertured in accordance with the present disclosure.

Referring to FIG. 5, a schematic illustration of an example cross-sectional view of a patterned apertured web 10 comprising two layers is illustrated. Although the examples of the patterned apertured webs of FIG. 5-10 comprise more than one layer, patterned apertured webs of the present disclosure may only have one layer (see, for example, FIGS. 1-4). The patterned apertured web 10 may comprise a patterned apertured layer 16 and a non-apertured layer 18. The patterned apertured layer 16 may comprise any of the various aperture patterns disclosed herein, for example. The patterned aperture layer 16 may be combined with, bonded to, adhesively joined to, or joined to the non-apertured layer 18 to form a laminate. The patterned apertured layer 16 may have apertures and land areas at least partially, or fully, surrounding the apertures.

If both or all layers of a multi-layer patterned apertured web are apertured, the apertures may be aligned or overlapping, not aligned or not overlapping, or partially aligned or partially overlapping in the Z-direction. For instance, the apertures in one layer may be 100% aligned or overlapping in the Z-direction with the apertures in a second layer thus forming apertures through both layers of the patterned apertured web. In such an instance, the apertures may be formed by overbonding both layers together to join the layers and then rupturing the overbonds to form apertures in both of the layers (or more than two of the layers). In other instances, the apertures may be less than 100% aligned or overlapping in the Z-direction. Stated another way, the apertures in one layer may be offset in the CD, MD, or other direction or different patterns of apertures may be formed in each layer to create the misalignment of the apertures. In such instances, the area of the apertures in one layer may overlap the area of the apertures in another layer, in the Z-direction, by 10% to 90%, 10% to 100%, 10% to 80%, 25% to 75%, 25%, 50%, or 75%, for example, specifically reciting all 0.5% increments within the specified ranges and all ranges formed therein or thereby.

In instances where more than one layer of a patterned apertured web includes apertures, the apertures may be coincident in the Z-direction, i.e., penetrate through both layers. In a form, this may be achieved by forming the apertures after bonding, joining and/or laminating the two or more layers together. Alternatively, the apertures in one layer may have a different pattern, size, and/or shape from the apertures in a second layer and/or may be oriented in a different direction. In a form, this may be achieved by forming the apertures in each of the layers prior to combining the two or layers into a laminated structure. In absorbent article forms comprising a patterned apertured web having an apertured layer and a non-apertured layer, the apertured layer may be oriented on the wearer-facing side of the patterned apertured web or on the garment-facing side of the patterned apertured web. In still other forms, the patterned apertured layer may be positioned intermediate two non-apertured layers or may be positioned under one or more non-apertured layers. In yet another form, two patterned apertured layers may sandwich one or more non-apertured layers in a patterned apertured web.

A first layer of a patterned apertured web may have the same or a different hydrophilicity as another layer of the same patterned apertured web. Both layers may be hydrophilic or hydrophobic, but one may be more hydrophilic or hydrophobic. As an example, a wearer-facing layer of a patterned apertured web may be hydrophobic while a garment-facing layer of the patterned apertured web may be hydrophilic to help wick fluid into the apertures and into an absorbent core. As another example, a first layer of a patterned apertured web may be a hydrophobic topsheet with apertures and a second layer of a patterned apertured web may be hydrophilic acquisition layer or material. This can promote fluid wicking or drainage into the absorbent core and provide depth perception.

In an instance, again referring to FIG. 5, the patterned apertured layer 16 may have a different color as the non-apertured layer 18, such that the apertures in the layer 16 are easily visible or more readily apparent to a user. The aperture pattern in the patterned apertured layer 16 may also form indicia that may indicate the correct orientation of an absorbent article comprising the patterned apertured web 10 on a wearer. Such indicia may include any object or shape that has a commonly understood vertical orientation, such as a heart shape, a face, a building, a letter or numeral, a car, for example. This may also apply to other patterned apertured webs described herein, regardless of how many apertured or non-apertured layers are provided.

Any of the patterned apertured webs described herein may have gradients of color to indicate which side of the product comprising the web is the top and which side is the bottom or to indicate depth in an absorbent article or to provide an enhanced depth perception.

The layers of the patterned apertured webs of the present disclosure may have the same basis weights or different basis weights. In an instance, again referring to FIG. 5, the layer 16 may have a higher basis weight than the layer 18. This may provide better softness on a surface of the layer 16 (e.g., a topsheet contacting a baby's skin), while also providing enhanced fluid penetration owing to the apertures in the layer 16. The various layers of the patterned apertured webs of the present disclosure may also be the same or different in material compositions, density, caliper, opacity, lotion concentration, or any other properties of nonwoven materials.

The basis weight of a patterned apertured web, or a layer thereof, may in the range of about 6 gsm to about 200 gsm, about 10 gsm to about 100 gsm, about 10 gsm to about 50 gsm, or about 10 gsm to about 40 gsm, specifically reciting all 0.1 gsm increments within the above-specified range and all ranged formed therein or thereby. Basis weight is measured according to the Basis Weight Test herein.

The predominant fiber orientation of the fibers in the layers of the multi-layer patterned apertured webs may be the same or different. In an instance, a predominant fiber orientation may be about 45 degrees to about 135 degrees, for example, off-axis relative to a machine direction, while another layer may have a predominant fiber orientation substantially along a machine direction or +/–about 10 to about 20 degrees from the machine direction. Providing different layers in a patterned apertured web with different predominant fiber orientations may provide increased strength and resistance to tearing of the patterned apertured web when the two or more layers are joined or bonded together.

Figure 6:
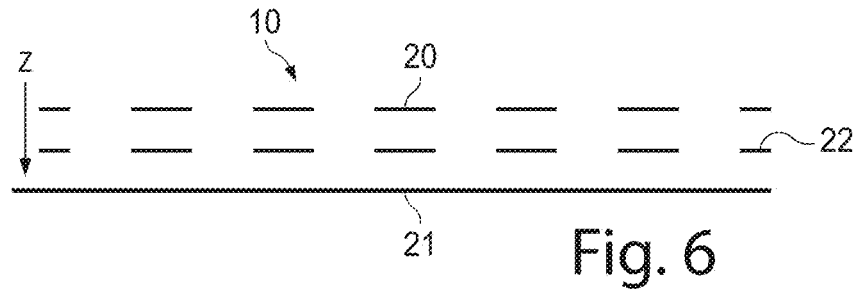
FIG. 6 is a schematic representation of a cross-sectional view of a patterned apertured web having two layers, with both layers having patterned apertures and with the apertures in the layers being aligned in accordance with the present disclosure.

Referring to FIG. 6, a schematic illustration of an example cross-sectional view of another patterned apertured web 10 is illustrated. The patterned apertured web 10 may comprise a first patterned apertured layer 20 and a second patterned apertured layer 22. Apertures of the first patterned apertured layer 20 in FIG. 6 may be about 80%, about 85%, about 90%, about 95%, about 80% to about 100%, or about 100% aligned, in the Z-direction (indicated by arrow Z), with apertures in the second patterned apertured layer 22, specifically reciting all 0.5% increments within the specified range and all ranges formed therein. The first patterned apertured layer 20 may be combined with, bonded to, or joined to the second patterned aperture layer 22 to form a laminated patterned apertured web. The patterned apertured web 10 of FIG. 6, or any of the other patterned apertured webs of the present disclosure, may comprise a third layer 21 (or more than three layers) that may be non-apertured or apertured. The second patterned apertured layer 22 may be combined with, bonded to, or joined to the third non-apertured layer 21.

Again referring to FIG. 6, the apertures in the second patterned apertured layer 22 may be smaller than (e.g., about 10% less area, about 20% less area, about 30% less area etc.) the apertures in the first patterned apertured layer 20. Such a feature may allow BM penetration through the first layer while also providing adequate liquid bodily exudate (e.g., urine and menses) fluid strikethrough through the second layer 22 or rewet from the first layer compared to a non-apertured second layer.

Figure 7:
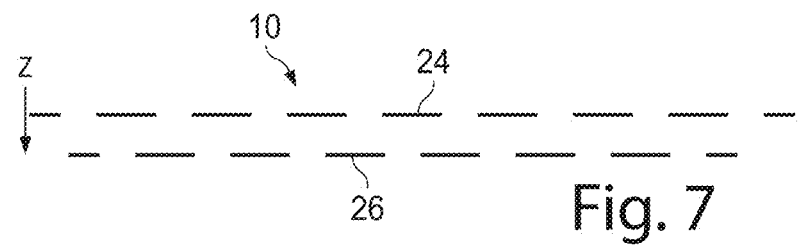
FIG. 7 is a schematic representation of a cross-sectional view of a patterned apertured web having two layers, with both layers having patterned apertures and with the apertures in one layer being fully overlapped by land areas in the other layer in accordance with the present disclosure.

Referring to FIG. 7, a schematic illustration of an example cross-sectional view of another patterned apertured web 10 is illustrated. The patterned apertured web 10 may comprise a first patterned apertured layer 24 and a second patterned apertured layer 26. Apertures of the first patterned apertured layer 24 may be fully overlapped by non-apertured portions or "land areas" of the second patterned apertured layer 26 in the Z-direction (indicated by arrow Z). The first patterned apertured layer 24 may be combined with, bonded to, or joined to the second patterned aperture layer 26 to form a laminated patterned apertured web.

Figure 8:
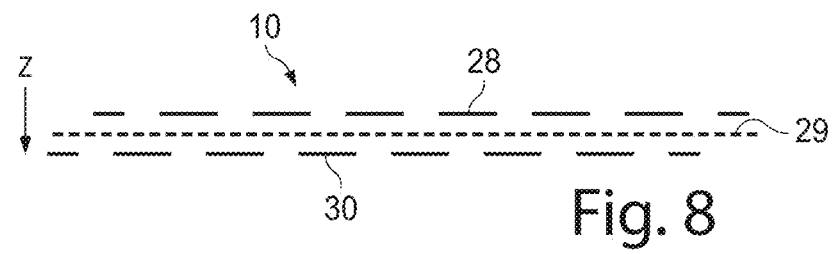
FIG. 8 is a schematic representation of a cross-sectional view of a patterned apertured web having two layers, with both layers having patterned apertures and with the apertures in one layer being partially overlapped by land areas in the other layer in accordance with the present disclosure.

Referring to FIG. 8, a schematic illustration of an example cross-sectional view of another patterned apertured web 10 is illustrated. The patterned apertured web 10 may comprise a first patterned apertured layer 28 and a second patterned apertured layer 30. Apertures of the first patterned apertured layer 28 may be partially overlapped by non-apertured portions or "land areas" of the second patterned apertured layer 30 in the Z-direction (indicated by arrow Z). The first patterned apertured layer 28 may be combined with, bonded to, or joined to the second patterned aperture layer 30 to form a laminated patterned apertured web. The overlap of the areas of the apertures in the first patterned apertured layer 28 and the areas of the apertures in the second patterned apertured layer may be in the range of about 5% to about 95%, about 10% to about 90%, about 20% to about 80%, about 25% to about 75%, about 25%, about 50%, or about 75%, specifically reciting all 0.5% increments within the specified ranges and all ranges formed therein or thereby.

The example patterned apertured web 10 of FIG. 8 may also comprise a pigmented substance (full continuous layer) or a patterned pigmented substance 29 at least partially intermediate the first and second patterned apertured layers 28 and 30. This concept may also apply to any of the examples in FIGS. 5-10 or other examples herein. The pigmented substance may also be positioned on either of the layers 28 and 30. The pigmented substance or patterned pigmented substance 29 may comprise graphics, inks, pigmented adhesives or other pigmented substances and may be viewable through the overlapping areas of the apertures from either side of the patterned apertured web 10. In a form, the pigmented substance or patterned pigmented substance 29 may be positioned under the second patterned apertured layer 30 and may still be viewable through the overlapping areas of the apertures when viewing from the first patterned apertured layer 28. The first patterned apertured layer 28, the second patterned apertured layer 30, and the pigmented substance or the patterned pigmented substance 29 may be the same color or may each be a different color. Alternatively, the patterned apertured layers 28 and 30 may have a different color as the pigmented substance or the patterned pigmented substance 29. Such forms allow for a three-dimensional appearance to be provided in the patterned apertured web 10 without actually making the patterned apertured web 10 three-dimensional, such as through embossing, for example.

Materials

Any of the layers of the patterned apertured webs described herein may comprise any materials known in the art including, but not limited to, nonwovens, wovens, cellulosic materials, films, elastic materials, non-elastic materials, highloft materials, and/or foams. The patterned apertured webs may also comprise one or more layers of one or more nonwoven materials, one or more films, combinations of different nonwoven materials, combinations of different films, combinations of one or more films and one or more nonwoven materials, or combinations of one or more different materials, for example. Patterned apertured webs having one or more layers of the same or similar materials are also within the scope of the present disclosure. The basis weight, color, opacity, hydrophilicity, Average Interaperture Distance, Average Absolute Feret Angle, Effective Aperture Area, Effective Open Area, or other parameters or characteristics of the various materials in the various layers may be the same or different.

Some precursor web materials for the patterned apertured webs may comprise PE/PP bicomponent fiber spunbond webs. Other suitable precursor webs may comprise spunbond webs comprising side-by-side crimped fibers (e.g., PE/PP or PP/PP) that are bonded via calendar (thermal point) bonding or through-air bonding. Other suitable precursor webs may comprise carded, through-air bonded or resin bonded (highloft) nonwovens comprising PE/PP or PE/PET fibers. The precursor webs may comprise microfibers and/or nanofibers, optionally with other fibers. In some circumstances, multiple layer webs may be desired over a single layer webs (even at the same basis weight) due to increased uniformity/opacity and the ability to combine webs having different properties. For example, an extensible spunbond nonwoven carrier layer may be combined with a soft, highloft nonwoven (spunbond or carded) to create an apertured web that is both soft and strong. The layers may have the same or different surface energy. For example, the top layer may be hydrophobic and the lower layer may be hydrophilic. The layers may have different permeability/capillarity, e.g. the upper layer may have higher permeability and the lower layer have higher capillarity in order to set up a capillary gradient and aid in moving fluid away from the surface (or topsheet) of an absorbent article and into an absorbent core of the absorbent article.

Fibers of the precursor web materials may comprise any suitable thermoplastic polymers. Example thermoplastic polymers are polymers that melt and then, upon cooling, crystallize or harden, but that may be re-melted upon further heating. Suitable thermoplastic polymers may have a melting temperature (also referred to as solidification temperature) from about 60° C. to about 300° C., from about 80° C. to about 250° C., or from about 100° C. to about 215° C., specifically reciting all 0.5° C. increments within the specified ranges and all ranges formed therein or thereby. And, the molecular weight of the thermoplastic polymer may be sufficiently high to enable entanglement between polymer molecules and yet low enough to be melt spinnable.

The thermoplastic polymers may be derived from any suitable material including renewable resources (including bio-based and recycled materials), fossil minerals and oils, and/or biodegradeable materials. Some suitable examples of thermoplastic polymers include polyolefins, polyesters, polyamides, copolymers thereof, and combinations thereof. Some example polyolefins include polyethylene or copolymers thereof, including low density, high density, linear low density, or ultra-low density polyethylenes such that the polyethylene density ranges between about 0.90 grams per cubic centimeter to about 0.97 grams per cubic centimeter or between about 0.92 and about 0.95 grams per cubic centimeter, for example. The density of the polyethylene may be determined by the amount and type of branching and depends on the polymerization technology and co-monomer type. Polypropylene and/or polypropylene copolymers, including atactic polypropylene; isotactic polypropylene, syndiotactic polypropylene, and combination thereof may also be used. Polypropylene copolymers, especially ethylene may be used to lower the melting temperature and improve properties. These polypropylene polymers may be produced using metallocene and Ziegler-Natta catalyst systems. These polypropylene and polyethylene compositions may be combined together to optimize end-use properties. Polybutylene is also a useful polyolefin and may be used in some forms. Other suitable polymers include polyamides or copolymers thereof, such as Nylon 6, Nylon 11, Nylon 12, Nylon 46, Nylon 66; polyesters or copolymers thereof, such as maleic anhydride polypropylene copolymer, polyethylene terephthalate; olefin carboxylic acid copolymers such as ethylene/acrylic acid copolymer, ethylene/maleic acid copolymer, ethylene/methacrylic acid copolymer, ethylene/vinyl acetate copolymers or combinations thereof; polyacrylates, polymethacrylates, and their copolymers such as poly(methyl methacrylates).

The thermoplastic polymer component may be a single polymer species or a blend of two or more thermoplastic polymers e.g., two different polypropylene resins. As an example, fibers of a first nonwoven layer of a patterned apertured web may comprise polymers such as polypropylene and blends of polypropylene and polyethylene, while a second nonwoven layer of the patterned apertured web may comprise fibers selected from polypropylene, polypropylene/polyethylene blends, and polyethylene/polyethylene terephthalate blends. In some forms, the second nonwoven layer may comprise fibers selected from cellulose rayon, cotton, other hydrophilic fiber materials, or combinations thereof. The fibers may also comprise a super absorbent material such as polyacrylate or any combination of suitable materials.

The fibers of the layer of the patterned apertured web may comprise monocomponent fibers, bi-component fibers, and/or bi-constituent fibers, round fibers or non-round fibers (e.g., capillary channel fibers), and may have major cross-sectional dimensions (e.g., diameter for round fibers) ranging from about 0.1 microns to about 500 microns. The fibers may also be a mixture of different fiber types, differing in such features as chemistry (e.g. polyethylene and polypropylene), components (mono- and bi-), denier (micro denier and >2 denier), shape (i.e. capillary and round) and the like. The fibers may range from about 0.1 denier to about 100 denier.

Example materials are contemplated where a first plurality of fibers and/or a second plurality of fibers comprise additives in addition to their constituent chemistry. For example, suitable additives include additives for coloration, antistatic properties, lubrication, softness, hydrophilicity, hydrophobicity, and the like, and combinations thereof. These additives, for example titanium dioxide for coloration, may generally be present in an amount less than about 5 weight percent and more typically less than about 2 weight percent or less.

As used herein, the term "monocomponent fiber(s)" refers to a fiber formed from one extruder using one or more polymers. This is not meant to exclude fibers formed from one polymer to which small amounts of additives have been added for coloration, antistatic properties, lubrication, hydrophilicity, etc.

As used herein, the term "bi-component fiber(s)" refers to fibers which have been formed from at least two different polymers extruded from separate extruders but spun together to form one fiber. Bi-component fibers are also sometimes referred to as conjugate fibers or multicomponent fibers. The polymers are arranged in substantially constantly positioned distinct zones across the cross-section of the bi-component fibers and extend continuously along the length of the bi-component fibers. The configuration of such a bi-component fiber may be, for example, a sheath/core arrangement wherein one polymer is surrounded by another, or may be a side-by-side arrangement, a pie arrangement, or an "islands-in-the-sea" arrangement. Some specific examples of fibers which may be used in the first nonwoven layer include polyethylene/polypropylene side-by-side bi-component fibers. Another example is a polypropylene/polyethylene bi-component fiber where the polyethylene is configured as a sheath and the polypropylene is configured as a core within the sheath. Still another example is a polypropylene/polypropylene bi-component fiber where two different propylene polymers are configured in a side-by-side configuration. Additionally, forms are contemplated where the fibers of a nonwoven layer are crimped.

Bi-component fibers may comprise two different resins, e.g. a first polypropylene resin and a second polypropylene resin. The resins may have different melt flow rates, molecular weights, or molecular weight distributions. Ratios of the 2 different polymers may be about 50/50, 60/40, 70/30, 80/20, or any ratio within these ratios. The ratio may be selected to control the amount of crimp, strength of the nonwoven layer, softness, bonding or, the like.

As used herein, the term "bi-constituent fiber(s)" refers to fibers which have been formed from at least two polymers extruded from the same extruder as a blend. Bi-constituent fibers do not have the various polymer components arranged in relatively constantly positioned distinct zones across the cross-sectional area of the fiber and the various polymers are usually not continuous along the entire length of the fiber, instead usually forming fibrils which start and end at random. Bi-constituent fibers are sometimes also referred to as multi-constituent fibers. In other examples, a bi-component fiber may comprise multiconstituent components.

As used herein, the term "non-round fiber(s)" describes fibers having a non-round cross-section, and includes "shaped fibers" and "capillary channel fibers." Such fibers may be solid or hollow, and they may be tri-lobal, delta-shaped, and may be fibers having capillary channels on their outer surfaces. The capillary channels may be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, TN. T-401 fiber is a polyethylene terephthalate (PET polyester).

Other example nonwoven materials for the patterned apertured webs may comprise spunbond materials, carded materials, melt blown materials, spunlace materials, needle punched materials, wet-laid materials, or air-laid materials, for example.

Some other example materials for at least one layer of the patterned apertured webs of the present disclosure are those that are capable of elongation in the cross-machine direction of greater than about 100%, greater than about 120%, or greater than about 150%. This enables the web to extend upon stretching and minimizes the number of broken fibers and/or tears between apertures. One example of this type of web is a spunbond web comprising sheath/core bicomponent fibers of polyethylene in the sheath and polypropylene in the core. An example may be a 25 gsm nonwoven comprising fibers that are 2.8 denier per filament with a 50/50 polyethylene/polypropylene ratio available from Fitesa in Washougal, WA.

It may be desirable for individual precursor materials, or at least one of the layer within a patterned apertured web, to be capable of undergoing an elongation of greater than or equal to about one of the following amounts: about 100% (that is double its unstretched length), about 110%, about 120%, or about 130% up to about 200%, or more, at or before reaching the peak tensile force. It may also be desirable for the precursor materials to be capable of undergoing plastic deformation to ensure that the structure of the deformations is "set" in place so that the nonwoven laminate will not tend to recover or return to its prior configuration. However, in the case crimped fiber spunbond layers, it may be desirable for the precursor material for these specific layer(s) to be capable of experiencing no or minimal plastic deformation during processing.

In contrast to spunbond nonwoven layers, the constituent fibers of the crimped fiber spunbond nonwoven layers typically are uncoiled and/or displaced when processed. Because the crimped fibers tend to coil to some extent, the processing typically displaces/uncoils the crimped fibers as opposed to elongating the crimped fibers.

Extensibility of a nonwoven layer may be impacted by bonding between constituent fibers. This is true for both spunbond nonwoven layer and crimped fiber spunbond nonwoven layers. For example, to increase extensibility in a nonwoven layer, it may be desirable for the nonwoven layer to be underbonded as opposed to optimally bonded prior to processing. A thermally bonded nonwoven web's tensile properties may be modified by changing the bonding temperature. A web may be optimally or ideally bonded, underbonded or overbonded. Optimally or ideally bonded webs are characterized by the highest peak tensile strength and elongation at tensile peak with a rapid decay in strength after tensile peak. Under strain, bond sites fail and a small amount of fibers pull out of the bond site. Thus, in an optimally bonded nonwoven, the fibers may stretch and break around the bond sites when the nonwoven web is strained beyond a certain point. Often there is a small reduction in fiber diameter in the area surrounding the thermal point bond sites. Underbonded webs have a lower peak tensile strength and elongation at tensile peak when compared to optimally bonded webs, with a slow decay in strength after tensile peak. Under strain, some fibers will pull out from the thermal point bond sites. Thus, in an underbonded nonwoven, at least some of the fibers can be separated easily from the bond sites to allow the fibers to pull out of the bond sites and rearrange when the material is strained. Overbonded webs also have a lowered peak tensile strength and elongation at tensile peak when compared to optimally bonded webs, with a rapid decay in strength after tensile peak. The bond sites look like films and result in complete bond site failure under strain.

Joining of Layers

If more than one layer is provided in a particular patterned apertured web, the layers may be bonded together using any bonding methods known to those of skill in the art, such as adhesive bonding, patterned adhesive coating, ultrasonic bonding, thermal bonding, mechanical bonding, or any combination of these bonding methods. Alternatively, the various layers may be bonded together only at the perimeter of the apertures, or partially the perimeter of the apertures, through an overbonding process. The bonding may be done in a pattern of bonds or in arrays of bonds. The pattern may be a regular, homogeneous and uniform pattern or an irregular, non-uniform and non-homogeneous pattern. The bonding patterns may comprise a substantially continuous bond pattern or may be formed of discrete bonding points. The discrete bonding points may form a pattern. The pattern of bonding points may be homogeneous or non-homogeneous. A bond pattern in one region of a patterned apertured web may differ from a bond pattern in another region of the patterned apertured web. For example, the bond pattern may be different in the machine direction or the cross-machine direction of the patterned apertured web laminate. An absorbent article including the patterned apertured web may have a different bond pattern in the front region vs. the back region, the center region vs. side regions, the crotch region vs. waist regions, or a first portion and a second portion of a topsheet or an outer cover, of the absorbent article, for example. Bonding in patterned apertured webs is typically accomplished by joining the land areas of various layers of the patterned apertured webs. If an adhesive is used in the bonding process, the adhesive may be tinted, pigmented, and/or patterned to create a complementary or contrasting pattern compared to the aperture pattern or patterns.

Color/Printing/Adhesives

Any of the layers of the patterned apertured webs may have a color that is the same or different than another layer of the patterned apertured web, regardless of whether a layer is apertured or non-apertured. For instance, in a two layer patterned apertured web, a first layer may be blue and a second layer may be white, or a first layer may be dark blue and the second layer may be light blue. There may be a Delta E difference between at least some of the layers. The layers may also have the same opacity or a different opacity, as described in further detail below. Single layer patterned apertured webs may also have a color.

Figure 9:
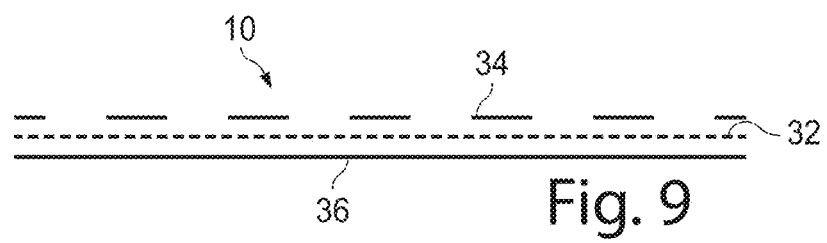
FIG. 9 is a schematic representation of a cross-sectional view of a patterned apertured web having two layers, with a first patterned apertured layer and a second non-apertured layer and with printing or ink on one of the layers in accordance with the present disclosure.

Either in addition to or in lieu of the various layered being colored, referring to FIG. 9, one or more of the layers of the patterned apertured webs 10 of the present disclosure may comprise printing 32, e.g., with ink or a pigmented or colored pattern. Single layer patterned apertured webs may also comprise ink or a pigmented or colored pattern. The ink may be deposited via any printing process known in the art including, but not limited to, flexographic printing and digital inkjet printing. The printing may form graphics or other indicia. The printing may be on an external surface of a first layer 34 of the patterned apertured web 10, between the first and second layers 34, 36 (as illustrated) of the patterned apertured web 10, or may be on a surface beneath the second layer 36 of the patterned apertured web 10. The printing may also be situated in any suitable location if the patterned apertured web has more than two layers (e.g., on the surface of any of the layers). The printing may also be deposited in zones of the patterned apertured web, or layers thereof, and/or in patterns throughout the patterned apertured web, or layers thereof. The printing may be different or the same in different zones of the patterned apertured web, or layers thereof. If the printing is covered by one of the layers (e.g., layer 34), the covering layer (e.g., layer 34) may have a relatively low opacity to enhance the visual appearance of the printing. The density of the printing (e.g., clarity and contrast) may be enhanced by including small-denier fibers in the printed layer including, but not limited to, melt-blown fibers, microfibers, and nanofibers. In an instance, the printing may indicate the proper orientation of an absorbent article on a wearer (e.g., front/rear). It will be understood that printing may be used with any of the various forms and configurations of the patterned apertured webs disclosed herein. In some forms, more than one type or color, for example, of printing may be used in a single patterned apertured web, or layer thereof. Additional layers may also be provided in a pattered apertured web having one or more prints.

Figure 10:
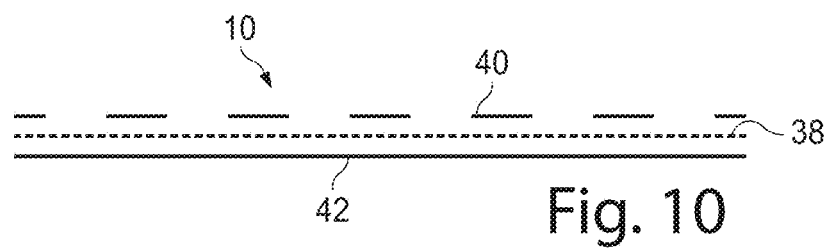
FIG. 10 is a schematic representation of a cross-sectional view of a patterned apertured web having two layers, with a first patterned apertured layer and a second non-apertured layer and with a colored adhesive on one of the layers or positioned intermediate the layers in accordance with the present disclosure.
Figure 11:
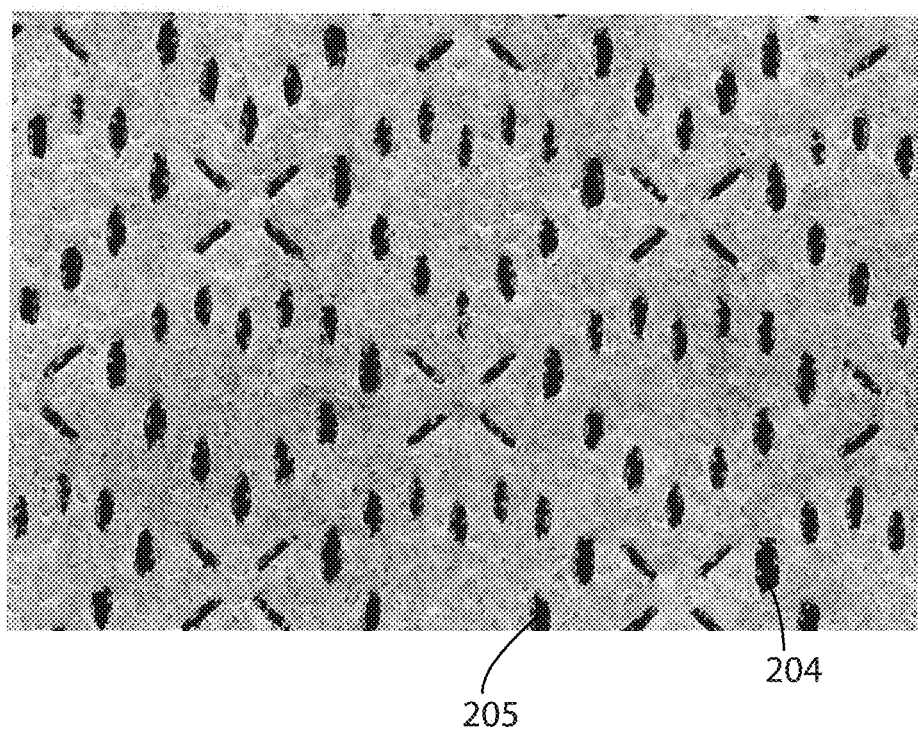
FIGS. 11-15 are example patterned apertured webs in accordance with the present disclosure.
Figure 12:
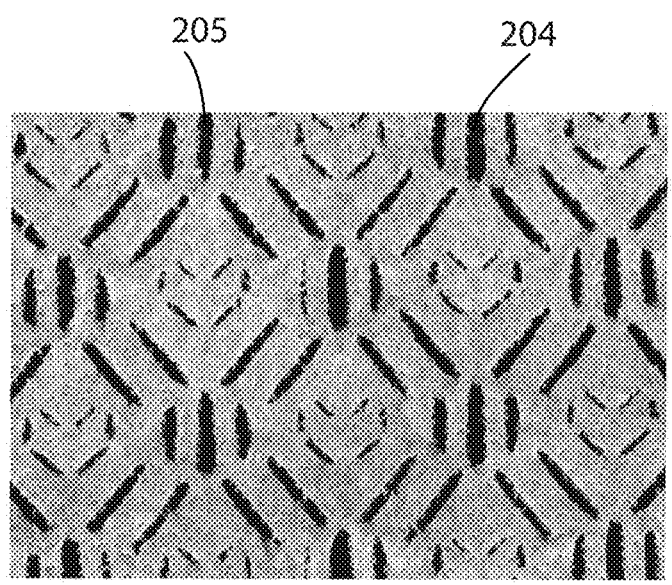
Figure 13:
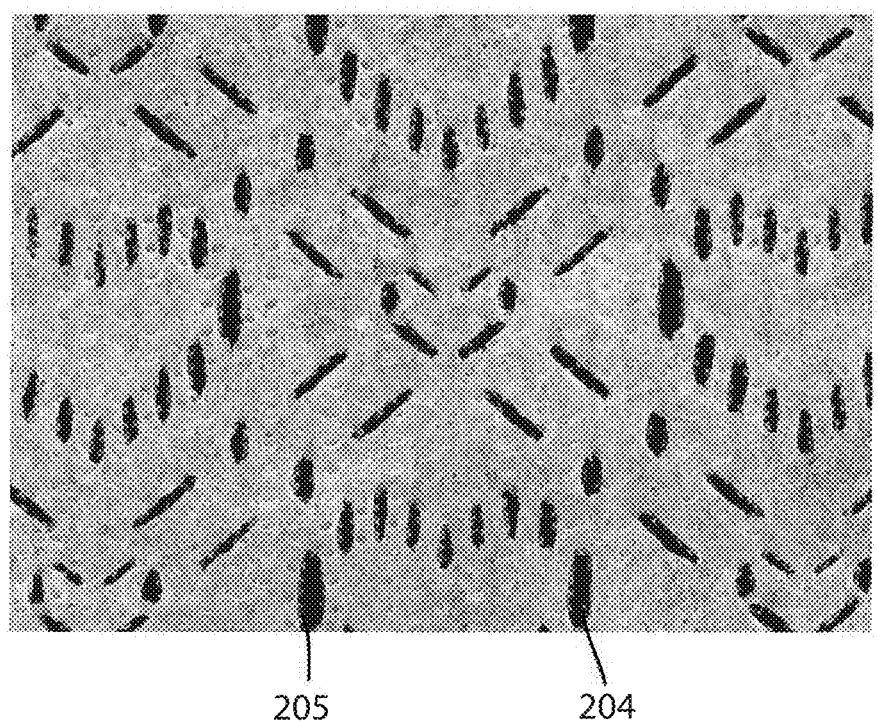
Figure 14:
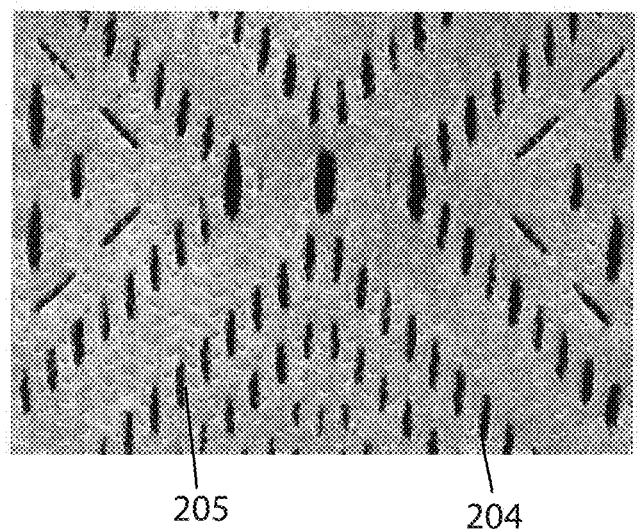
Figure 15:
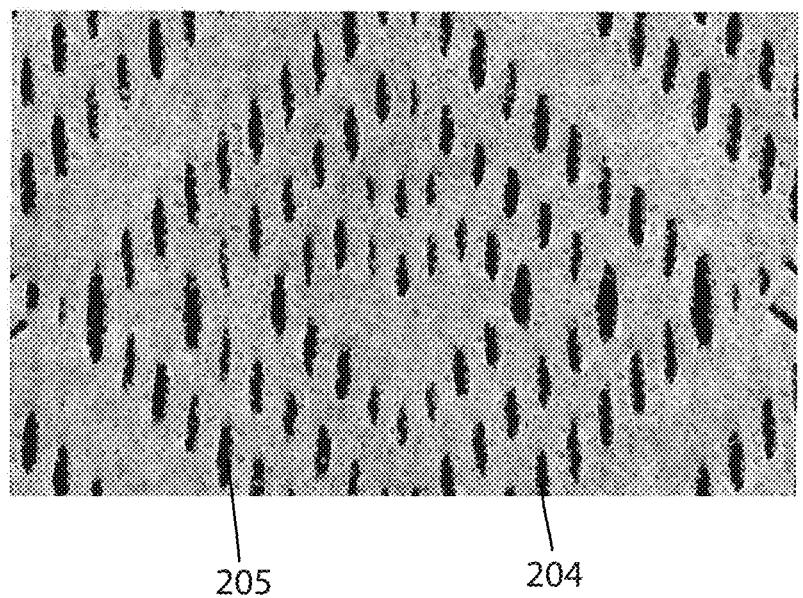

Either in addition to or in lieu of the various layered being colored and/or having printing, referring to FIG. 10, the patterned apertured webs may comprise a pigmented adhesive 38 or other pigmented substance (hereinafter "colored adhesive"). The pigmented adhesive 38 may include a dye, for example. The colored adhesive, in a form, may be positioned between a first layer 40 and second layer 42 of a patterned apertured web 10. The colored adhesive may be formed in a pattern that corresponds with, coordinates with, matches, or does not correspond with, does not coordinate with, or does not match the aperture pattern in one or more aperture layers 40. It will be understood that a pigmented adhesive may be used with any of the various forms and configurations of the patterned apertured webs disclosed herein. In some forms, more than one colored adhesive may be used in a single patterned apertured web. The pigmented adhesive may also be situated in any suitable location if the patterned apertured web has more than two layers (e.g., on the surface of or intermediate any of the layers). The pigmented adhesive may also be deposited in zones of the patterned apertured web, or layers thereof, and/or in patterns throughout the patterned apertured web, or layers thereof. The pigmented adhesive may be different or the same in different zones of the patterned apertured web, or layers thereof. The pigmented adhesive may be positioned intermediate the two layers 40, 42 or positioned on any other surfaces of the layers 40, 42. Additional layers may also be provided in a patterned apertured web having one or more colored adhesives.

In an instance, a colored adhesive may be positioned between two low basis weight materials (e.g., about 15 gsm or less, about 10 gsm or less) forming a patterned apertured web, so that the colored adhesive may be visible from either side of the patterned apertured web. In a topsheet context, this can provide a high basis weight multilayer topsheet to achieve improved softness, while still retaining the benefit of seeing the colored adhesive from either side of the patterned apertured web.

Example Patterned Apertured Webs

Additional examples of patterned apertured webs 10 are illustrated in FIGS. 11-15.

Opacity

The opacity of at least one of the layers of a patterned apertured web may differ from the opacity of at least one of the other layers of the patterned apertured web. Opacity is measured according to the Opacity Test herein. In some instances, the layer of the patterned apertured web closest to an external observer may have a lower opacity than an underlying layer in order to maximize observable contrast differences between the layers and/or to observe printing or colored adhesives. Alternatively, the layer of the patterned apertured web closest to an external observer may have a higher opacity than an underlying layer in order to more effectively mask bodily exudates (e.g., urine, menses, or BM) or to provide for greater color contrast with the layers below. When a patterned apertured web is used as a fluid-permeable topsheet, the layer closest to an external observer would be the wearer-facing surface. In a form, where the patterned apertured web is located on the external surface of an absorbent article (e.g., an outer cover, fastening system element, stretch ear, wing of a sanitary napkin, belt, or side panel), the layer closest to an external observer would be the garment-facing surface. For example, the opacity of a non-apertured layer may be lower than that of a patterned apertured layer, or vice versa, depending on the specific orientation of a patterned apertured web in an absorbent article.

A nonwoven web may have a high opacity. This enables an aperture pattern to be more easily distinguished, provides contrast to any colors and materials underneath, and in the case of a diaper topsheet or a sanitary napkin topsheet, masks the presence of bodily fluids contained within the absorbent core, providing a cleaner appearance to the wearer. To achieve this benefit, opacities of about 30%, about 40%, about 50%, about 60%, about 70%, about 80%, about 90%, in the range of about 40% to about 100%, or about 50% to about 90%, specifically reciting all 0.1% increments within the specified ranges and all ranges formed therein or thereby, may be desired. Increases in opacity may be achieved via any known mechanisms including fillers (e.g. TiO2), fiber shape (e.g. Trilobal vs. round), smaller fiber diameters (including microfibers and/or nano fibers), etc. One example of such a web may have an SMS construction. Another example is a nonwoven comprising nanofibers, such as those produced by melt film fibrillation (e.g., U.S. Pat. No. 8,487,156 and U.S. Pat. Appl. Publ. Serial No. 2004/0266300).

Components of Absorbent Articles

The patterned apertured webs of the present disclosure may be used as components of absorbent articles. More than one patterned apertured web may be used in a single absorbent article. In such a context, the patterned apertured webs may form at least a portion of: a topsheet; a topsheet and an acquisition layer; a portion of a sanitary napkin, a wing of a sanitary napkin, a topsheet and a distribution layer; a topsheet, an acquisition layer, and a distribution layer (and any other layers intermediate the topsheet and an absorbent core, such as a carrier layer for a distribution layer as disclosed in U.S. patent application Ser. No. 14/844,037, filed on Sep. 3, 2015, an acquisition layer and a distribution layer; an outer cover; an outer cover and a backsheet, wherein a film (non-apertured layer) of the patterned apertured web forms the backsheet and a nonwoven material forms the outer cover; a leg cuff; an ear or side panel; a fastener; a waist band; a belt, or portion thereof; or any other suitable portion of an absorbent article. The patterned apertured webs may take on different configurations and patterns of land and aperture areas depending on their particular use in an absorbent article on other product. The number of layers in a patterned apertured web may also be determined by the patterned apertured webs' particular use.

As referenced above, any of the patterned apertured webs of the present disclosure may be disposed on an external surface of the absorbent article (i.e., the outer cover or garment facing-surface). In such an instance, the patterned apertures or properties of the same may be the same or different in different regions of the external surface. In an outer cover example, effective aperture areas and effective open areas may be higher in a waist region than in a crotch region of the outer cover for better breathability. In another outer cover form, the waist regions may include patterned apertures of the present disclosure, while the crotch region comprises more uniform aperture patterns or no apertures. In each of these forms, the effective aperture area and effective open area, or apertures may provide higher air porosity in the waist region than in the crotch region, allowing more sweat evaporation and better breathability in the tightly occluded waist area Feminine Hygiene Products The patterned apertured webs may also be used as components of absorbent articles, such as feminine hygiene products, including sanitary napkins (or wings thereof), liners, and tampons. More than one patterned apertured web may be used in a single feminine hygiene product. In a sanitary napkin context, the patterned apertured webs may form at least a portion of: a topsheet; a topsheet and an acquisition layer; a topsheet and a distribution layer; a topsheet and a secondary topsheet; an outer cover; an outer cover and a backsheet; wings; wings and a topsheet or a backsheet; an outer covering for a tampon; or any other suitable portion of a feminine hygiene product. The patterned apertured webs may take on different configurations and patterns of land and aperture areas depending on their particular use in a feminine hygiene product. The number of layers in a patterned apertured web may also be determined by the patterned apertured webs' particular use.

Other Consumer Products

The patterned apertured webs may also be used as components of absorbent articles, such as cleaning substrates, dusting substrates, and/or wipes. More than one patterned apertured web may be used in a single cleaning or dusting substrate and/or a single wipe. The patterned apertured webs may take on different configurations and patterns of land and aperture areas depending on their particular use in a cleaning substrate, dusting substrate, and/or a wipe. The number of layers in a patterned apertured web may also be determined by the patterned apertured webs' particular use.

Physical Characteristics

The patterned apertured webs of the present disclosure may take on different physical characteristics depending on their intended or desired use in absorbent articles, feminine hygiene products, cleaning substrates, dusting substrates, wipes, or other consumer products. For instance, the properties of density, basis weight, aperture pattern, land area pattern, caliper, opacity, three-dimensionality, and/or elasticity, for example, may be varied depending on the desired use of the patterned apertured web. More than one patterned apertured web may be combined with other, similar or different, patterned apertured webs in some instances for certain design criteria.

Methods of Making

The patterned apertured webs of the present disclosure may be made generally by using the process generally described in U.S. Pat. No. 5,628,097 entitled "Method for Selectively Aperturing a Nonwoven Web" which issued May 13, 1997 and U.S. Patent Publication 2003/0021951 entitled "High Elongation Apertured Nonwoven Web and Method of Making" which published Jan. 20, 2003. This process is described in further detail below. The patterned apertured webs may also be made by hydroforming carded webs, laser cutting, punching with a patterned roll, or other suitable methods.

Figure 16:
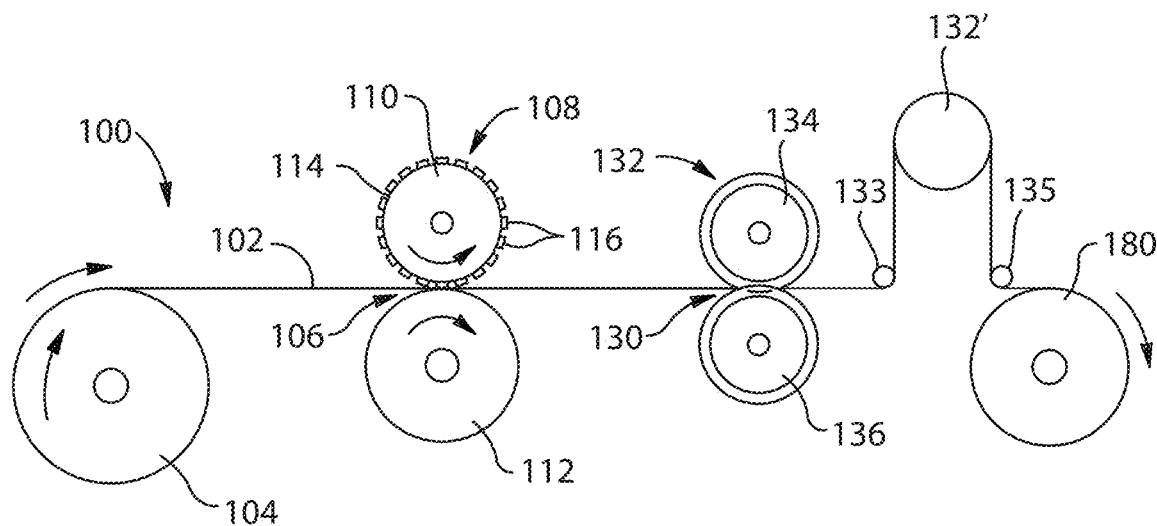
FIG. 16 is a schematic representation of an example method for producing the patterned apertured webs of the present disclosure in accordance with the present disclosure.

Referring to FIG. 16 there is schematically illustrated at 100 one process for forming the patterned apertured webs of the present disclosure.

First, a precursor material 102 is supplied as the starting material. The precursor material 102 can be supplied as discrete webs, e.g. sheets, patches, etc. of material for batch processing. For commercial processing, however, the precursor material 102 may be supplied as roll stock, and, as such it can be considered as having a finite width and an infinite length. In this context, the length is measured in the machine direction (MD). Likewise, the width is measured in the cross machine direction (CD).

The precursor material 102 may be one or more nonwoven materials (same or different), one or more films (same or different), a combination of one or more nonwoven materials and one or more films, or any other suitable materials or combinations thereof. The precursor material 102 may be purchased from a supplier and shipped to where the patterned apertured webs are being formed or the precursor material 102 formed at the same location as where the patterned apertured web are being produced.

The precursor material 102 may be extensible, elastic, or nonelastic. Further, the precursor material 102 may be a single layer material or a multilayer material. In an instance, the precursor material 102 may be joined to a polymeric film to form a laminate.

The precursor material 102 may comprise or be made of mono-component, bi-component, multi-constituent blends, or multi-component fibers comprising one or more thermoplastic polymers. In an example, the bicomponent fibers of the present disclosure may be formed of a polypropylene core and a polyethylene sheath. Further details regarding bi-component or multi-component fibers and methods of making the same may be found in U.S. Patent Application Publ. No. 2009/0104831, published on Apr. 23, 2009, U.S. Pat. No. 8,226,625, issued on Jul. 24, 2012, U.S. Pat. No. 8,231,595, issued on Jul. 31, 2012, U.S. Pat. No. 8,388,594, issued on Mar. 5, 2013, and U.S. Pat. No. 8,226,626, issued on Jul. 24, 2012. The various fibers may be sheath/core, side-by-side, islands in the sea, or other known configurations of fibers. The fibers may be round, hollow, or shaped, such as trilobal, ribbon, capillary channel fibers (e.g., 4DG). The fibers may comprise microfibers or nanofibers.

The precursor material 102 may be unwound from a supply roll 104 and travel in a direction indicated by the arrow associated therewith as the supply roll 104 rotates in the direction indicated by the arrow associated therewith. The precursor material 102 passes through a nip 106 of a weakening roller (or overbonding) arrangement 108 formed by rollers 110 and 112, thereby forming a weakened precursor material. The weakened precursor material 102 has a pattern of overbonds, or densified and weakened areas, after passing through the nip. At least some of, or all of, these overbonds are used to form apertures in the precursor material 102. Therefore, the overbonds correlate generally to the patterns of apertures created in the precursor material 102.

Figure 17:
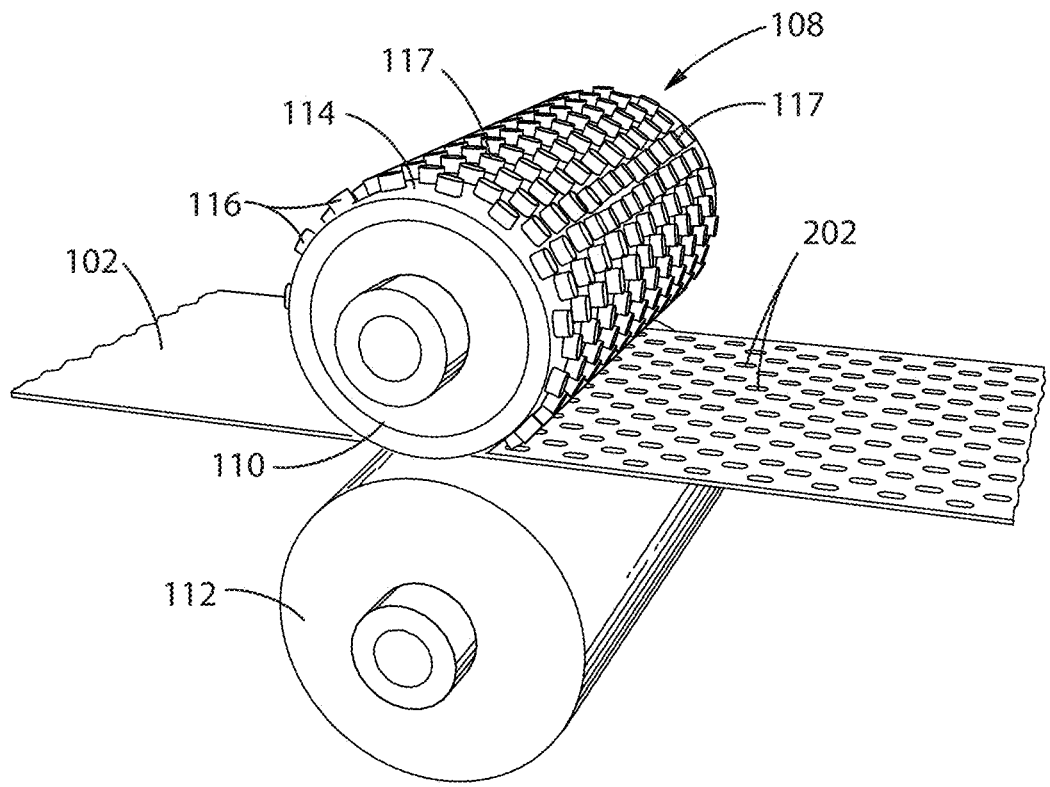
FIG. 17 is a perspective view of a web weakening arrangement of FIG. 16 in accordance with the present disclosure.

Referring to FIG. 17, the precursor material weakening roller arrangement 108 may comprises a patterned calendar roller 110 and a smooth anvil roller 112. One or both of the patterned calendar roller 110 and the smooth anvil roller 112 may be heated and the pressure between the two rollers may be adjusted by known techniques to provide the desired temperature, if any, and pressure to concurrently weaken and melt-stabilize (i.e., overbond) the precursor material 102 at a plurality of locations 202. The temperature of the calendar roller 110 (or portions thereof) and/or the smooth anvil roller 112 (or portions thereof) may be ambient temperature or may be in the range of about 100° C. to about 300° C., about 100° C. to about 250° C., about 100° C. to about 200° C., or about 100° C. to about 150° C., specifically reciting all 0.5° C. increments within the specified ranges and all ranges formed therein or thereby. The pressure between the calendar roller 110 and the smooth anvil roller 112 may be in the range of about 2,000 pli (pounds per linear inch) to about 10,000 pli, about 3,000 pli to about 8,000 pli, or about 4,500 to about 6,500 pli, specifically reciting all 0.1 pli increments within the specified ranges and all ranges formed therein or thereby. As will be discussed in further detail below, after the precursor material 102 passes through the weakening roller arrangement 108, the precursor material 102 may be stretched in the CD, or generally in the CD, by a cross directional tensioning force to at least partially, or fully, rupture the plurality of weakened, melt stabilized locations 202, thereby creating a plurality of at least partially formed apertures in the precursor material 102 coincident with the plurality of weakened, melt stabilized locations 202.

The patterned calendar roller 110 is configured to have a cylindrical surface 114, and a plurality of protuberances or pattern elements 116 which extend outwardly from the cylindrical surface 114. The pattern elements 116 are illustrated as a simplified example of a patterned calendar roller 110, but more detailed patterned calendar rollers that can be used to produce patterned apertured webs of the present disclosure will be illustrated in subsequent figures. The protuberances 116 may be disposed in a predetermined pattern with each of the protuberances 116 being configured and disposed to precipitate a weakened, melt-stabilized location in the precursor material 102 to affect a predetermined pattern of weakened, melt-stabilized locations 202 in the precursor material 102. The protuberances 116 may have a one-to-one correspondence to the pattern of melt stabilized locations in the precursor material 102. As shown in FIG. 17, the patterned calendar roller 110 may have a repeating pattern of the protuberances 116 which extend about the entire circumference of surface 114. Alternatively, the protuberances 116 may extend around a portion, or portions of the circumference of the surface 114. Also, a single patterned calendar roller may have a plurality of patterns in various zones (i.e., first zone, first pattern, second zone, second pattern). The protuberances 116 may have a cross-directional width in the range of about 0.1 mm to about 10 mm, about 0.1 mm to about 5 mm, about 0.1 mm to about 3 mm, about 0.15 mm to about 2 mm, about 0.15 mm to about 1.5 mm, about 0.1 mm to about 1 mm, about 0.1 mm to about 0.5 mm, or about 0.2 to about 0.5 mm, specifically reciting all 0.05 mm increments within the specified ranges and all ranges formed therein or thereby. The protuberances 116 may have an aspect ratio in the range of about 10:1, about 9:1, about 8:1, about 7:1, about 6:1, about 5:1, about 4:1, about 3:1, about 2:1, about 1.5:1, or about 1.1:1, for example. Other aspect ratios of the protuberances 116 are also within the scope of the present disclosure. The protuberances 116, in some forms, may be angled, relative to the machine direction on either side, in the range of about 60 degrees to about 1 degree, about 50 degrees to about 2 degrees, about 45 degrees to about 2 degrees, about 45 degrees to about 5 degrees, about 40 degrees to about 5 degrees, or about 35 degrees to about 5 degrees, specifically reciting all 0.1 degree increments within the specified ranges and all ranges formed therein or thereby. Spacing between adjacent protuberances 116 in any direction may be greater than about 0.5 mm, greater than about 0.6 mm, greater than about 0.7 mm, greater than about 0.8 mm, greater than about 0.9 mm, greater than about 1 mm, greater than about 1.1 mm, greater than about 1.2 mm, greater than about 1.3 mm, greater than about 1.4 mm, greater than about 1.5 mm, greater than about 2 mm, greater than about 3 mm, or may be in the range of about 0.7 mm to about 20 mm, or about 0.8 to about 15 mm, specifically reciting all 0.1 mm increments within the specified ranges and all ranges formed therein or thereby.

Figure 18:
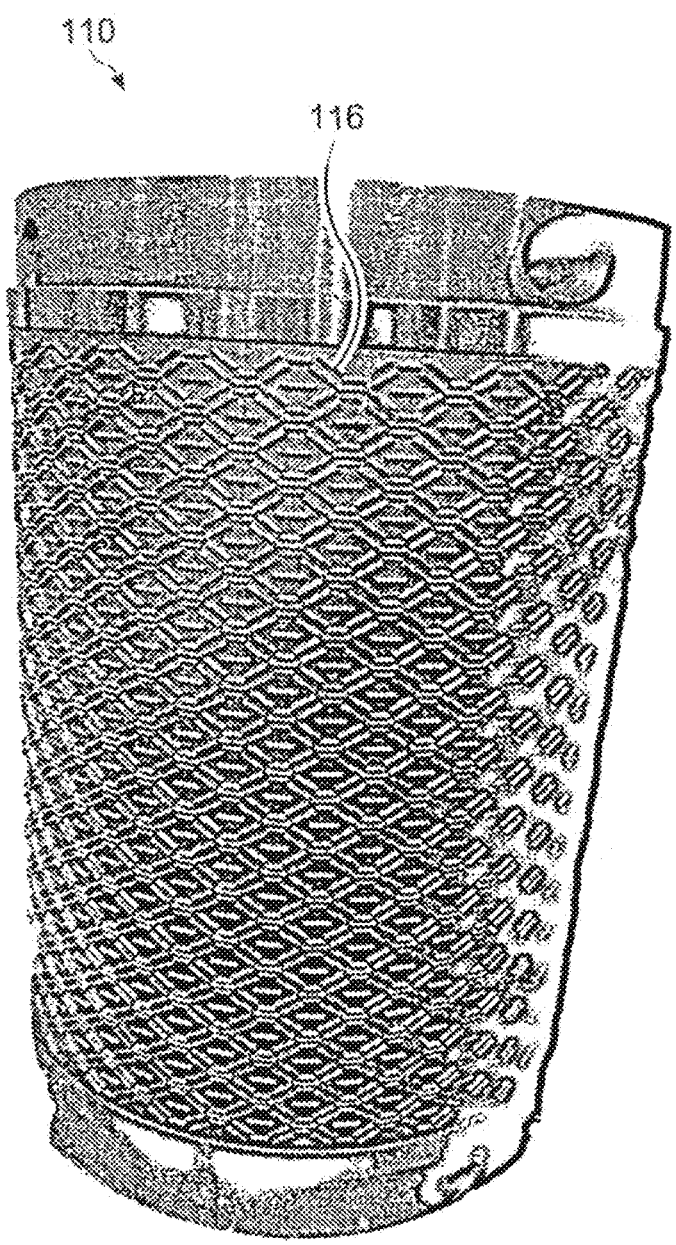
FIG. 18 is a photograph of an example roller that can be used as roller 110 in the weakening arrangement of FIG. 17 in accordance with the present disclosure.
Figure 19:
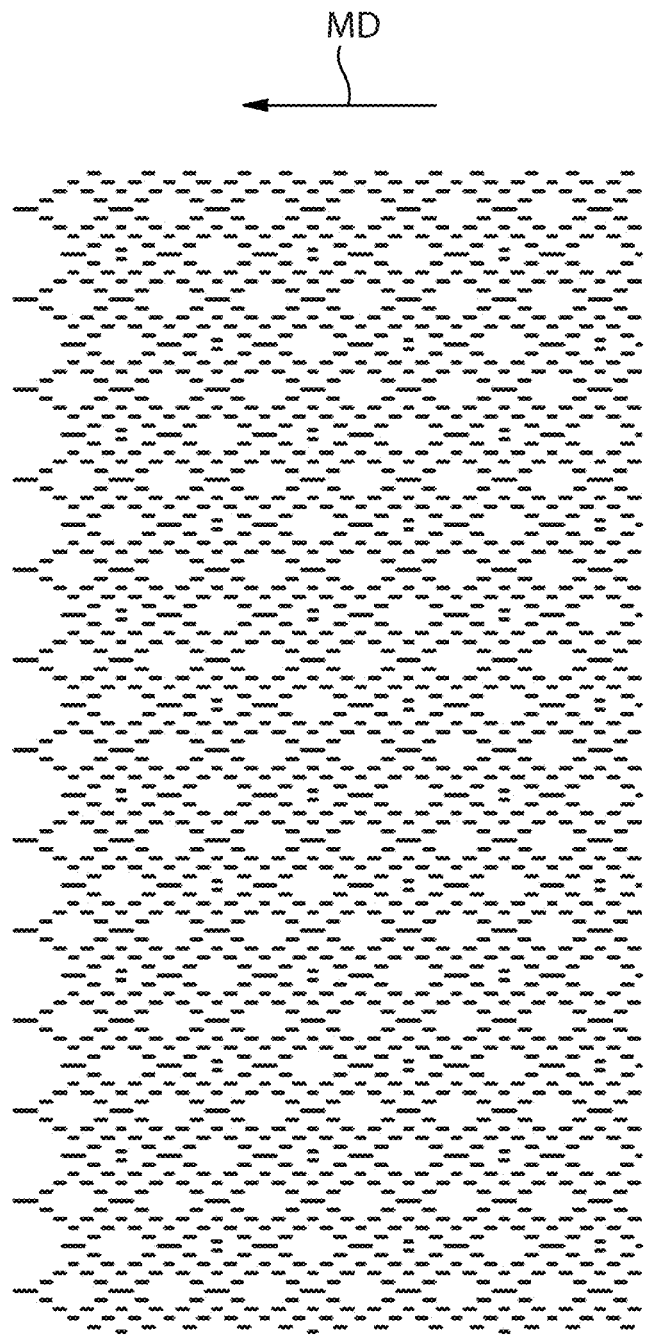
FIGS. 19-23 are example overbond patterns for roller 110 of FIG. 17 used to produce patterned apertured webs in accordance with the present disclosure.
Figure 20:
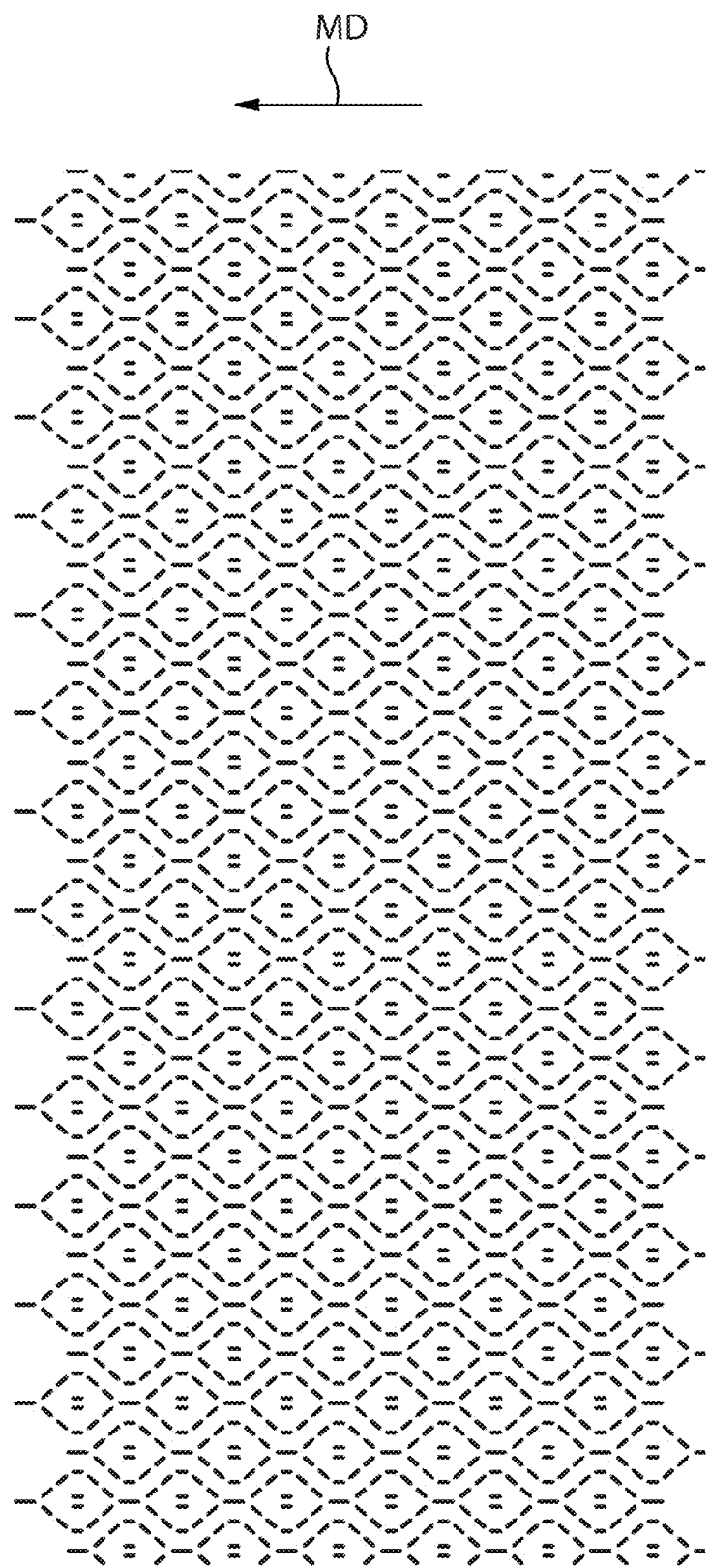
Figure 21:
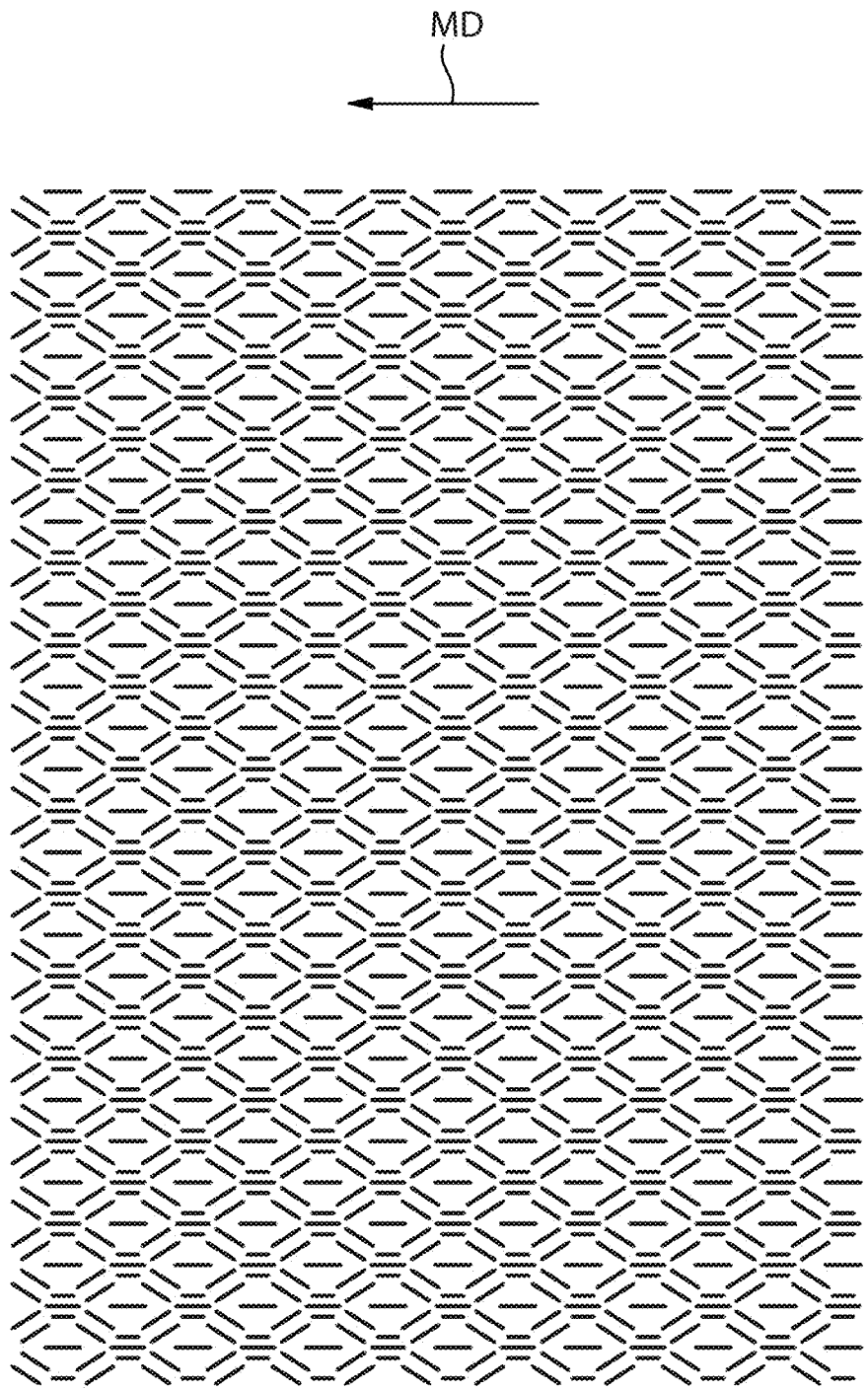
Figure 22:
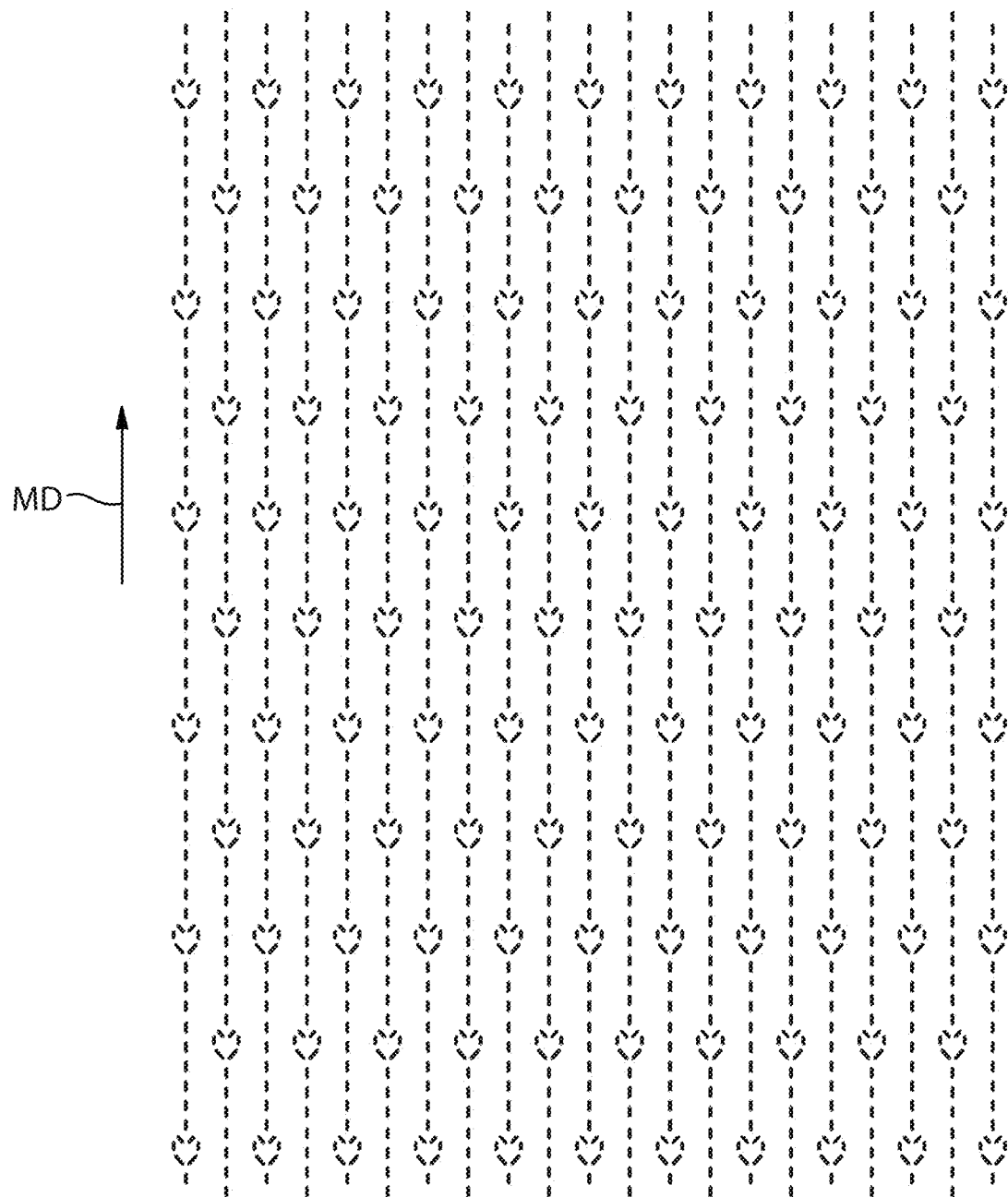
Figure 23:
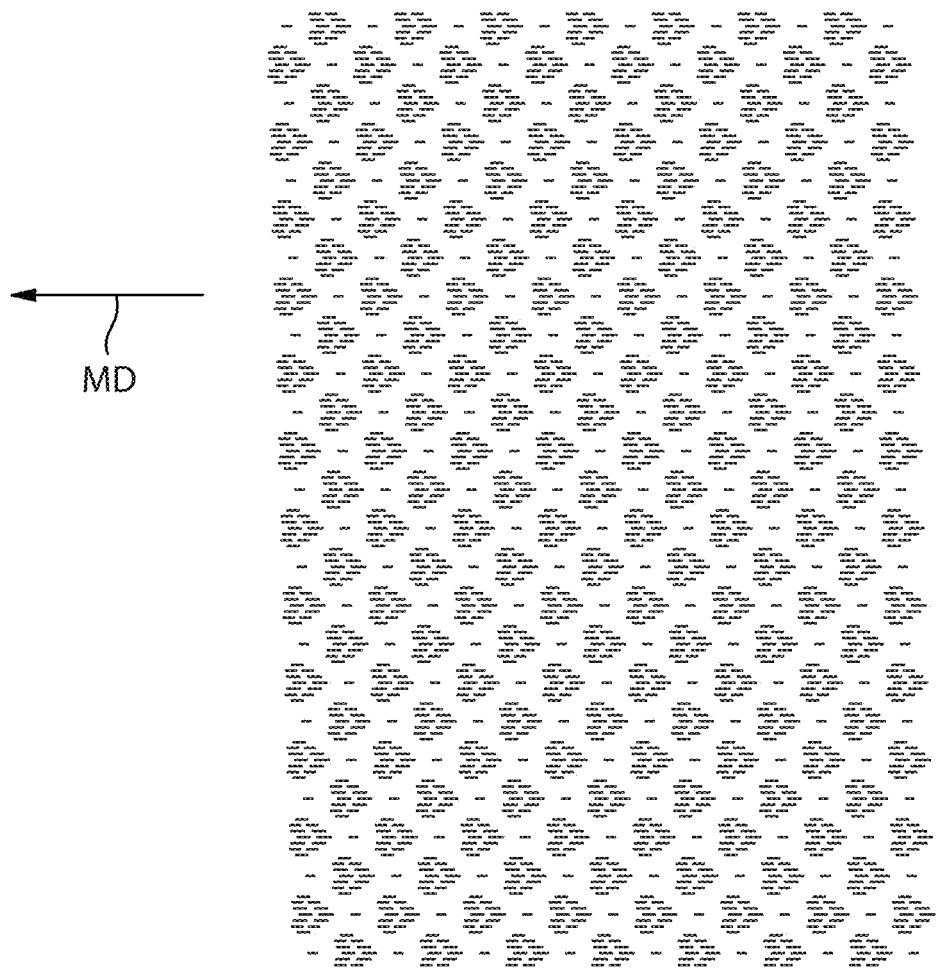

A photograph of an example roller that may be used as patterned calendar roller 110 in the process 100 of FIG. 16 to produce the patterned apertured webs of the present disclosure is illustrated in FIG. 18. The pattern of protuberances 116 on the roller in FIG. 18 would be formed in the precursor web 102, much like the melt-stabilized locations 202 of FIG. 17.

The protuberances 116 may extend radially outwardly from surface 114 and have distal end surfaces 117. The anvil roller 112 may be a smooth surfaced, circular cylinder of steel, rubber or other material. The anvil roller 112 and the patterned calendar roller 110 may be switched in position (i.e., anvil on top) and achieve the same result.

From the weakening roller arrangement 108, the material 102 passes through a nip 130 formed by an incremental stretching system 132 employing opposed pressure applicators having three-dimensional surfaces which at least to a degree may be complementary to one another.

Additional example patterns for protuberances 116 of roller 110 of FIG. 17 are illustrated in FIGS. 19-23. The machine direction "MD" of the patterns is indicated. The pattern of FIG. 22 was used to produce the patterned apertured web of FIG. 3.

Figure 24:
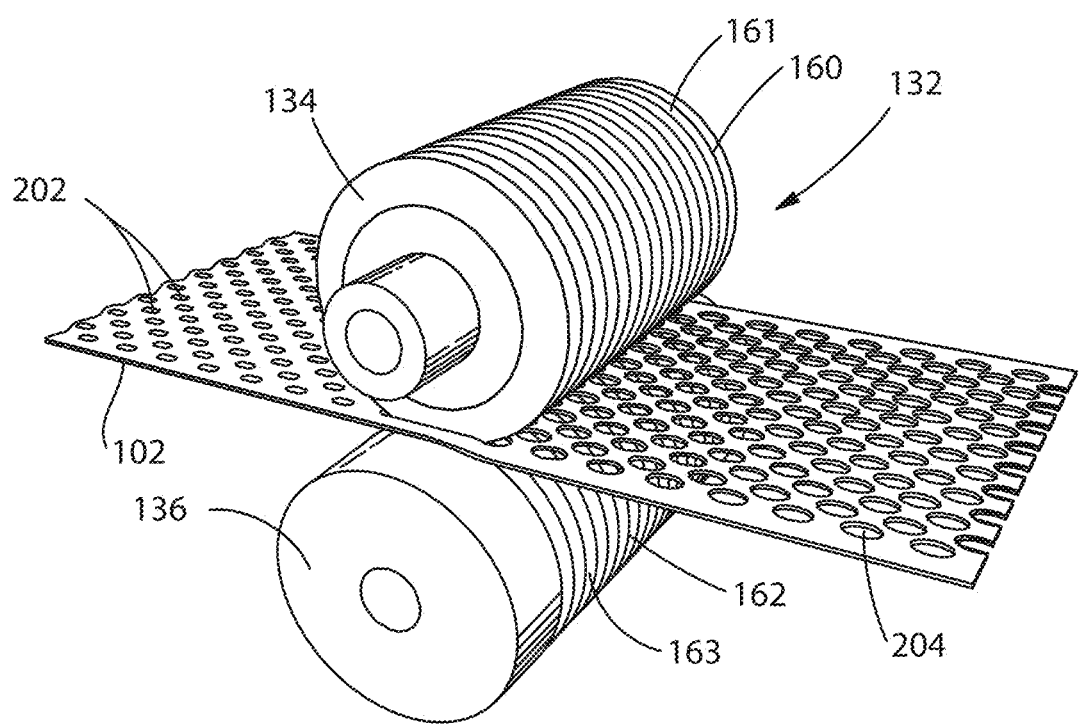
FIG. 24 is a perspective view of an incremental stretching system of the method of FIG. 16 in accordance with the present disclosure.

Referring now to FIG. 24, there is shown a fragmentary enlarged view of the incremental stretching system 132 comprising two incremental stretching rollers 134 and 136. The incremental stretching roller 134 may comprise a plurality of teeth 160 and corresponding grooves 161 which may about the entire circumference of roller 134. The incremental stretching roller 136 may comprise a plurality of teeth 162 and a plurality of corresponding grooves 163. The teeth 160 on the roller 134 may intermesh with or engage the grooves 163 on the roller 136 while the teeth 162 on the roller 136 may intermesh with or engage the grooves 161 on the roller 134. The spacing and/or pitch of the teeth 162 and/or the grooves 163 may match the pitch and/or spacing of the plurality of weakened, melt stabilized locations 202 in the precursor material 102 or may be smaller or larger. As the precursor material 102 having weakened, melt-stabilized locations 202 passes through the incremental stretching system 132 the precursor material 102 is subjected to tensioning in the CD causing the material 102 to be extended (or activated) in the CD, or generally in the CD. Additionally the material 102 may be tensioned in the MD, or generally in the MD. The CD tensioning force placed on the material 102 is adjusted such that it causes the weakened, melt-stabilized locations 202 to at least partially, or fully, rupture thereby creating a plurality of partially formed, or formed apertures 204 coincident with the weakened melt-stabilized locations 202 in the material 102. However, the bonds of the material 102 (in the non-overbonded areas) are strong enough such that they do not rupture during tensioning, thereby maintaining the material 102 in a coherent condition even as the weakened, melt-stabilized locations rupture. However, it may be desirable to have some of the bonds rupture during tensioning.

Figure 25:
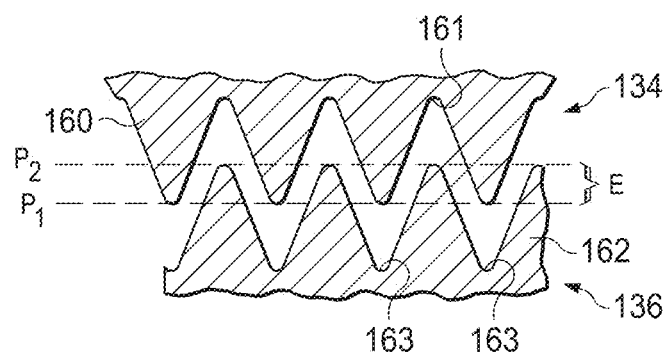
FIG. 25 is an enlarged view showing the details of teeth of the incremental stretching system of FIG. 24 in accordance with the present disclosure.

Referring to FIG. 25, a more detailed view of the teeth 160 and 162 and the grooves 161 and 163 on the rollers 134 and 136 is illustrated. The term "pitch" refers to the distance between the apexes of adjacent teeth. The pitch may be between about 0.02 inches to about 0.30 inches (about 0.51 mm to about 7.62 mm) or may be between about 0.05 inches and about 0.15 inches (about 1.27 mm to about 3.81 mm), specifically reciting all 0.001 inch increments within the above-specified ranges and all ranges formed therein or thereby. The height (or depth) of the teeth is measured from the base of the tooth to the apex of the tooth, and may or may not be equal for all teeth. The height of the teeth may be between about 0.010 inches (about 0.254 mm) and about 0.90 inches (about 22.9 mm) or may be between about 0.025 inches (about 0.635 mm) and about 0.50 inches (about 12.7 mm), specifically reciting all 0.01 inch increments within the above-specified ranges and all ranges formed therein or thereby. The teeth 160 in one roll may be offset by about one-half of the pitch from the teeth 162 in the other roll, such that the teeth of one roll (e.g., teeth 160) mesh in the valley (e.g., groove 163) between teeth in the mating roll. The offset permits intermeshing of the two rolls when the rolls are "engaged" or in an intermeshing, operative position relative to one another. The teeth of the respective rolls may only be partially intermeshing in some instances. The degree to which the teeth on the opposing rolls intermesh is referred to herein as the "depth of engagement" or "DOE" of the teeth. The DOE may be constant or not constant. As shown in FIG. 25, the DOE, indicated as "E", is the distance between a position designated by plane P1 where the apexes of the teeth on the respective rolls are in the same plane (0% engagement) to a position designated by plane P2 where the apexes of the teeth of one roll extend inward beyond the plane P1 toward the groove on the opposing roll. The optimum or effective DOE for particular laminate webs may be dependent upon the height and the pitch of the teeth and/or the structure of the material. Some example DOEs may in the range of about 0.01 inches to about 0.5 inches, about 0.03 inches to about 0.2 inches, about 0.04 inches to about 0.08 inches, about 0.05 inches, or about 0.06 inches, specifically reciting all 0.001 inch increments within the above-specified ranges and all ranges formed therein or thereby.

As the material 102 having the weakened, melt-stabilized locations 202 passes through the incremental web stretching apparatus 132, the material 102 is subjected to tensioning in the cross machine direction, or substantially in the cross machine direction, thereby causing the nonwoven web 102 to be extended in the cross machine direction. The tensioning force placed on the material 102 may be adjusted by varying the pitch, DOE, or teeth size, such that the incremental stretching is sufficient to cause the weakened, melt-stabilized locations 202 to at least partially, or fully rupture, thereby creating, or at least partially creating, a plurality of apertures 204 coincident with the weakened, melt-stabilized locations 202 in the material 102.

Figure 26:
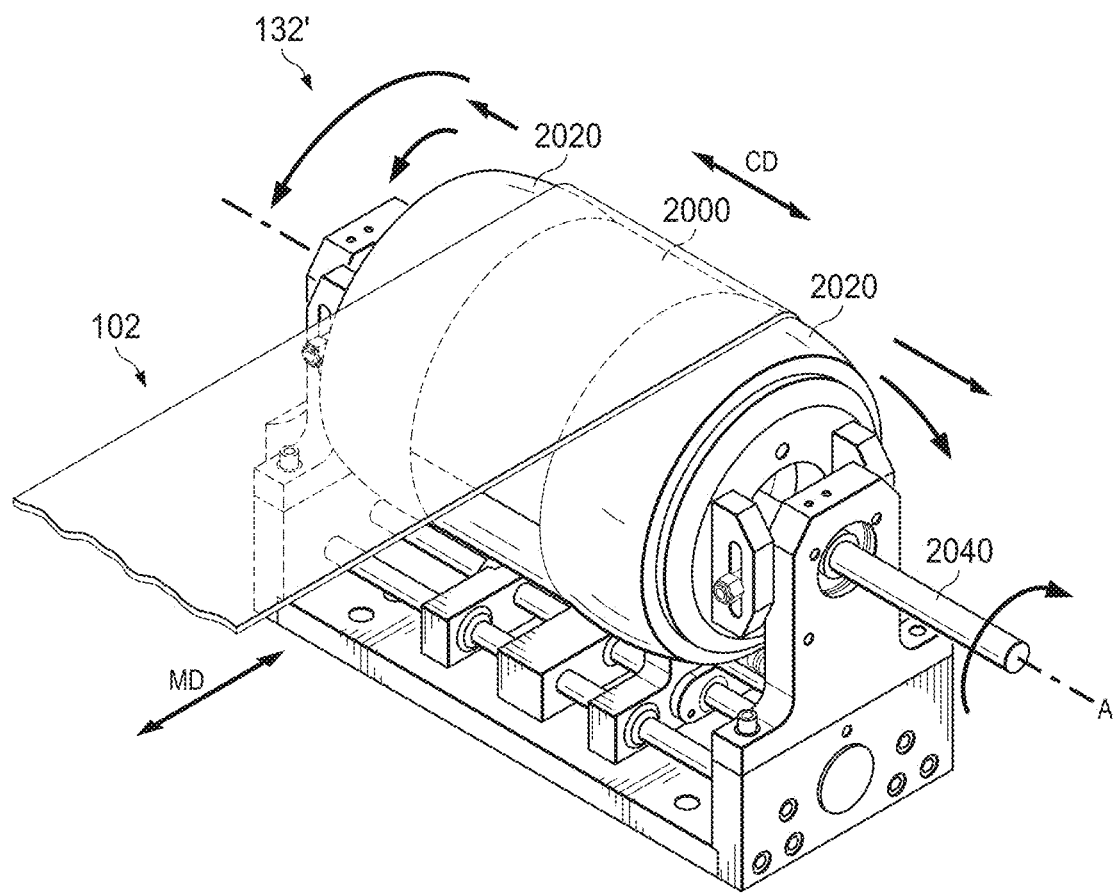
FIG. 26 is a perspective view of an example cross machine directional tensioning apparatus of the method of FIG. 16 in accordance with the present disclosure.

After the material 102 passes through the incremental web stretching apparatus 132, the web 102 may be advanced to and at least partially around a cross machine directional tensioning apparatus 132' (see e.g., FIGS. 16 and 26). The cross machine directional tensioning apparatus 132' may be offset from the main processing line by running the web partially around two idlers 133 and 135 or stationary bars, for example. In other instances, the cross machine tensioning apparatus 132' may be positioned in line with the main processing line. The cross machine directional tensioning apparatus 132' may comprise a roll that comprises at least one outer longitudinal portion that expands along a longitudinal axis, A, of the roll, relative to a middle portion of the roll, to stretch and/or expand the material 102 in the cross machine direction. Instead of or in addition to expanding along the longitudinal axis, A, of the roll, the outer longitudinal portion may be angled relative to the longitudinal axis, A, of the roll in a direction away from the material 102 being advanced over the roll to stretch the material 102 in the cross machine direction or generally in the cross machine direction. In an instance, the roll may comprise two outer longitudinal portions that each may expand in opposite directions generally along the longitudinal axis, A, of the roll. The two outer portions may both be angled downwards in a direction away from the material 102 being advanced over the roll. This movement or positioning of the outer longitudinal portions of the roll allows for generally cross machine directional tensioning of the material 102, which causes the plurality of weakened locations 202 to rupture and/or be further defined or formed into apertures 204.

The outer longitudinal portions of the roll may comprise vacuum, a low tack adhesive, a high coefficient of friction material or surface, such as rubber, and/or other mechanisms and/or materials to hold the material 102 to the outer lateral portions of the roll during movement of the outer longitudinal portion or portions relative to the middle portion of the roll. The vacuum, low tack adhesive, high coefficient of friction material or surface, and/or other mechanisms and/or materials may prevent, or at least inhibit, the held portions of the material 102 from slipping relative to the longitudinal axis, A, of the roll during stretching of the outer lateral portions of the material in the cross machine direction or generally in the cross machine direction.

FIG. 26 is a top perspective view of the example cross machine directional tensioning apparatus 132'. The cross machine directional tensioning apparatus 132' may comprise a roll comprising a middle portion 2000 and two outer longitudinal portions 2020 situated on either end of the middle portion 2000. The roll may rotate about its longitudinal axis, A, on a drive shaft 2040. The roll may rotate relative to the drive shaft 2040 or in unison with the drive shaft 2040, as will be recognized by those of skill in the art. The material 102 may be advanced over the entire cross machine directional width of the middle portion 2000 and at least portions of the cross machine directional widths of the outer longitudinal portions 2020. The material 102 may be advanced over at least about 5% up to about 80% of the circumference of the roll so that the cross machine directional stretching may be performed.

Figure 27:
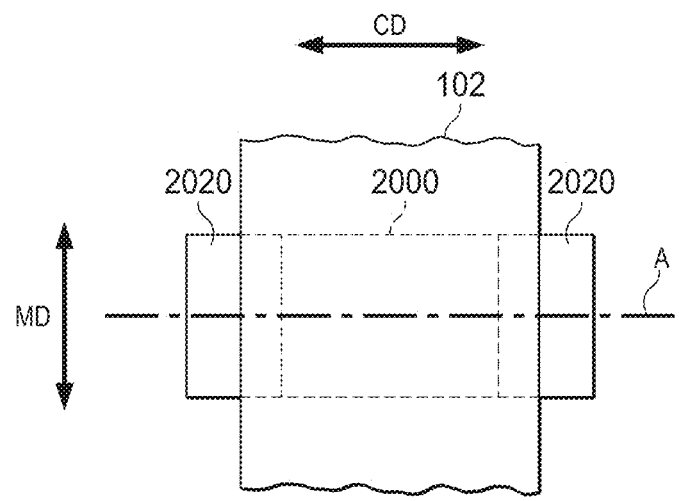
FIG. 27 is a schematic representation of a front view of an example cross machine directional tensioning apparatus with outer longitudinal portions in an unexpanded and non-angled position relative to a middle portion in accordance with the present disclosure.
Figure 28:
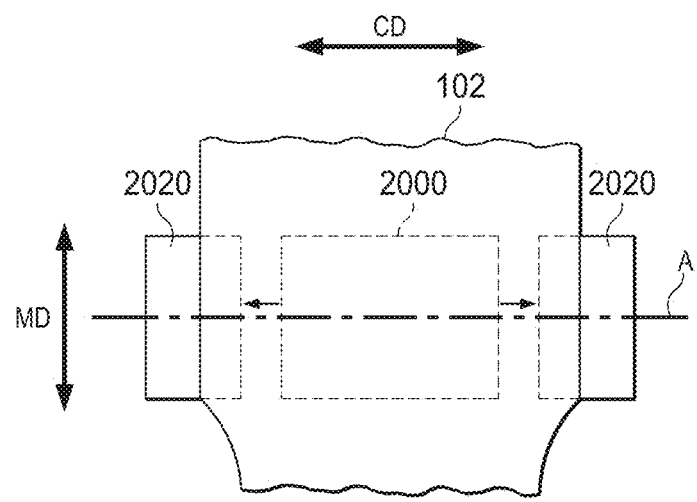
FIG. 28 is a schematic representation of a front view of the cross machine directional tensioning apparatus of FIG. 27 with the outer longitudinal portions in a longitudinally expanded position relative to the middle portion in accordance with the present disclosure.
Figure 29:
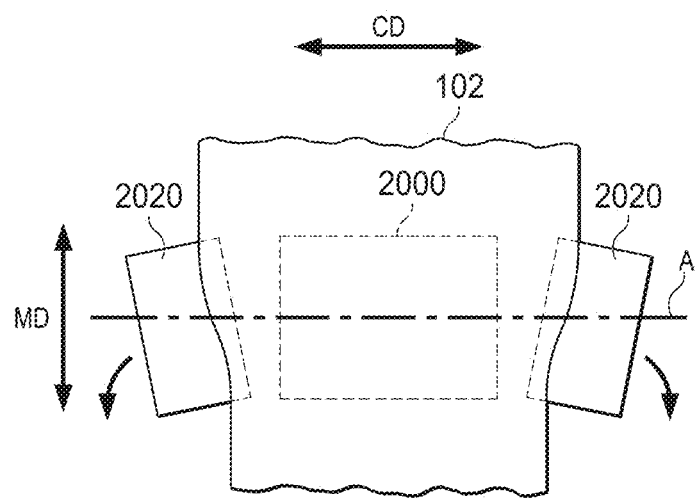
FIG. 29 is a schematic representation of a front view of the cross machine directional tensioning apparatus of FIG. 27 with the outer longitudinal portions in an angled and expanded position relative to the middle portion in accordance with the present disclosure.
Figure 30:
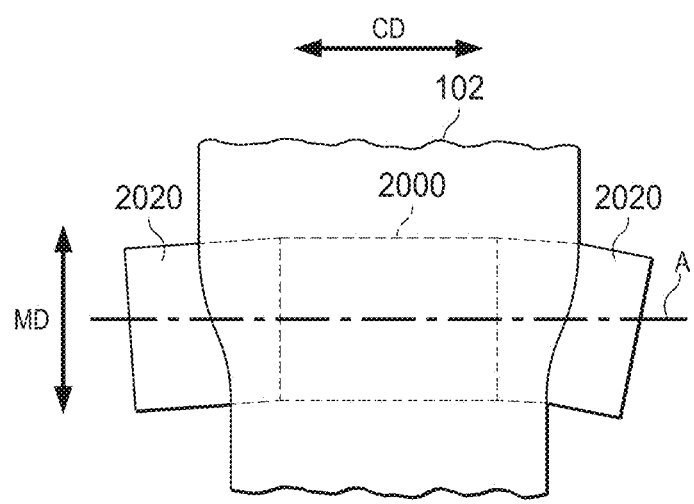
FIG. 30 is a schematic representation of a front view of a cross machine directional tensioning apparatus with outer longitudinal portions fixed in an angled position relative to a middle portion in accordance with the present disclosure.

FIG. 27 is a schematic representation of a front view of an example cross machine directional tensioning apparatus with outer longitudinal portions 2020 in an unexpanded or non-angled position relative to the middle portion 2000. FIG. 28 is a schematic representation of a front view of the cross machine directional tensioning apparatus of FIG. 27 with the outer longitudinal portions 2020 in a longitudinally expanded position relative to the middle portion 2000. FIG. 29 is a schematic representation of a front view of the cross machine directional tensioning apparatus of FIG. 27 with the outer longitudinal portions 2020 in an angled and expanded position relative to the middle portion 2000. In regard to FIG. 29, the outer longitudinal portions 2020 may merely move or slide in a direction generally perpendicular to the machine direction of the material passing over the roll to apply the cross machine directional tensioning force to the material 102. FIG. 30 is a schematic representation of a front view of a cross machine directional tensioning apparatus with the outer longitudinal portions 2020 fixed in an angled position relative to the middle portion 2000 to apply the cross machine directional tensioning force to the material 102. In such a form, the middle portion 2000 and each of the outer longitudinal portions 2020 may comprise a separate roll.

Regardless of whether one or both of the outer longitudinal portions 2020 is moved, slid, rotated, fixed, and/or expanded relative to the middle portion 2000, this relative motion or positioning between the outer longitudinal portions 2020 and the middle portion 2000 stretches the materials 102 in a cross machine direction to further rupture or further define the weakened locations 2020 in the material 102 and create, or further form, a plurality the apertures 2040 the material 102. The cross machine directional tensioning force applied by the cross machine directional tensioning apparatus 132' may be, for example, 10-25 grams or 15 grams. In an instance, the cross machine directional tensioning apparatus may be similar to, or the same as, the incremental stretching apparatus 132 to apply the cross machine directional tensioning force. In still other instances, any suitable cross machine directional tensioning apparatus may be used to apply the cross machine directional tensioning force to the material 102.

If desired, the incremental stretching step or the cross machine directional stretching step described herein may be performed at elevated temperatures. For example, the material 102 and/or the rolls may be heated. Utilizing heat in the stretching step may serve to soften the material, and may aid in extending the fibers without breaking.

Referring again to FIG. 16, the material 102 may be taken up on wind-up roll 180 and stored. Alternatively, the material 102 may be fed directly to a production line where it is used to form a portion of an absorbent article or other consumer product.

It is important to note that the overbonding step illustrated in FIGS. 16 and 17 could be performed by the material supplier and then the material may be shipped to a consumer product manufacturer to perform step 132. In fact, the overbonding step may be used in the nonwoven production process to form overbonds, which may be in addition to, or in lieu of, primary bonds formed in the nonwoven production process. Alternatively, the material supplier may fully perform the steps illustrated in FIG. 16 and then the material may be shipped to the consumer product manufacturer. The consumer product manufacturer may also perform all of the steps in FIG. 16 after obtaining a nonwoven material from a nonwoven material manufacturer.

One of ordinary skill in the art will recognize that it may be advantageous to submit the material 102 to multiple incremental stretching processes depending on various desired characteristics of the finished product. Both the first and any additional incremental stretching may either be done on-line or off-line. Furthermore, one of ordinary skill will recognize that the incremental stretching may be done either over the entire area of the material or only in certain regions of the material depending on the final desired characteristics.

Returning now to FIGS. 11-15, there is shown photographs of example patterned apertured webs after having been subjected to the tensioning force applied by the incremental stretching system 132 and the cross machine directional tensioning apparatus 132'. As can be seen in the photographs of FIGS. and 11-15, the patterned apertured webs now include a plurality of apertures 204 which are coincident with the weakened, melt-stabilized locations made by the roller 110 (with various patterns). A portion of the circumferential edges of an aperture 204 may include remnants 205 of the melt-stabilized locations. It is believed that the remnants 205 help to resist further tearing of the material particularly when the material is used as a portion of an absorbent article or another consumer product.

Percent of CD Stretch

Figure 31:
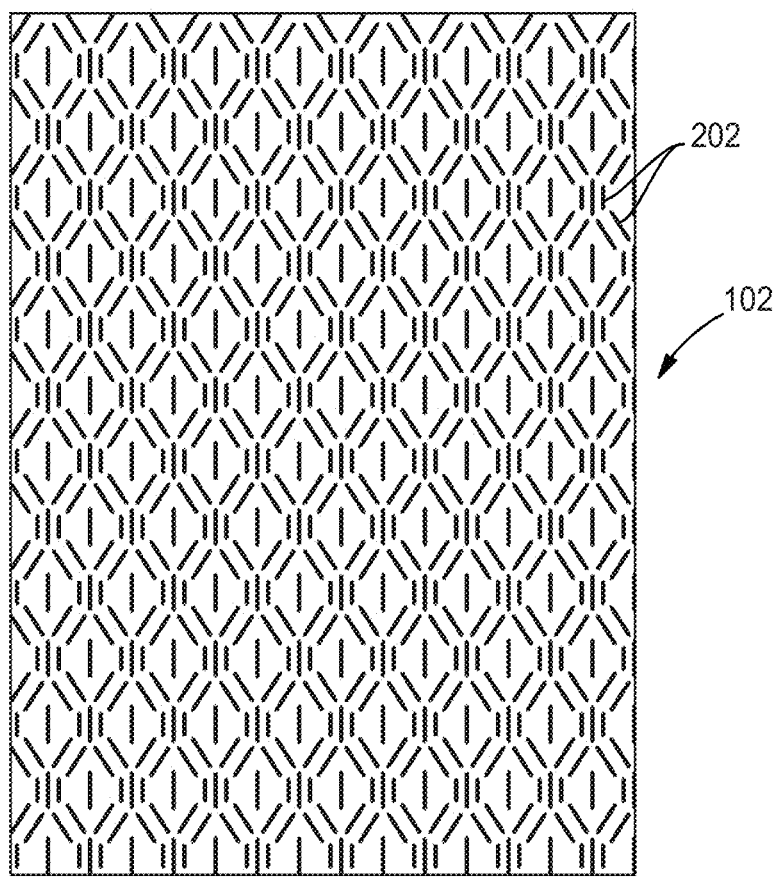
FIG. 31 is an example overbond pattern for the roller 110 of FIG. 17 in accordance with the present disclosure.
Figure 32:
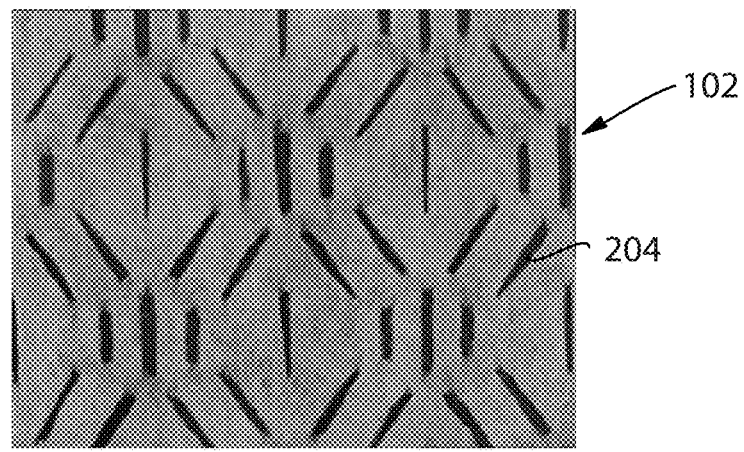
FIG. 32 is a photograph of an example patterned apertured web produced using the overbond pattern of FIG. 31 and having been subjected to a 25% cross directional stretch using the equipment illustrated in FIG. 26 in accordance with the present disclosure.
Figure 33:
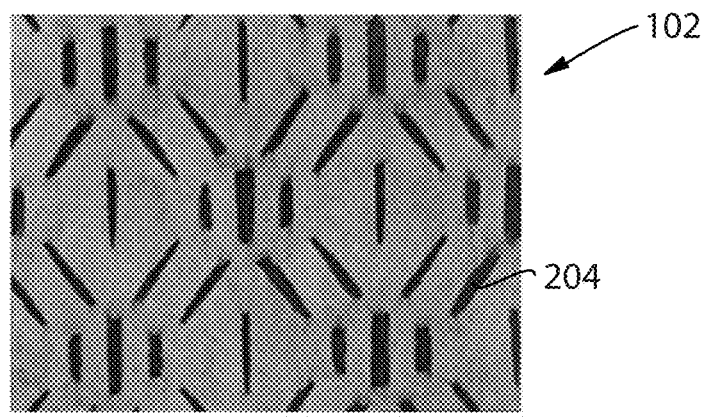
FIG. 33 is a photograph of an example patterned apertured web produced using the overbond pattern of FIG. 31 and having been subjected to a 35% cross directional stretch using the equipment illustrated in FIG. 26 in accordance with the present disclosure.
Figure 34:
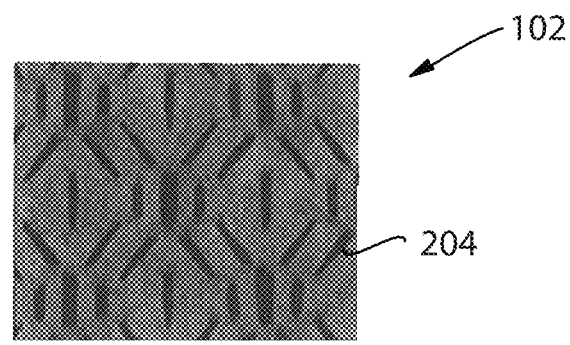
FIG. 34 is a photograph of an example patterned apertured web produced using the overbond pattern of FIG. 31 and having been subjected to a 45% cross directional stretch using the equipment illustrated in FIG. 26 in accordance with the present disclosure.
Figure 35:
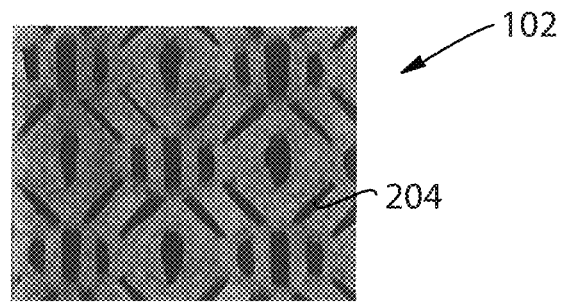
FIG. 35 is a photograph of an example patterned apertured web produced using the overbond pattern of FIG. 31 and having been subjected to a 55% cross directional stretch using the equipment illustrated in FIG. 26 in accordance with the present disclosure.

The extent to which the material 102 is stretched in the CD may have a correlation to the size, shape, and area of the apertures. In general, the apertures may have a larger area and be more open the more the material 102 is stretched in the CD direction by the cross machine directional tensioning apparatus 132'. As such, a manufacturer can further vary an aperture pattern based on the amount of CD tensioning applied to a material even when the melt-stabilized pattern in the material is the same. As an example, FIG. 31 illustrates an overbond pattern in a material 102 prior to the incrementally stretching step 132 and the cross machine directional tension step 132'. The plurality of melt-stabilized locations are indicated as 202. The material is then run through the incrementally stretching step 132 and the cross machine directional tensioning apparatus 132'. The cross machine directional tensioning apparatus 132' may be set to extend the material 102 to over 100% of its CD width "W" after exiting the incremental stretching apparatus 132, such as 125%, 135%, 145%, 155% of W. In other instances, the material 102 may be stretched in the cross machine direction in the range of about 110% to about 180% of W, about 120% to about 170% of W, specifically reciting all 0.5% increments within the specified ranges and all ranged formed therein or thereby. FIG. 32 illustrates an example of the material 102 with the overbond pattern of FIG. 31 and stretched to 125% of W. FIG. 33 illustrates an example of the material 102 with the overbond pattern of FIG. 31 and stretched to 135% of W. FIG. 34 illustrates an example of the material 102 with the overbond pattern of FIG. 31 and stretched to 145% of W. FIG. 35 illustrates an example of the material 102 with the overbond pattern of FIG. 31 and stretched to 155% of W. As illustrated, the amount of CD stretch can be a significant factor on the patterned apertured web produced.

Absorbent Article

Figure 36:
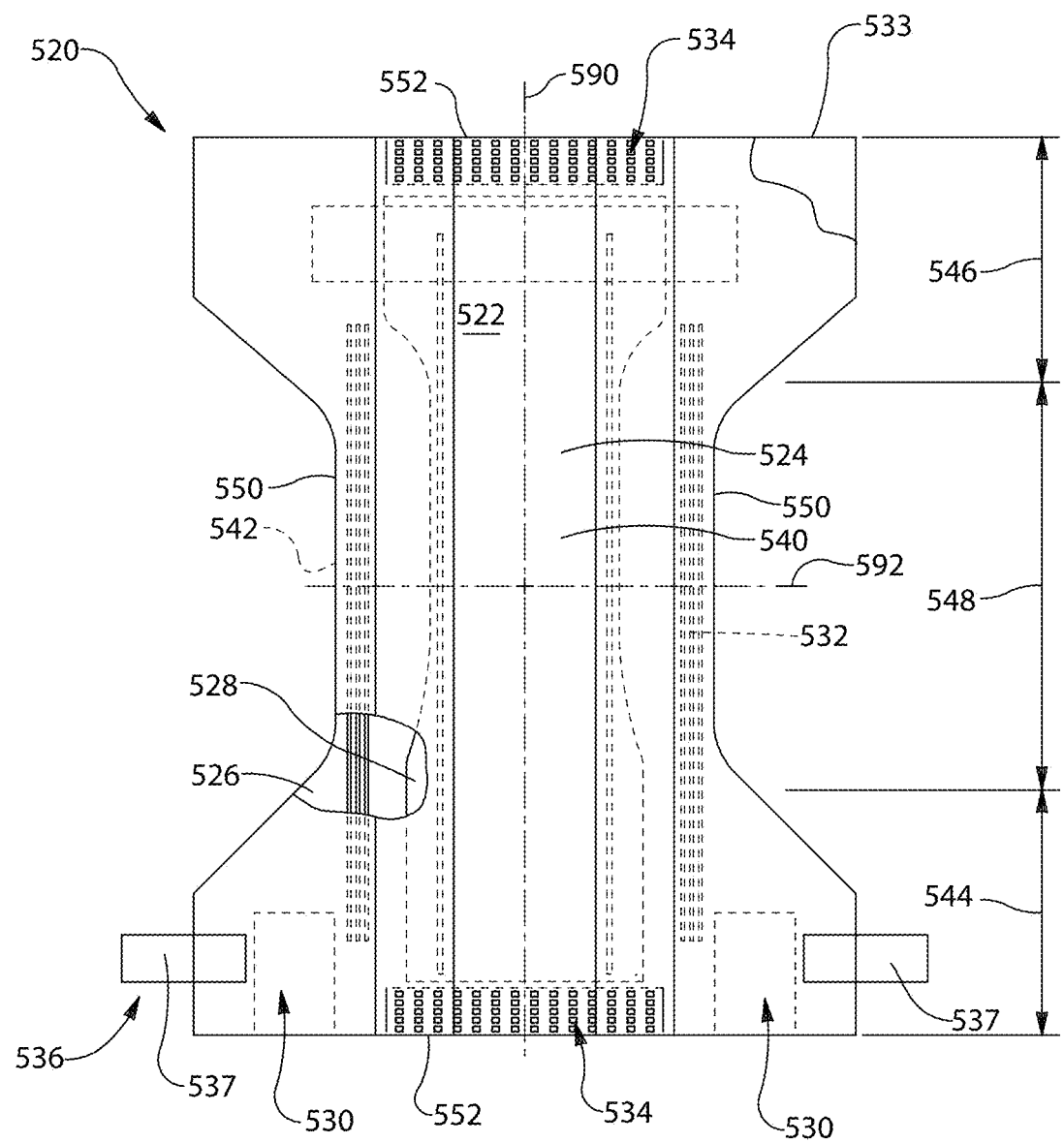
FIG. 36 is a plan view of an example disposable absorbent article having portions cut away to reveal underlying structure that may comprise one or more patterned apertured webs, the inner surface of the absorbent article is facing the viewer, in accordance with the present disclosure.

As described herein, the patterned apertured webs of the present disclosure may be used as one or more components of an absorbent article. An example absorbent article is set forth below. FIG. 36 is a plan view of an example absorbent article that is a diaper 520 in its flat-out, uncontracted state (i.e., with elastic induced contraction pulled out) with portions of the structure being cut-away to more clearly show the construction of the diaper 520 and with the portion of the diaper 520 which faces the wearer, the inner surface 540, facing the viewer. The diaper 520 may comprise a chassis 522 comprising a liquid pervious topsheet 524, a liquid impervious backsheet 26 joined to the topsheet, and an absorbent core 528 positioned at least partially between the topsheet 24 and the backsheet 26. The diaper 520 may comprise elasticized side panels 530, elasticized leg cuffs 532, elasticized waistbands 534, and a fastening system 536 that may comprise a pair of securement members 537 and a landing member or landing zone on a garment-facing surface or outer surface 542. The diaper 520 may also comprise an outer cover 533 that may comprise one or more of the patterned adhesive webs of the present disclosure. The outer cover 533 may comprise nonwoven materials and/or films.

The diaper 520 is shown to have an inner surface 540 (facing the viewer in FIG. 36), an outer surface 542 opposed to the inner surface 540, a rear waist region 544, a front waist region 546 opposed to the rear waist region 544, a crotch region 548 positioned between the rear waist region 544 and the front waist region 546, and a periphery which is defined by the outer perimeter or edges of the diaper 520 in which the longitudinal edges are designated 550 and the end edges are designated 552. The inner surface 540 of the diaper 520 comprises that portion of the diaper 520 which is positioned adjacent to the wearer's body during use (i.e., the inner surface 540 generally is formed by at least a portion of the topsheet 524 and other components joined to the topsheet 524). The outer surface 542 comprises that portion of the diaper 520 which is positioned away from the wearer's body (i.e., the outer surface 542 is generally formed by at least a portion of the backsheet 526 and other components joined to the backsheet 526). The rear waist region 544 and the front waist region 546 extend from the end edges 552 of the periphery to the crotch region 548.

The diaper 520 also has two centerlines, a longitudinal centerline 590 and a transverse centerline 592. The term "longitudinal", as used herein, refers to a line, axis, or direction in the plane of the diaper 520 that is generally aligned with (e.g., approximately parallel with) a vertical plane which bisects a standing wearer into left and right halves when the diaper 520 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The chassis 522 of the diaper 520 is shown in FIG. 36 as comprising the main body of the diaper 520. The containment assembly 522 may comprise at least the topsheet 524, the backsheet 526, and the absorbent core 528. When the absorbent article 520 comprises a separate holder and a liner, the chassis 522 may comprise the holder and the liner (i.e., the chassis 522 comprises one or more layers of material to define the holder while the liner comprises an absorbent composite such as a topsheet, a backsheet, and an absorbent core.) For unitary absorbent articles (or one piece), the chassis 522 comprises the main structure of the diaper with other features added to form the composite diaper structure. Thus, the chassis 522 for the diaper 520 generally comprises the topsheet 524, the backsheet 526, and the absorbent core 528.

FIG. 36 shows a form of the chassis 522 in which the topsheet 524 and the backsheet 526 have length and width dimensions generally larger than those of the absorbent core 528. The topsheet 524 and the backsheet 526 extend beyond the edges of the absorbent core 528 to thereby form the periphery of the diaper 520. While the topsheet 524, the backsheet 526, and the absorbent core 528 may be assembled in a variety of well known configurations know to those of skill in the art.

The absorbent core 528 may be any absorbent member which is generally compressible, conformable, non-irritating to the wearer's skin, and capable of absorbing and retaining liquids such as urine and other certain body exudates. As shown in FIG. 36, the absorbent core 528 has a garment-facing side, a body-facing side, a pair of side edges, and a pair of waist edges. The absorbent core 528 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. The absorbent core may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials. The absorbent core may also comprise SAP and air felt in any suitable ranges.

The configuration and construction of the absorbent core 528 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 528 may also be varied to accommodate wearers ranging from infants through adults. However, the total absorbent capacity of the absorbent core 528 should be compatible with the design loading and the intended use of the diaper 520.

Figure 37:
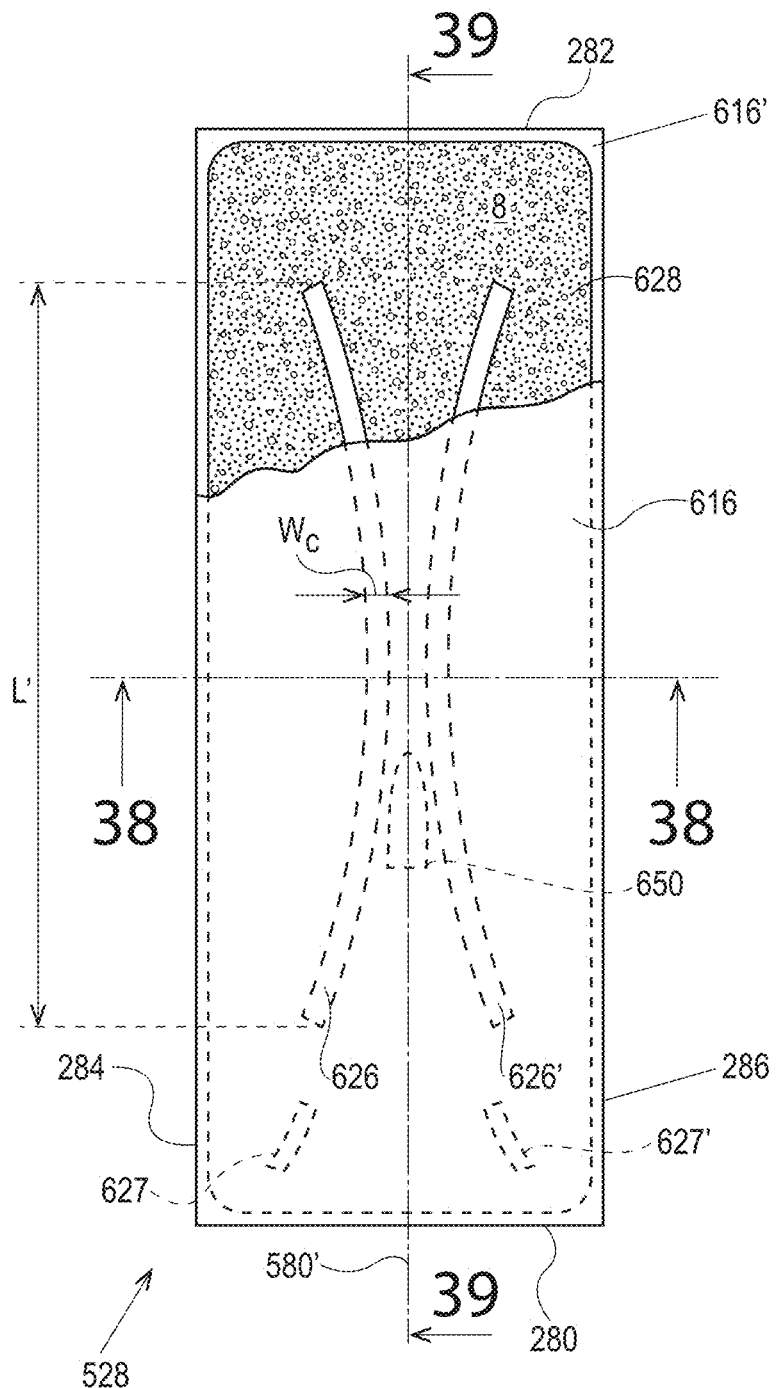
FIG. 37 is a top view of an example absorbent core of an absorbent article with some layers partially removed, wherein the absorbent core comprises one or more channels in accordance with the present disclosure.
Figure 38:
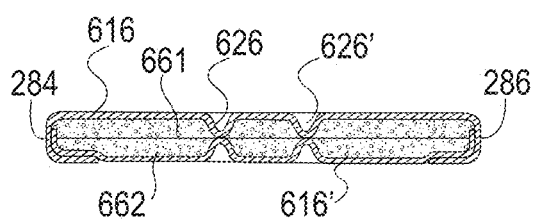
FIG. 38 is a cross-sectional view of the absorbent core taken about line 38-38 of FIG. 37 in accordance with the present disclosure.
Figure 39:
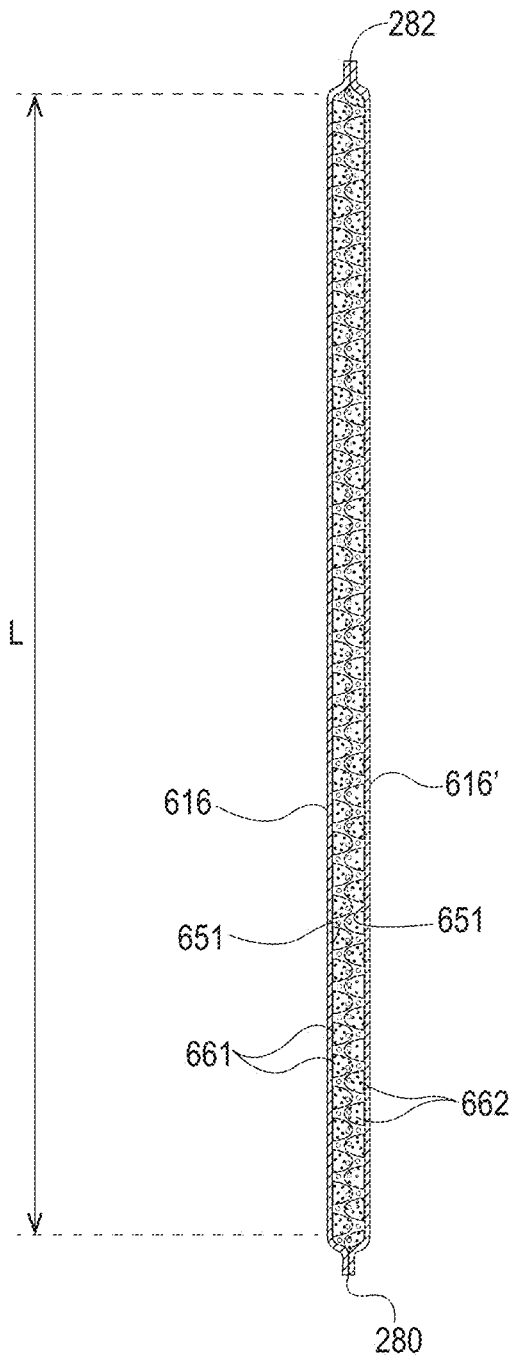
FIG. 39 is a cross-sectional view of the absorbent core taken about line 39-39 of FIG. 37 in accordance with the present disclosure.

Referring to FIGS. 37-39, the absorbent core 528 of the absorbent articles may comprise one or more channels 626, 626', 627, 627' (627 and 627' are shown in dash in FIG. 36), such as two, three, four, five, or six channels. The absorbent core 528 may comprise a front side 280, a rear side 282, and two longitudinal sides 284, 286 joining the front side 280 and the rear side 282. The absorbent core 528 may comprise one or more absorbent materials. The absorbent material 628 of the absorbent core 528 may be distributed in higher amounts towards the front side 280 than towards the rear side 282 as more absorbency may be required at the front of the absorbent core 528 in particular absorbent articles. The front side 280 may be positioned generally in the front waist region of an absorbent article and the rear side 282 may be positioned generally in the rear waist region of an absorbent article.

A core wrap (i.e., the layers enclosing the absorbent material of the absorbent core 528) may be formed by two nonwoven materials, substrates, laminates, films, or other materials 616, 616'. The core wrap may be at least partially sealed along the front side 280, the rear side 282, and/or the two longitudinal sides 284, 286 of the absorbent core 528 so that substantially no absorbent material is able to exit the core wrap. In a form, the core wrap may only comprise a single material, substrate, laminate, or other material wrapped at least partially around itself. The first material, substrate, or nonwoven 616 may at least partially surround a portion of the second material, substrate, or nonwoven 116' to form the core wrap, as illustrated as an example in FIG. 37. The first material 616 may surround a portion of the second material 616' proximate to the first and second side edges 284 and 286 and/or the front side 280 and the rear side 282. Patterned apertured webs of the present disclosure may have forms where the patterned apertures in, for example a topsheet, a wearer-facing laminate, an outer cover, and/or a garment-facing laminate may only have patterned apertures overlapping at least some of the core channels (e.g., channels 626 and 626' of FIG. 37). In other instances, the patterned apertures in the topsheet, the wearer-facing laminate, the outer cover, and/or the garment-facing laminate may coordinate with or compliment the core channels in such a way as the core channels are highlighted to a caregiver or wearer. This concept may also apply to sanitary napkins having core channels.

The absorbent core 528 of the present disclosure may comprise one or more adhesives, for example, to help immobilize the SAP or other absorbent materials within the core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

The absorbent material may comprise one or more continuous layers present within the core wrap with channels having no, or little (e.g., 0.1%-10%) absorbent material positioned therein. In other forms, the absorbent material may be formed as individual pockets or stripes within the core wrap. In the first case, the absorbent material may be, for example, obtained by the application of the continuous layer(s) of absorbent material, with the exception of the absorbent material free, or substantially free, channels. The continuous layer(s) of absorbent material, in particular of SAP, may also be obtained by combining two absorbent layers having discontinuous absorbent material application patterns, wherein the resulting layer is substantially continuously distributed across the absorbent particulate polymer material area, as disclosed in U.S. Pat. Appl. Pub. No. 2008/0312622A1 to Hundorf et al., for example. The absorbent core 528 may comprise a first absorbent layer and at least a second absorbent layer. The first absorbent layer may comprise the first material 616 and a first layer 661 of absorbent material, which may be 100% or less of SAP, such as 85% to 100% SAP, 90% to 100% SAP, or even 95% to 100% SAP, specifically including all 0.5% increments within the specified ranges and all ranges formed therein or thereby. The second absorbent layer may comprise the second material 616' and a second layer 662 of absorbent material, which may also be 100% or less of SAP (including the ranges specified above). The absorbent core 528 may also comprise a fibrous thermoplastic adhesive material 651 at least partially bonding each layer of the absorbent material 661, 662 to its respective material 616, 616'. This is illustrated in FIGS. 38 and 39, as an example, where the first and second SAP layers have been applied as transversal stripes or "land areas" having the same width as the desired absorbent material deposition area on their respective substrate before being combined. The stripes may comprise different amount of absorbent material (SAP) to provide a profiled basis weight along the longitudinal axis 580' of the core 528.

The fibrous thermoplastic adhesive material 651 may be at least partially in contact with the absorbent material 661, 662 in the land areas and at least partially in contact with the materials 616 and 616' in the channels 626, 626'. This imparts an essentially three-dimensional structure to the fibrous layer of thermoplastic adhesive material 651, which in itself is essentially a two-dimensional structure of relatively small thickness, as compared to the dimension in length and width directions. Thereby, the fibrous thermoplastic adhesive material 651 may provide cavities to cover the absorbent material in the land areas, and thereby immobilizes this absorbent material, which may be 100% or less of SAP (including the ranges specified above).

The channels 626, 626' may be continuous or discontinuous and may have a length of L' and a width, $W_c$, for example, or any other suitable length or width. The channels 626, 626', 627, and 627' may have a lateral vector component and a longitudinal vector component or may extend entirely longitudinally or entirely laterally. The channels may each have one or more arcuate portions. One or more channels may extend across the lateral axis or the longitudinal axis 580' of the absorbent core 528, or both.

Referring to FIG. 38, it can be seen that the channels 626 and 626' do not comprise absorbent material. In other instances, the channels 626 and 626' may comprise a relatively small amount (compared to the amount of the absorbent material within the remainder of the absorbent core 528) of absorbent material. The relatively small amount of absorbent material within the channels may be in the range of 0.1% to 20%, specifically reciting all 0.1% increments within the specified ranges and all ranges formed therein.

Referring again to FIG. 37, the absorbent core 528 may comprise one or more pockets 650 (shown in dash). The one or more pockets 650 may be provided in addition to the one or more channels or instead of the one or more channels. The pockets 650 may be areas in the absorbent core 528 that are free of, or substantially free of absorbent material, such as SAP (including the ranges specified above). The pockets 650 may overlap the longitudinal axis 580' and may be positioned proximate to the front side 280, the rear side 282, or may be positioned at a location intermediate the front side 280 and the rear side 282, such as longitudinally centrally, or generally longitudinally centrally between the front side 280 and the rear side 282.

Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

The diaper 520 may have an asymmetric, modified T-shaped absorbent core 528 having ears in the front waist region 546 but a generally rectangular shape in the rear waist region 544. Example absorbent structures for use as the absorbent core 528 of the present disclosure that have achieved wide acceptance described in U.S. Pat. No. 4,610,678, entitled "High-Density Absorbent Structures" issued to Weisman et al., on Sep. 9, 1986; U.S. Pat. No. 4,673,402, entitled "Absorbent Articles With Dual-Layered Cores", issued to Weisman et al., on Jun. 16, 1987; U.S. Pat. No. 4,888,231, entitled "Absorbent Core Having A Dusting Layer", issued to Angstadt on Dec. 19, 1989; and U.S. Pat. No. 4,834,735, entitled "High Density Absorbent Members Having Lower Density and Lower Basis Weight Acquisition Zones", issued to Alemany et al., on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345 entitled "High Efficiency Absorbent Articles For Incontinence Management", issued to Young et al. on Sep. 15, 1992.

The backsheet 526 is positioned adjacent the garment-facing surface of the absorbent core 528 and may be joined thereto by attachment methods (not shown) such as those well known in the art. For example, the backsheet 526 may be secured to the absorbent core 528 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art. Forms of the present disclosure are also contemplated wherein the absorbent core is not joined to the backsheet 526, the topsheet 524, or both in order to provide greater extensibility in the front waist region 546 and the rear waist region 544.

The backsheet 526 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 526 may prevent, or at least inhibit, the exudates absorbed and contained in the absorbent core 528 from wetting articles which contact the diaper 520 such as bed sheets and undergarments, however, the backsheet 526 may permit vapors to escape from the absorbent core 528 (i.e., is breathable). Thus, the backsheet 526 may comprise a polymeric film such as thermoplastic films of polyethylene or polypropylene. A suitable material for the backsheet 526 is a thermoplastic film having a thickness of from about 0.012 mm (0.5 mil) to about 0.051 mm (2.0 mils), for example.

The topsheet 524 is positioned adjacent the body-facing surface of the absorbent core 528 and may be joined thereto and to the backsheet 526 by attachment methods (not shown) such as those well known in the art. Suitable attachment methods are described with respect to joining the backsheet 526 to the absorbent core 528. The topsheet 524 and the backsheet 526 may be joined directly to each other in the diaper periphery and may be indirectly joined together by directly joining them to the absorbent core 528 by the attachment methods (not shown).

The topsheet 524 may be compliant, soft feeling, and non-irritating to the wearer's skin. Further, the topsheet 524 may be liquid pervious permitting liquids (e.g., urine) to readily penetrate through its thickness. A suitable topsheet 524 may comprise one or more of the patterned apertured webs of the present disclosure forming one or more layers. As described herein, the patterned apertured webs of the present disclosure may form any other suitable components, or portions thereof, of an absorbent article or the example diaper 520, such as an outer cover; an outer cover and a backsheet; a carrier layer (as referenced above); an ear panel; an acquisition material; a distribution material; an acquisition material and a topsheet; a distribution material and a topsheet; a first acquisition material; a second acquisition material; a first acquisition or distribution material and a second acquisition or distribution material; a topsheet, a first acquisition or distribution material, and a second acquisition or distribution material; a topsheet, a patch joined to or positioned on a topsheet; and a topsheet and a secondary topsheet, for example. Apertures may be formed through any or all of these materials, for example. In an example, an apertured or patterned apertured topsheet may be embossed or otherwise joined to an acquisition material, to an acquisition material and a distribution material, or to an acquisition material, a distribution material and a carrier layer, for example.

In an instance of a patterned apertured web, a first layer may comprise a topsheet and a second layer may comprise an acquisition material or layer. The acquisition material or layer may be a discrete patch that is not as long and/or wide as the topsheet or that may be the same size as the topsheet. The first layer and/or the second layer may have patterned apertures having any of the features described herein. Either of the layers may be pre-strained prior to being joined to the other layer, as described herein, thereby creating three-dimensional features in the topsheet/acquisition material laminate. By providing a patterned apertured web comprising a topsheet as a first layer and comprising an acquisition material as a second layer, improved fluid acquisition may be achieved as well as improved depth perception of the absorbent article owing to the relatively high basis weight of the acquisition material. In a feminine care context, the acquisition material may be a secondary topsheet.

Sanitary Napkin

Figure 40:
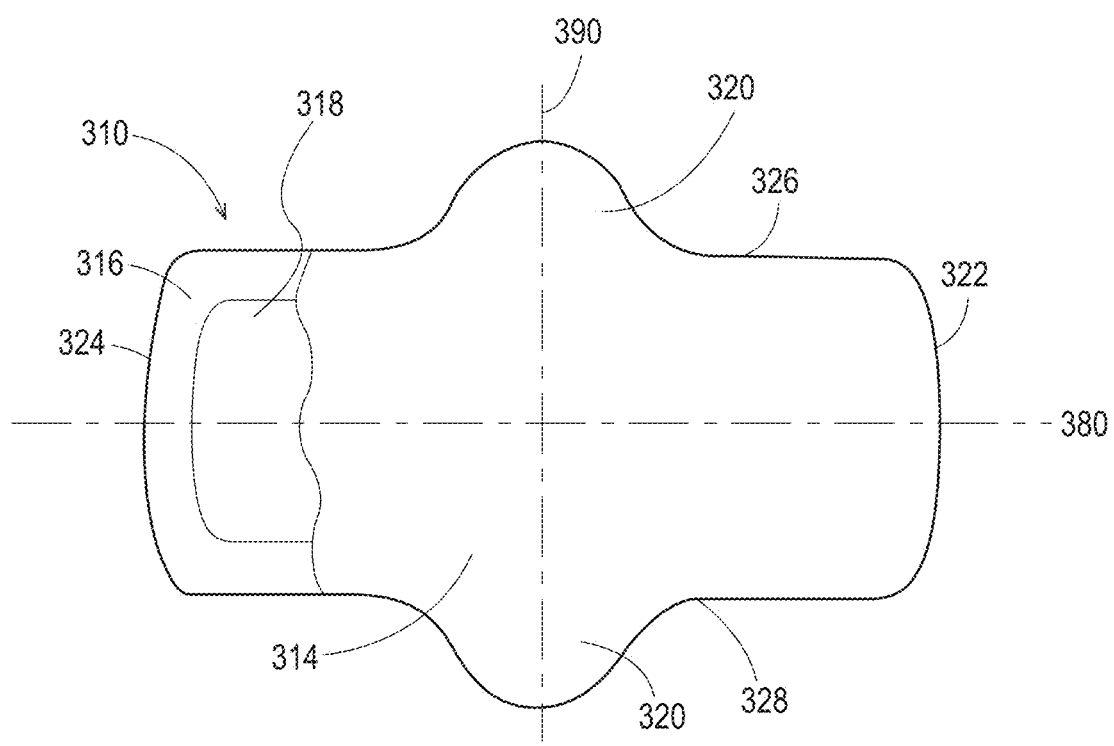
FIG. 40 is a top view of an absorbent article of the present disclosure, having portions cut away to reveal underlying structure, that is a sanitary napkin in accordance with the present disclosure.

Referring to FIG. 40, the absorbent article may be a sanitary napkin 310. A topsheet, a secondary topsheet, wings, or another portion of the sanitary napkin may comprise one or more of the patterned apertured webs of the present disclosure. The sanitary napkin 310 may comprise a liquid permeable topsheet 314, a liquid impermeable, or substantially liquid impermeable, backsheet 316, and an absorbent core 318 positioned intermediate the topsheet 314 and the backsheet 316. The absorbent core 318 may have any or all of the features described herein with respect to the absorbent cores 28 and, in some forms, may have a secondary topsheet instead of the acquisition layer(s) disclosed above. The sanitary napkin 310 may comprise wings 320 extending outwardly with respect to a longitudinal axis 380 of the sanitary napkin 310. The sanitary napkin 310 may also comprise a lateral axis 390. The wings 320 may be joined to the topsheet 314, the backsheet 316, and/or the absorbent core 318. The sanitary napkin 310 may also comprise a front edge 322, a rear edge 324 longitudinally opposing the front edge 322, a first side edge 326, and a second side edge 328 longitudinally opposing the first side edge 326. The longitudinal axis 380 may extend from a midpoint of the front edge 322 to a midpoint of the rear edge 324. The lateral axis 390 may extend from a midpoint of the first side edge 328 to a midpoint of the second side edge 328. The sanitary napkin 310 may also be provided with additional features commonly found in sanitary napkins as is known in the art.

Patterned Adhesive

Any of the patterned apertured webs and/or absorbent articles of the present disclosure, or portions thereof, may comprise one or more patterned adhesives applied thereto or printed thereon. The patterned adhesives may be present on the patterned apertured webs or under the patterned apertured webs such that at least a portion of the patterned adhesives may be viewable through the patterned apertured webs, either though apertures or non-apertured areas. Patterned adhesives are adhesives that are applied to one or more layers of the patterned apertured webs, or between layers of the same, in particular patterns to provide the absorbent articles, or portions thereof, with certain patterns, visible patterns, and/or certain textures.

Figure 41:
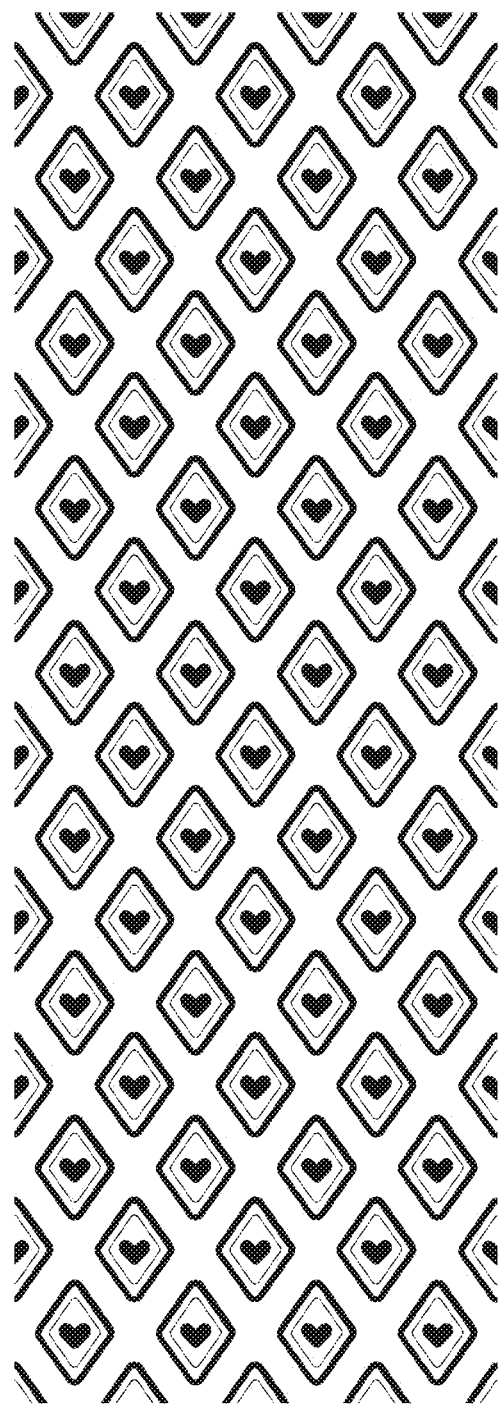
FIG. 41 is a top view of a patterned adhesive applied to a substrate in accordance with the present disclosure.
Figure 42:
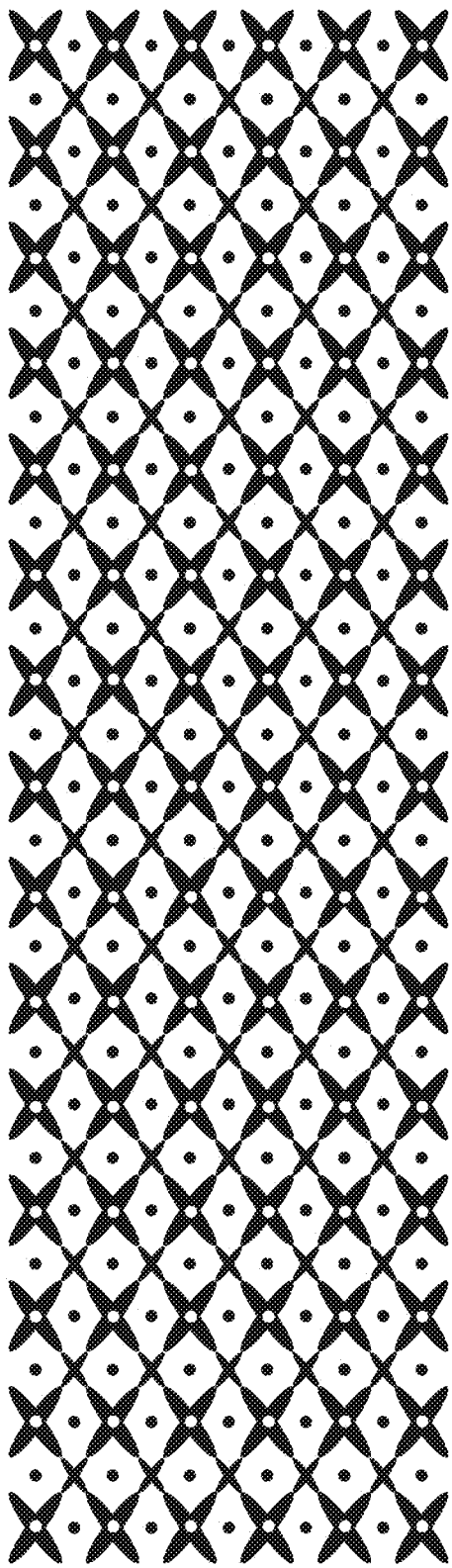
FIG. 42 is a top view of another patterned adhesive applied to a substrate in accordance with the present disclosure.

FIGS. 41 and 42 illustrate example patterns of adhesives, or pigmented adhesives, that can be used with the patterned apertured webs of the present disclosure. For example, these adhesive patterns may be used with the example patterned apertured web pattern of FIG. 15. These patterned adhesives can also be used with non-apertured layers having overbonds or embossments. The patterned adhesives may be printed on one or more apertured or non-apertured layers of the patterned apertured webs or patterned webs having embossments or overbonds. Other adhesive patterns having any suitable configuration are also within the scope of the present disclosure. The patterned adhesives may be printed on or otherwise applied to any suitable layer of the patterned apertured webs or applied above or beneath them. Methods for applying patterned adhesives to layers or substrates by adhesive printing are disclosed, for example, in U.S. Pat. No. 8,186,296, to Brown et al., issued on May 29, 2012, and in U.S. Pat. Appl. Publ. No., 2014/0148774, published on May 29, 2014, to Brown et al. Other methods of applying patterned adhesives to substrates known to those of skill in the art are also within the scope of the present disclosure.

A patterned adhesive may have the same color or a different color as at least one layer of a patterned apertured web. In some instances, the patterned adhesive may have the same or a different color as both or all layers of a patterned apertured web. In some instances, aperture patterns in at least one layer of a patterned apertured web may coordinate with a patterned of a patterned adhesive to visually create a three-dimensional appearance. The apertured patterns may be the same or different than patterns of the patterned adhesive.

In an instance, a patterned apertured web may comprise a first layer comprising a plurality of apertures and a plurality of land areas and a second layer comprising a plurality of apertures and a plurality of land areas. A patterned pigmented substance, such as ink or a patterned adhesive, may be positioned at least partially intermediate the first layer and the second layer. The patterned pigmented substance may be positioned on land areas of the first layer and/or the second layer. The plurality of apertures of the first layer may be at least partially aligned with the plurality of apertures of the second layer (see e.g., FIG. 8). The patterned pigmented or colored substance (e.g., 29 of FIG. 8) may be at least partially viewable through the apertures in one of the first or second layers.

Patterns

Figure 43:
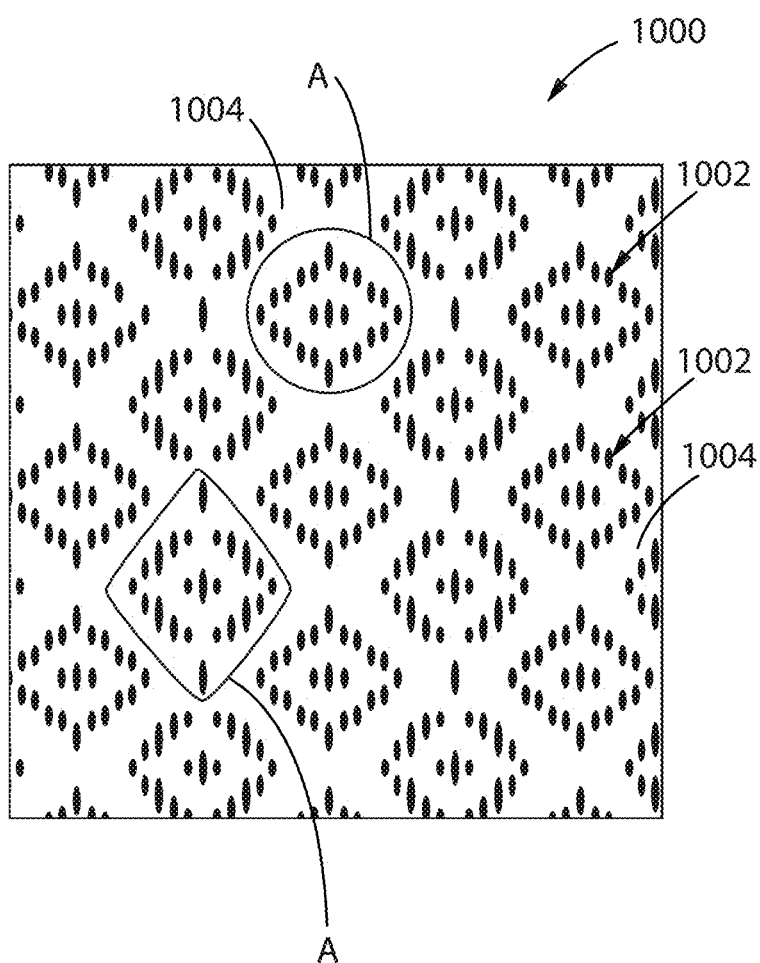
FIGS. 43-52 represent schematic illustrations of patterned apertures and land area in various patterned apertured webs, with the apertures being the black portions and the land areas being the white portions, in accordance with the present disclosure.
Figure 44:
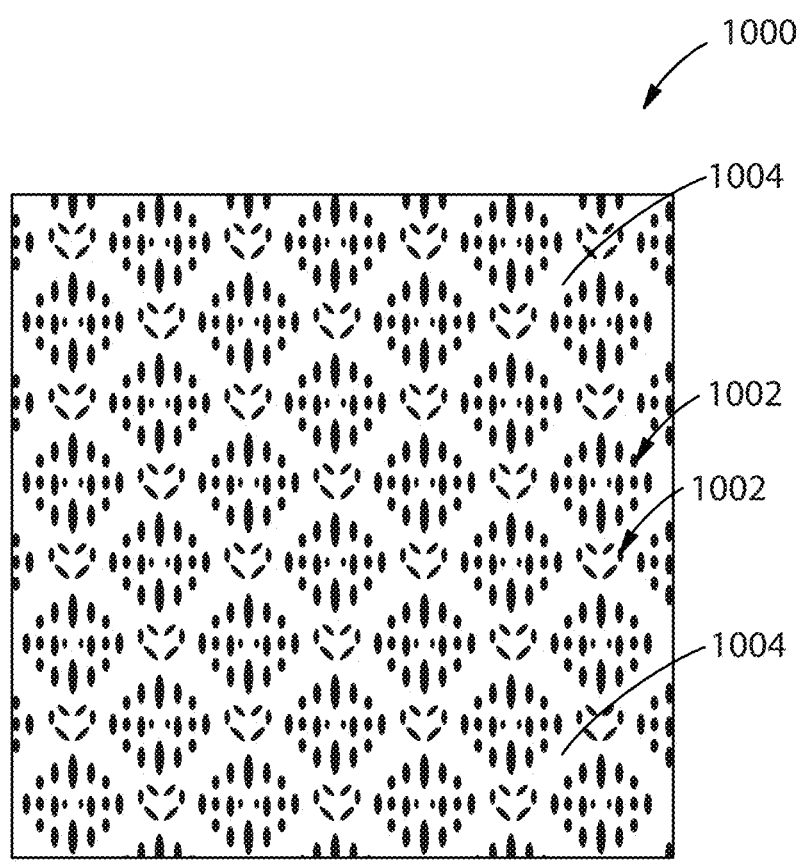

The apertures in at least one layer of a patterned apertured web may be grouped in spaced arrays of apertures (see e.g., FIGS. 1-4 and 43). FIG. 43 shows example arrays of apertures, labeled as "A". An aperture array may include two or more, or three or more apertures having much closer spacing between the apertures than the distance between the aperture arrays. The distance between the array and other apertures may be at least about 1.5, at least about 2 times, or at least about 3 times the maximum distance between apertures in the array. The aperture arrays may form a regular or recognizable shape, such as a heart shape, polygon, ellipse, arrow, chevron, and/or other shapes known in the pattern art. The apertures arrays may differ in one portion of the patterned apertured web compared to another portion of the patterned apertured web. In an absorbent article context, the aperture arrays may differ in one region of the absorbent article compared to another region of the absorbent article. The aperture arrays may have perimeters that are concave, convex, or may include concavities and convexities. The aperture arrays may be organized into "macro-arrays" having a higher order structure. For example, referring to FIGS. 43 and 44, a patterned apertured web 1000 is illustrated with aperture arrays 1002 that may be separated by a continuous, inter-connected land area pattern 1004. In such an instance, the land area pattern 1004 may function as a fluid distribution pathway and the aperture arrays 1002 may function as fluid "drains" thereby promoting fluid access to the underlying absorbent material or absorbent core. The shape of the aperture arrays may enhance the ability of the arrays to manage fluid, such as bodily exudates (i.e., urine, runny BM, menses). For example, aperture arrays including a concavity facing a fluid insult location in an absorbent article may function as fluid collection "traps" as the fluid may travel along the "land area" in the concavity to a point where the concavity ends. At this location, the fluid may enter the apertures in the direction of the fluid path or those on either side of the concavity if the fluid turns in either lateral direction. Example aperture array shapes having a concavity include heart shapes, star shapes, some polygons, crescents, and chevrons, to name a few examples.

Figure 45:
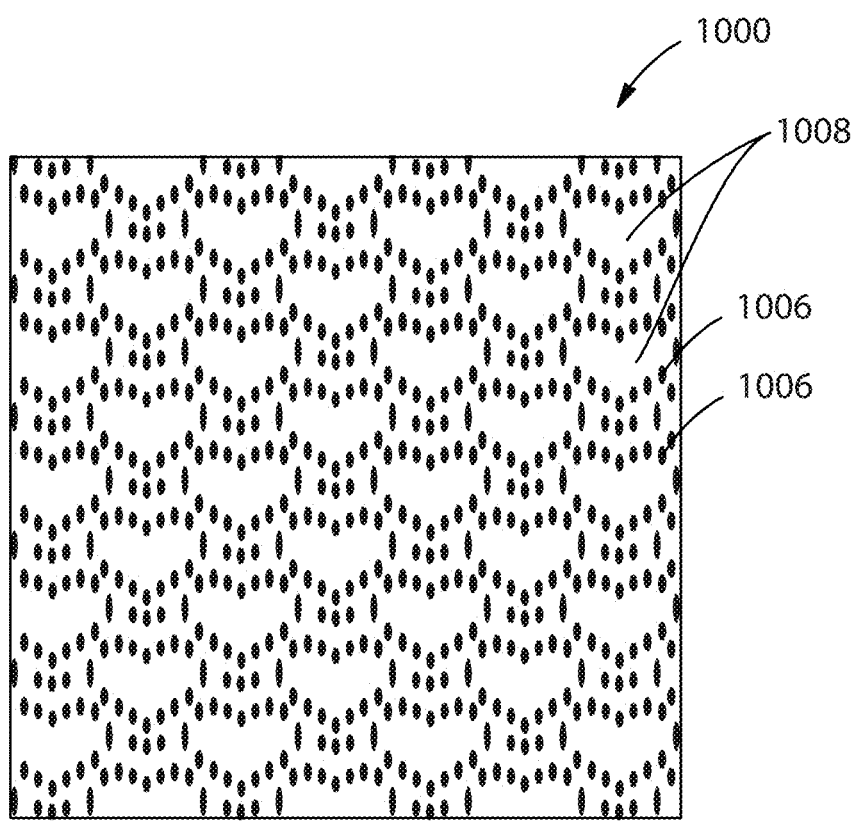
Figure 46:
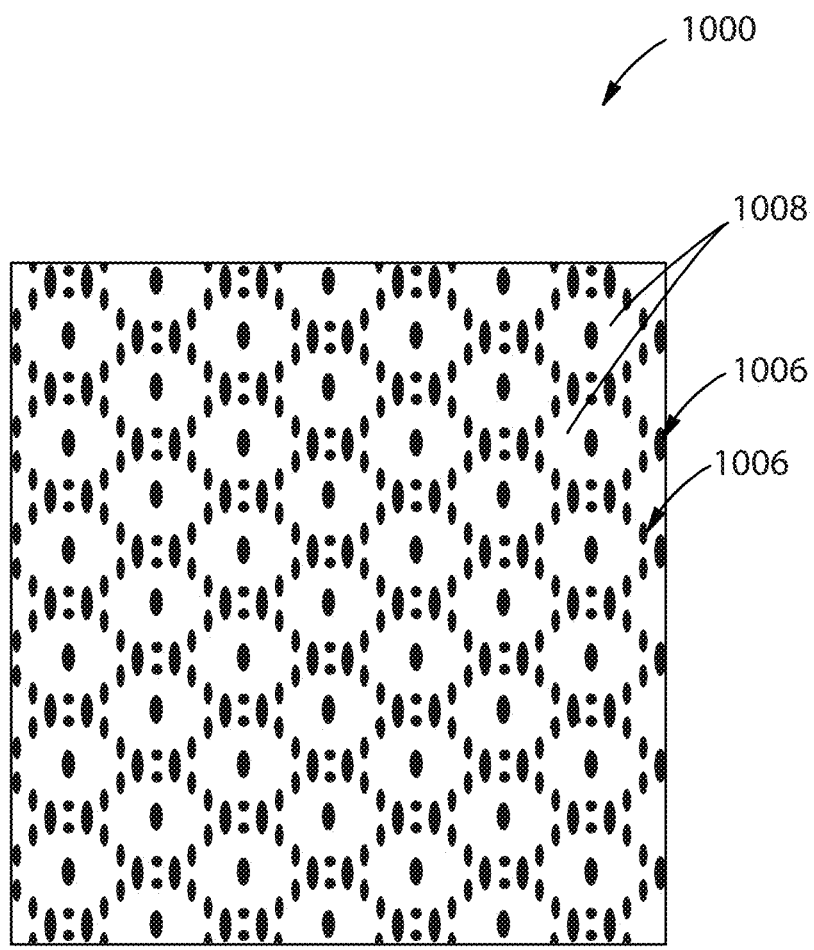
Figure 47:
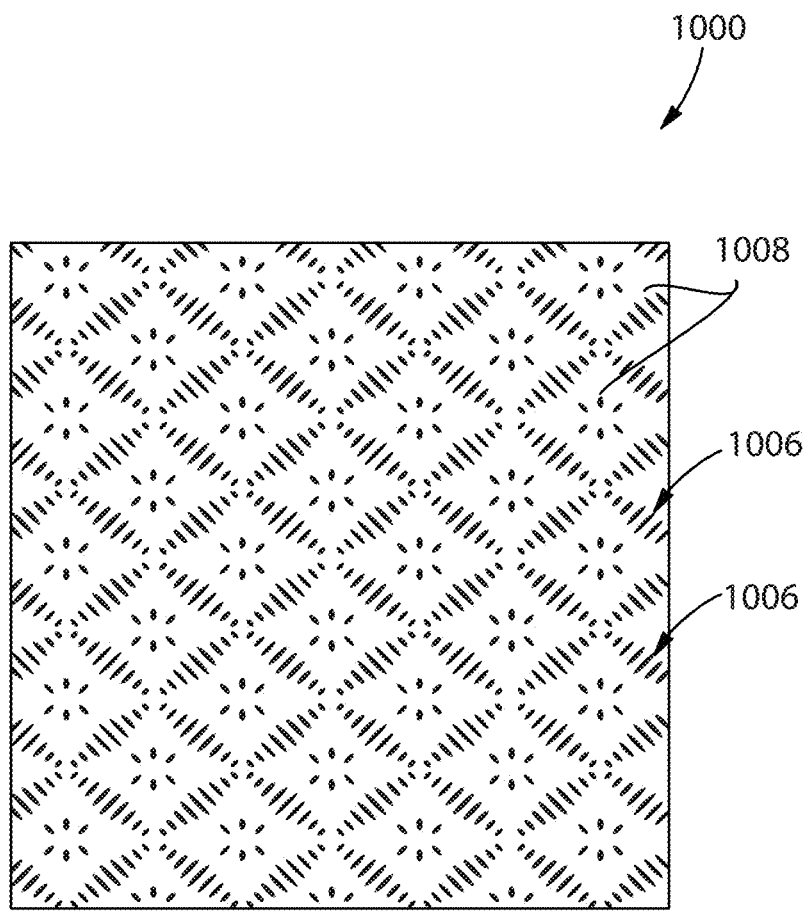
Figure 48:
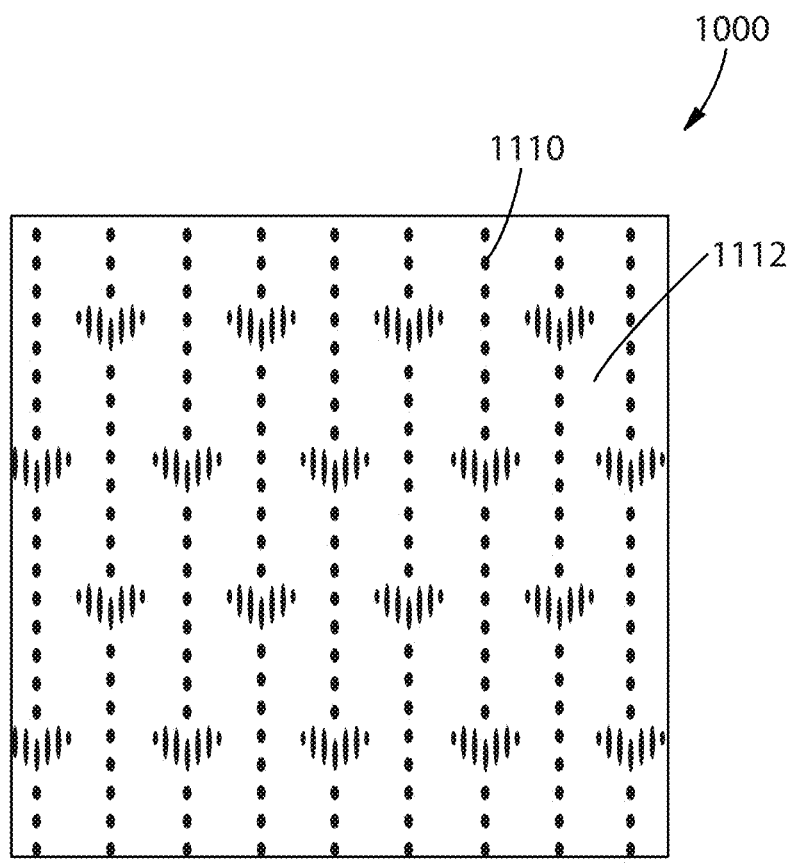
Figure 49:
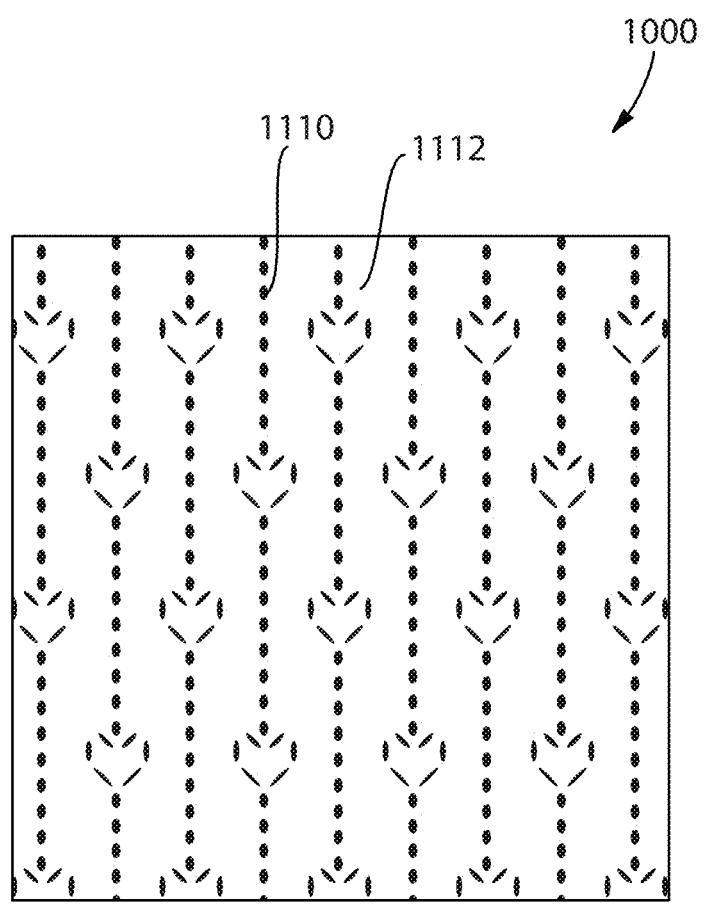
Figure 50:
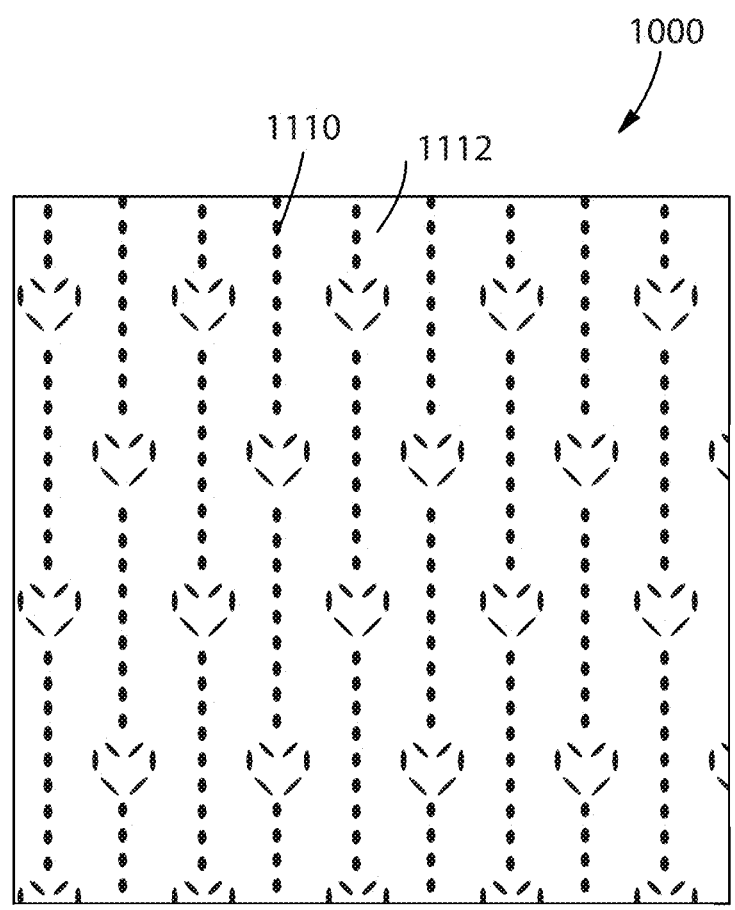
Figure 51:
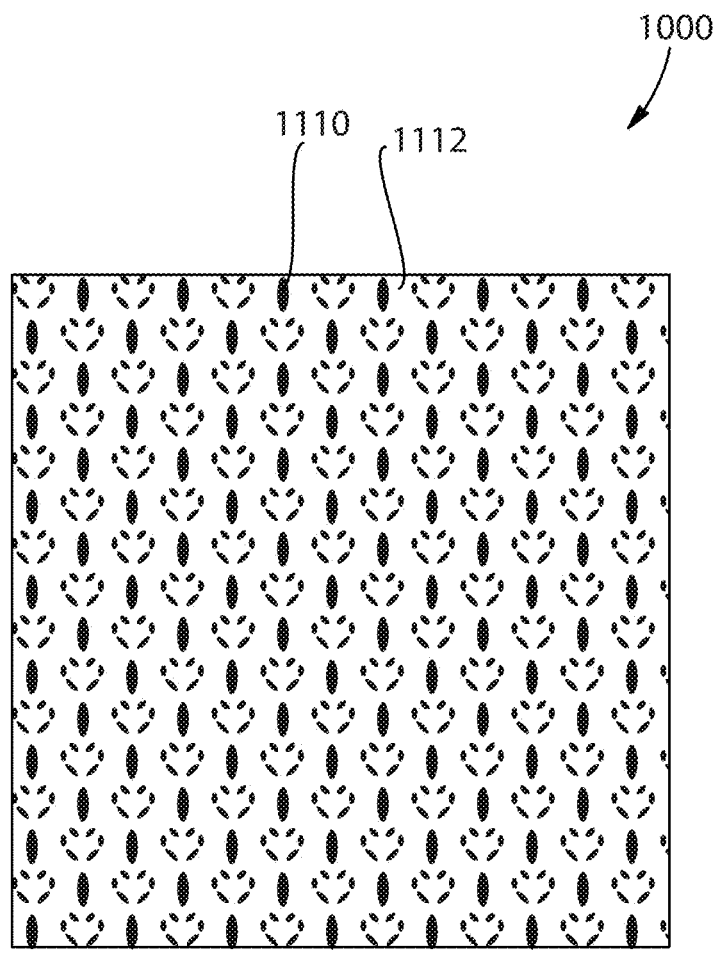
Figure 52:
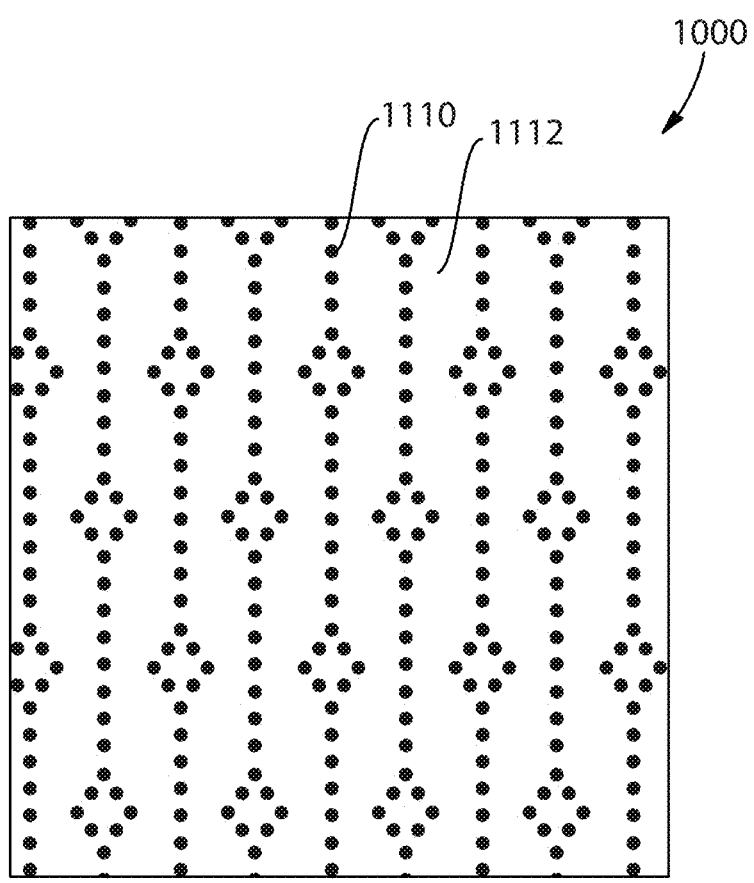

In an instance, referring to FIGS. 45-47, apertures, or arrays thereof, in a patterned apertured web 1000, may form one or more continuous or semi-continuous patterns 1006, resulting in discrete "macro" land areas 1008. In such an instance, the discrete macro land areas 1008 may function as fluid deposition regions. Fluid moving from the discrete macro land areas 1008 in any direction may be absorbed into the apertures of the continuous or semi-continuous pattern 1006.

In an instance, referring to FIGS. 48-52, the apertures, or aperture arrays thereof, in a patterned apertured web 1000 may form linear patterns 1110 alternating with continuous or semi-continuous land areas 1112. The patterned apertured webs may include unidirectional or multi-directional (and intersecting) aperture or aperture array patterns. Linear aperture or array patterns may be oriented parallel to the longitudinal or lateral axis, or at an angle between 0 and 90 degrees, specifically reciting all 0.5 degree increments within the specified range and all ranges formed therein, from either the longitudinal or lateral axis. Linear apertures or aperture array patterns may function to restrict fluid movement along the patterned apertured web to a greater degree in one direction compared to another direction.

The aperture pattern in a patterned apertured web may coordinate with graphics, indicia, printing, inks, color, and/or patterned adhesives, for example, located beneath the patterned apertured web or within the patterned apertured web. In an instance, the patterned apertured web may be used a topsheet, an outer cover, an ear, wings of a sanitary napkin, or other portion of an absorbent article.

The aperture pattern in a patterned apertured web may coordinate with features under it, such as bond sites, material edges, channels, and/or discolored or colored materials. By coordinating with these features it is meant that the patterned apertured web may be used to accentuate or block/hide these features. The aperture patterns of a patterned apertured web may also be used to indicate the correct front vs. rear, left vs. right orientation of an absorbent article or other consumer product.

If a patterned apertured web is used as part, or all of, an outer cover (garment-facing layer) of an absorbent article, the aperture pattern or patterns may provide enhanced breathability in certain regions (e.g., waist, hips) or reduced breathability in areas over an absorbent core, for example. The aperture pattern or patterns in a patterned apertured web used as an outer cover may also provide enhanced textures and/or signals in certain regions of the outer cover. Such texture and/or signals may provide intuitive instructions on how to property apply the absorbent article, where to grip the absorbent article, and/or where/how to fasten the absorbent article, among other functions, such as to enhance graphics or aesthetics.

If a patterned apertured web is used as a portion of a leg cuff of an absorbent article, an apertured pattern of the patterned apertured web of the leg cuff may coordinate with an aperture pattern of a patterned apertured web used as a topsheet and/or an outer cover of the same absorbent article to signal a holistic function.

If a patterned apertured web is used as a portion of a fastener (e.g., taped fastener) of an absorbent article, an apertured pattern of a patterned apertured web of the fastener may indicate how to grip and fasten the fastener and indicate when it is and is not fastened correctly. An apertured pattern of the patterned apertured web used as a fastener, or portion thereof, may coordinate with an aperture pattern of a patterned apertured web used as a topsheet and/or an outer cover of the same absorbent article to signal a holistic function.

The optimum balance of bodily exudate acquisition speed and rewet in an absorbent article comprising a patterned apertured web as a topsheet and/or topsheet and acquisition system may be derived from a combination of aperture diameter, shape or area, depth or thickness of the patterned apertured web, and the spacing between the various apertures or aperture arrays within the patterned apertured web.

An absorbent article comprising a patterned apertured web as a topsheet and/or a topsheet and an acquisition system may comprise a longitudinal axis, much like the longitudinal axis of 590 of FIG. 36. Arrays of apertures in the patterned apertured web may repeat themselves along a line that is angled about 20 degrees to about 160 degrees, specifically reciting all 1 degree increments within the specified range and all ranges formed therein, relative to the longitudinal axis. Additionally, there may be a plurality of aperture sizes, shapes, or areas along the line or the spacing between the apertures may not the same between all of the apertures along the line for purposes of channeling liquid bodily exudates into preferred areas of the absorbent article or the absorbent core thereof to help avoid leakage.

An aperture pattern in a patterned apertured web may form a recognizable visual element, such as a heart or a water droplet, for example. An aperture pattern that forms one or more water droplet shapes in a patterned apertured web used as a topsheet or an outer cover of an absorbent article may be used to aid communication of absorbency and/or wetness. Such a feature may be combined with a wetness indicator of an absorbent article.

Various commonly understood shapes may be created in a patterned apertured web. These shapes may be shapes that have commonly understood proper orientations, such as hearts, for example. An example is the use of one or more hearts on an outer cover or a topsheet of a front waist region and/or a back waist region of a diaper. The caregiver would understand to place the diaper on the wearer with the point of the heart facing toward the wearer's feet because of the common knowledge of the orientation of hearts.

In an instance, a patterned apertured web may comprise a first non-apertured layer comprising a pattern having a color and a second patterned apertured layer comprising a pattern of apertures. The pattern on the first non-apertured layer may be printed on the layer, for example, and may form graphics or other indicia. At least 50% to 100% of the pattern on the first non-apertured layer may be aligned with the pattern of apertures in the second patterned apertured layer to draw attention to the apertures. The alignment, or partial alignment, of the pattern of apertures on the first layer with the pattern having a color of the second layer may make aid in aligning the product on a wearer if the patterned apertured web is provided on an absorbent article.

Zones

In any context of a patterned apertured web, but especially in an absorbent article context, the patterned apertured webs may be employed in a zonal fashion. For instance, a first zone of a topsheet or outer cover of an absorbent article may have a first patterned apertured web having a first pattern, while a second zone of the topsheet or the outer cover of the absorbent may have a second patterned apertured web having a second, different pattern. In a topsheet context, for example, the patterns in the different zones may be configured to receive certain bodily exudates or inhibit or encourage their flow in any desired direction. For example, the first pattern may be better configured to receive and/or direct the flow of urine, while the second pattern may be better configured to receive and/or direct the flow of runny BM. In other instances where the patterned apertured webs are used as a topsheet of an absorbent article, a first patterned apertured web having a first pattern may be configured to receive heavy gushes of bodily exudates, while a second patterned apertured web having a second different pattern may be configured to restrict lateral bodily exudate flow in any desired direction. The first pattern may be situated in, for instance, the middle of the absorbent article or in the crotch region, while the second pattern may be situated in the front and rear waist regions or outer perimeter topsheet regions of the absorbent article.

The zones in a patterned apertured web may be positioned in the machine direction, the cross direction, or may be concentric. If a product, such as an absorbent article, has two different zones in the machine direction, the zones may have the same or a similar cross-direction width (e.g., +/−2 mm) for ease in processing. One or more of the zones may have curved or straight boundaries or partial boundaries.

Any suitable zones, including more than two, of different or the same patterned apertured webs, are envisioned within the scope of the present disclosure. The various zones may be in the topsheet as mentioned above, but may also be present on an outer cover, a barrier leg cuff, or any other portion of ab absorbent article or other product, for example. In some instances, the same or a different pattern of zones of patterned apertured webs may be used on the wearer-facing surface (e.g., topsheet) and the garment-facing surface (e.g., outer cover).

In an instance, a topsheet or other portion of an absorbent article may have two or more zones in a patterned apertured web. A first zone of the patterned apertured web may have a different aperture pattern than a second zone. The first zone and the second zone may have different functionalities owing to the different aperture patterns. A functionality of the first zone may be to provide liquid bodily exudate distribution (fluid moving on the patterned apertured web), while the functionality of the second zone may be to provide liquid bodily exudate acquisition (fluid penetrating the patterned apertured web). Benefits of such a zoned patterned apertured web can be better use of an absorbent core and more efficient liquid bodily exudate distribution within the absorbent core.

In an instance, an absorbent article may comprise a patterned apertured web that forms a first portion and a second, different portion thereof. Aperture patterns in each portion of the patterned apertured web may be the same, substantially similar, or different. In another instance, an absorbent article may comprise a patterned apertured web that comprises a first portion of an absorbent article, and wherein a second portion of the absorbent article has graphics, printing, patterned adhesives, or other indicia that forms a pattern that is similar to, substantially similar to, coordinates with, or is different than an aperture pattern in the patterned apertured web.

In an instance, a patterned apertured web may have a plurality of zones. A first zone may have at least some apertures having a first angle (central longitudinal axis of aperture vs. MD), first size, and/or first shape, while a second zone (or third or fourth zone etc.) may have apertures having a second, different angle (central longitudinal axis of aperture vs. MD), second, different size, and/or second, different shape.

Visual Texture

Apertures, patterned apertures, aperture arrays, three-dimensional elements, printing, patterned adhesives, or any combinations of these "texture elements" may impart a variable visually observed texture in a patterned apertured web. Variations in observable textures have been extensively studied in the psychological and neurological sciences. Some small texture elements are much more readily ("instantly") detected by the human visual perception system than others. Most texture patterns having similar "second order" (iso-dipole) statistics cannot be discriminated in a brief "flash" observation. However, exceptions to this (i.e., iso-dipole texture elements that are easily discriminated) have been defined and are known in the literature as "textons". Patterned apertured webs including texture elements forming texton shapes provide a way to create easily recognizable "zones" on a laminate or in an absorbent article, signaling regions having different functions, and/or providing strong cues as to correct product orientation on a wearer (e.g., front/back). Forms of the patterned apertured webs of the present disclosure may include texture elements forming texton shapes, including quasi-collinearity, corner features, and closure of local features. A reference is Julesz, B., et al, *Visual Discrimination of Textures with Identical Third-Order Statistics*, Biological Cybernetics vol. 31, 1978, pp. 137-140).

Effective Open Area

A patterned apertured web may have an Effective Open Area between about 3% to about 50%, about 5% to about 50%, about 5% to about 40%, about 10% to about 40%, about 10% to about 35%, about 10% to about 30%, or about 15% to about 30%, specifically reciting all 0.1% increments within the specified ranges and all ranges formed therein or thereby. All Effective Open Area percents are determined using the Aperture Test described herein. Patterned apertured webs having a higher Effective Open Area may have utility as a topsheet or acquisition layer or system in an absorbent article (more functional to absorbent bodily exudates), while patterned apertured webs having a lower Effective Open Area may have utility as an outer cover of an absorbent article (more decorative or for breathability purposes).

Effective Aperture Area

A patterned apertured web may have apertures having an Effective Aperture Area in the range of about 0.3 $mm^2$ to about 15 mm 2, 0.3 $mm^2$ to about 14 mm 2, 0.4 $mm^2$ to about 12 mm 2, 0.3 $mm^2$ to about 10 mm 2, 0.5 $mm^2$ to about 8 mm 2, or 1.0 $mm^2$ to about 8 $mm^2$, specifically reciting all 0.05 mm increments within the specified ranges and all ranges formed therein or thereby. All Effective Aperture Areas are determined using the Aperture Test described herein. A plurality of the apertures in a patterned apertured web may be different in Effective Aperture Areas. The Relative Standard Deviation of the Effective Aperture Areas in a patterned apertured web may be at least about 50%, or at least about 55%, or at least about 60%, for example.

Aperture Aspect Ratio

The apertures of the patterned apertured webs of the present disclosure may have an aspect ratio of greater than one, for example, greater than two, greater than 3, greater than 5, or greater than 10, but typically less than 15, according to the Aperture Test herein. The aperture patterns in the patterned apertured web may comprise apertures having more than one aspect ratio, such as two or more distinct populations or having a substantially continuous distribution of aspect ratios having a slope greater than zero. Additionally, the aperture patterns of the patterned apertured webs may comprise apertures with more than two effective aperture areas, either as two or more distinct populations or as a distribution of aperture areas having a slope greater than zero. The Relative Standard Deviation of the aperture aspect ratios in a patterned apertured web may be at least about 30%, at least about 40%, or at least about 45%.

Aperture Density

The apertures of the patterned aperture webs of the present disclosure may have an Aperture Density, according to the Aperture Test herein, of at least about 150, at least about 175, at least about 200, or at least about 300, for example.

Method

A method of producing a patterned apertured web is provided. The method may comprise providing a web having a central longitudinal axis. The web may comprise a plurality of overbonds extending substantially parallel to, or parallel to, the central longitudinal axis. Substantially parallel means +/−5 degrees or +/−3 degrees or less. The method may comprise conveying the web in a machine direction. The machine direction may be substantially parallel to, or parallel to, a direction of extension of the central longitudinal axis of the web. The method may comprise stretching the web in a cross-machine direction that is substantially perpendicular (+/−5 degrees or +/−3 degrees or less) to the machine direction to cause at least some of, most of, or all of, the overbonds to at least partially rupture, or fully rupture, and at least partially form, or form, patterned apertures in the web. At least some of the patterned apertures may have Absolute Feret Angles, according to the Aperture Test herein, of at least about 10 degrees, at least about 15 degrees, at least about 20 degrees, at least about 25 degrees, at least about 30 degrees, at least about 35 degrees, at least about 40 degrees, at least about 45 degrees, or in the range of about 10 degrees to about 45, or about 15 to about 35 degrees, specifically reciting all 0.1 degree increments within the specified ranges and all ranges formed therein or thereby. At least some of the patterned apertures may have an Aspect Ratio, according to the Aperture Test herein, of greater than about 1.5:1, greater than about 1.8:1, greater than about 2:1, greater than about 2.5:1, greater than about 3:1, or in the range of about 1.5:1 to about 10:1, about 2:1 to about 6:1, about 2:1 to about 5:1, or about 2:1 to about 4:1, specifically reciting all 0.1 increments (e.g., 1.6:1, 1.7:1, 1.8:1) within the specified ranges and all ranges formed therein or thereby. The overbond may be at least partially ruptured, or fully ruptured, to form the patterned apertures using the process illustrated and described with respect to FIGS. 16, 17, and 24-30, for example.

At least some of the patterned apertures may have Absolute Feret Angles, according to the Aperture Test herein, in the range of about 0 degrees to about five degrees, or about 0 degrees (i.e., +/−2 degrees). Thus, some of the patterned apertures may be angled relative to the machine direction, while others may not. The patterned apertures may comprise a first plurality of patterned apertures and a second plurality of patterned apertures. Central longitudinal axes of the first plurality of patterned apertures may extend in a first direction relative to the machine direction. Central longitudinal axes of the second plurality of apertures may extend in a second, different direction relative to the machine direction. The second different direction may be at least about 5 degrees, at least about 10 degrees, at least about 15 degrees, at least about 20 degrees, at least about 30 degrees, at least about 40 degrees, at least about 50 degrees, at least about 60 degrees, at least about 70 degrees, at least about 80 degrees, at least about 90 degrees, or in the range of about 10 degrees to about 90 degrees, or about 20 degrees to about 70 degrees, specifically reciting all 0.1 degree increments within the above-specified ranges and all ranges formed therein or thereby, different than the first direction. The first direction may have a positive slope relative to the machine direction and the second direction may have a negative slope relative to the machine direction. In other instances, the first direction and the second direction may both have a positive slope or may both have a negative slope. At least some of the plurality of the overbonds may form a diamond-shaped or diamond-like pattern in the web. Land areas may be formed at least partially around, or fully around, at least some of the plurality of the overbonds or the patterned apertures. At least some of the patterned apertures, such as 2 or more, 3 or more, or 4 or more may be non-homogenous meaning that they are designed to have a different size, shape, Absolute Feret Angle, according to the Aperture Test herein, and/or Aspect Ratio, according to the Aperture Test herein.

A method of forming patterned apertures in a web is provided. The method may comprise providing a web having a central longitudinal axis, conveying the web in a machine direction that is substantially parallel to the central longitudinal axis, and creating a plurality of overbonds in the web. The overbonds may have central longitudinal axes that are substantially parallel to the central longitudinal axis of the web. The method may comprise stretching the web in a cross-machine direction that is substantially perpendicular to, or perpendicular to, the machine direction to at least partially form, or fully form, patterned apertures in the web at, at least some of, or most of, or all of, the overbonds. At least some of the patterned apertures may have Absolute Feret Angles, according to the Aperture Test herein, of at least about 20 degrees (and other numbers and ranges set forth above). At least some of the patterned apertures may have an Aspect Ratio, according to the Aperture Test herein, of greater than about 2:1 (and other numbers and ranges set forth above). At least some of patterned apertures may have Absolute Feret Angles, according to the Aperture Test herein, of at least about 30 degrees (and other numbers and ranges set forth above). The patterned apertures may comprise a first plurality of patterned apertures and a second plurality of patterned apertures. Central longitudinal axes of the first plurality of patterned apertures may extend in a first direction. Central longitudinal axes of the second plurality of patterned apertures may extend in a second, different direction. The second different direction may be at least about 10 degrees or at least about 30 degrees (and other numbers and ranges set forth above) different than the first direction.

A method of producing a patterned apertured web is provided. The method may comprise providing a web having a central longitudinal axis. The web may comprise a plurality of overbonds extending substantially parallel to, or parallel to, the central longitudinal axis. The method may comprise conveying the web in a machine direction that is substantially parallel to, or parallel to, a direction of extension of the central longitudinal axis of the web. The method may comprise stretching the web in a cross-machine direction that is substantially perpendicular to, or perpendicular to, the machine direction to cause at least some of, or most of, or all of, the overbonds to at least partially rupture, or fully rupture, and at least partially form, or fully form, apertures in the web. At least some of the apertures have Absolute Feret Angles, according to the Aperture Test herein, that are at least about 25 degrees (and other numbers and ranges set forth above). At least some of the apertures have an Aspect Ratio, according to the Aperture Test herein, in the range of about 2:1 to about 6:1 (and other ratios and ranges as set forth above. At least two, three, four, or five of the apertures may be nonhomogeneous.

Patterned apertured webs having apertures having different Absolute Feret Angles may provide liquid bodily exudate handling benefits when the patterned apertured webs are used as topsheets in absorbent articles, for example. For example, fluid run-off may be reduced in the front or back of the absorbent article when all of the Absolute Feret Angles are not all about 0 degrees, but instead are greater than 0 degrees, such as about 15 degrees, about 20 degrees, about 30 degrees, about 45 degrees, or even about 90 degrees, as the apertures can more readily acquire the liquid bodily exudates. Therefore, it may be desirable to have apertures having different Absolute Feret Angles to most effectively acquire liquid bodily exudates running along the surface of the patterned apertured web and prevent, or at least inhibit, run-off and soiling of garments.

Figure 53:
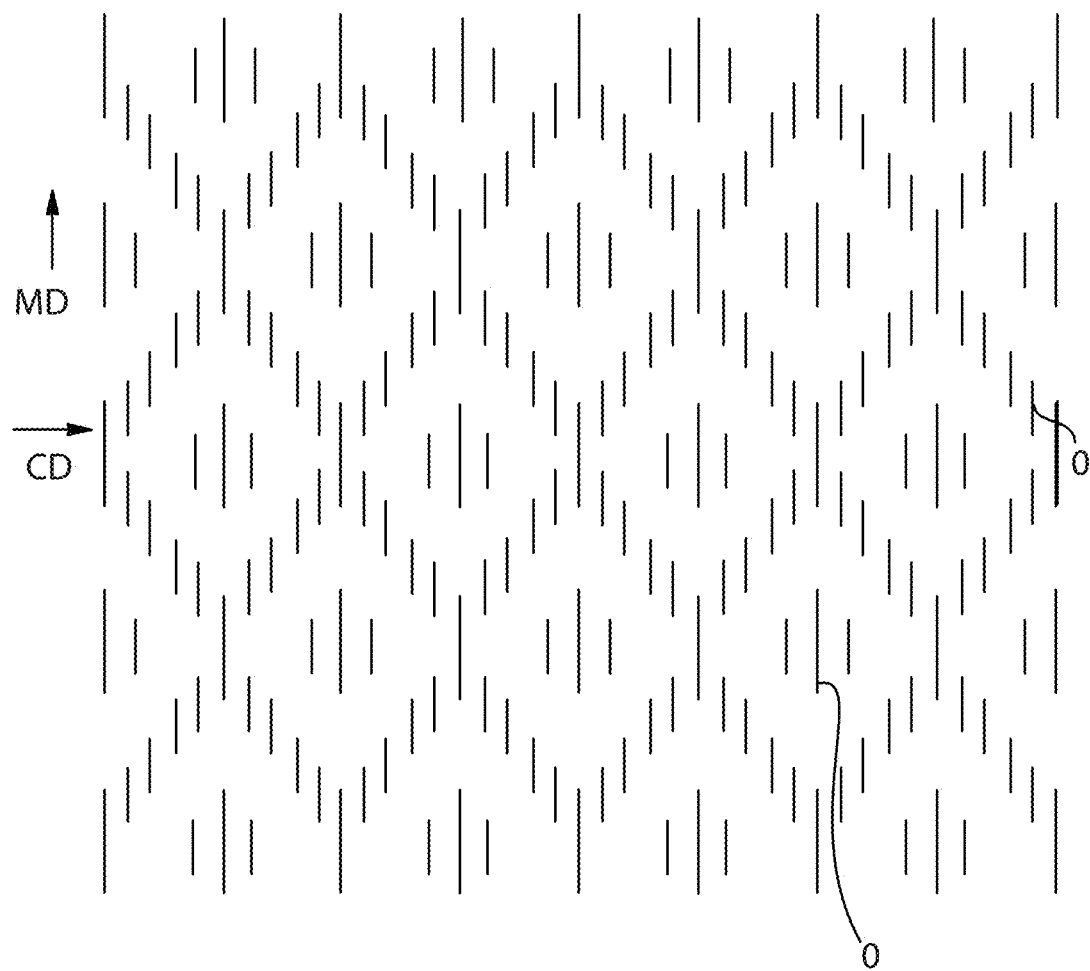
FIG. 53 represents a schematic illustration of an example overbond pattern having overbonds with central longitudinal axes that are substantially parallel to a machine direction in accordance with the present disclosure.
Figure 53A:
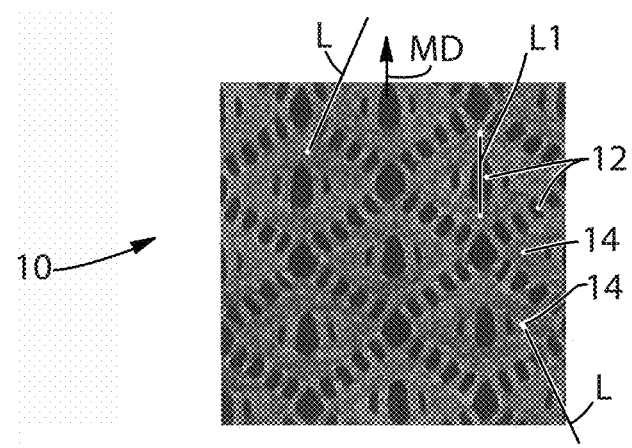
FIG. 53A is a photograph of a patterned apertured web produced using an overbond roll having the overbond pattern of FIG. 53 in according with the present disclosure.

In some example patterned apertured webs of the present disclosure, a pattern of overbonds, each of which is oriented solely in the machine direction, or substantially in the machine direction (i.e., +/−5 degrees+/−3 degrees or less from the machine direction), may be used to create a patterned apertured web with apertures having Absolute Feret Angles or central longitudinal axes that are not all oriented in the machine direction or, stated another way, that are angled more than 5 degrees with respect to the machine direction or have Absolute Feret Angles that are greater than 5 degrees, greater than 10 degrees, greater than 15 degrees, greater than 25 degrees, or greater than 30 degrees. Referring to FIG. 53, an example overbond pattern having overbonds "O" oriented solely in the machine direction are illustrated. The overbond pattern of FIG. 53 may be used to produce the patterned apertured web of FIG. 53A, for example. The patterned apertured web 10 of FIG. 53A may have some apertures 12 having a central longitudinal axis, L, having an angle with respect to the machine direction or an Absolute Feret Angle greater than 5 degrees. The Absolute Feret Angle may be any of the numbers or ranges set for the above. Some of the apertures 12 in the patterned apertured web 10 may also have a central longitudinal axis, L1, that extends parallel to, or substantially parallel to (e.g., +/−less than 5 degrees), the machine direction or apertures 12 having Absolute Feret Angles in the range of about 0 to about 5 degrees. The cross directional stretching step or steps described herein may be used to create the apertures and to orient the central longitudinal axes, L, of at least some of the apertures in a direction not parallel to, or substantially parallel to, the machine direction. At least some of the apertures in a patterned apertured web having their central longitudinal axes not parallel to, or substantially parallel to, the machine direction may have a first plurality of apertures having central longitudinal axes extending in a first direction with respect to the machine direction and a second plurality of apertures having central longitudinal axes extending at a second, different direction relative to the machine direction. Those of skill in the art will recognize that other angles relative to the machine direction are also within the scope of the present disclosure.

The apertures in a patterned apertured web having a central longitudinal axis angled with respect to the machine direction and produced by machine direction overbonds may be more open (i.e., have a lower aspect ratio) than they would have been if the overbonds had been oriented at an angle (5 degrees or more) with respect to the machine direction. Overbonds oriented at an angle with respect to the machine direction typically produce apertures having higher aspect ratios post cross-directional stretching that are less open.

Fused Portions

Figure 54:
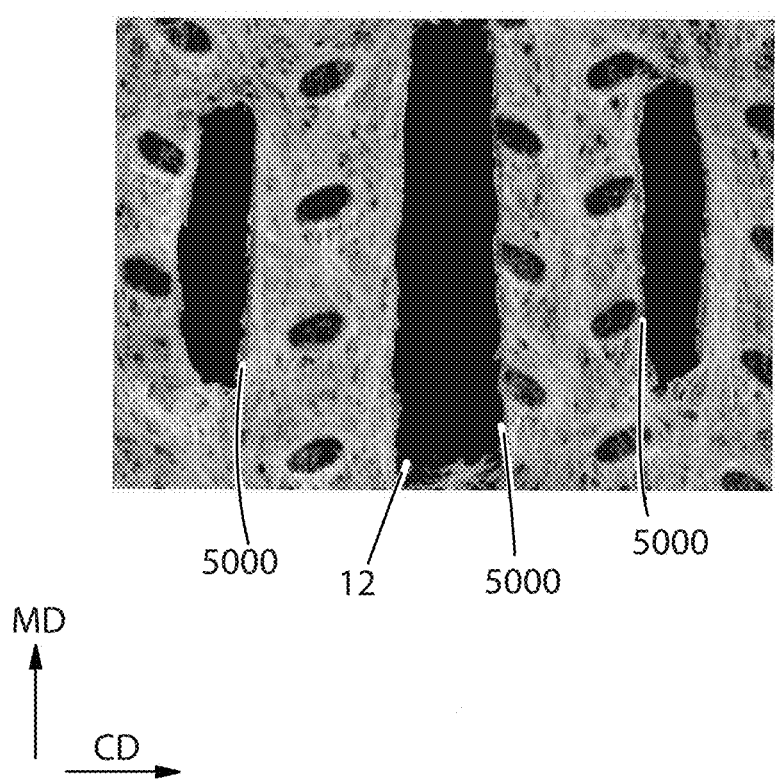
FIG. 54 is a photograph of a portion of a patterned apertured web comprising fused or melted portions surrounding the apertures in accordance with the present disclosure.
Figure 55:
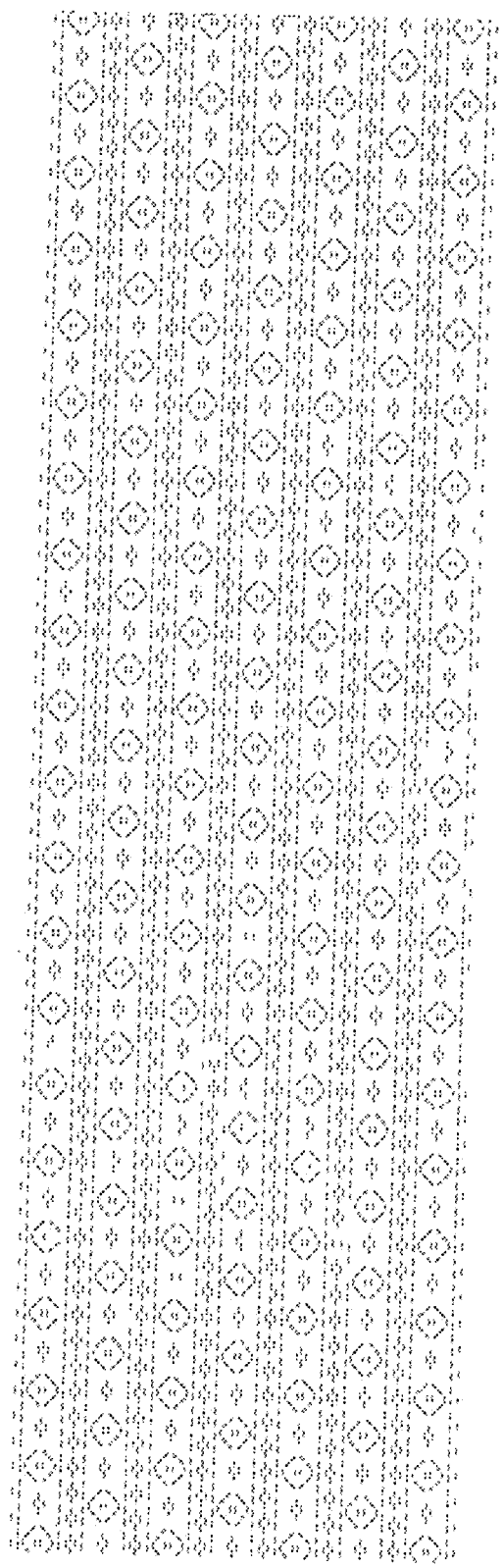
FIGS. 55-60 illustrate schematic illustrations of example overbond roller patterns used to create patterns of overbonds in webs in accordance with the present disclosure.
Figure 56:
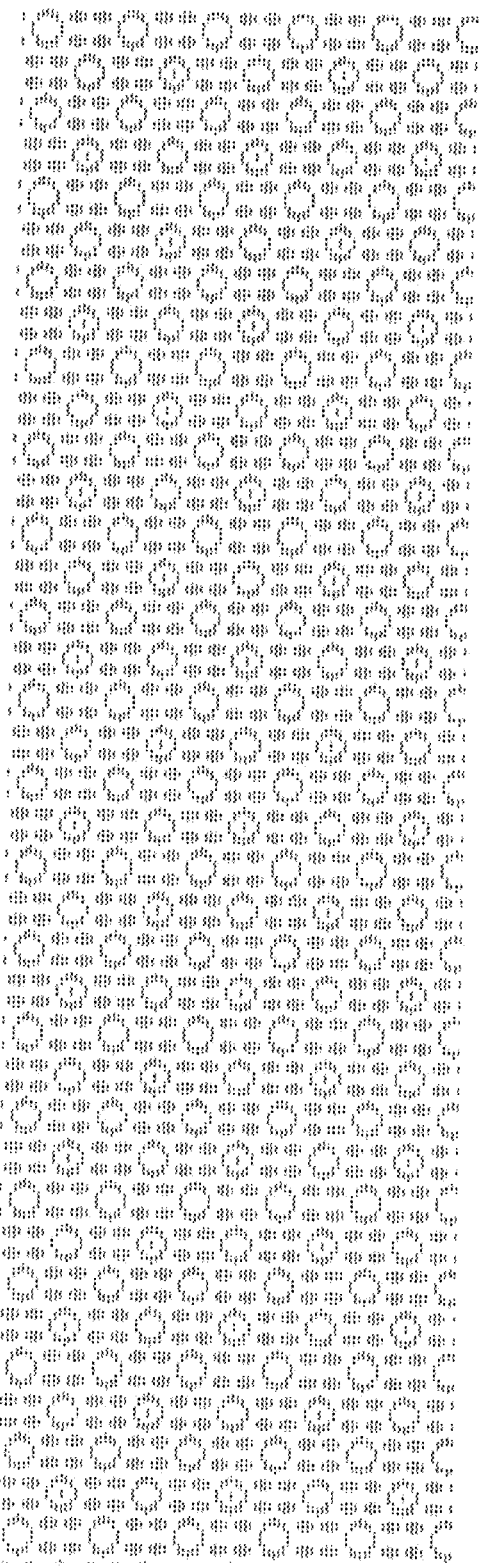
Figure 57:
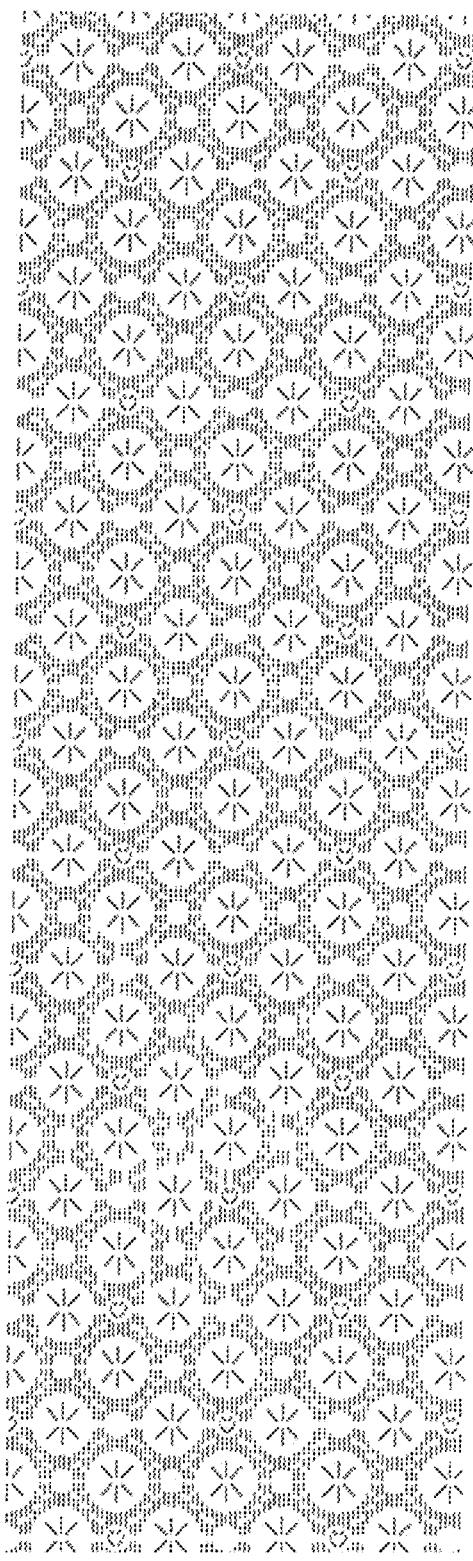
Figure 58:
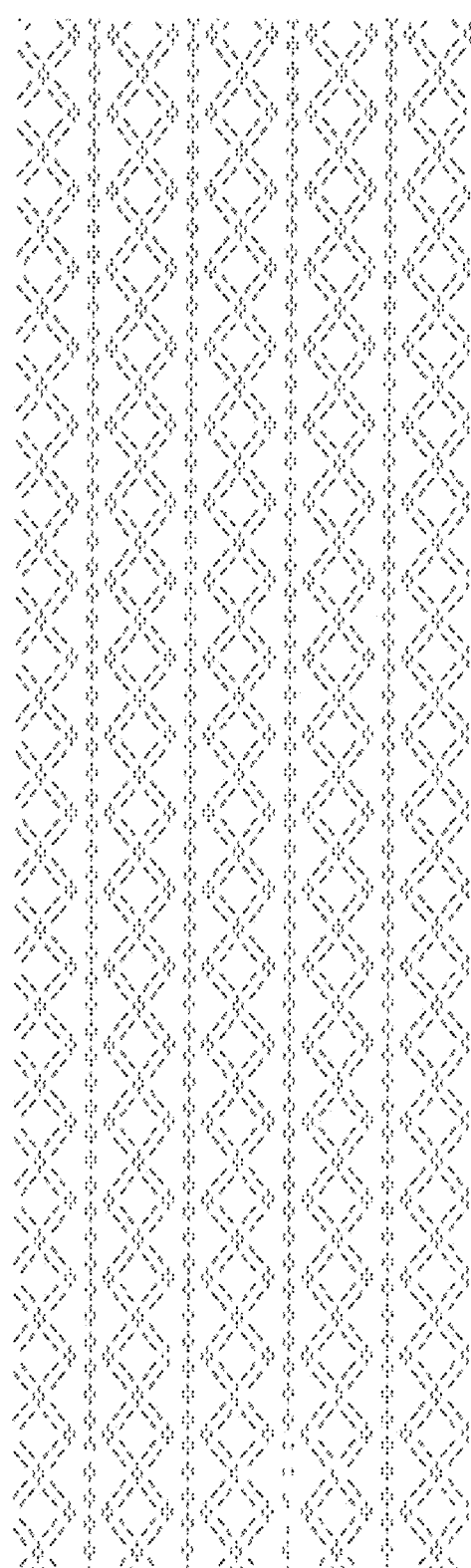
Figure 59:
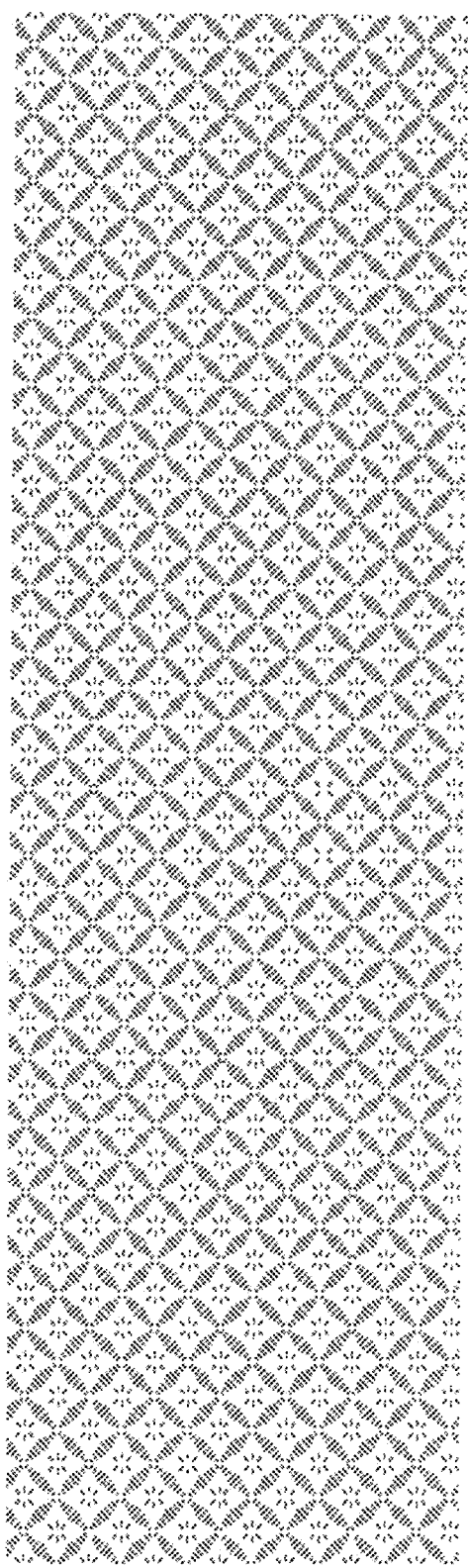
Figure 60:
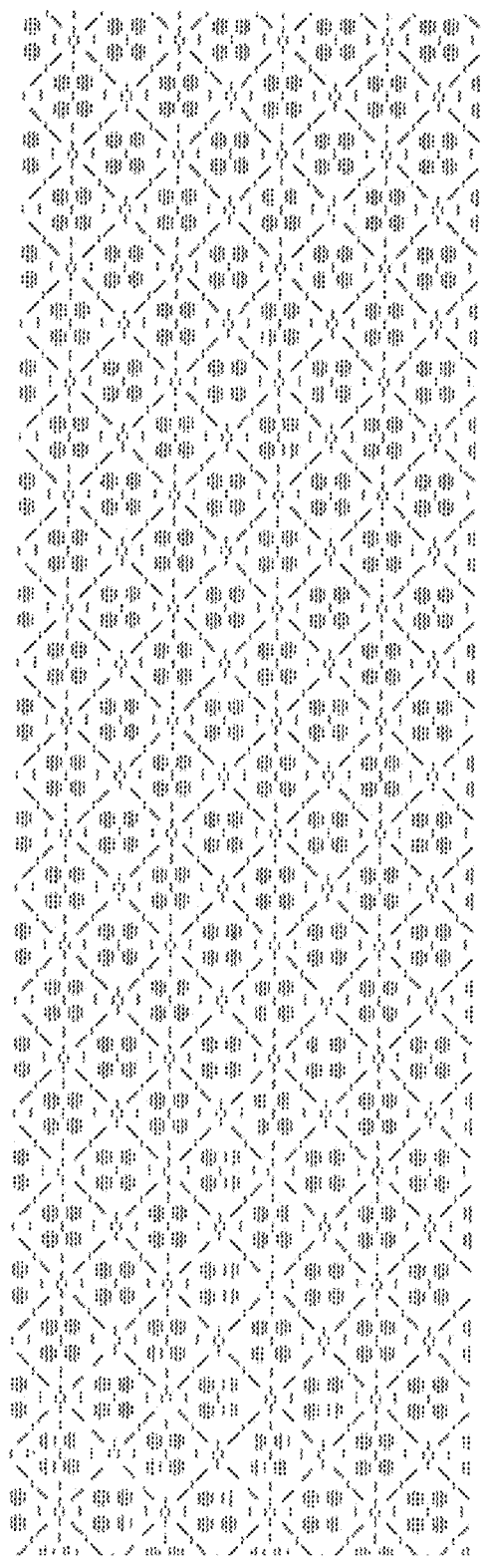

Referring to FIG. 54, areas surrounding at least a portion of an aperture 12 in a patterned apertured web of the present disclosure may comprise one or more fused portions 5000. The fused portions 5000 may at least partially surround the apertures 12, or fully surround the apertures 12. The fused portions 5000 may surround at least 25% of a perimeter of the apertures 12 up to about 100% of the perimeter of the apertures 12. In some instances, the fused portions 5000 may be formed on the lateral sides of the apertures 12 and not on the leading and trailing edges of the apertures 12 (see MD and CD arrows for reference in FIG. 54). The fused portions 5000 are believed to be formed during the overbonding step and are believed to add strength to the patterned apertured webs.

Example Overbond Patterns for Patterned Apertured Webs

Some example schematic representations of additional overbond patterns that could be used on an overbonding roller, like roller 110 of FIG. 16 are illustrated in FIGS. 55-60. Those of skill in the art will recognize that other suitable overbond patterns are also within the scope of the present disclosure, along with variations of the illustrated patterns.

Interaperture Distance and Average Interaperture Distance

The patterned apertured webs or layers thereof may have apertures that have an Average Interaperture Distance of less than about 3.5 mm, less than about 3 mm, less than about 2.5 mm, less than about 2 mm, less than about 1.5 mm, less than about 1 mm, in the range of about 1 mm to about 3.5 mm, in the range of about 1 mm to about 3 mm, in the range of about 1 mm to about 2.5 mm, or in the range of about 3.5 mm to about 10 mm, specifically reciting all 0.1 mm increments within the above-specified ranges and all ranges formed therein or thereby, according to the Aperture Test herein.

A patterned apertured web may have Interaperture Distances, calculated according to the Aperture Test herein. The Interaperture Distances may have a distribution having a mean and a median. The mean may be greater than, different than, or less than the median. The mean may be greater than, different than, or less than the median in the range of about 3% to about 25%, about 4% to about 25%, about 5% to about 20%, about 8% to about 20%, or about 4% to about 15%, for example, specifically reciting all 0.1% increments within the above-specified ranges and all ranges formed therein or thereby. A first zone of a patterned apertured web may have Interaperture Distances. The Interaperture Distances of the first zone may have a first distribution having a first mean and a first median. The first mean may be greater than, different than, or less than the first median by the ranges set forth above in this paragraph. A second zone of the patterned apertured web may have Interaperture Distances. The Interaperture Distances of the second zone may have a second distribution having a second mean and a second median. The second mean may be greater than, less than, or different than the second median by the ranges set forth above in this paragraph. A third zone of the patterned apertured web may have Interaperture Distances. The Interaperture Distances of the third zone may have a third distribution having a third mean and a third median. The third mean may be greater than, different than, or less than the third median by the ranges set forth above in this paragraph. The first, second, and third means may be the same or different. The first, second, and third medians may be the same or different. The first, second, and third zones may be in a topsheet, a topsheet layer, an acquisition layer, an outer cover, an outer cover layer, or any other component of an absorbent article or other consumer products.

In other instances, a first portion of an absorbent article or other consumer product may have a first patterned apertured web that has Interaperture Distances, according to the Aperture Test herein. The Interaperture Distances of the first portion have a first distribution. A second portion of an absorbent article or other consumer product may have a second patterned apertured web that has Interaperture Distances, according to the Aperture Test herein. The Interaperture Distances of the second portion have a second distribution. A third portion of an absorbent article or other consumer product may have a third patterned apertured web that has Interaperture Distances, according to the Aperture Test herein. The Interaperture Distances of the third portion have a third distribution. The first, second, and third distributions may be the same or different. The first distribution may have a first mean and a first median. The first mean may be greater than, less than, or different than the first median in the range of about 3% to about 25%, about 4% to about 25%, about 5% to about 20%, about 8% to about 20%, or about 4% to about 15%, for example, specifically reciting all 0.1% increments within the above-specified ranges and all ranges formed therein or thereby. The second distribution may have a second mean and a second median. The second mean may be greater than, different than, or less than the second median by the ranges set forth above in this paragraph. The third distribution may have a second mean and a second median. The second mean may be greater than, different than, or less than the second median by the ranges set forth above in this paragraph. The first, second, and third means may be the same or different. The first, second, and third medians may be the same or different. The Relative Standard Deviation of the Interaperture Distances of a patterned apertured web may be at least about 50%, or at least about 55%. The Maximum Interaperture Distance in a given patterned apertured web may be at least about 8 mm, or at least about 10 mm, for example.

Average Absolute Feret Angle and Absolute Feret Angle

A patterned apertured web may have one or more apertures having an Absolute Feret Angle, according to the Aperture Test herein, of at least about 15 degrees, at least about 18 degrees, at least about 20 degrees, at least about 22 degrees, at least about 25 degrees, at least about 30 degrees, at least about 35 degrees, at least about 40 degrees, in the range of about 15 degrees to about 80 degrees, in the range of about 20 degrees to about 75 degrees, in the range of about 20 degrees to about 70 degrees, or in the range of about 25 degrees to about 65 degrees, specifically reciting all 0.1 degrees increments within the above-specified ranges and all ranges formed therein or thereby.

A patterned apertured web may have a plurality of apertures having an Average Absolute Feret Angle, according to the Aperture Test, of at least about 15 degrees, at least about 18 degrees, at least about 20 degrees, at least about 22 degrees, at least about 25 degrees, at least about 30 degrees, at least about 35 degrees, at least about 40 degrees, in the range of about 15 degrees to about 80 degrees, in the range of about 20 degrees to about 75 degrees, in the range of about 20 degrees to about 70 degrees, or in the range of about 25 degrees to about 65 degrees, specifically reciting all 0.1 degrees increments within the above-specified ranges and all ranges formed therein or thereby. These apertures may all be within a single repeat unit of the patterned apertured web. The Relative Standard Deviation of the Absolute Feret Angles in a patterned apertured web may be at least about 30%, or at least about 40%, or at least about 50%. A repeat unit is an area in a patterned apertured web that can be identified as having a full aperture pattern or array. Multiple repeat units may be present in a patterned apertured web, with one full aperture pattern or array being present in each repeat unit.

At least two, at least 3, at least 4, at least 5, at least 6, at least 7, at least 8, at least 9, or at least of the apertures in a patterned apertured web, or a repeat unit of a patterned apertured web, may each have a different Absolute Feret Angle, according to the Aperture Test herein. In other instances, some of the apertures may have Absolute Feret Angles that are the same, while other of the apertures may have Absolute Feret Angles that are different. In addition to having different Absolute Feret Angles, the at least two, at least 3, at least 4, at least 5, at least 6, at least 7, at least 8, at least 9, or at least 10 apertures may have different sizes and/or shapes. At least some of the at least two, at least 3, at least 4, at least 5, at least 6, at least 7, at least 8, at least 9, or at least 10 apertures may also have the same size and/or shape, while having different Absolute Feret Angles. The Absolute Feret Angles of at least some of the apertures within a repeat unit may differ by at least about 5 degrees, at least about degrees, at least about 15, degrees, at least about 20 degrees, at least about 25 degrees, or at least about 30 degrees, for example.

Pre-Strained Laminates

One or more layers of a laminate may comprise one or more pre-strained layers. The pre-strained layers may be apertured or non-apertured. Other layers of the laminate may be apertured or non-apertured. The apertured layer(s) may have uniformly sized and spaced apertures or may have nonhomogeneous patterned apertures, such as the various patterned aperture patterns described herein. The patterned apertures may have any of the features or parameters described herein. The layers may comprise nonwovens, films, cellulosic webs, foams, or other materials. In some instances, non-apertured layers may comprise a plurality of overbonds arranged in a pattern. The pre-strained layer or layers may be joined to the non-pre-strained layer or layers to form a three-dimensional laminate upon the release of the pre-strain. The pre-strained layers may be pre-strained in an amount of about 5% of their length or width to about 40% of their length or width or about 5% of their length or width to about 20% of their length or width, specifically reciting all 0.1% increments within the specified ranges and all ranges formed therein or thereby. In other instances, the pre-strained layers may be pre-strained in an amount of about 5%, about 10%, about 15%, or about 20%, for example. The pre-strained layer should at least partially recover after being joined to a non-pre-strained layer to create three-dimensional features in the non-pre-strained layer.

Figure 61:
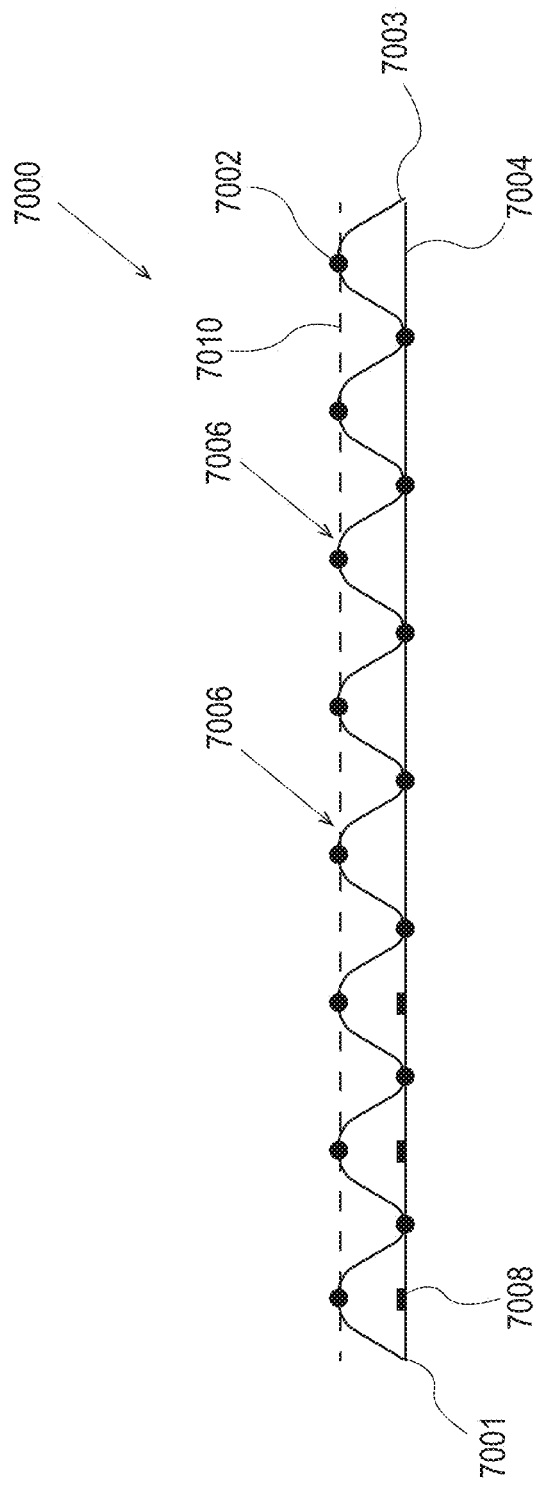
FIG. 61 is a schematic illustration of a patterned apertured web with one of the layers being pre-strained prior to being joined to at least one of the other layers in accordance with the present disclosure.

In an instance, referring to FIG. 61, an example schematic cross-sectional view of a laminate 7000 may comprise a first layer 7002 and a second layer 7004. The second layer 7004 was pre-strained prior to being joined to the first layer 7002, thereby resulting in the three-dimensional features 7006 in the first layer 7002 upon relaxation of the laminate. Either or both of the first layer 7002 and the second layer 7004 may comprise uniform and homogeneous apertures, nonhomogeneous patterns of apertures, overbonds (either homogeneous or non-homogeneous), or embossments. The first layer 7002 and/or the second layer 7004 (or any additional layer) may also comprise indicia 7008. The indicia 7008 may comprise a patterned adhesive, a patterned pigmented adhesive, a printed ink, or a printed pigmented ink, for example. The indicia 7008 may be at least partially visible through apertures or patterned apertures in one layer of the laminate 7000 or through a non-apertured layer of the laminate 7000. The indicia 7008 may be a different color than the first layer 7002 and/or the second layer 7004. For example, the indicia may be teal and the first and second layers may be white. The first and second layers 7002 and 7004 may also have different or the same colors or opacities. Although the example laminate 7000 is described in a two layer form, it will be understood that laminates having any suitable number of layers are within the scope of the present disclosure. In such instances, any suitable number of the layers may comprise indicia, apertures, patterned apertures, embossments, overbonds, and/or may be pre-strained. As an example, a third layer 7010, illustrated in dash, may be joined to the first layer 7002. The third layer 7010 may also be joined to the second layer 7004, for example. The third layer 7010 may be apertured or non-apertured.

Figure 62:
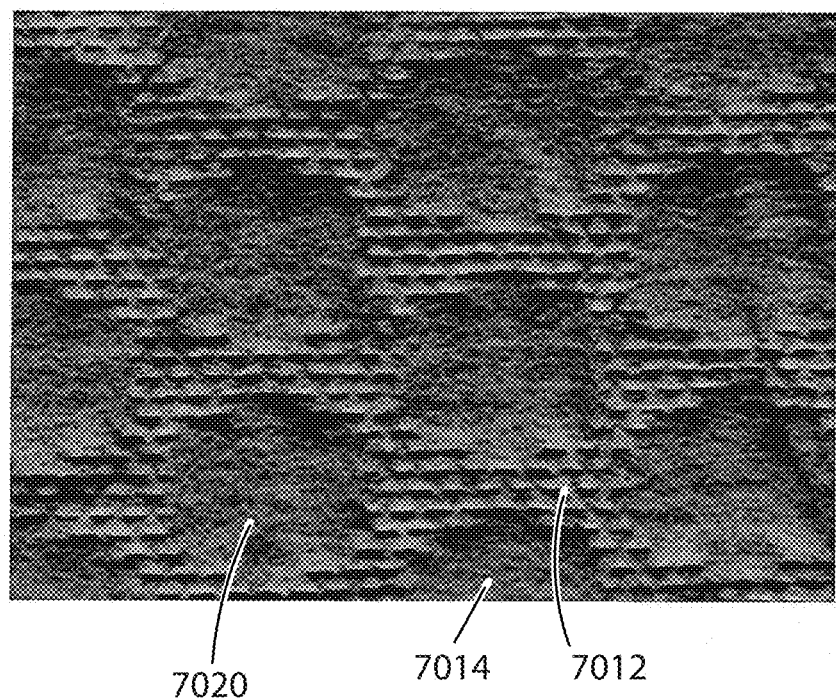
FIG. 62 is a photograph of a portion of a patterned apertured web with at least one of the layers being pre-strained prior to being joined to at least one of the other layers in accordance with the present disclosure.
Figure 63:
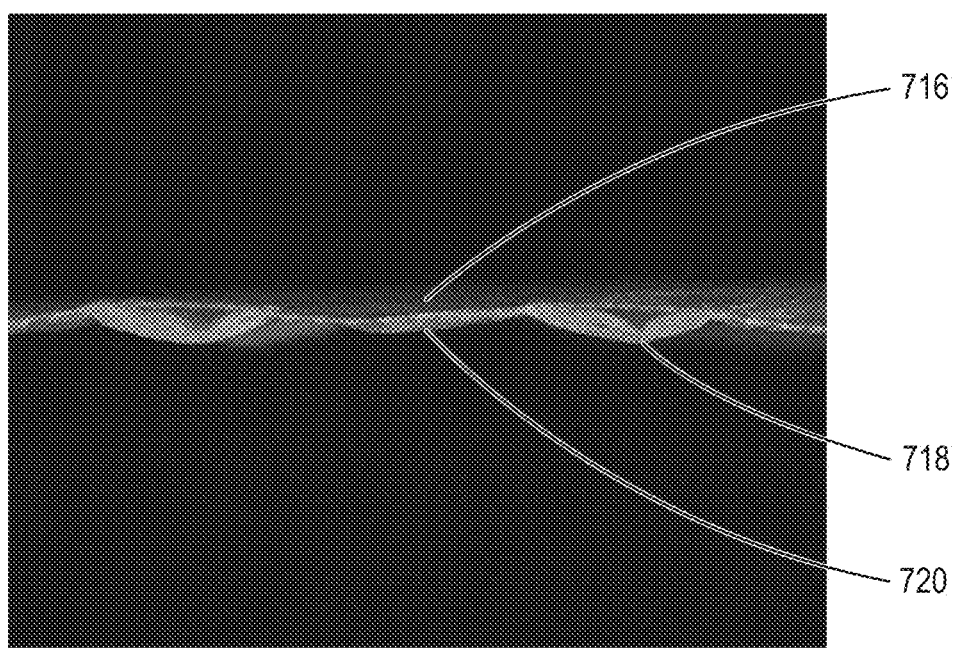
FIG. 63 is a cross-sectional view of a patterned apertured web with at least one of the layers being pre-strained prior to being joined to at least one of the other layers in accordance with the present disclosure.
Figure 64:
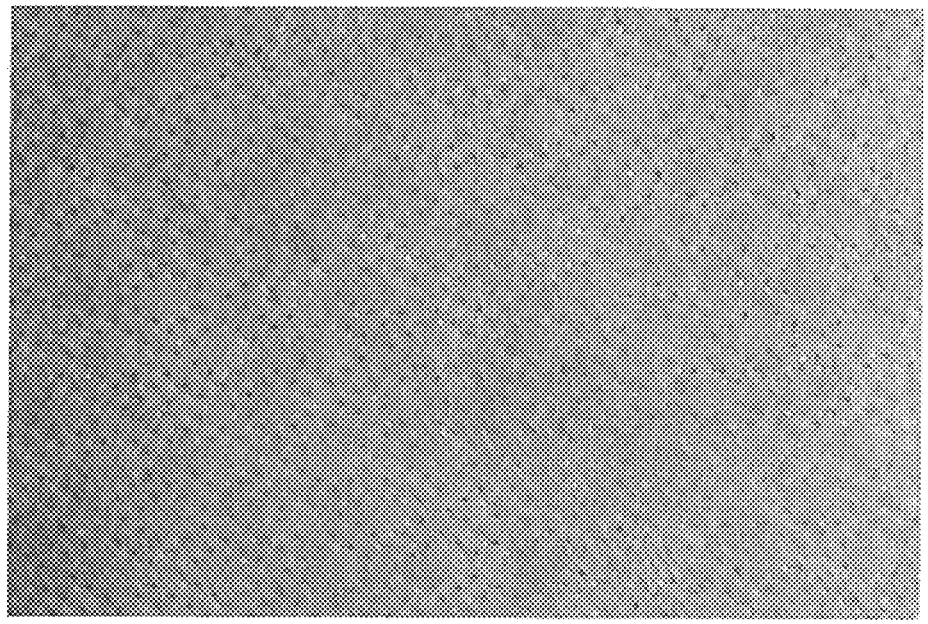
FIG. 64 is a photograph of an overbonded web free of any pre-strained layers in accordance with the present disclosure.
Figure 65:
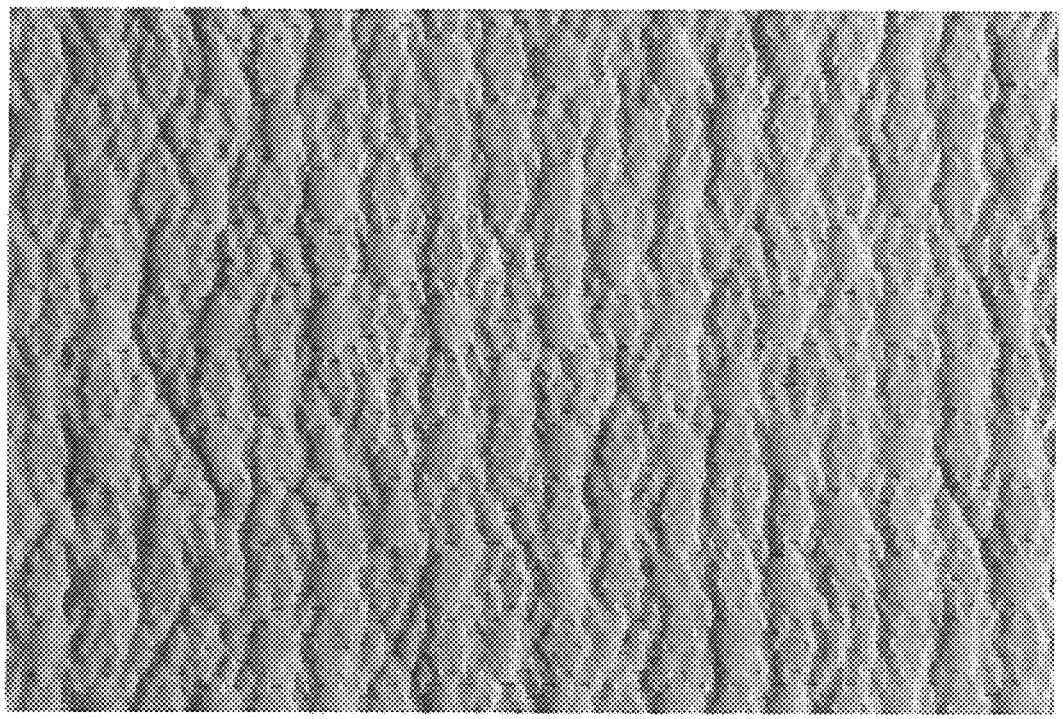
FIG. 65 is a photograph of the overbonded web of FIG. 64 with a pre-strained layer in accordance with the present disclosure.
Figure 66:
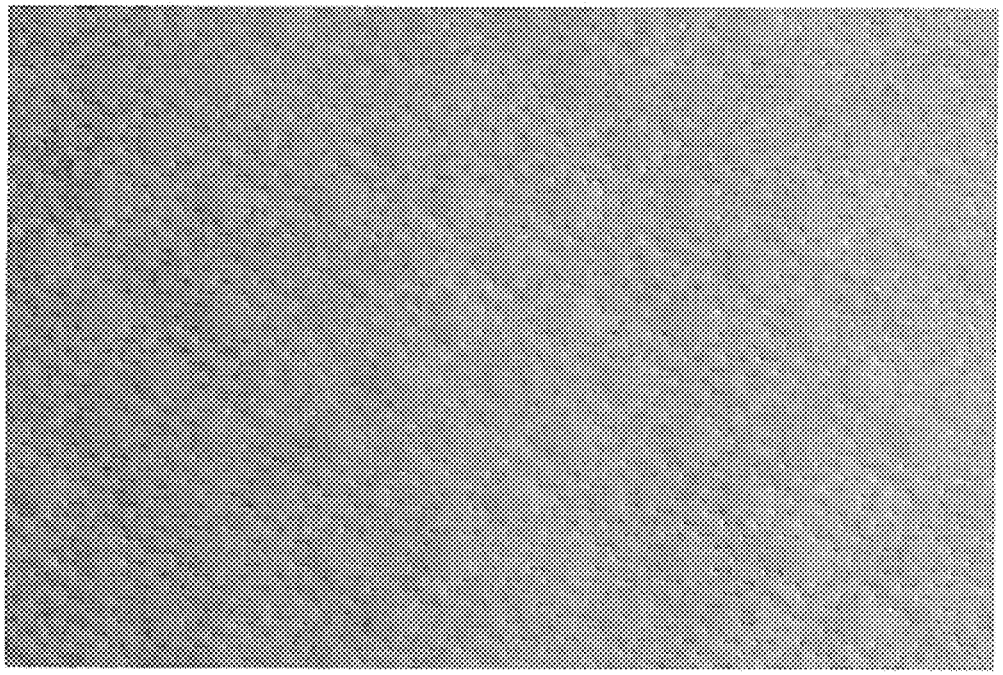
FIG. 66 is a photograph of an overbonded web free of any pre-strained layers in accordance with the present disclosure.
Figure 67:
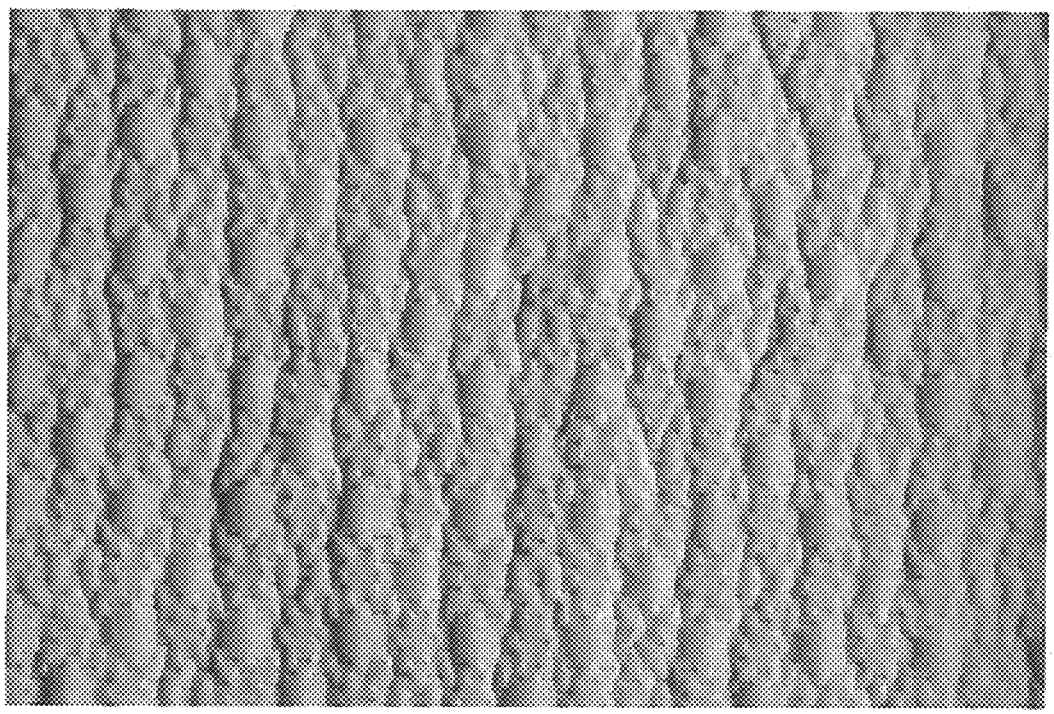
FIG. 67 is a photograph of the overbonded web of FIG. 66 with a pre-strained layer in accordance with the present disclosure.
Figure 68:
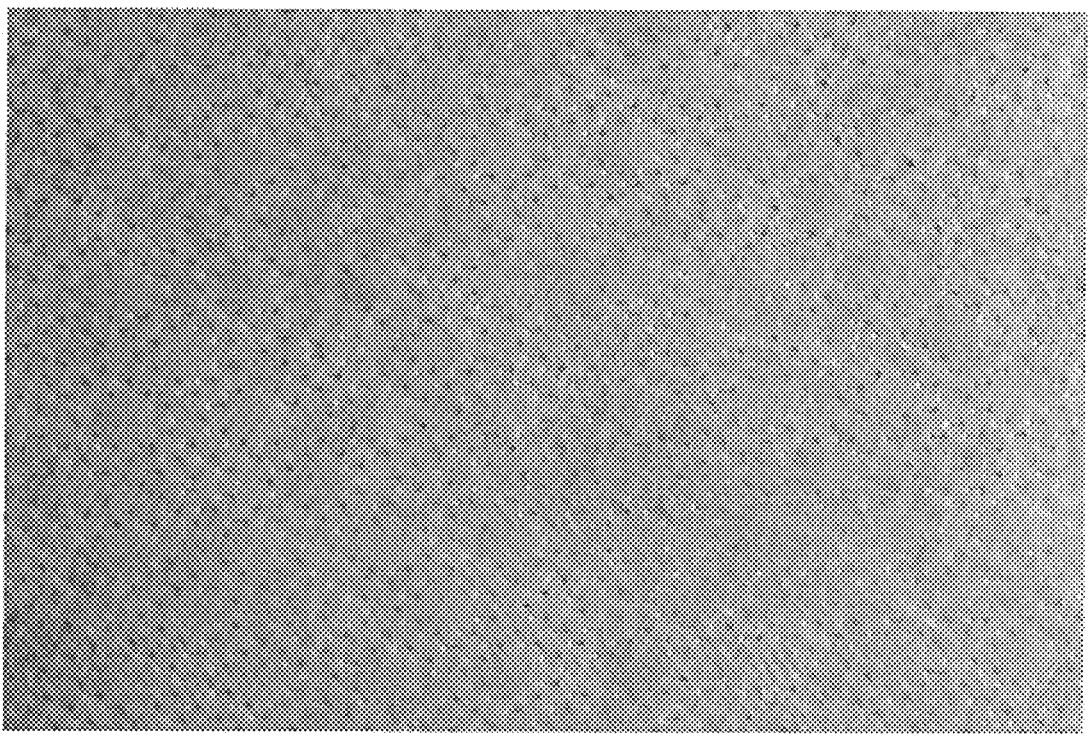
FIG. 68 is a photograph of a patterned apertured web free of any pre-strained layers in accordance with the present disclosure.
Figure 69:
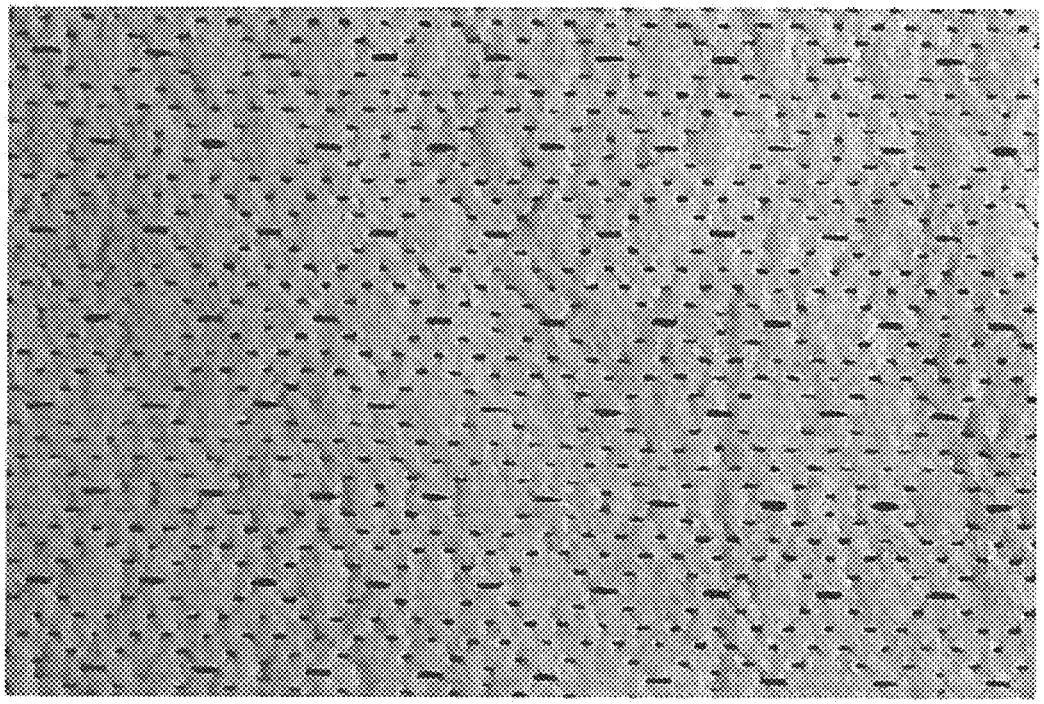
FIG. 69 is a photograph of the patterned apertured web of FIG. 68 with a pre-strained layer in accordance with the present disclosure.
Figure 70:
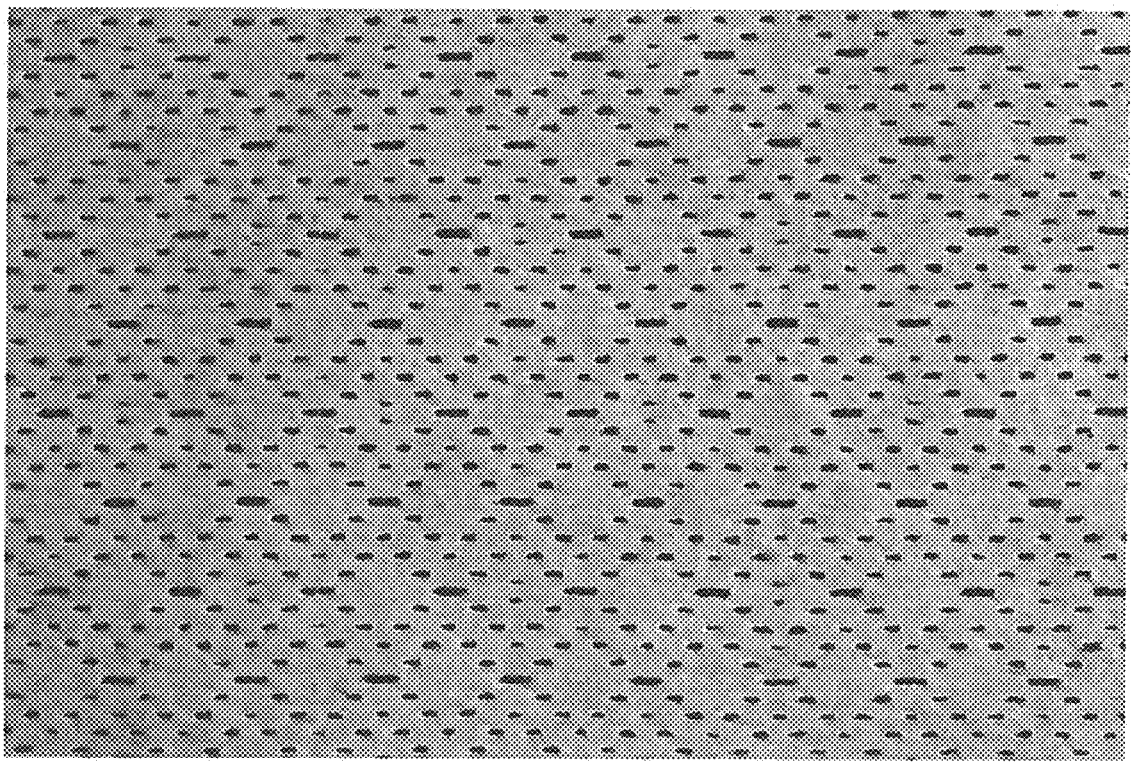
FIG. 70 is a photograph of a patterned apertured web free of any pre-strained layers in accordance with the present disclosure.
Figure 71:
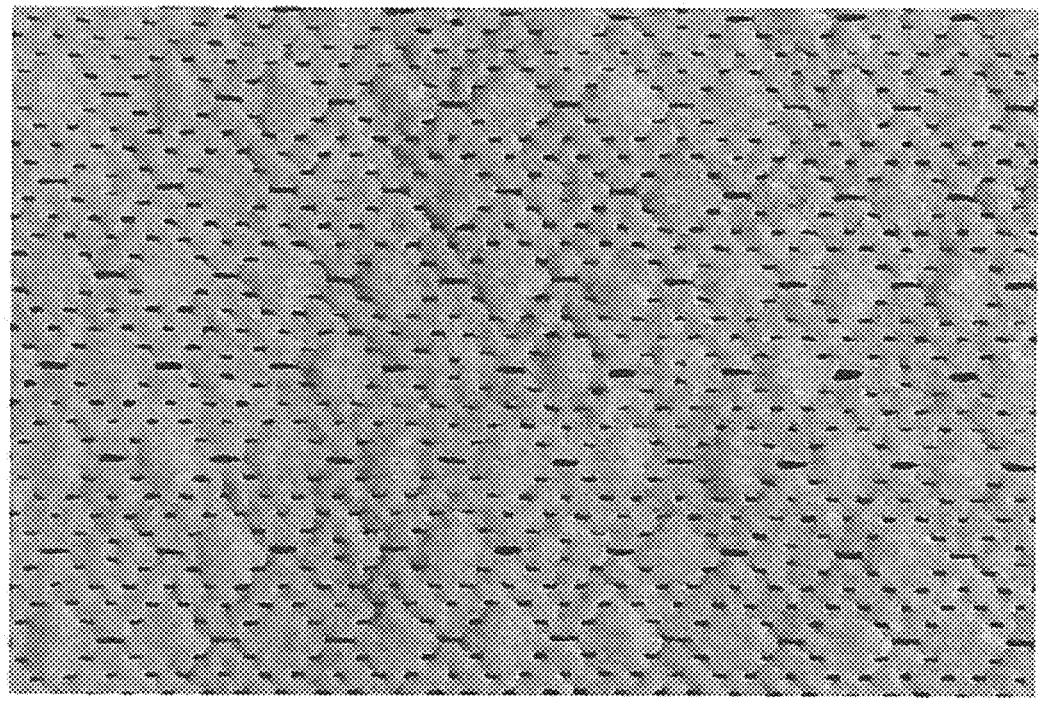
FIG. 71 is a photograph of the patterned apertured web of FIG. 70 with a pre-strained layer in accordance with the present disclosure.

An example of a top view of a pre-strained laminate is illustrated in FIG. 62. A cross-sectional view of the pre-strained laminate of FIG. 62 is illustrated in FIG. 63. The laminate has apertured areas 7012 and non-apertured areas 7014. The laminate has one pre-strained layer 7016 and one non-pre-strained layer 7018. Upon release of the pre-strain force of the pre-strained layer 7016, three dimensional features 7020 are formed in the non-pre-strained layer 7018.

Again referring to FIG. 61 the first layer 7002 having the three-dimensional features 7006 may have a greater path length than the second layer 7004 that was pre-strained. The path length is the distance traveled between a first edge 7001 of the material and a second edge 7003 of the material (following the material from the left to the right in FIG. 61). If the third layer 7010 is attached to the first layer 7002 or to the second layer 7004, the third layer may have a different path length or the same path length as the first layer 7002 or the second layer 7004.

In an instance, both the first and second layers 7002 and 7004 may each have a plurality of apertures or patterned apertures. At least some of the apertures in the first layer 7002 may at least partially, or fully, align with at least some of the apertures in the second layer 7004. In other instances, all of, or most of, the apertures may align or at least partially align. In such configurations, portions of, or all of, perimeters of at least some apertures in the first layer 7002 may be bonded (e.g., mechanically or adhesively) to portions of, or all of, perimeters of at least some apertures in the second layer 7004. In other configurations, the first and second layers 7002 and 7004 may be joined by a plurality of and/or a pattern of mechanical or adhesive bonds.

The first layer 7002 may be formed of a different material than the second layer 7004 and/or the third layer 7010. In an example, the first layer 7002 may be formed of a first nonwoven material and the second and/or third layers 7004, 7010 may be formed of a different nonwoven material or other material, such as a film, for example.

The patterned apertures in any of the layers may have the Absolute Feret Angles, the Average Absolute Feret Angles, the Interaperture Distances, Effective Aperture Areas, and/or the Average Interaperture Distances described herein. Further, any of the layers may have the Effective Open Areas specified herein, such as in the range of about 5% to about 50%.

Absorbent articles may comprise one or more of these pre-strained laminates. Example absorbent articles, as described above, may comprise a liquid permeable topsheet, a liquid impermeable backsheet, and outer cover nonwoven material, and an absorbent core, among other features. The pre-strained laminates may be used as topsheets, outer covers, outer cover nonwoven material/backsheet laminates, portions of garment-facing surfaces of the absorbent articles, portions of wearer-facing surfaces of the absorbent articles, portions of belts, hip areas, waist areas, and/or portions of barrier leg cuffs, for example. These pre-strained laminates may also be used in cleaning substrates, dusting substrates, wipes, medical substrates, and/or any other suitable products or consumer products, for example.

Some examples of pre-strained laminates are illustrated below.

The materials used in Charts 1 and 2 are specified below.

Material A: 25 gsm spunbond nonwoven material comprising 50/50 PE/PP sheath/core bicomponent fibers having an average fiber size of 2.8 denier per filament, available from Fitesa Nonwovens in Washougal, WA.

Material B: 24 gsm carded, through-air bonded nonwoven material comprising 2.0 dpf PE/PET fibers, available from Xiamen Yanjan Industries, Inc.

In all instances in Charts 1 and 2 below, Layer 2 was pre-strained in the machine direction by the % shown and then the two layers were overbonded together, using the overbonding process described herein with respect to FIG. 16. The pre-strain force was applied by decreasing the speed of an infeed roll by 0% (i.e., no pre-strain), 5%, 10%, or 15% (according to the Charts) relative to the speed of the rolls 112 and 114 of FIG. 16. The pre-strain in Layer 2 was then released. Examples without the overbonds ruptured are Examples 1-8 and FIGS. 64-67. Examples with the overbonds ruptures are Examples 9-16 and FIGS. 68-71. In the latter, the overbonds were ruptured to form apertures in both layers using the steps and equipment 132 and 132' described herein with respect to FIG. 15 (with additional details described in view of FIGS. 23-29). For Examples 9-16, the depth of engagement (see e.g., FIG. 24) was 0.065 inches and the line speed was 1,000 feet per minute.

As the amount of pre-strain on Layer 2 increases, the caliper of the resultant pre-strained laminate may also increase, by an amount than is greater than the increase in basis weight would predict. The example substrates of FIGS. 65, 67, 69, and 71 with a pre-strained layer show significant puckering or three-dimensionality as compared to the non-pre-strained examples of FIGS. 64, 66, 68, and 70.

CHART 1

Overbond Only, No Apertures

| Example # | Layer 1 | Layer 2 (pre-strain) | % Pre-Strain | Caliper (mm) | Total Basis Weight (BW) (gsm) | Normalized Caliper (Caliper/BW) |
|---|---|---|---|---|---|---|
| 1 (FIG. 64) | A | A | 0 | 0.45 | 51.8 | 0.009 |
| 2 | A | A | 5 | 0.66 | 56.0 | 0.012 |
| 3 (FIG. 65) | A | A | 10 | 1.01 | 61.6 | 0.016 |
| 4 | A | A | 15 | 1.38 | 69.0 | 0.020 |
| 5 (FIG. 66) | B | A | 0 | 0.57 | 49.3 | 0.012 |
| 6 | B | A | 5 | 0.89 | 52.7 | 0.017 |
| 7 (FIG. 67) | B | A | 10 | 1.31 | 62.6 | 0.021 |
| 8 | B | A | 15 | 1.53 | 68.5 | 0.022 |

CHART 2

Overbond and Apertures

| Example # | Layer 1 | Layer 2 (pre-strain) | % Pre-Strain | Caliper (mm) |
|---|---|---|---|---|
| 9 (FIG. 68) | A | A | 0 | 0.66 |
| 10 | A | A | 5 | 0.69 |
| 11 (FIG. 69) | A | A | 10 | 0.70 |
| 12 | A | A | 15 | 0.76 |
| 13 (FIG. 70) | B | A | 0 | 0.81 |
| 14 | B | A | 5 | 0.92 |
| 15 (FIG. 71) | B | A | 10 | 0.95 |
| 16 | B | A | 15 | 1.01 |

Various method of producing pre-strained laminates will now be discussed. For example, two non-apertured layers may be provided. One layer may be pre-strained in the CD or MD direction. The layers may then be overbonded (see e.g., FIG. 16 for overbonding and associated disclosure) to join them together, or joined together and then overbonded. The pre-strain force may then be released to create a plurality of three-dimensional features in the non-pre-strained layer or in both layers. Optionally, at least some of, most of, or all of the overbonds may then be ruptured to create apertures in the first and second layers. Such rupturing may be done by stretching the first and second layers in the CD or MD direction (see e.g., FIGS. 23-29 for example overbond rupturing). In some instances, the pre-strain force may not be released until the apertures are ruptured. At least a third layer may also be combined into the laminate. The at least third layer may be apertured or non-apertured, pre-strained, or non-pre-strained. At least one of the layers may be formed of a different material than the remaining layers (e.g., film/nonwoven, first nonwoven/second nonwoven, or first film/second film).

In an instance, one apertured layer may be combined with one non-apertured layer, or two apertured layers may be combined, using mechanical or adhesive bonding. The apertures may be formed in the layer or layers using any suitable aperturing technique, such as needle punching, for example. Either of the layers may be pre-strained prior to joining the layers. Upon release of the pre-strain force, three-dimensional features may be formed in the layer that was not pre-strained, or in both layers. At least a third layer may also be combined into the laminate. The at least third layer may be apertured or non-apertured, pre-strained or non-pre-strained. At least one of the layers may be formed of a different material than the remaining layers (e.g., film/nonwoven, first nonwoven/second nonwoven, or first film/second film).

In an instance, one overbonded layer may be combined with one non-apertured or apertured layer, or two overbonded layers may be combined, using mechanical or adhesive bonding. Either of the layers may be pre-strained prior to joining the layers. Upon release of the pre-strain force, three-dimensional features may be formed in the layer that was not pre-strained, or in both layers. At least a third layer may also be combined into a laminate. The at least third layer may be overbonded or non-overbonded, apertured or non-apertured, pre-strained or non-pre-strained. At least one of the layers may be formed of a different material than the remaining layers (e.g., film/nonwoven, first nonwoven/second nonwoven, or first film/second film).

In an instance, a method of forming a three-dimensional laminate for an absorbent article is provided. The method may comprise providing a first layer and a second layer (and optionally additional layers). The first and second layers may be the same or different. For example, the layers may comprise the same nonwoven materials, the same film materials, two different nonwoven materials, two different film materials, or a film material and a nonwoven material. In some instances, any of these layers may be apertured or non-apertured, overbonded or non-overbonded. The apertures patterns or overbonds patterns may be homogeneous or non-homogeneous. The method may comprise applying a pre-strain force to the first or second layers. The pre-strain force may be applied in any suitable direction, such as substantially in the machine direction or substantially in the cross-machine direction, for example. The layers may then be joined by adhesive or mechanical bonding, or other suitable methods of joining layers. If at least one of the first or second layers is not apertured or overbonded, the joining step may comprise an overbonding step (see e.g., FIG. 16 for overbonding as associated disclosure) or embossing. The first and second layers may be joined to each other while the first or second layer remains in a pre-strained state or condition. Suitable adhesives, patterned adhesive, pigmented patterned adhesives, pigmented printed inks, or printed inks may be applied to the first or second layers pre-joining or post-joining, if desired. If an overbonding step is used, the layers, post-joining, may be stretched in a suitable direction, such as substantially in the cross-machine direction or substantially in the machine direction to at least partially rupture, or fully rupture at least some of, most of, or all of the overbonds to thereby at least partially form, or form apertures in the layers (see e.g., FIGS. 23-29 for such rupturing). The pre-strain force may then be released to form a plurality of three-dimensional features in the laminate. The plurality of three-dimensional features may be formed in the non-pre-strained layer or in both of the layers (including the pre-strained layer).

Any of the laminates with at least one layer pre-strained may be free of elastic strands or elastic films.

The methods may comprise applying a pre-strain force to one of the layers (pre-layer joining) in a substantially machine direction, a machine direction, or other direction. The pre-strain force causes the layer being pre-strained to elongate in the direction the pre-strain force is being applied by at least 5%, at least 10%, at least 15%, at least 20%, in the range of about 5% to about 40%, or in the range of about 5% to about 20%, specifically reciting all 0.1% increments within the specified ranges and all ranges formed therein or thereby. The pre-strain force may be applied by suppling a continuous web of pre-strained laminate where an infeed roll is rotating at a slower speed than overbonding rolls or an output roll.

If a layer, or more than one layer, of the pre-strained laminate has a plurality of overbonds, the overbonds may comprise a first overbond, a second overbond, and at least a third overbond. The first, second, and at least third overbonds may all be different in size, shape, feret angle, and/or orientation. Alternatively, at least two of the first, second, and third overbonds may be different in size, shape, feret angle, and/or orientation.

One or more layers of a laminate (pre-strained layer or no pre-strained layer) may have a first overbond having a central longitudinal axis extending in a first direction, a second overbond having a central longitudinal axis extending in a second direction, and a third overbond having a central longitudinal axis extending in a third direction. At least two of, or all of the first, second, and third directions may be different. At least two of, or all of, the first, second, and third directions may be at least about 5 degrees, at least about 10 degrees, at least about 15 degrees, at least about 20 degrees, apart from each other. In other instances, at least two of, or all of, the first, second, and third directions may be different from each other in the range of about 5 degrees to about 40 degrees, about 5 degrees to about 30 degrees, or about 10 degrees to about 25 degrees, specifically reciting all 0.1 degree increments within the specified ranges and all ranges formed therein or thereby. More than three overbonds having central longitudinal axes may also be provided. The central longitudinal axes of the more than three overbonds may also extend in different directions than the first, second, and third central longitudinal axes, as described in this paragraph.

Another method of forming a three-dimensional laminate for an absorbent article is provided. The method may comprise providing a first layer and providing a separate, second layer. The layers may be the same or different in material, basis weight, and/or properties, for example. The method may comprise applying a pre-strain force to the first layer or to the second layer and overbonding the first layer and the second layer while the first layer or the second layer is in a pre-strained condition to join the first layer and the second layer. The method may further comprise releasing the pre-strain force to form the three-dimensional laminate and three-dimensional features in the non-pre-strained layer. Before or after the pre-strain force is released, the method may comprise stretching the first and second layers to cause at least some of, most of, or all of the overbonds to at least partially rupture and at least partially form, or form, apertures in the first and second layers. This stretching may be substantially (e.g., +/−1 degree, +/−3 degrees, or +/−5 degrees) in the cross-machine direction, while the pre-strain force may be substantially in the machine direction (e.g., +/−1 degree, +/−3 degrees, or +/−5 degrees). In other instances, the stretching may be substantially in the machine direction, while the pre-strain force may be substantially in the cross-machine direction.

Another method of forming a three-dimensional laminate for an absorbent article is provided. The method may comprise providing a nonwoven first layer and providing a separate, nonwoven second layer. The method may comprise applying a pre-strain force substantially in the machine direction to the first nonwoven layer or to the second nonwoven layer and overbonding the first layer and the second layer while the first layer or the second layer is in a pre-strained condition to join the first layer and the second layer. The method may comprise stretching the first and second nonwoven layers in a substantially cross-machine direction to cause at least some of, most of, or all of the overbonds to at least partially rupture and at least partially form, or form apertures in the first and second nonwoven layers. The method may comprise releasing the pre-strain force to form the three-dimensional laminate and form three-dimensional features in the non-pre-strained layer. The three-dimensional laminate may be free of elastic strands or elastic films.

Garment-Facing Layer/Garment-Facing Laminate

Absorbent article of the present disclosure may comprise a garment-facing layer or garment facing laminates comprising at least one apertured or patterned apertured layer. The absorbent articles may comprise a liquid permeable topsheet on a wearer-facing side of the absorbent article and a garment-facing laminate or a garment-facing layer on a garment-facing side of the absorbent article. The garment-facing laminate may comprise a first layer or a first nonwoven layer and a second layer joined to the nonwoven layer. The first layer or the first nonwoven layer may comprise a plurality of apertures. In some instances, at least 3, at least 5, or at least 10 of the apertures in a repeat unit have one or more of a different size, a different shape, or a different Absolute Feret Angle, according to the Aperture Test herein. At least 3, at least 5, or at least 10 of the plurality of apertures in the first nonwoven layer may be non-homogeneous apertures within the repeat unit. The garment-facing layer may only comprise a single layer having the features of the first layer or first nonwoven layer of the garment-facing laminate. The absorbent article may comprise an absorbent core that is disposed at least partially intermediate the liquid permeable topsheet and the garment-facing laminate or the garment-facing layer. Either of the first or second layers of the garment-facing laminate may be pre-strained as described herein to create three-dimensional features in the non-pre-strained layer or in both layers. The first or second layer that is pre-strained may be free of apertures.

The second layer of the garment-facing laminate may be a second nonwoven layer. The second nonwoven layer may be positioned on the outermost surface of the garment-facing surface or intermediate the first nonwoven layer and a liquid impermeable backsheet. If the second nonwoven layer is positioned on the outermost surface, the first nonwoven layer comprising the apertures or patterned apertures may be visible through the second nonwoven layer. In an instance, the second nonwoven layer may comprise apertures or patterned apertures, as the patterned apertured are described herein. The second nonwoven layer may also be non-apertured. In other instances, the second layer of the garment-facing laminate may comprise a liquid impermeable backsheet film. A patterned adhesive, a pigmented patterned adhesive, a printed ink, or a pigmented printed ink (together "indicia") may be on the backsheet film such that this indicia is visible through the first and/or second layers and/or through the apertures or the patterned apertures in one of the layers. This indicia may also be on the first nonwoven layer or the second nonwoven layer in other instances. In an instance, a first portion of the indicia may be on the first nonwoven layer and a second portion of the indicia may be on the second layer.

The first nonwoven layer may be joined to the second layer or the second nonwoven layer by a patterned of mechanical or adhesive bonds. In other instances, the first nonwoven layer may be joined to the second layer or the second nonwoven layer by a patterned adhesive or a pigmented patterned adhesive. The patterned adhesive or pigmented patterned adhesive may have a first color that is different than the color of the first nonwoven layer or the second layer or the nonwoven layer. For example, the adhesive may be teal, while the first and second layers are white. The first and second layers may also have colors that are different.

Figure 72:
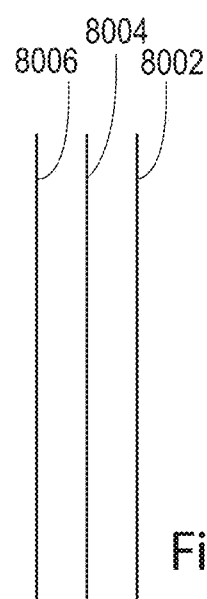
FIGS. 72-75 are schematic representations of layers of various webs in accordance with the present disclosure.

FIGS. 72-75 illustrate example layering of garment-facing laminates. In the example of FIG. 72, a first layer 8002 may be a liquid impermeable backsheet, a second layer 8004 may be a material, such as a nonwoven material, that is apertured or non-apertured, and a third layer 8006 may be a material, such as a nonwoven material, that is apertured or non-apertured. If any of the layers are non-apertured, they may comprise embossments or overbonds. One or more of layers 8002, 8004, and 8006 may be pre-strained prior to being joined to the other layers. In some instances, the first layer 8002 may also be a nonwoven material. Any or all of the layers may be apertured or have patterned apertures. In some instances, especially in cases where the first layer 8002 is a liquid impervious backsheet film, the second layer 8004 and/or the third layer 8006 may be apertured or have patterned apertures. In other instances, only one of the second layer 8004 and the third layers 8006 may have apertures or patterned apertures, with the other layer being non-apertured. In an instance, it may be desirable to have only the second layer 8004 have apertures or patterned apertures with the third layer 8006 being non-apertured to provide an absorbent article with a smooth garment-facing surface. Layer 8006 may form a portion of a garment-facing surface of an absorbent article.

Figure 73:
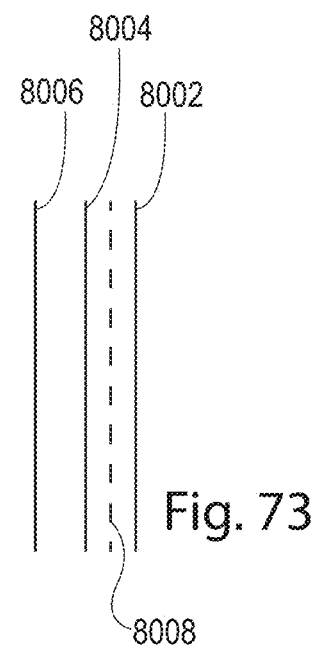
Figure 74:
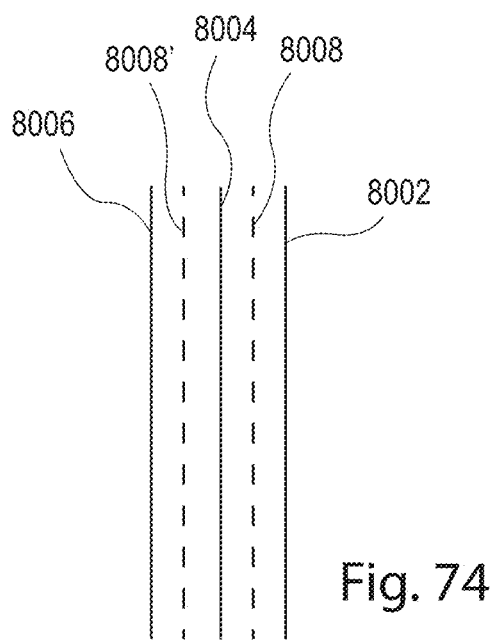

FIG. 73 illustrates the garment-facing laminate of FIG. 72, but with an indicia 8008 positioned on one of the layers; in the example, the first layer 8002 or the second layer 8004. The indicia 8008 may also be positioned intermediate the first and second layers 8002 and 8004. The indicia 8008 may be a patterned adhesive, a pigmented patterned adhesive, a printed ink, and/or a pigmented printed ink, for example. As shown in the example of FIG. 74, a first indicia 8008 may be positioned on the first and second layers 8002 and 8004, or may be positioned intermediate the first and second layers 8002 and 8004. A second indicia 8008' may be positioned on the second and third layers 8004 and 8006, or may be positioned intermediate the second and third layers 8004 and 8006. The second indicia 8008' may be a patterned adhesive, a pigmented patterned adhesive, a printed ink, and/or a pigmented printed ink. In some instances, only the second indicia may be provided. The first indicia 8008 may be the same as or different than the second indicia 8008'. In FIGS. 73 and 74, the first, second, and third layers 8002, 8004, and 8006 may be the same as described with respect to FIG. 72. If two or more nonwoven materials are provided as two or more of the layers, the nonwoven materials may be the same or different (i.e., different in basis weight, material, methods of manufacture, properties, effective open area). The third layer 8006 may form a portion of a garment-facing surface of an absorbent article.

Figure 75:
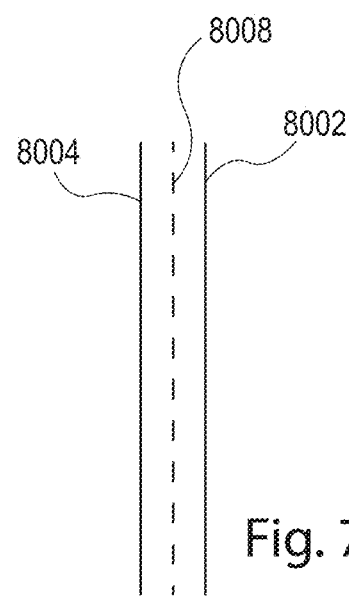

FIG. 75 illustrates a two layer garment-facing laminate. The first layer 8002 and the second layer 8004 may be the same or different. At least one of the layers may be a nonwoven material. In some instances, the first layer 8002 may comprise a liquid impermeable backsheet, while the second layer 8004 may comprise a garment-facing surface of an absorbent article. In such an instance, the first layer 8002 may be non-apertured, while the second layer 8004 may be apertured, have patterned apertures, or comprise a plurality of overbonds or embossments. Either of the first and second layers 8002 and 8004 may be pre-strained prior to being joined together to create a three-dimensional laminate. An indicia may be positioned on the first or second layers 8002 or 8004, or may be placed intermediate the first and second layers 8002 or 8004. The indicia may be the same as described above with respect to FIG. 73.

The plurality of apertures, patterned apertures, overbonds, or embossments in the first nonwoven layer or the second layer or second nonwoven layer may have a first pattern in a first area and a second, different pattern in a second, different area. The first area may comprise one or more of a waist region, a hip region, a belt portion, a crotch region, a front region, a back region, and/or a buttocks region. The second area may comprise a different one or more of the waist region, the hip region, the belt portion, the crotch region, the front region, the back region, and/or the buttocks region. The first pattern may be different from the second, different pattern in size and shape, shape and frequency, or size and frequency, for example.

Figure 76:
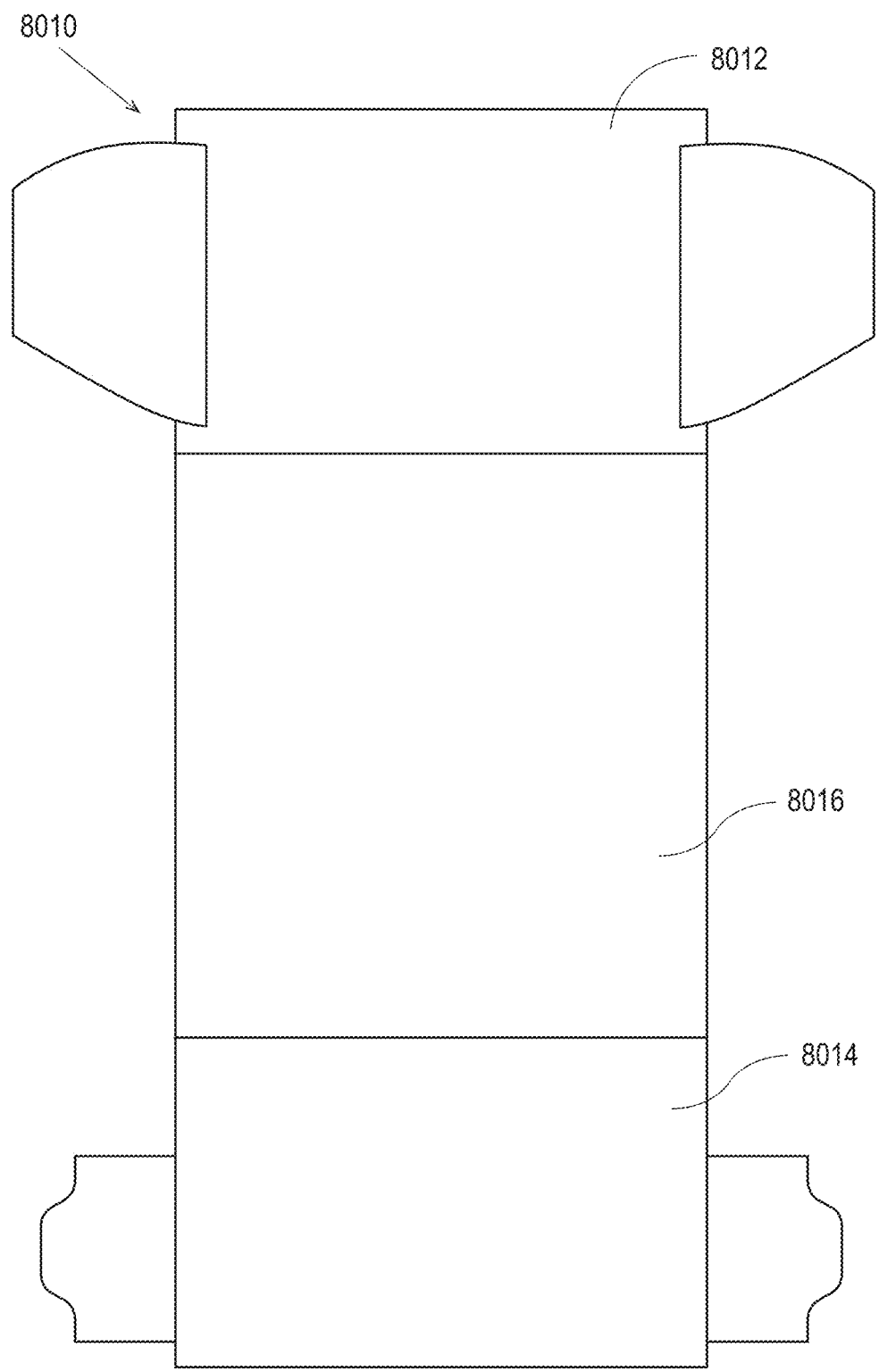
FIGS. 76-79 are plan views of absorbent articles, garment-facing surfaces facing the viewer, in accordance with the present disclosure.
Figure 77:
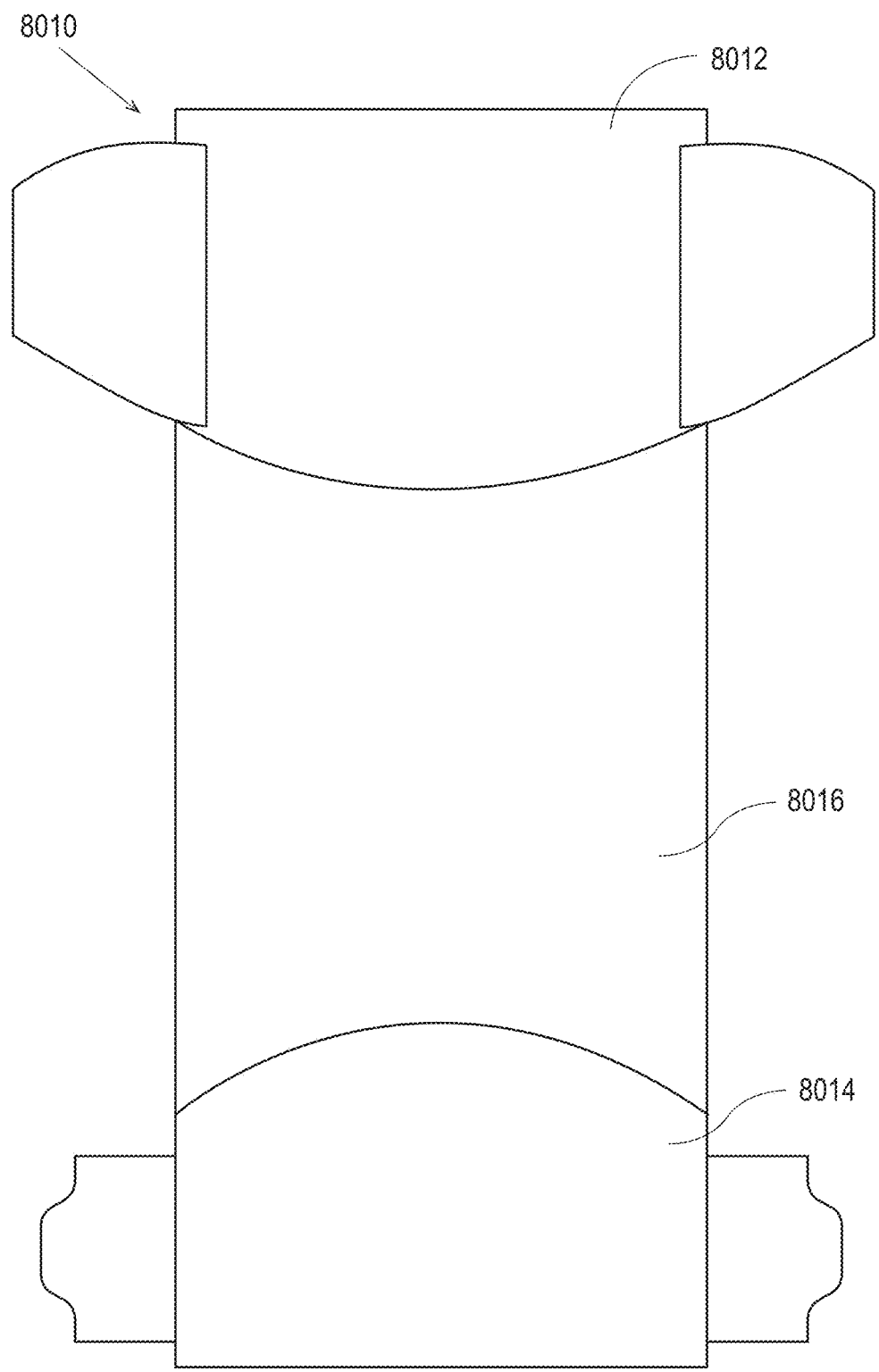

Referring to FIGS. 76 and 77, example garment-facing laminates or garment-facing layers on an absorbent article 8010 are illustrated. The garment-facing laminates or layers may be the same as described above in construction, but may have different zones. The absorbent articles 8010 may have a first zone 8012, a second zone 8014, and a third zone 8016. The first and second zones 8012, 8014 may form waist or hip portions (or front or rear regions) of the absorbent article 8010, while the third zone 8016 may form a crotch and/or buttocks portion of the absorbent article 8010. Any suitable number of zones may also be provided in a garment-facing laminate or layer. At least some of the zones 8012, 8014, 8016 may have apertures or patterned apertures. In some instances, two or more of the zones 8012, 8014, and 8016, or portions thereof, may have apertures or patterned apertures. In still other instances, one or more zones may have apertures and other zones may have patterned apertures. In yet other instances, one more zones may have overbonds that are not ruptured or may have overbonds that are partially ruptured, as will be described in further detail below. One or more of the zones may comprise embossments. The apertures or patterned apertures may be the same or different in different zones. In an instance, the first and second zones 8012 and 8014 may have the same pattern of apertures or patterned apertures, overbonds, or embossments, while the third zones 8016 may have a different pattern of apertures or patterned apertures, overbonds, or embossments. Any of the zones may also comprise indicia as described herein. The indicia may be the same or different in various zones.

Figure 78:
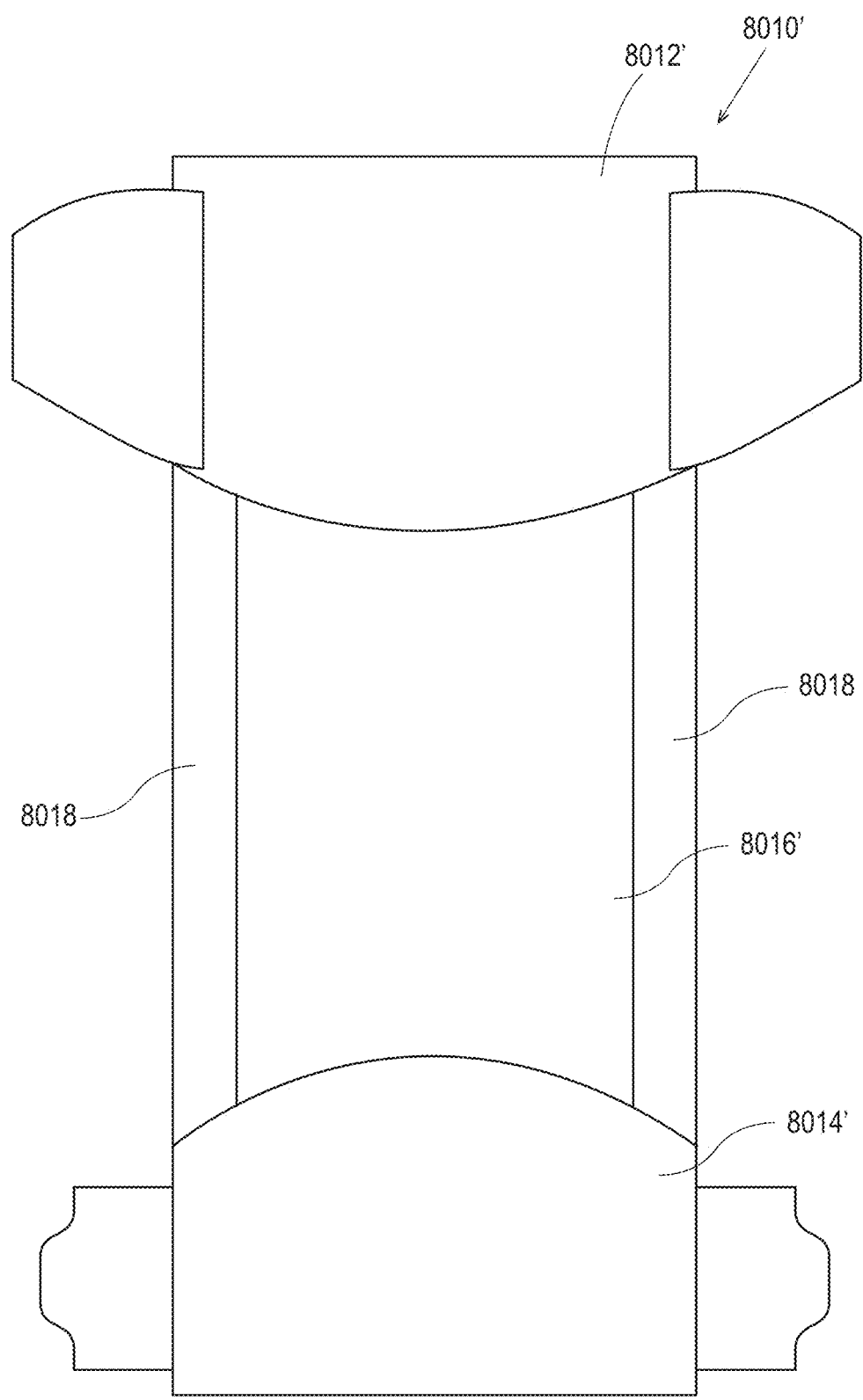

FIG. 78 illustrates an example absorbent article 8010' with a first zone 8012', a second zone 8014', a third zone 8016', and fourth zone 8018. Any of the first, second, third, and fourth zones 8012', 8014', 8016', and 8018 may be apertured, have patterned apertures, and/or comprise overbonds and/or embossments. The apertures, patterned apertures, overbonds, and/or embossments may be the same or different in the various zones. In an instance, at least two zones may have the same pattern of apertures, patterned apertures, overbonds and/or embossments. Any of the zones may also comprise indicia as described herein. In an instance, the first and second zones 8012' and 8014' may have the same pattern of apertures, patterned apertures, embossments, and/or overbonds, while the third zone 8016' or the fourth zone 8018 may have a different pattern of apertures, patterned apertures, embossments, and/or overbonds.

Figure 79:
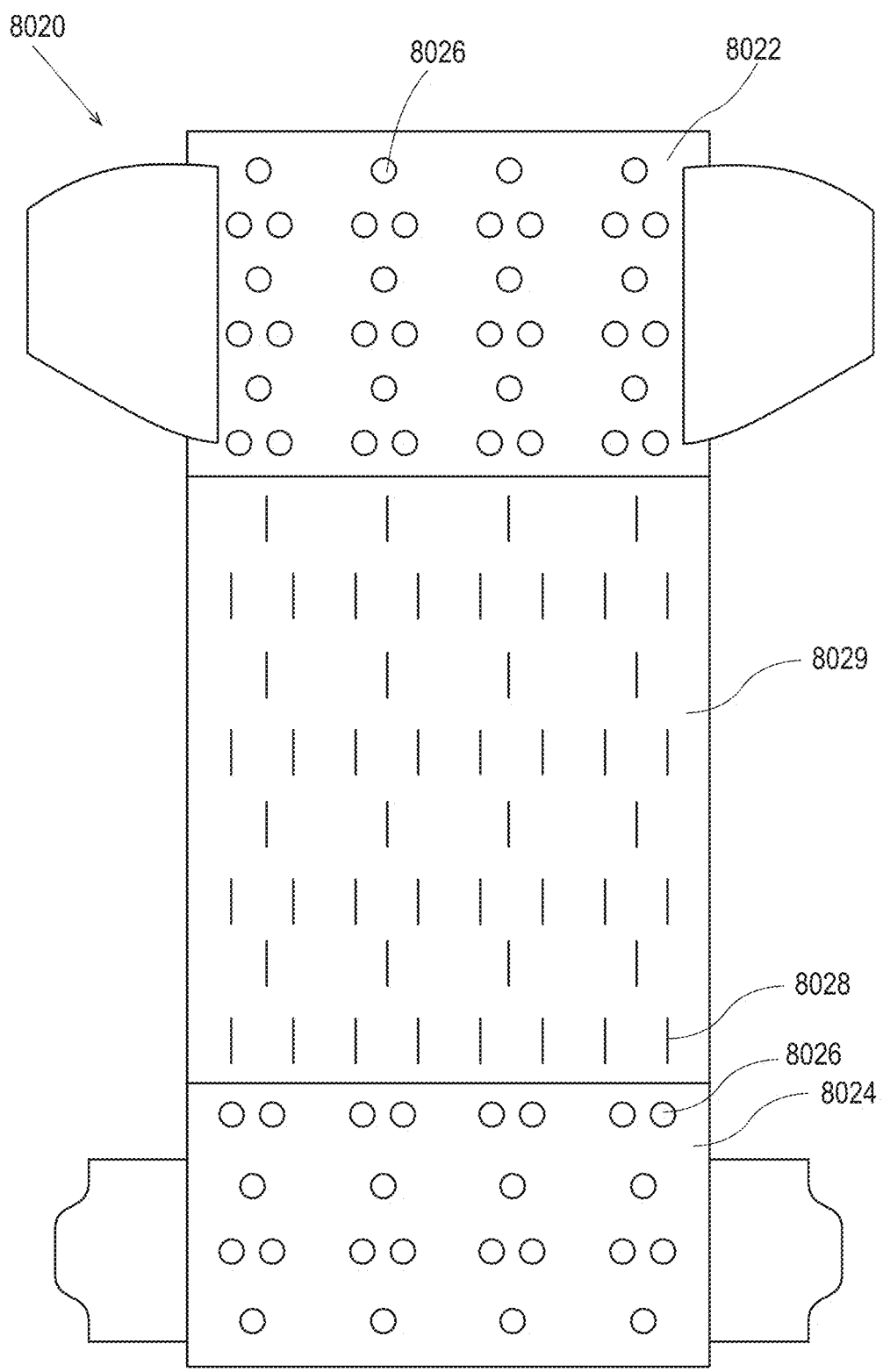

FIG. 79 is another example of an absorbent article 8020 with zones in a garment-facing layer or laminate. A first zone 8022 and a second zone 8024 comprise a plurality of apertures 8026 or patterned apertures, while a third zone 8029 comprises a pattern of unopened overbonds 8028 or embossments. Stated another way, the first zone 8022 and the second zone 8024 comprise a plurality of ruptured overbonds 8026, while the third zone 8029 comprises a plurality of unruptured overbonds 8028. To create such a structure, a material may be overbonded and then certain regions (e.g., the first and second zones 8022 and 8024) may be stretched (e.g., in the cross-machine direction) to at least partially, or fully, rupture the overbonds, with other regions not being stretched (e.g., the third zone 8029). In such a configuration, the garment-facing layer or laminate may signify that the waist, hip, or belt potions (i.e., the first and second zones 8022 and 8024 (with apertures or patterned apertures)) are breathable, while the third zone 8029 (with only overbonds or embossing) is designed for absorbency and/or performance. Ruptured overbonds (or apertures) and unruptured overbonds may be positioned in any suitable zones.

Figure 80:
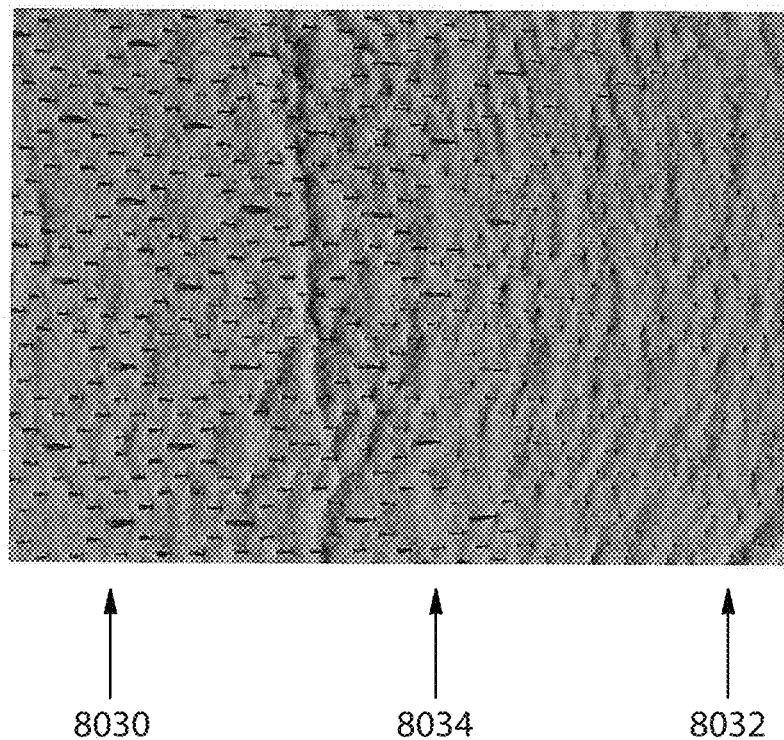
FIGS. 80 and 81 are photographs of webs with only some of the overbonds ruptured to form apertures in accordance with the present disclosure.

FIG. 80 is a photograph of a nonwoven material or laminate with ruptured overbonds forming apertures in a first section (or zone) 8030 (left side) and unruptured overbonds in a second section 8032 (or zone) (right side). FIG. 80 also illustrates a third, transition section 8034 positioned intermediate the first section 8030 and the second section 8032. In the third, transition section 8034, at least some of the overbonds are partially ruptured. Such a material may be used as a portion of the garment-facing laminate of FIG. 79.

Figure 81:
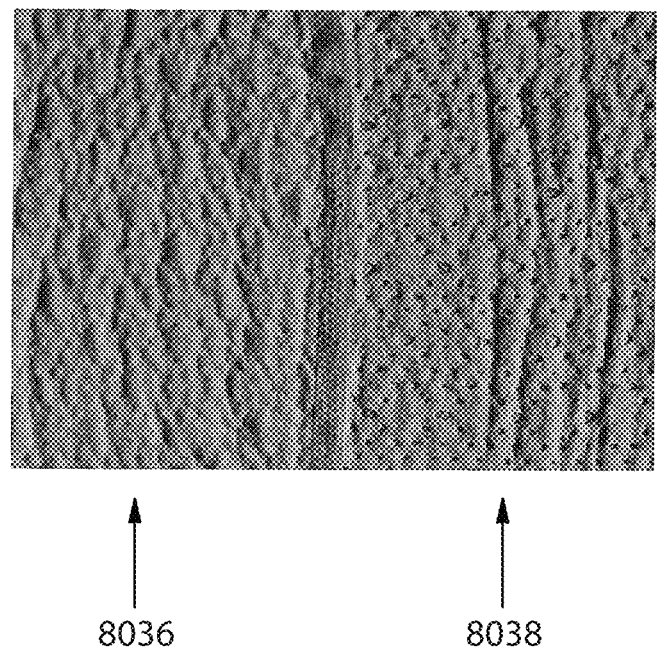

FIG. 81 is a photograph of a nonwoven laminate with overbonds or embossments in a first section 8036. The first section (or zone) 8036 may also have a layer that was pre-strained prior to being joined to another layer, thereby producing the three-dimensional features. A second section (or zone) 8038 may comprise a plurality of apertures or a plurality of patterned apertures with or without a pre-strained layer. The first section 8036 may represent a first zone in a garment-facing laminate and the second section 8038 may represent a second zone in the garment-facing laminate.

An absorbent article may comprise a liquid permeable topsheet on a wearer-facing side of the absorbent article and a garment-facing laminate on a garment-facing side of the absorbent article. The garment-facing laminate may comprise a first layer or a first nonwoven layer and a second layer or a second nonwoven layer joined to the first layer when the first layer or the second layer is in a pre-strained condition and when the other of the first layer or the first nonwoven layer or the second layer or the second nonwoven layer is in a non-pre-strained condition to form a three-dimensional material. Details of the pre-strained layers and laminates comprising a pre-strained layer are described above. The first nonwoven layer may comprise a plurality of apertures or a plurality of patterned apertures as described herein. At least 3, at least 5, or at least 10 of the apertures may be nonhomogeneous apertures. The second layer may comprise a film or may comprise a backsheet film. The laminate may comprise one or more patterned adhesives and/or printed inks, as described herein. The absorbent article may comprise an absorbent core is disposed at least partially intermediate the liquid permeable topsheet and the garment-facing laminate.

An absorbent article may comprise a liquid permeable topsheet on a wearer-facing side of the absorbent article and a garment-facing layer on a garment-facing side of the absorbent article. The garment-facing layer may comprise a nonwoven material. The garment-facing layer may comprise a first zone comprising a plurality of overbonds and a second zone comprising a plurality of apertures or patterned apertures. The second zone may at least partially form a waist region, hip region, or belt portion, of the absorbent article and the second zone may at least partially form a crotch region of the absorbent article. At least 3, at least 5, or at least 10 of the plurality of apertures in a repeat unit may have a different size, a different shape, and/or a different Absolute Feret Angle, according to the Aperture Test herein. The absorbent article may comprise a liquid impermeable backsheet and an absorbent core is disposed at least partially intermediate the liquid permeable topsheet and the backsheet.

Figure 82:
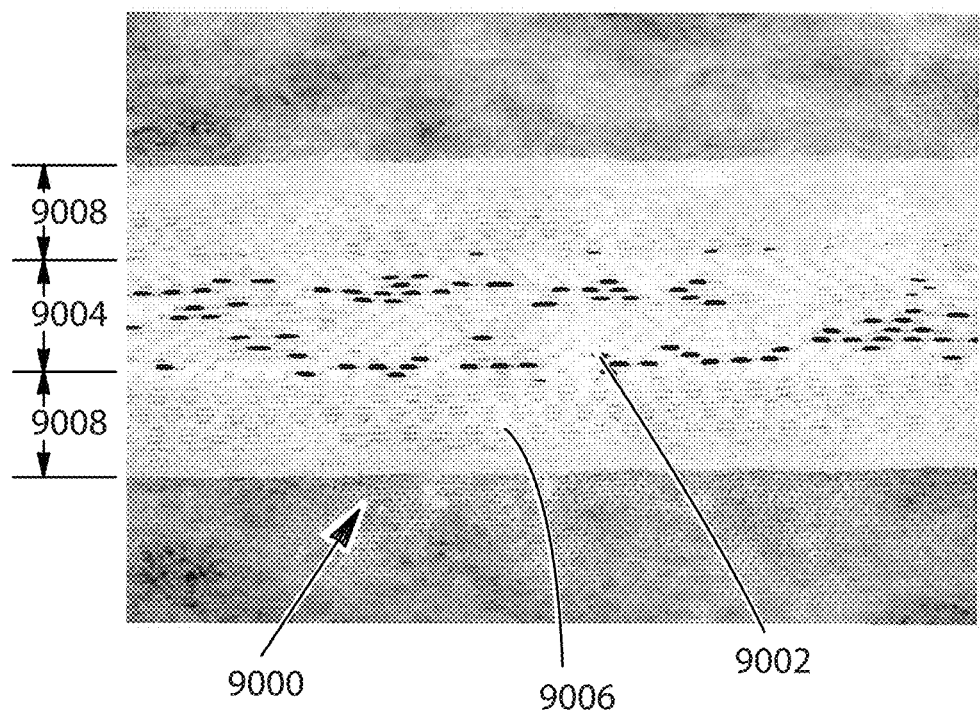
FIG. 82 is a photograph of a patterned apertured web for a feminine hygiene product, wherein outer portions of the web have embossed areas in accordance with the present disclosure.

FIG. 82 is an example patterned apertured web 9000 with patterned apertures 9002 in a central region 9004 thereof and with embossed areas 9006 in outer portions 9008 thereof. The patterned apertured web 9000 may be used in a feminine hygiene product, as a topsheet, for example, or may be used in other absorbent articles.

Figure 83:
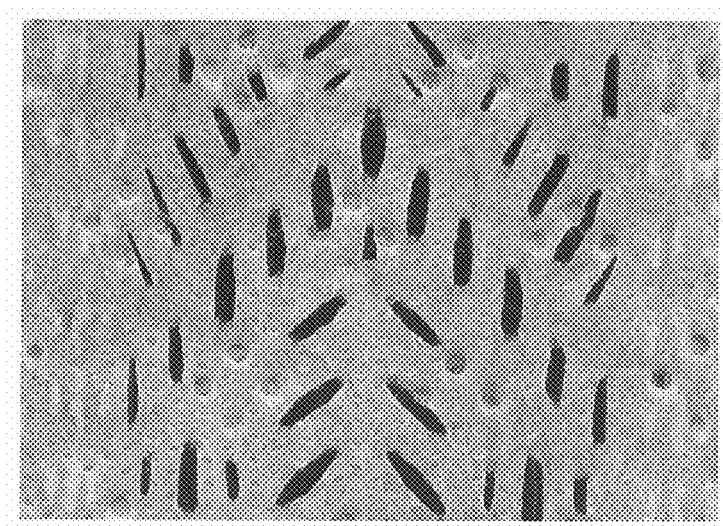
FIG. 83 is a photograph of an example patterned apertured web in accordance with the present disclosure.

FIG. 83 is another example patterned apertured web 9010.

Moiré Effect Laminates and Methods for Making the Same

The present disclosure also envisions laminates that provide a moiré effect. The moiré effect is a visual image that is evident when one pattern in a first material is superimposed over another pattern in a second material while one pattern is displaced or moved relative to the other pattern. More than two materials may also be used, optionally with additional patterns. Providing the moiré effect in various layers of consumer products or absorbent articles is highly consumer desired because of the interesting appearance of the product or article. In an absorbent article context, providing the moiré effect may provide the consumer with the impressions of depth, absorbency, quality, improved wicking, and/or and air flow.

Figure 84:
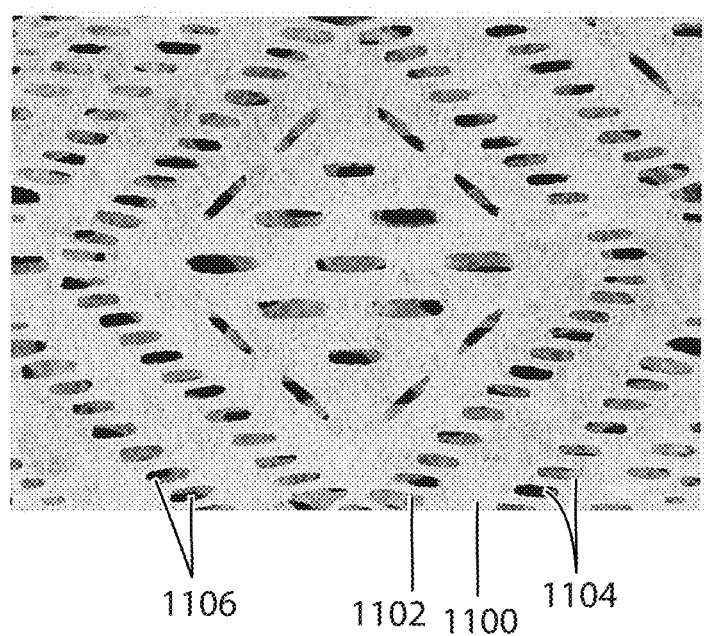
FIG. 84 is a photograph of an example moiré effect laminate with a first layer in a first position relative to a second layer, wherein a first portion of a second pattern of the second layer is at least partially visible through a first portion of a first pattern of the first layer, in accordance with the present disclosure.
Figure 85:
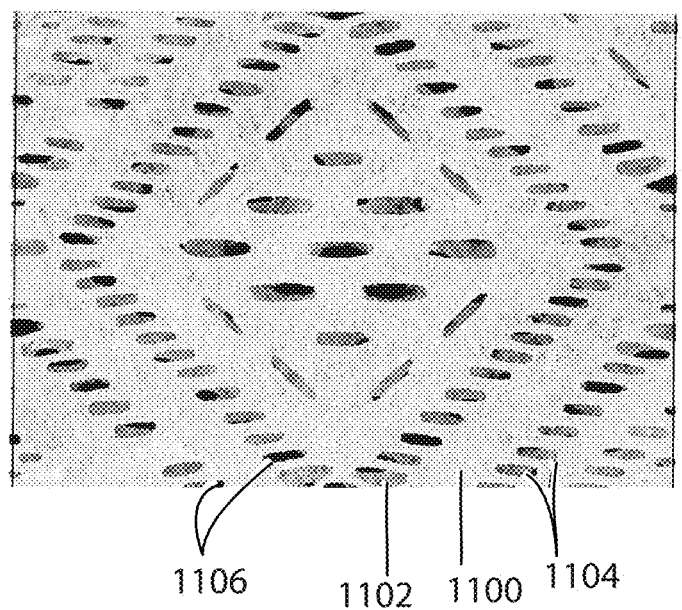
FIG. 85 is a photograph of the example moiré effect laminate of FIG. 84 with the first layer in a second position relative to the second layer, wherein a second portion of the second pattern is at least partially visible through a second portion of the first pattern, in accordance with the present disclosure.
Figure 86:
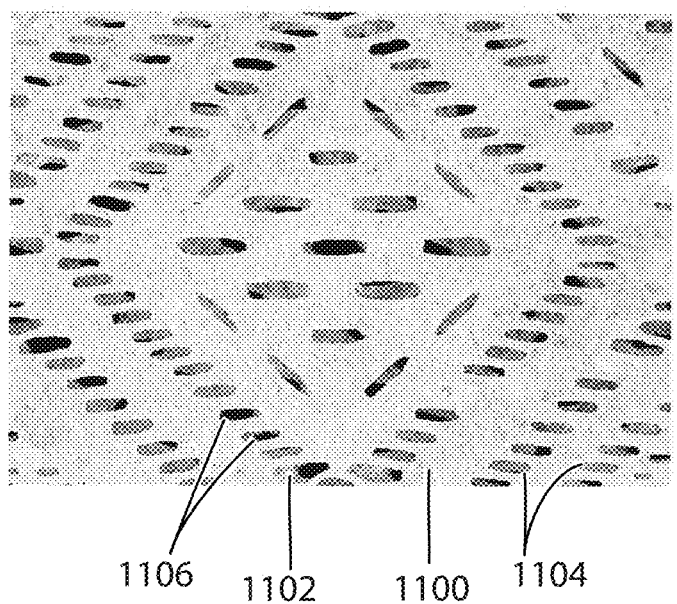
FIG. 86 is a photograph of the example moiré effect laminate of FIG. 84 with the first layer in a third position relative to the second layer, wherein a third portion of the second pattern is at least partially visible through a third portion of the first pattern, in accordance with the present disclosure.
Figure 87:
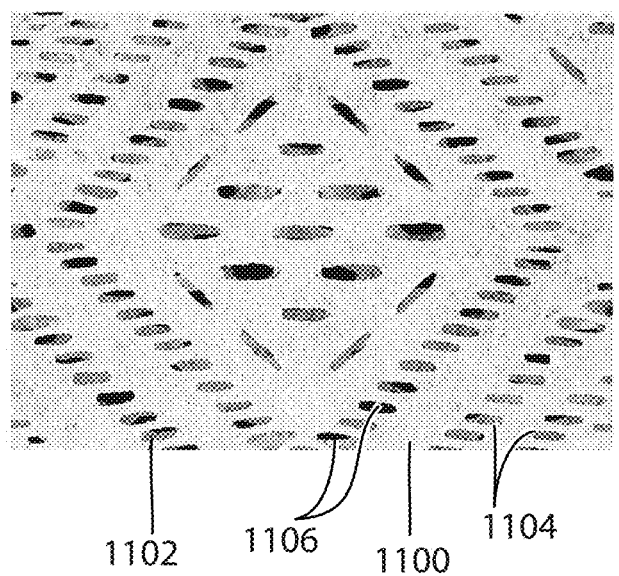
FIG. 87 is a photograph of the example moiré effect laminate of FIG. 84 with the first layer in a fourth position relative to the second layer, wherein a fourth portion of the second pattern is at least partially visible through a fourth portion of the first pattern, in accordance with the present disclosure.

Some examples of patterned apertured nonwoven materials providing the moiré effect are illustrated in FIGS. 84-87. In FIG. 84, a first layer 1100 is in a first position relative to the second layer 1102. The first layer 1100 has a plurality of patterned apertures 1104 (as described herein) and the second layer 1102 has a plurality of uniformly spaced and homogeneous apertures 1106. FIG. 85 illustrates the first layer 1100 in a second position relative to the second layer 1102. FIG. 86 illustrates the first layer 1100 in a third position relative to the second layer 1102. FIG. 87 illustrates the first layer 1100 in a fourth position relative to the second layer 1102. When viewing FIGS. 84-87 together, the moiré effect is illustrated. This may be accomplished by having non-bonded spans between the first and second layers 1100 and 1102. By having non-bonded spans in the first and second layers, the first and second layers may move relative to each other, even when the first and second layers are at least intermittently joined together into a laminate. Even if the first and second layers do not move relative to each other, the moiré effect may appear as the viewer moves relative to the laminate. FIGS. 84-87 are merely examples of the moiré effect, and further forms are discussed below.

A moiré effect laminate may have two or more layers. A first layer may comprise a nonwoven, a cellulosic material, a coform material, a woven, a film, any other suitable material, or combinations thereof. A second layer may also comprise a nonwoven, a cellulosic material, a coform material, a woven a film, any other suitable material, or combinations thereof. The first layer or the second layer may comprise apertures (uniform and homogenous) or patterned apertures as described herein. In other instances, only one of the layers may comprise apertures or patterned apertures. In still other instances, neither of the layers may comprise apertures or patterned apertures.

One of the layers may comprise a plurality of lower opacity zones in a pattern positioned within a higher opacity zone. Stated another way, a material having a first opacity (higher opacity) may have certain zones that have a reduced opacity (lower opacity). The lower opacity zones should have an area of at least about 1 mm$^2$, at least about 2 mm$^2$, at least about 3 mm$^2$, at least about 4 mm$^2$, at least about 5 mm$^2$, at least about 6 mm$^2$, at least about 7 mm$^2$, at least about 8 mm$^2$, or in the range of about 1 mm$^2$ to about 20 mm$^2$, about 1 mm$^2$ to about 15 mm$^2$, about 2 mm$^2$ to about 10 mm$^2$, specifically reciting all 0.1 mm$^2$ increments within the specified ranges and all ranges formed therein or thereby. These lower opacity zones, in some instances, may be at least partially, or fully, formed by apertures. The lower opacity zones positioned within a higher opacity zone may enable viewing a portion of a pattern behind the material with the lower opacity zones. Stated another way, the lower opacity zones essentially create "windows" in the material, thereby allowing a pattern behind the material to be at least partially visible.

The higher opacity zone may have an opacity of at least about 1.1 times, at least about 1.5 times, at least about 2 times, at least about 2.5 times, or at least about 3 times greater than the opacity of the lower opacity zones, according to the Opacity Test herein. Alternatively, the higher opacity zone may have an opacity in the range of about 1.1 times to about 5 times greater than the lower opacity zones, according to the Opacity Test herein, specifically reciting all 0.1 increments within the specified range and all ranges formed therein. Also, the higher opacity zone may have an opacity that is at least about 3 percentage points, at least about 5 percentage points, at least about 10 percentage points, at least about 15 percentage points, at least about 20 percentage points, or at least about 25 percentage points greater than an opacity of the lower opacity zones, according to the Opacity Test herein. Alternatively, the higher opacity zone may have an opacity that is in the range of about 3 percentage points to about 20 percentage points greater than the opacity of the lower opacity zones, specifically reciting all 0.1 percentage point increments within the specified ranges an all ranges formed therein, according to the Opacity Test herein. If the lower opacity zones are apertures, their opacity would be 0% or about 0%, or about 0% to 5%, specifically reciting all 0.1% increments within the specified range and all ranges formed therein, according to the Opacity Test herein.

The higher opacity zone may have a light transmission of at least about 1.1 times, at least about 1.5 times, at least about 2 times, at least about 2.5 times, or at least about 3 times less than the light transmission of the lower opacity zones, according to the Light Transmission Test herein. Alternatively, the higher opacity zone may have a light transmission in the range of about 1.1 times to about 5 times less than the lower opacity zones, according to the Light Transmission Test herein, specifically reciting all 0.1 increments within the specified range and all ranges formed therein. Also, the higher opacity zone may have a light transmission that is at least about 3 percentage points, at least about 5 percentage points, at least about 10 percentage points, at least about 15 percentage points, at least about 20 percentage points, or at least about 25 percentage points less than a light transmission of the lower opacity zones, according to the Light Transmission Test herein. Alternatively, the higher opacity zone may have a light transmission that is in the range of about 3 percentage points to about percentage points less than the light transmission of the lower opacity zones, according to the Light Transmission Test herein. If the lower opacity zones are apertures, their light transmission would be about 95-100%, specifically reciting all 0.1% increments within the specified range and all ranges formed therein, according to the Light Transmission Test herein.

The layers of the moiré effect laminate may comprise the same materials or different materials. By different, the layers could be different in basis weight, opacity, fiber composition, fiber type, fiber size, method of production, caliper, and/or color, for example. In some instances, a first layer may be a nonwoven material and a second layer may be a different type of nonwoven material or a film.

In some instances, a first pattern in a first layer of a moiré effect laminate may be a printed pattern, a patterned adhesive, a pattern of homogeneous and uniform apertures, patterned apertures (as described herein), lower opacity zones positioned in a higher opacity zone, and/or a pattern of embossments. Likewise, a second pattern in a second layer of a moiré effect laminate may be a printed pattern, a patterned adhesive, a pattern of homogeneous and uniform apertures, patterned apertures, lower opacity zones positioned in a higher opacity zone, a pattern of embossments, or combinations thereof. The first and second patterns, in the first and second layers, respectively, may be the same or different, in size, scale, shape, area, color, and/or orientation, for example. As a further example, a first pattern in a first layer may comprise patterned apertures and a second pattern in a second layer may comprise a printed pattern or a patterned adhesive. As another example, a first pattern in a first layer may comprise lower opacity zones positioned within a higher opacity zone and a second pattern in a second layer may comprise a printed pattern or a patterned adhesive. As still another example, a first pattern in a first layer may comprise lower opacity zones positioned within a higher opacity zone, apertures, or patterned apertures and a second pattern in a second layer may comprise apertures, patterned apertures, and/or a pattern of embossments. The first layer may be the layer facing the viewer, but the second layer could be as well.

As referenced above, the color of the layers in a moiré effect laminate may be the same or different. As an example, a first layer may be white and a second layer may be blue. As another example, a first layer may be light blue and a second layer may be dark blue. Any of the layers may be the same or a different color as the patterns of printed ink or patterned adhesive.

In an instance, a first layer of a moiré effect laminate may comprise a garment-facing nonwoven layer and a second layer may comprise a backsheet film or other film. The garment-facing nonwoven layer may have apertures, patterned apertures (as described herein), or lower opacity zones within a higher opacity zone. These apertures, patterned apertures, or lower opacity zones may form the first pattern in the first layer. The first layer may comprise one or more substrates as a laminate. The second layer comprising the backsheet film or other film may comprise a second pattern comprising apertures, patterned apertures, printed inks, patterned adhesives, and/or patterns of embossments. The second pattern may be at least partially visible through the first pattern in the first layer.

The first layer of the moiré effect laminate may be intermittently joined or bonded to the second layer of the moiré effect laminate (or additional layers) using any suitable type of joining or bonding. Examples of suitable joining or bonding include ultrasonic bonding or joining, adhesive bonding or joining, mechanically bonding or joining, interpenetration of one layer into another layer, mechanical entanglement, and/or thermal joining or bonding, for example. The bonds or joined portions may be placed at least about 15 mm, at least about 20 mm, at least about 25 m, at least about 30 mm, at least about 35 mm, at least about 40 mm, at least about 45 mm, or at least about 50 mm apart. In other instances, the bonds or joined portions may be positioned in the range of about 15 mm to about 150 mm apart, about 20 mm to about 140 mm apart, about 20 mm to about 120 mm apart, about 30 mm to about 100 mm apart, specifically reciting all 0.1 mm increments within the above-referenced ranges and all ranges formed therein or thereby. In larger products, the bonds or joined portions may be positioned in the range of about 25 mm to about 1000 mm apart, about 100 mm to about 750 mm apart, or about 100 mm to about 500 mm apart, specifically reciting all 0.1 mm increments within the above-referenced ranges and all ranges formed therein or thereby.

Figure 88:
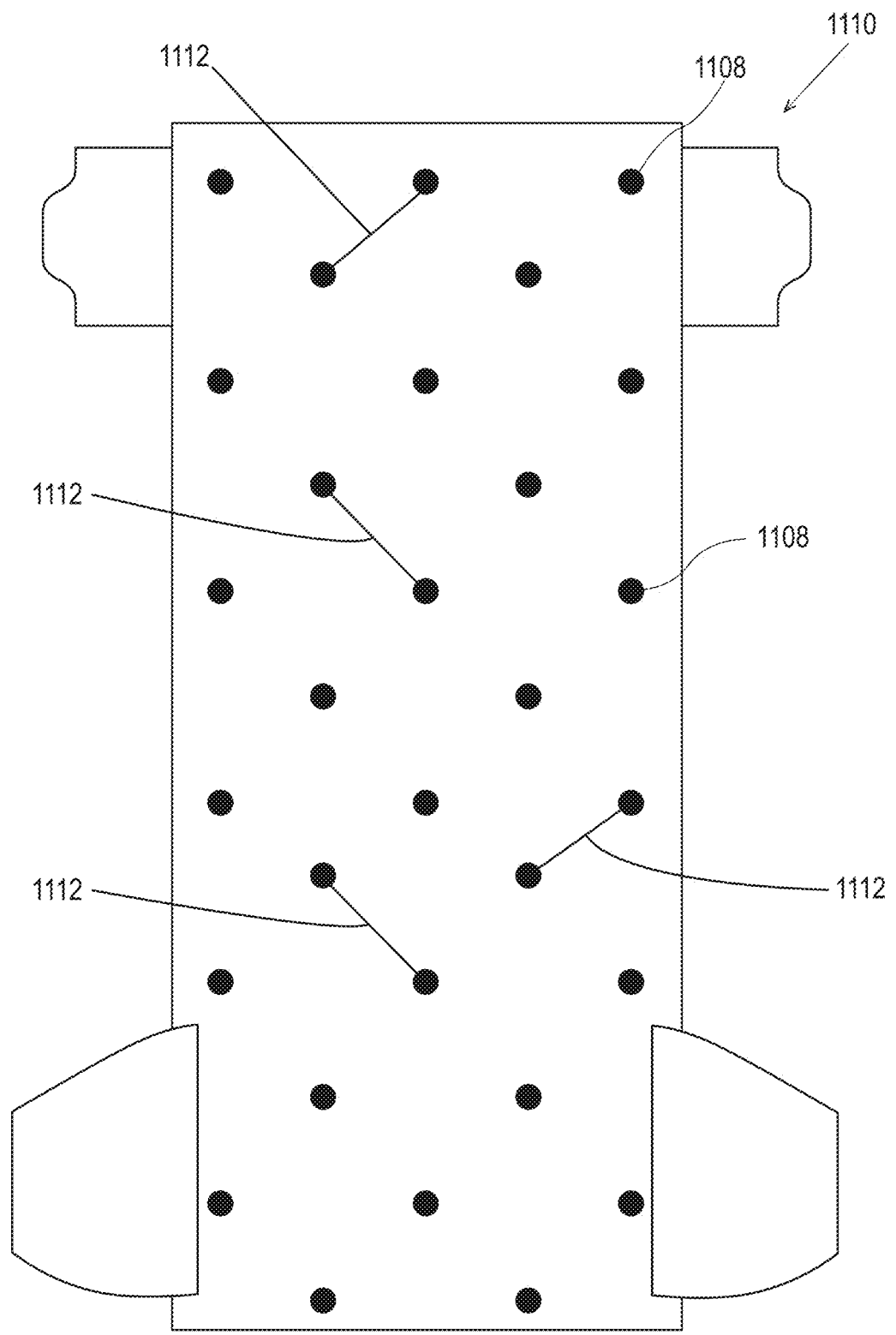
FIGS. 88-90 are example absorbent articles with bonds or joined portions, garment-facing surfaces removed to show the position of the bond or joined portions, in accordance with the present disclosure.
Figure 89:
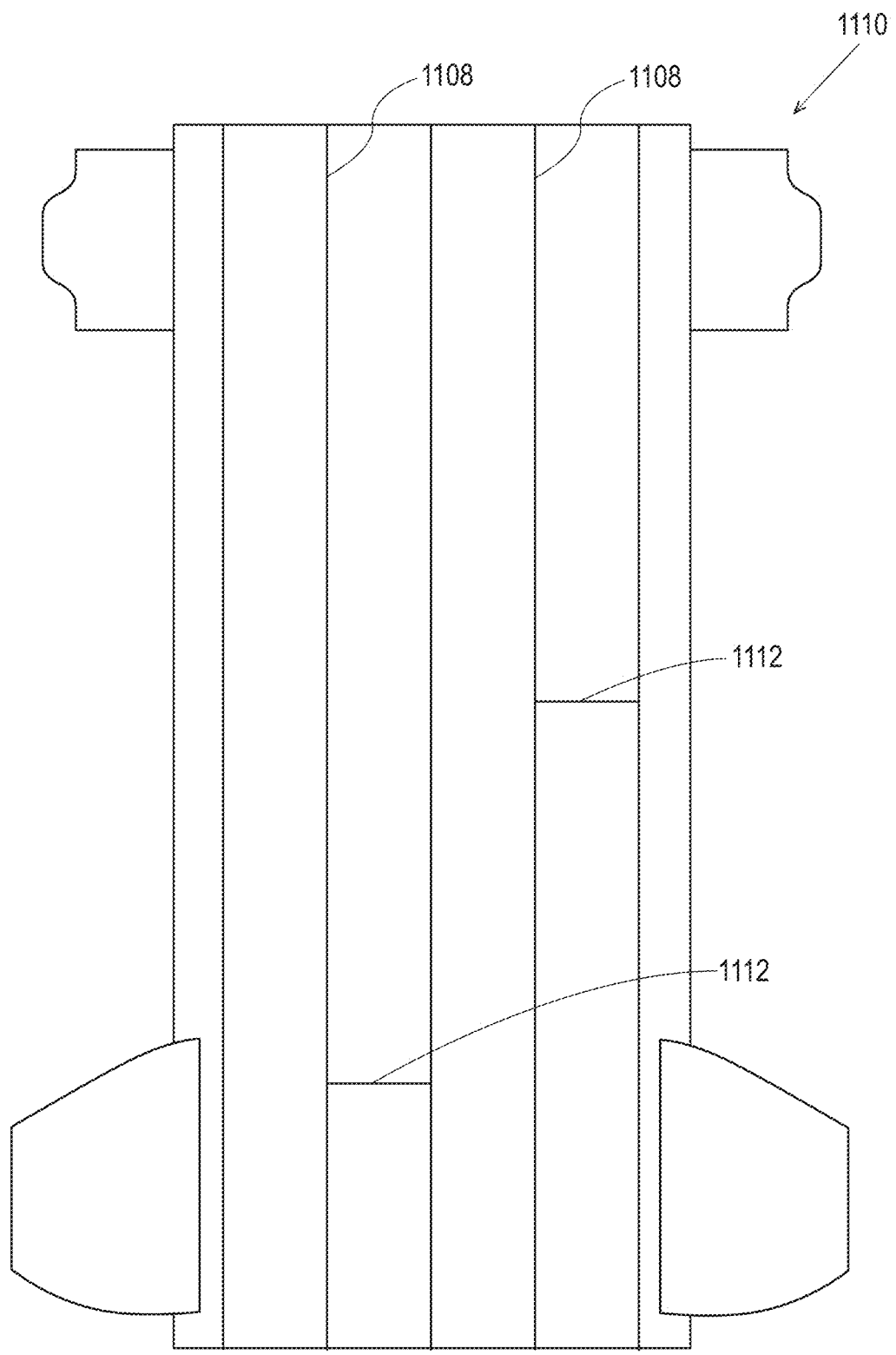
Figure 90:
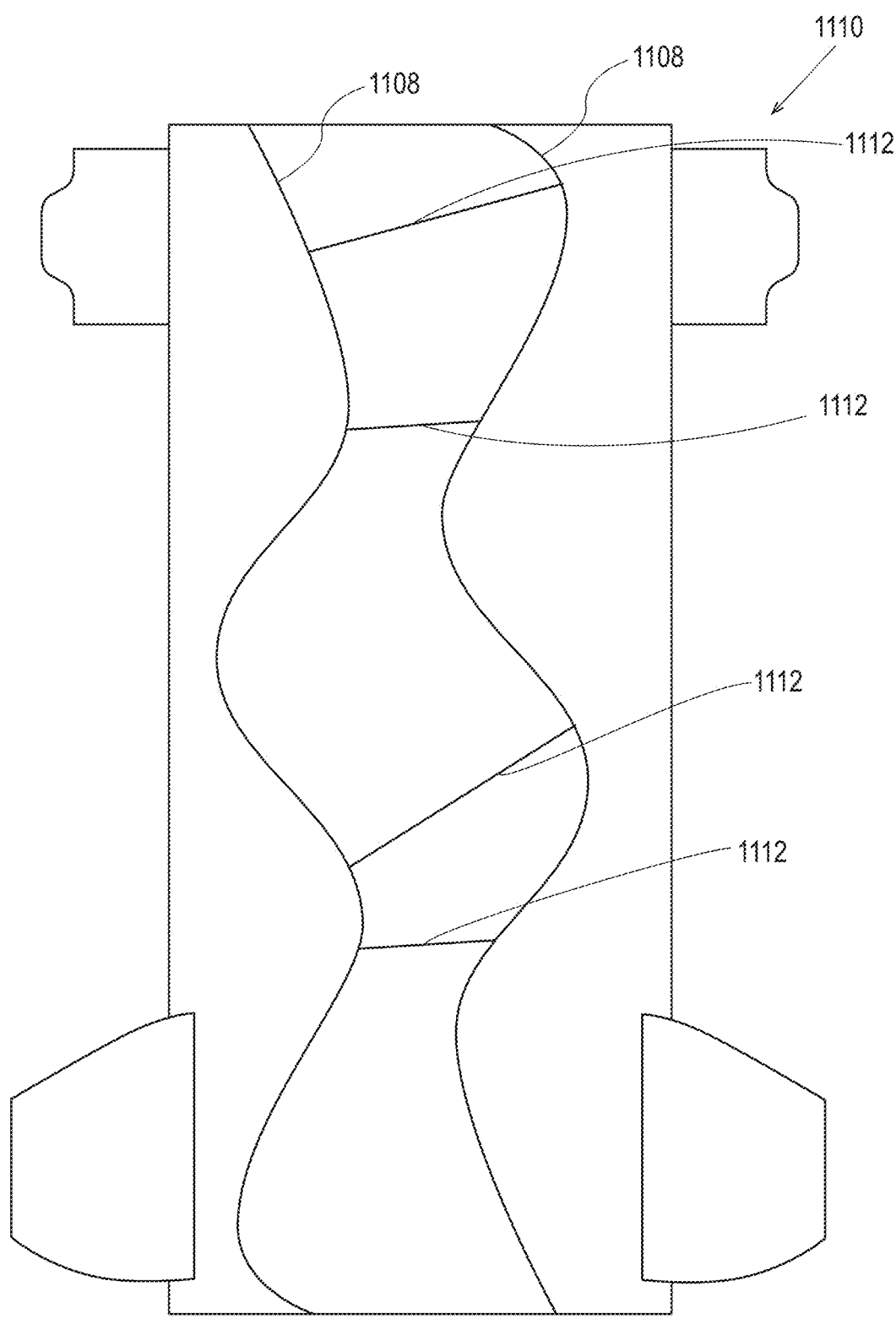

Referring to FIGS. 88-90, example bonds or joined portions 1108 are illustrated in simplistic views for ease in understanding. The bonds or joined portions 1108 may be between the first and second layers (or additional layers) of a moiré effect laminate. In FIGS. 88-90, an example absorbent article 1110 is illustrated with a garment-facing surface (or first layer) removed to show the locations of the bonds or joined portions, although the bonding or joining concept applies to any moiré effect laminate, regardless of where used in an absorbent article or another consumer product. For example, the moiré effect laminates could be used as topsheets, topsheets and acquisition layers, topsheets and distribution layers, waist bands, outer covers, leg cuffs, belts, fastening systems, wipes, or as any other component of consumer products or absorbent articles that have natural movement when in use (e.g., ears). The bonds or joined portions 1108 may be discrete (see FIG. 88), linear and continuous (see FIGS. 89 and 90), discontinuous and linear, or discontinuous, for example. In various instances, the bonds or joined portions may form any suitable or desired patterns.

In view of the bond or joined portion spacing described above, again referring to FIGS. 88-90, non-joined spans 1112 may exist intermediate the bonds or joined portions 1108 in a moiré effect laminate. These non-joined spans 1112 are areas where the first layer is not joined or bonded to the second layer (or an additional layer, if provided in a moiré effect laminate). They can also be referred to as non-bonded spans. The non-bonded spans may extend in any suitable direction between the bonds or joined portions. The first and second layers within the non-joined spans 1112 may be moveable relative to each other, even if just slightly to allow for the moiré effect. The non-joined spans may have distances in the range of at least about 15 mm, at least about 20 mm, at least about 25 mm, at least about 30 mm, at least about 35 mm, at least about 40 mm, at least about 45 mm, or at least about 50 mm, for example. In other instances, the non-joined spans may be positioned in the range of about 15 mm to about 150 mm apart, about 20 mm to about 140 mm apart, about 20 mm to about 120 mm apart, about 30 mm to about 100 mm apart, specifically reciting all 0.1 mm increments within the above-referenced ranges and all ranges formed therein or thereby. In larger products, the non-joined spans may be positioned in the range of about 25 mm to about 1000 mm apart, about 100 mm to about 750 mm apart, or about 100 mm to about 500 mm apart, specifically reciting all 0.1 mm increments within the above-referenced ranges and all ranges formed therein or thereby.

Figure 91:
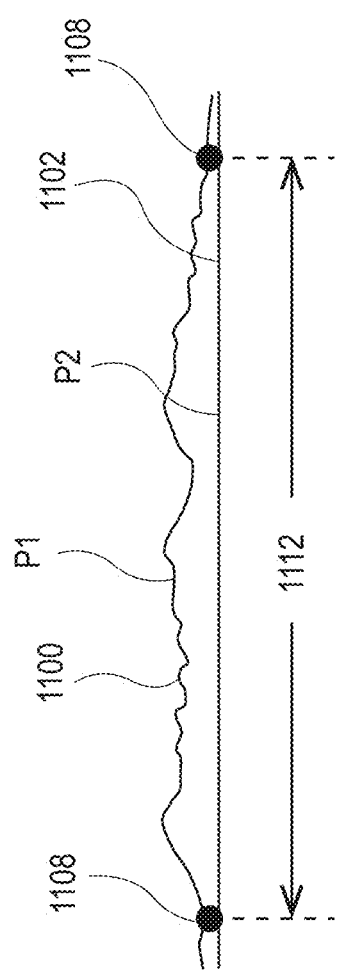
FIG. 91 is an example illustration of a moiré effect laminate or other laminate of the present disclosure with a first layer having a different path length of a second layer, in accordance with the present disclosure.

In some instances, a path length in a non-joined or non-bonded span may be greater, less, the same, or different in one of the layers of a moiré effect laminate relative to another one of the layers. Referring to FIG. 91, a first layer 1100 may have a greater path length, P1, than a path length P2, of the second layer 1102 in a non-joined span 1112. Path length is the distance traveled when moving over a surface from one bond or joined portion 1108 to another. As can be seen, the distance traveled would be greater for the first layer 1100 than the second layer 1102. Stated another way, the first layer 1100 is longer than the second layer 1102 in the non-joined span. The opposite may also be true with the path length of the second layer 1102 being greater than the first layer 1100. Providing a laminate with two layers, where the two layers have different path lengths may be provided by pre-straining one layer before joining it to another non-pre-strained layer, as described in greater detail herein. By providing this path length differential, a moiré effect laminate may provide three dimensional features in at least one layer, while also increasing the visual significance of the moiré effect as one layer is allowed to move more relative to another layer within the non-joined or non-bonded span 1112. In the example of FIG. 91, the first layer 1100 may have apertures, patterned apertures, or lower opacity zones in a first pattern and the second layer 1102 may have a printed pattern, a printed ink, a patterned adhesive, apertures, and/or patterned apertures that are at least partially visible through the apertures, patterned apertures, or lower opacity zones in the first layer. The path length of a first layer may be at least about 0.5%, about 1%, about 1.5%, about 2%, about 2.5%, about 3%, about 4%, about 5%, about 6%, about 7%, about 8%, about 9%, about 10%, or in the range of about 0.5% to about 40% greater than or different than the path length of a second layer in a moiré effect laminate, specifically reciting all 0.1% increments with the specified range and all ranges formed therein.

Even without a different path length between the layers in the non-joined spans, the first and second layers within the non-joined span may still be able to move relative to each other. This allows the moiré effect to be observed. Movement between the first and second layers in the non-bonded span or span may be caused by movement of a wearer of an absorbent article and/or movement of the consumer product that the moiré laminate is part of.

Figure 92:
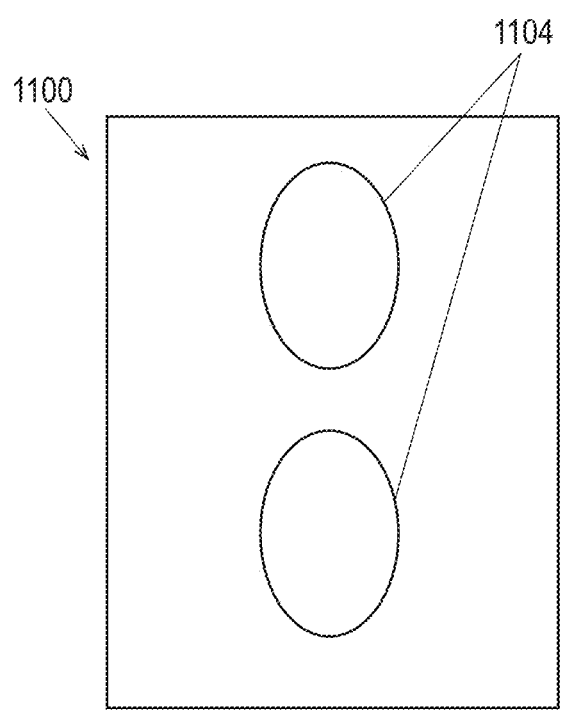
FIG. 92 is an example of a first layer having a first pattern of a moiré effect laminate, in accordance with the present disclosure.
Figure 93:
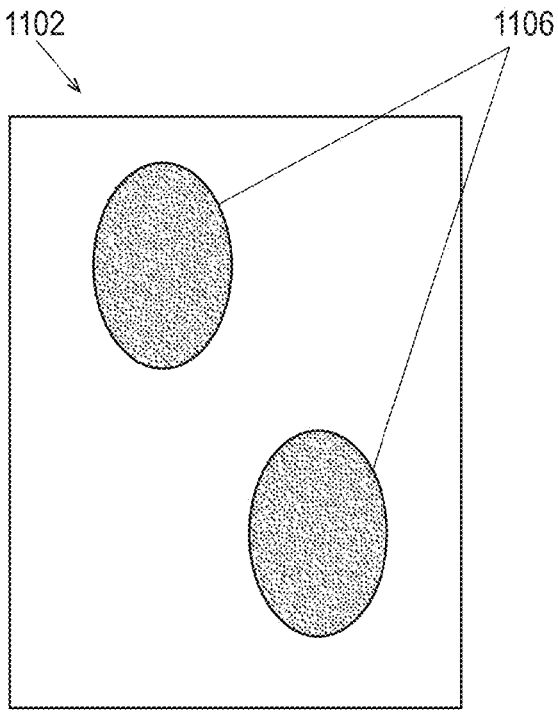
FIG. 93 is an example of a second layer having a second pattern of moiré effect laminate, in accordance with the present disclosure.
Figure 94:
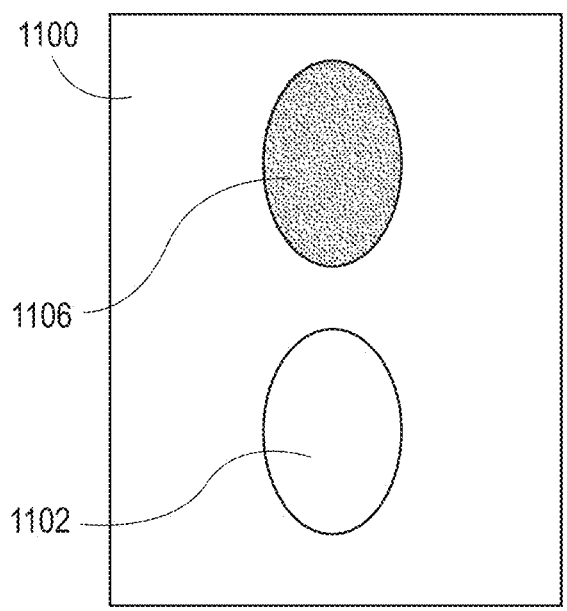
FIG. 94 is an example the first layer of FIG. 92 overlaid on the second layer of FIG. 93 to form a moiré effect laminate, wherein the first layer is in a first position relative to the second layer, in accordance with the present disclosure.
Figure 95:
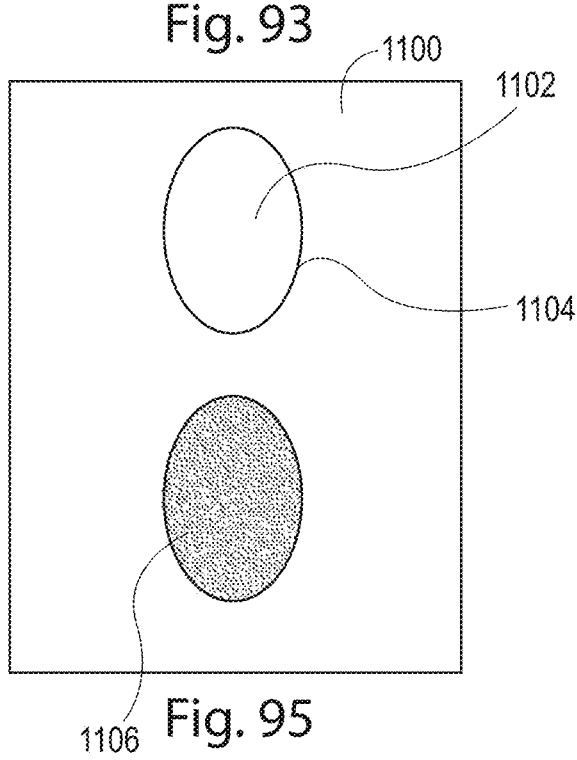
FIG. 95 is an example the first layer of FIG. 92 overlaid on the second layer of FIG. 93 to form a moiré effect laminate, wherein the first layer is in a second position relative to the second layer, in accordance with the present disclosure.

FIG. 92 illustrates an example of a first layer 1100 of a moiré effect laminate having a first pattern 1004. The first pattern may comprise apertures, patterned apertures, or lower opacity zones positioned within a higher opacity zone. FIG. 93 illustrates an example of a second layer 1102 of a moiré effect laminate having a second pattern 1106. The second pattern 1106 may comprise apertures, patterned apertures, printed inks, patterned adhesives, and/or embossments, for example. FIG. 94 illustrates the first layer 1100 in a first position relative to the second layer 1102 in a non-joined span. FIG. 95 illustrates the first layer 1100 in a second position relative to the second layer 1102 in the same non-joined span. As can be seen, a first portion of the second pattern 1106 is visible through the first pattern 1104 when the first layer 1100 is in the first position and a second portion of the second pattern 1106 is visible through the first pattern 1104 when the first layer 1102 is in the second position. The first pattern 1104 and the second pattern 1106 may be the same size and shape.

Figure 96:
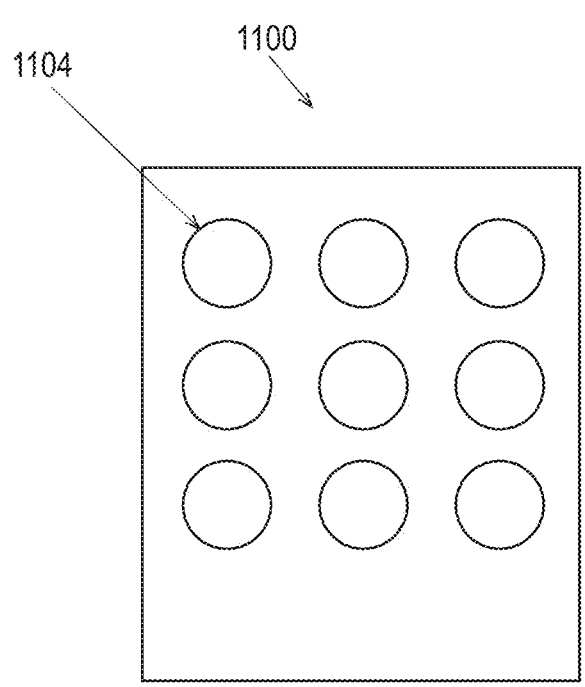
FIG. 96 is an example of a first layer having a first pattern of a moiré effect laminate, in accordance with the present disclosure.
Figure 97:
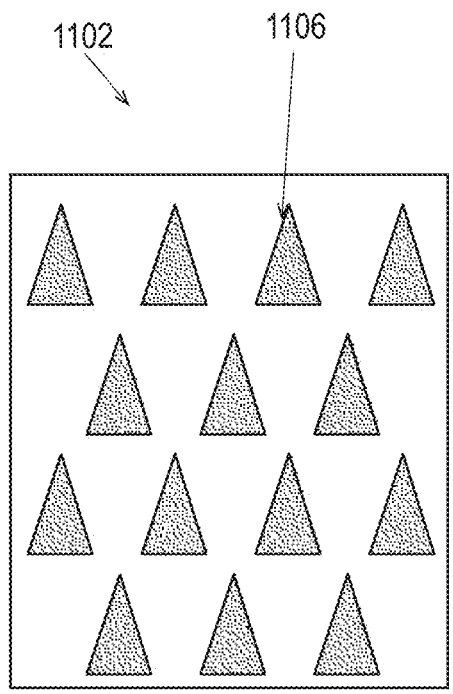
FIG. 97 is an example of a second layer having a second pattern of moiré effect laminate, in accordance with the present disclosure.
Figure 98:
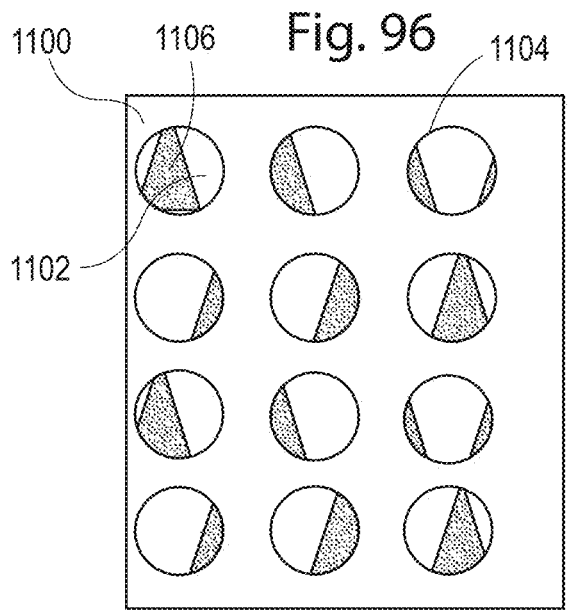
FIG. 98 is an example the first layer of FIG. 96 overlaid on the second layer of FIG. 97 to form a moiré effect laminate, wherein the first layer is in a first position relative to the second layer, in accordance with the present disclosure.
Figure 99:
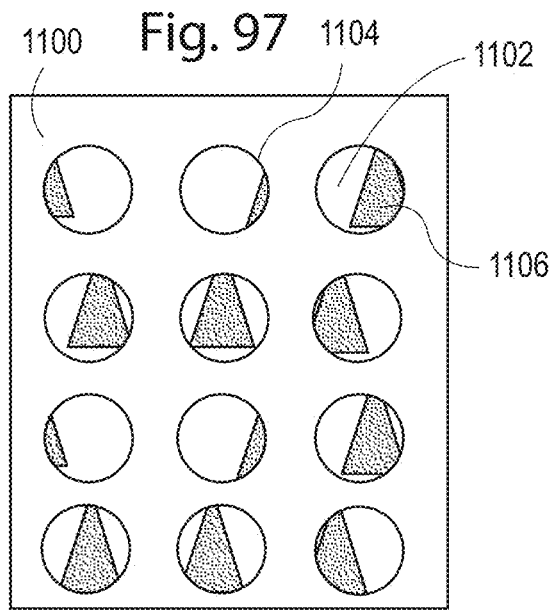
FIG. 99 is an example the first layer of FIG. 96 overlaid on the second layer of FIG. 97 to form a moiré effect laminate, wherein the first layer is in a second position relative to the second layer, in accordance with the present disclosure.

FIG. 96 illustrates an example of another first layer 1100 of a moiré effect laminate having a first pattern 1104. The first pattern may comprise apertures, patterned apertures, or lower opacity zones positioned within a higher opacity zone. FIG. 97 illustrates an example of a second layer 1102 of a moiré effect laminate having a second pattern 1106. The second pattern 1106 may comprise apertures, patterned apertures, printed inks, patterned adhesives, and/or embossments, for example. FIG. 98 illustrates the first layer 1100 in a first position relative to the second layer 1102 in a non-joined span. FIG. 99 illustrates the first layer 1100 in a second position relative to the second layer 1102 in the same non-joined span. As can be seen, a first portion of the second pattern 1106 is visible through the first pattern 1104 when the first layer 1100 is in the first position and a second portion of the second pattern 1106 is visible through the first pattern 1104 when the first layer 1102 is in the second position. The first pattern 1104 and the second pattern 1106 may be a different size and shape.

FIG. 100 illustrates a cross-sectional illustration of a portion of a non-joined span of a moiré effect laminate, wherein the first layer 1100 is in a first position relative to the second layer 1102, and wherein a first portion of the second pattern 1106 is visible through the first pattern 1104. In such an example, the first pattern 1104 is a plurality of apertures or patterned apertures and the second pattern 1106 is a plurality of apertures or patterned apertures.

FIG. 101 illustrates another cross-sectional illustration of the portion of the non-joined span of the moiré effect laminate of FIG. 100, wherein the first layer 1100 has been moved into a second position relative to the second layer 1102, and wherein a second portion of the second pattern 1106 is visible through the first pattern 1004.

FIG. 102 illustrates a cross-sectional illustration of a portion of a non-joined span of a moiré effect laminate, wherein the first layer 1100 is in a first position relative to the second layer 1102, and wherein a first portion of the second pattern 1106 is visible through the first pattern 1104. In such an example, the first pattern 1104 is a plurality of lower opacity zones in a higher opacity zone and the second pattern 1106 is a plurality of apertures or patterned apertures.

FIG. 103 illustrates another cross-sectional illustration of the portion of the non-joined span of the moiré effect laminate of FIG. 101, wherein the first layer 1100 has been moved into a second position relative to the second layer 1102, and wherein a second portion of the second pattern 1106 is visible through the first pattern 1004.

Any of the moiré effect laminates disclosed herein may have a pattern formed by patterned apertures having any parameters of the patterned apertures set forth herein, such as Interaperture Distance and Average Absolute Feret Angle, for example.

A method of producing moiré effect laminate is provided. The method may comprise providing a first layer, a first nonwoven layer, or a first film layer, comprising a plurality of lower opacity zones positioned within a higher opacity zone (opacity differences are discussed above). The lower opacity zones may comprise or be apertures. The plurality of lower opacity zones may form a first pattern. The method may comprise providing a second layer, a second nonwoven layer, or a second film layer, comprising a second pattern and positioning the first layer in a face-to-face relationship with the second layer. The method may comprise intermittently joining the first layer to the second layer to form at least one non-joined span of the first and second layers such that at least a portion of the first layer is moveable relative to a portion of the second layer within the non-joined span. The non-joined span may have a dimension of at least 20 mm (or any of the dimensions set forth above for the non-joined or non-bonded spans). Portions of the second pattern may be aligned, or partially aligned, with portions of the first pattern in the non-joined span. A portion of the second pattern and a portion of the first pattern may be present in the non-joined span. The first pattern may be the same or different than the second pattern in size, shape, and/or orientation, for example. A first path length in the first layer of the non-joined span may be different than, greater than, or less than a second path length in the second layer of the non-joined span by any of the percentages disclosed above.

A method of producing an optical interference pattern in an absorbent article is provided. The method may comprise providing a first layer (nonwoven or film) as a first component of the absorbent article. The first layer may comprise a plurality of lower opacity zones positioned within a higher opacity zone (differences in opacity are described above). The plurality of lower opacity zones may form a first pattern. The lower opacity zones may comprise apertures. The method may comprise providing a second layer (nonwoven or film) as a second component of the absorbent article. The second layer may comprise a second pattern. The first layer, or a portion thereof, may be in a face-to-face relationship with the second layer, or a portion thereof, and is intermittently joined to the second layer to thereby form at least one non-joined span. The method may comprise allowing a portion of the first layer, in the non-joined span, to move relative to a portion of the second layer, in the non-joined span, to produce the optical interference pattern. A first portion of the second pattern, in the non-joined span, may be visible through a portion of the first pattern, in the non-joined span, when the portion of the first layer is in a first position relative to the portion of the second layer. A second portion of the second pattern, in the non-joined span, may be visible through the portion of the first pattern, in the non-joined span, when the portion of the first layer is in a second position relative to the portion of the second layer. The first component of the absorbent article may be a topsheet, an acquisition layer, or any other suitable component. The second component of the absorbent article may be a secondary topsheet, an acquisition layer, a backsheet, or any other suitable component.

Zonal Patterned Apertured Webs

Referring to FIGS. 104-107, aspects of zonal patterned apertured webs are illustrated. The various zones are represented as Z1, Z2, etc. to signify zone 1, zone 2 etc. Although the zonal patterned apertured web are illustrated as either a garment-facing layer or laminate or wearer-facing layer or laminate in FIGS. 104-107, it will be understood that zonal patterned apertured web, whether comprising one layer or multiple layers, may also be used for any portion of an absorbent article or other consumer product. For example, a zonal patterned apertured web may be used as part of an ear panel, a wipe, and/or a barrier leg cuff. The zonal patterned apertured webs may have one or more layers that is pre-strained and joined to non-pre-strained layers, as described herein.

Figure 104:
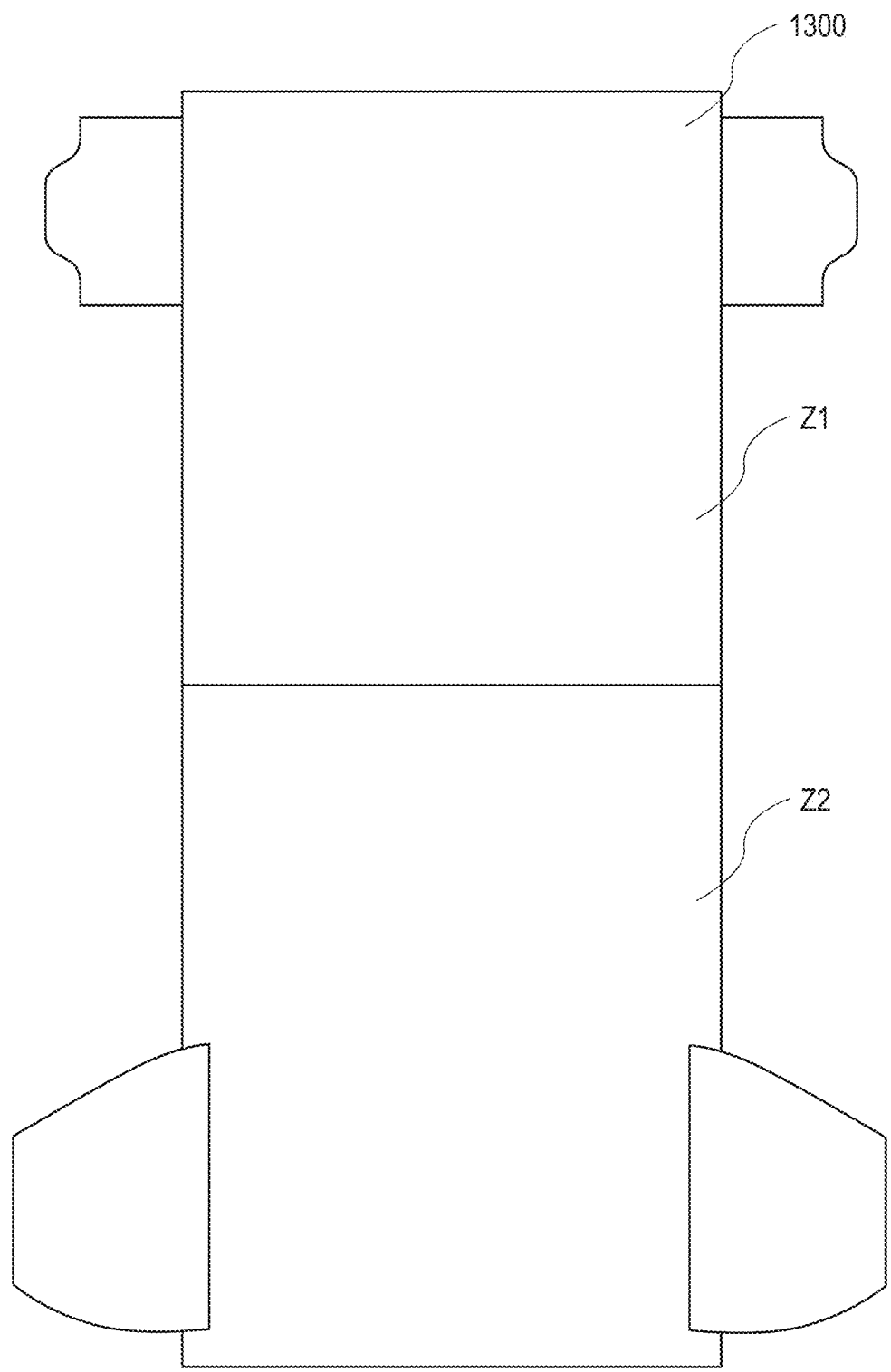
FIGS. 104-107 illustrate patterned apertured webs on an absorbent article that have various zones, in accordance with the present disclosure.

Referring to FIG. 104, a first zone, Z1, represents a front portion of an absorbent article while a second zone, Z2, represents a rear portion of an absorbent article. The first and second zones are formed in a patterned apertured web that may be a single layer or multiple layers. The patterned apertured web 1300 may comprise a plurality of first arrays forming the first zone, Z1. At least some of the first arrays may comprise a first plurality of land areas and a first plurality of apertures. At least some of the first plurality of land areas surround at least some of the first plurality of apertures. The first zone, Z1, may have a plurality of Interaperture Distances, according to the Aperture Test herein. The Interaperture Distances of the first zone, Z1, may have a first distribution having a first mean and a first median. The first mean may be greater than, less than, or different than the first median by at least 4% or other percentage, such as 8%, for example. The first arrays in the first zone, Z1, may have an Effective Open Area, according to the Aperture Test herein, in the range of about 5% to about 50%, also including any other ranges specified herein. An example of first arrays that may form the first zone, Z1, is illustrated in FIG. 1, along with land areas 14 and apertures 12. Any of the other patterned apertured webs of the present disclosure may also form all of or part of the first zone, Z1.

A plurality of second, different arrays may form the second zone, Z2, in the patterned apertured web 1300. At least some of the second arrays may comprise a second plurality of land areas and a second plurality of apertures. At least some of the second land areas may surround at least some of the second plurality of apertures. The second zone, Z2, may have a plurality of Interaperture Distances, according to the Aperture Test herein. The Interaperture Distances of the second zone, Z2, may have a second distribution having a second mean and a second median. The second mean may be greater than, less than, or different than the second median by at least 4% or other percentage, such as 8%, for example. The second arrays in the second zone, Z2, may have an Effective Open Area, according to the Aperture Test herein, of about 5% to about 50%, also including any other ranges specified herein. An example of second arrays that may form the second zone, Z2, is illustrated in FIG. 2, along with land areas 14 and apertures 12. Any of the other patterned apertured webs of the present disclosure may also form all of or part of the second zone, Z2.

The patterned apertured web in either of the zones, Z1 or Z2, may comprise one or more layers or may only comprise a single layer. The layer or layers may comprise films, nonwoven material or any of the other materials specified herein. In a multi-layer patterned apertured web, the layers may comprise the same materials or different materials, with at least one of the layers having patterned apertures. The layers may have the same or different colors. The first plurality of apertures in the first zone, Z1, may be the same as or different than the plurality of apertures in the second zone, Z2. The first plurality of apertures in the first array or the second plurality of apertures in the second array may form a substantially continuous pattern, a discrete pattern, or a linear pattern. The first plurality of land areas in the first array or the second plurality of land area in the second array may form a substantially continuous pattern, a discrete pattern, or a linear pattern.

The first zone, Z1, or the second zone, Z2, may indicate the correct orientation of the absorbent article on a wearer. The patterned apertured web 1300 may comprise a polyethylene/polypropylene bicomponent spunbond material, nanofibers, and/or crimped fibers.

A patterned apertured web (single or multi-layer) may comprise a plurality of first arrays forming a first zone, Z1, in the patterned apertured web 1300. At least some of the first arrays may comprise a first plurality of land areas and a first plurality of non-homogeneous apertures. At least some of the first plurality of land areas may surround at least some of the first plurality of apertures. The first plurality of apertures may have an Average Absolute Feret Angle of greater than about 20 degrees (or other degrees as set forth herein), according to the Aperture Test herein. The first arrays may have an Effective Open Area, according to the Aperture Test herein, in the range of about 5% to about 50% (or other percentages or ranges specified herein). A plurality of second, different arrays may form a second zone, Z2, in the patterned aperture web. At least some of the second arrays may comprise second plurality of land areas and a second plurality of non-homogeneous apertures, wherein at least some of the second plurality of land areas surround at least some of the second plurality of apertures. The second arrays may have an Effective Open Area, according to the Aperture Test, of about 5% to about 50% (or other percentages or ranges specified herein). The second plurality of apertures may also have an Average Absolute Feret Angle of greater than about 20 degrees, according to the Aperture Test herein.

A patterned apertured web (whether single or multi-layer) may comprise a plurality of first arrays forming a first zone, Z1, in the patterned apertured web. At least some of the first arrays may comprise a first plurality of land areas having a width greater than at least 5 mm, at least 8 mm, or at least 10 mm and a first plurality of apertures. At least some of the first plurality of land areas may surround at least some of the first plurality of apertures. The first zone, Z1, may have a plurality of Interaperture Distances, according to the Aperture Test herein, wherein the Interaperture Distance of the first zone, Z1, may have a first distribution having a first mean and a first median. The first mean may be greater than, less than, or different than the first median by at least 4% or at least 8%. The first arrays may have an Effective Open Area, according to the Aperture Test, in the range of about 5% to about 50% (or other percentages or ranges specified herein). A plurality of second arrays may form second zone, Z2, in the patterned apertured web 1300. At least some of the second arrays may comprise a second plurality of land areas having a width greater than at least 5 mm, at least 8 mm, or at least 10 mm and a second plurality of apertures. At least some of the second plurality of land areas may surround at least some of the second plurality of apertures. The second zone, Z2, may have a plurality of Interaperture Distances, according to the Aperture Test herein. The Interaperture Distances of the second zone, Z2, may have a second distribution having a second mean and a second median. The second mean may be greater than, less than, or different than the second median by at least 4% or at least 8% or in the range of about 4% to about 25%. The second arrays may have an Effective Open Area in the range of about 5% to about 50% (or other percentages or ranges specified herein).

A patterned apertured web may comprise a layer comprising a plurality of apertures and a plurality of land areas. The plurality of apertures may comprise a first set of apertures and a second set of apertures. The first set of apertures may have Interaperture Distances, according to the Aperture Test herein. The Interaperture Distances of the first set of apertures may have a first distribution having a first mean and a first median. The first mean may be greater than, less than or different than, the first median. The second set of apertures may have Interaperture Distances, according to the Aperture Test herein. The Interaperture Distances of the second set of apertures may have a second distribution having a second mean and a second median. The second mean may be greater than, less than, or different than the second median. The first and second sets of apertures may have different patterns. The patterned apertured web 1300 may comprise a third set of apertures. The third set of apertures may be different than the first and second sets of apertures. The third set of apertures may have Interaperture Distances, according to the Aperture Test herein. The e Interaperture Distances of the third set of apertures may have a third distribution having a third mean and a third median. The third mean may be greater than, less than or different than the third median. The patterned apertured web 1300 may have one or more layers. One or more of the layers may be apertured. In other instances, one or more of the layer may not be apertured. A first layer of the patterned apertured web may be apertured and a second layer of the patterned apertured web may not be apertured. In other instances, a first layer of a patterned apertured web may be apertured and a second layer of the patterned apertured web may be apertured. The layers may have a different in hydrophilicity as described herein. A portion of, or all of, the first layer or a portion of, or all of, the second layer may comprise a polyethylene/polypropylene bicomponent spunbond material, nanofibers, and/or crimped fibers.

Figure 105:
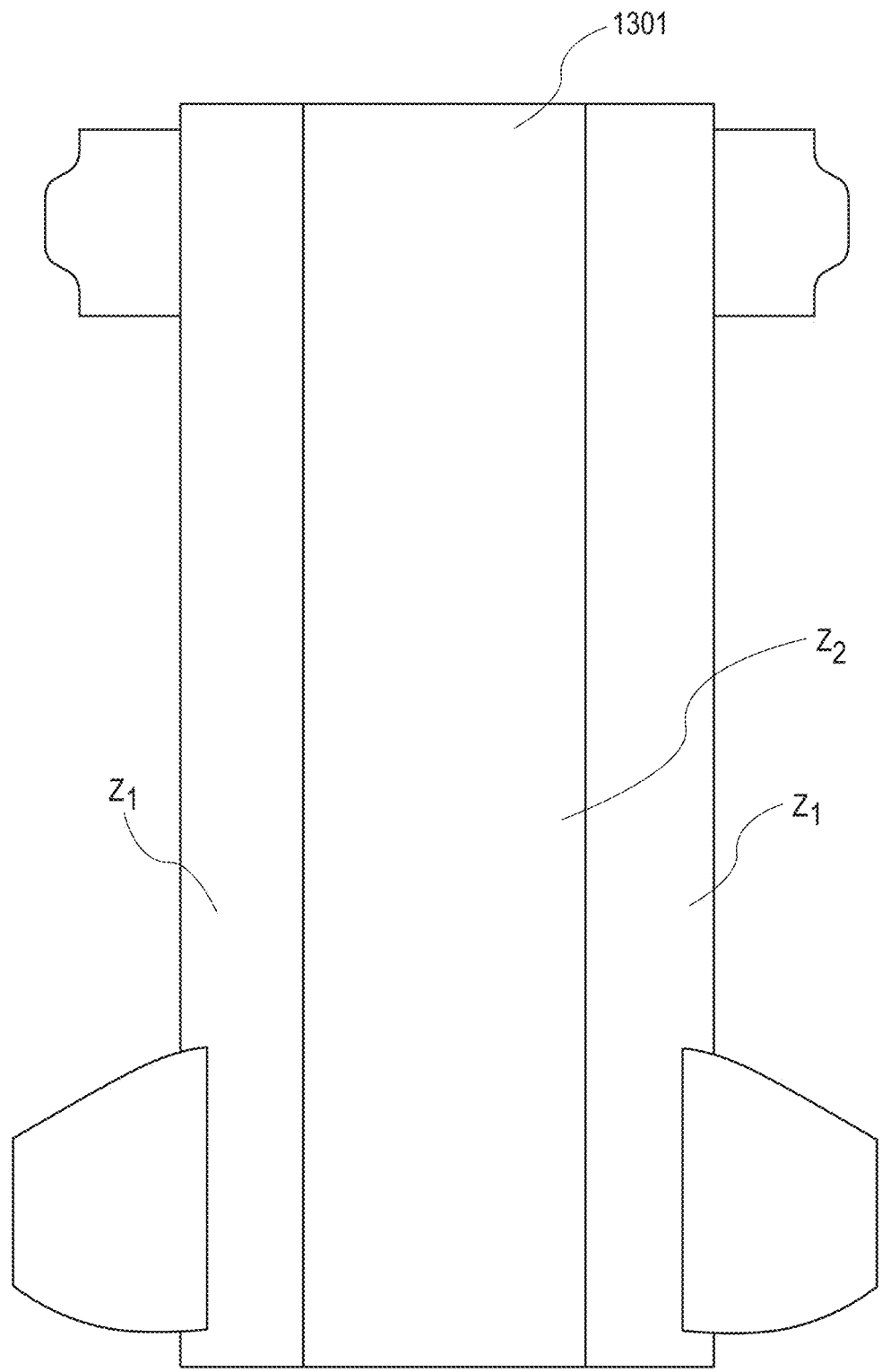
Figure 106:
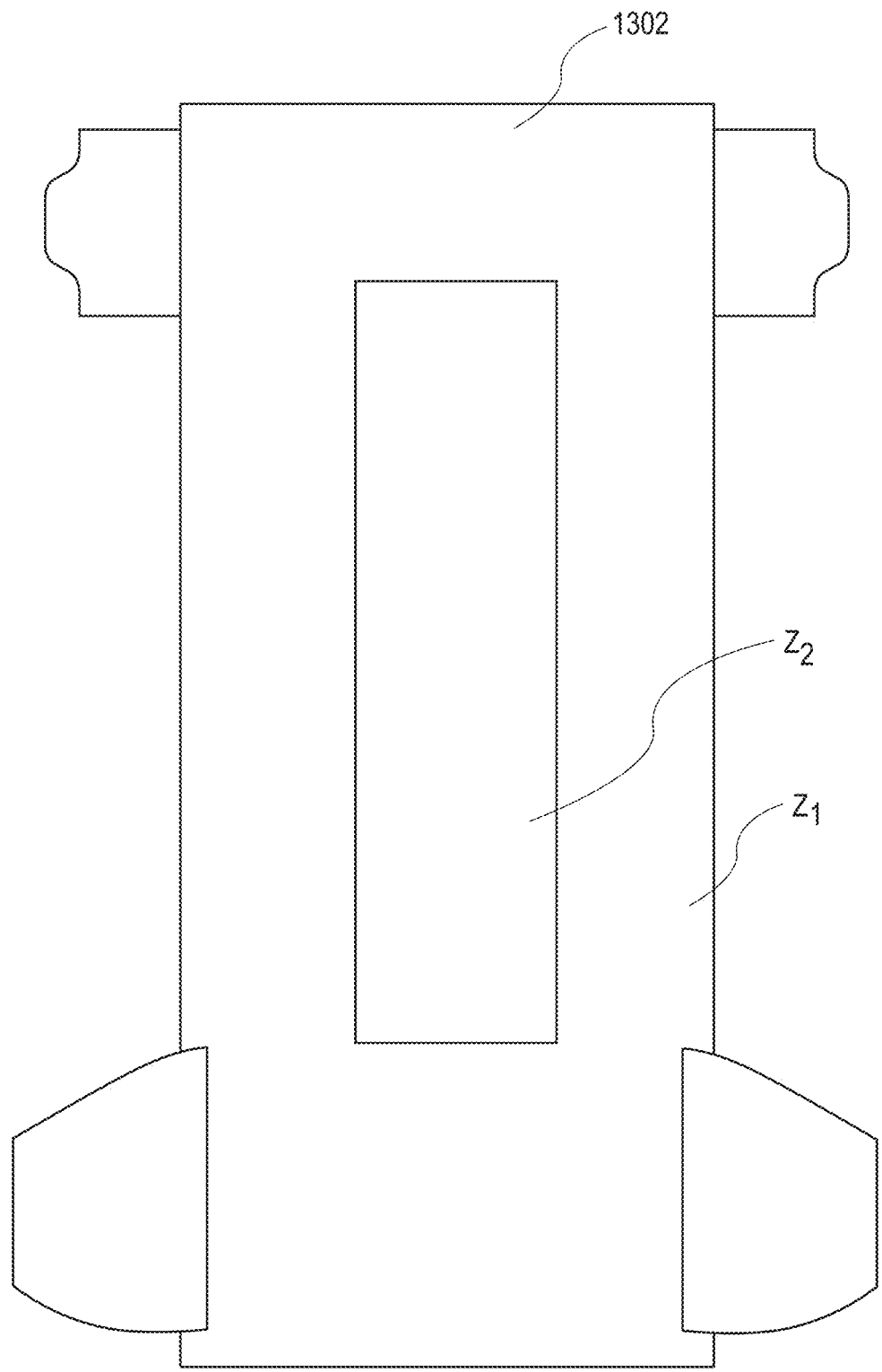

Referring to FIG. 105, a patterned apertured web 1301 may have a first zone, Z1, and a second zone, Z2. The first and second zones, Z1 and Z2, may have any of the features described above with respect to the patterned apertured web 1300 and FIG. 104. The same applies to the patterned apertured web 1302 of FIG. 106. In FIG. 106, the first zone, Z1, may be a first patterned apertured web, and the second zone, Z2, may be a second patterned apertured web. The first patterned apertured web may surround the second patterned apertured web or the second patterned apertured web may be a patch placed on or joined to the first patterned apertured web.

Figure 107:
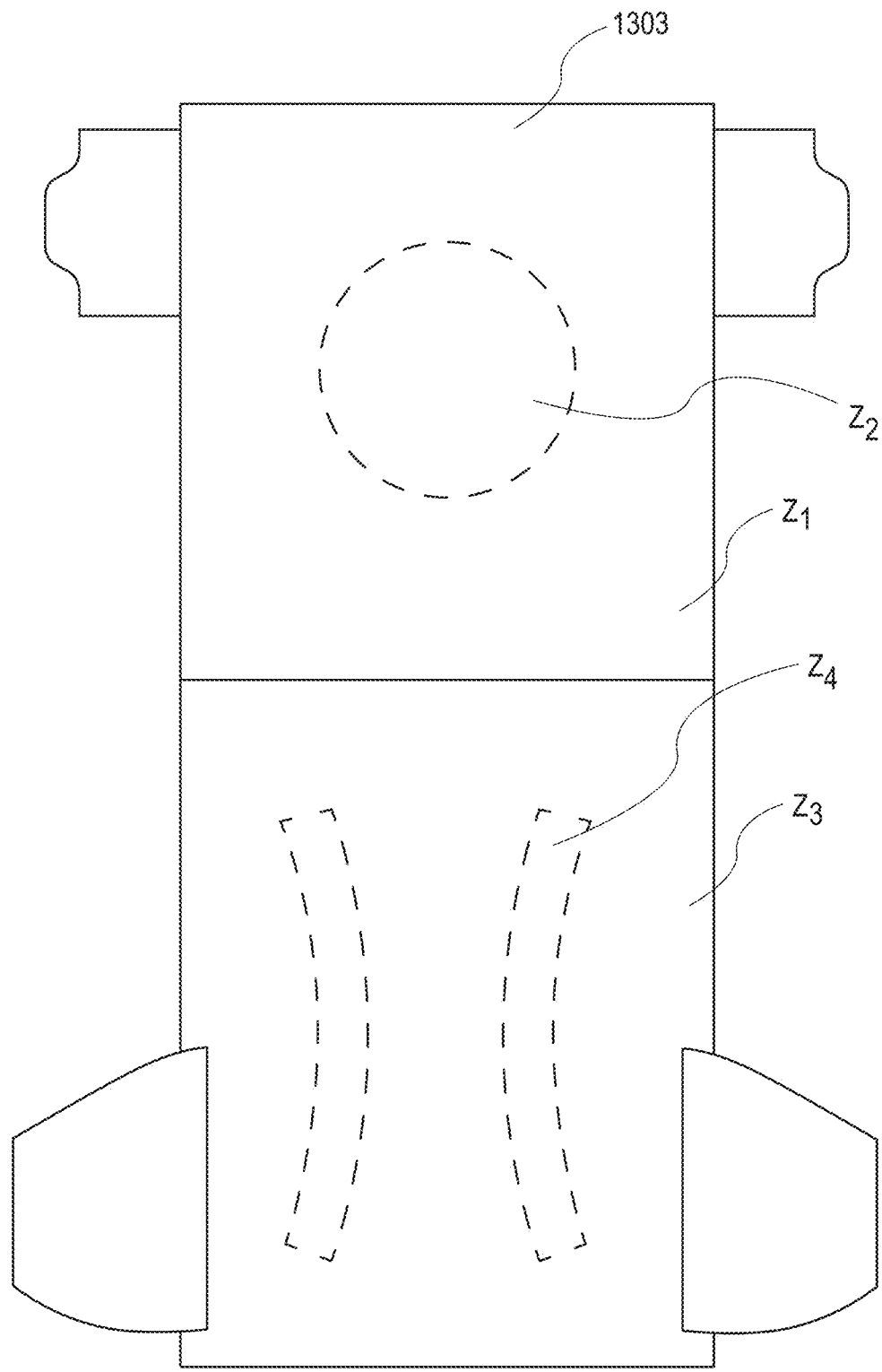

Referring to FIG. 107, a patterned apertured web 1303 may have a first zone, Z1, a second zone, Z2, a third zone, Z3, and a fourth zone, Z4. The first, second, third, and fourth zones, Z1-Z4, may have any of the features described above with respect to the patterned apertured web 1300 and FIG. 104.

At least some of the zones of FIGS. 104-107 may not have patterned apertures or apertures in some instances.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 108:
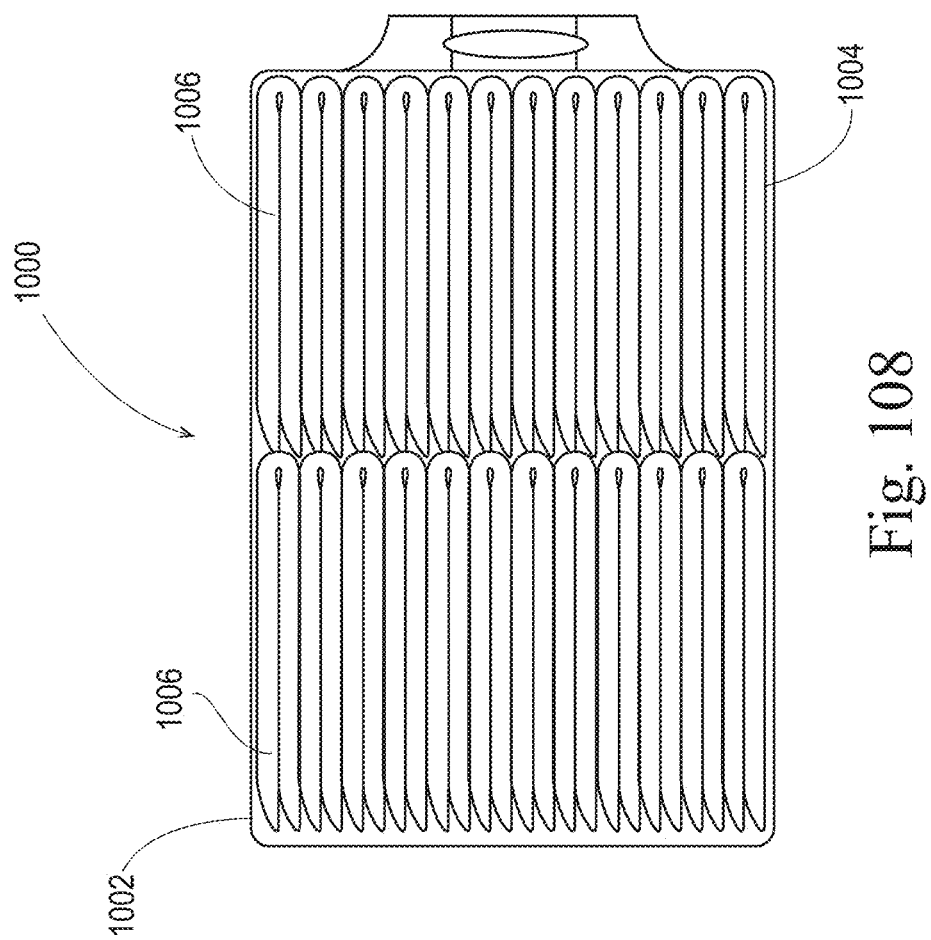
FIG. 108 is a side view of a package of absorbent articles in accordance with the present disclosure. The outer surface is illustrated as transparent for purposes of clarity.

FIG. 108 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Materials/Laminates Comprising Overbonds

Materials and/or laminates comprising overbonds are also within the scope of the present disclosure. The materials may be single self-sustaining webs, while the laminates may be one or more single self-sustaining webs that are joined together. In a laminate context, only one layer may comprise overbonds or all layers may comprise overbonds. If overbonds are provided in more than one layer of a laminate, they may have the same patterns or different patterns. Any of the layers of the laminate may be pre-strained. The webs may be films, nonwovens, any other suitable materials, and/or any other materials described herein. The overbonds may be arranged in any suitable patterns, such as the patterns of FIGS. 19-23, 31, 53, and 55-60, for example. The overbonds may be applied at a nonwoven supplier or nonwoven manufacture (without performing the cross-machine directional stretching step(s)) or may be applied at a site where the cross-machine directional stretching step(s) is/are also conducted. Examples of the cross-machine direction stretching steps are described herein with references to FIGS. 16 and 24-30. The overbonded materials and/or laminates may be used to produce the patterned apertured webs of the present disclosure.

Test Methods

Basis Weight Test

Basis weight of the patterned apertured webs may be determined by several available techniques, but a simple representative technique involves taking an absorbent article or other consumer product, removing any elastic which may be present and stretching the absorbent article or other consumer product to its full length. A punch die having an area of 45.6 cm 2 is then used to cut a piece of the patterned apertured web (e.g., topsheet, outer cover) from the approximate center of the absorbent article or other consumer product in a location which avoids to the greatest extent possible any adhesive which may be used to fasten the patterned apertured web to any other layers which may be present and removing the patterned apertured web from other layers (using cryogenic spray, such as Cyto-Freeze, Control Company, Houston, Texas, if needed). The sample is then weighed and dividing by the area of the punch die yields the basis weight of the patterned apertured web. Results are reported as a mean of 5 samples to the nearest 0.1 cm 2.

Aperture Test

Aperture dimensions, Effective Aperture Area, % Effective Open Area, Interaperture Distance measurements, among other measurements, are obtained from specimen images acquired using a flatbed scanner. The scanner is capable of scanning in reflectance mode at a resolution of 6400 dpi and 8 bit grayscale (a suitable scanner is an Epson Perfection V750 Pro from Epson America Inc., Long Beach CA or equivalent). The scanner is interfaced with a computer running an image analysis program (a suitable program is ImageJ v. 1.47 or equivalent, National Institute of Health, USA). The specimen images are distance calibrated against an acquired image of a ruler certified by NIST. A steel frame is used to mount the specimen, which is then backed with a black glass tile (P/N 11-0050-30, available from HunterLab, Reston, VA) prior to acquiring the specimen image. The resulting image is then thresheld, separating open aperture regions from specimen material regions, and analyzed using the image analysis program. All testing is performed in a conditioned room maintained at about 23±2° C. and about 50±2% relative humidity.

Sample Preparation:

To obtain a specimen, tape an absorbent article to a rigid flat surface in a planar configuration. Any leg elastics may be cut to facilitate laying the article flat. A rectilinear steel frame (100 mm square, 1.5 mm thick with an opening 60 mm square) is used to mount the specimen. Take the steel frame and place double-sided adhesive tape on the bottom surface surrounding the interior opening. Remove the release paper of the tape, and adhere the steel frame to the apertured layer of the article. Align the frame so that it is parallel and perpendicular to a machine direction (MD) and a cross direction (CD) of the apertured layer. Using a razor blade excise the apertured layer from the underlying layers of the article around the outer perimeter of the frame. Carefully remove the specimen such that its longitudinal and lateral extension is maintained to avoid distortion of the apertures. A cryogenic spray (such as Cyto-Freeze, Control Company, Houston TX) may be used to remove the specimen from the underlying layers if necessary. Five replicates obtained from five substantially similar articles are prepared for analysis. If the apertured layer of interest is too small to accommodate the steel frame, reduce the frame dimensions accordingly to accomplish the goals of removal of the specimen without distortion of the apertures while leaving an opening of sufficient size to allow for scanning a significant portion of the apertured layer. An apertured or patterned apertured substrate raw material is prepared for testing by extending or activating it under the same process conditions, and to the same extent, as it would be for use on the absorbent article, and then in its extended state adhering it to the steel frame as described above for testing. Condition the samples at about 23° C.±2 C.° and about 50%±2% relative humidity for 2 hours prior to testing.

Image Acquisition:

Place the ruler on the scanner bed, oriented parallel to sides of the scanner glass, and close the lid. Acquire a calibration image of the ruler in reflectance mode at a resolution of 6400 dpi (approximately 252 pixels per mm) and 8 bit grayscale, with the field of view corresponding to the dimensions of an interior of the steel frame. Save the calibration image as an uncompressed TIFF format file. Lift the lid and remove the ruler. After obtaining the calibration image, all specimens are scanned under the same conditions and measured based on the same calibration file. Next, place the framed specimen onto the center of the scanner bed, lying flat, with the outward facing surface of the specimen facing the scanner's glass surface. Orient the specimen so that sides of the frame are aligned parallel with and perpendicular to the sides of the scanner's glass surface, so that the resulting specimen image will have the MD vertically running from top to bottom. Place the black glass tile on top of the frame covering the specimen, close the lid and acquire a scanned image. Scan the remaining four replicates in like fashion. If necessary, crop all images to a rectangular field of view circumscribing the apertured region, and resave the files.

% Effective Open Area Calculation:

Open the calibration image file in the image analysis program and perform a linear distance calibration using the imaged ruler. This distance calibration scale will be applied to all subsequent specimen images prior to analysis. Open a specimen image in the image analysis program and set the distance scale. View the 8 bit histogram (0 to 255, with one bin per GL) and identify the gray level (GL) value for the minimum population located between the dark pixel peak of the aperture holes and the lighter pixel peak of the specimen material. Threshold the image at the minimum gray level value to generate a binary image. In the binary image the apertures appear as black, with a GL value of 255, and specimen as white, with a GL value of 0.

Using the image analysis program, analyze each of the discrete aperture regions. Measure and record all of the individual aperture areas to the nearest 0.01 mm$^2$, including partial apertures along the edges of the image. Discard any apertures with an area less than 0.3 mm$^2$ as "non-effective". Sum the remaining aperture areas (including whole and partial apertures), divide by the total area included in the image and multiply by 100. Record this value as the % effective open area to the nearest 0.01%.

In like fashion, analyze the remaining four specimen images. Calculate and report the average % effective open area values to the nearest 0.01% for the five replicates.

Effective Aperture Dimension Measurements:

Open the calibration image (containing the ruler) file in the image analysis program. Resize the resolution of the original image from 6400 dpi to 640 dpi (approximately 25.2 pixels per mm) using a bicubic interpolation. Perform a linear distance calibration using the imaged ruler. This distance calibration scale will be applied to all subsequent specimen images prior to analysis. Open a specimen image in the image analysis program. Resize the resolution of the original image from 6400 dpi to 640 dpi (approximately 25.2 pixels per mm) using a bicubic interpolation. Set the distance scale. View the 8 bit histogram (0 to 255, with one bin per GL) and identify the gray level (GL) value for the minimum population located between the dark pixel peak of the aperture holes and the lighter pixel peak of the specimen material. Threshold the image at the minimum gray level value to generate a binary image. In the binary image, the apertures appear as black, with a GL value of 255, and specimen as white, with a GL value of 0. Next, two morphological operations are performed on the binary image. First, a closing (a dilation operation followed by an erosion operation, iterations=1, pixel count=1), which removes stray fibers within an aperture hole. Second, an opening (an erosion operation followed by a dilation operation, iterations=1, pixel count=1), which removes isolated black pixels. Pad the edges of the image during the erosion step to ensure that black boundary pixels are maintained during the operation. Lastly, fill any remaining voids enclosed within the black aperture regions.

Using the image analysis program, analyze each of the discrete aperture regions. During the analysis exclude measurements of partial apertures along the edges of the image, so that only whole apertures are measured. Measure and record all of the individual effective aperture areas, perimeters, feret diameters (length of the apertures) along with its corresponding angle of orientation in degrees from 0 to 180, and minimum feret diameters (width of the apertures). Record the measurements for each of the individual elements areas to the nearest 0.01 mm$^2$, the perimeters and feret diameters (length and width), to the nearest 0.01 mm, and angles to the nearest 0.01 degree. Discard any apertures with an area less than 0.3 mm$^2$ as "non-effective". Record the number of remaining apertures, divide by the area of the image and record as the Aperture Density value. The angle of orientation for an aperture aligned with the MD (vertical in the image) will have an angle of 90 degrees. Apertures with a positive slope, increasing from left to right, will have an angle between zero and 90 degrees. Apertures with a negative slope, decreasing from left to right, will have an angle between 90 and 180 degrees. Using the individual aperture angles calculate an Absolute Feret Angle by subtracting 90 degrees from the original angle of orientation and taking its absolute value. In addition to these measurements, calculate an Aspect Ratio value for each individual aperture by dividing the aperture length by its width. Repeat this analysis for each of the remaining four replicate images. Calculate and report the statistical mean and standard deviation for each of the effective aperture dimension, the Absolute Feret Angle, and the Aspect Ratio measurements using all of the aperture values recorded from the replicates. Record the average of the individual Absolute Feret Angle measurements as the Average Absolute Feret Angle value. Calculate and report the % relative standard deviation (RSD) for each of the aperture dimension, the Absolute Feret Angle, and the Aspect Ratio measurements by dividing the standard deviation by the mean and multiplying by 100.

Inter-Aperture Distance Measurements:

The mean, standard deviation, median, and maximum distance between the apertures can be measured by further analyzing the binary image that was analyzed for the aperture dimension measurements. First, obtain a duplicate copy of the resized binary image following the morphological operations, and using the image analysis program, perform a Voronoi operation. This generates an image of cells bounded by lines of pixels having equal distance to the borders of the two nearest pattern apertures, where the pixel values are outputs from a Euclidian distance map (EDM) of the binary image. An EDM is generated when each intra-aperture pixel in the binary image is replaced with a value equal to that pixel's distance from the nearest pattern aperture. Next, remove the background zeros to enable statistical analysis of the distance values. This is accomplished by using the image calculator to divide the Voronoi cell image by itself to generate a 32-bit floating point image where all of the cell lines have a value of one, and the remaining parts of the image are identified as Not a Number (NaN). Lastly, using the image calculator, multiply this image by the original Voronoi cell image to generate a 32-bit floating point image where the distance values along the cell lines remain, and all of the zero values have been replaced with NaN. Next, convert the pixel distance values into actual inter-aperture distances by multiplying the values in the image by the pixel resolution of the image (approximately 0.04 mm per pixel), and then multiply the image again by 2 since the values represent the midpoint distance between apertures. Measure and record the mean, standard deviation, median and maximum inter-aperture distances for the image to the nearest 0.01 mm. Repeat this procedure for all replicate images. Calculate the % relative standard deviation (RSD) for the interaperture distance by dividing the standard deviation by the mean and multiplying by 100.

Opacity Test

Opacity by contrast ratio measurements are made using a 0°/45° spectrophotometer suitable for making standard CIE L*a*b* color measurements (e.g., Hunterlab Labscan XE spectrophotometer, Hunter Associates Laboratory Inc., Reston VA or equivalent). The diameter of the instrument's measurement port should be chosen such that only the region of interest is included within the measurement port. Analyses are performed in a room controlled at about 23° C.±2 C.° and 50%±2% relative humidity. Samples are conditioned at the same condition for 2 hours before testing.

Calibrate the instrument per the vender instructions using the standard black and white tiles provided by the vendor. Set the spectrophotometer to use the CIE XYZ color space, with a D65 standard illumination and 10° observer. If the specimen is a layer of an article, use cryogenic spray and scissors to carefully excise the specimen from the article for testing, otherwise obtain the specimen from a representative sample of material of sufficient size for testing. Place the specimen flat against the instrument with the outward facing surface toward the spectrophotometer's measurement port and the region of interest within the port. Ensure that no tears, holes or apertures are within the measurement port. Place the white standard tile onto the opposing surface of the specimen such that it completely covers the measurement port. Take a reading for XYZ and record to 0.01 units. Without moving the specimen, remove the white plate and replace it with the black standard plate. Take a second reading for XYZ and record to 0.01 units. Repeat this procedure at a corresponding site for a total of ten (10) replicate specimens.

Opacity is calculated by dividing the Y value measured using the black tile as backing, divided by the Y value measured using the white tile as backing, then multiplying the ratio by 100. Record the opacity value to the nearest 0.01%. Calculate opacity for the 10 replicates and report the average opacity to the nearest 0.01%.

Light Transmission Test

The light transmission test measures the average amount of light transmitted through specific regions of a specimen. A calibrated light transmission image is obtained using a flatbed scanner. A binary mask is generated to separate discrete aperture regions from the surrounding land area. The binary mask is then registered to the light transmission image, and used to exclude the apertures from the land area in the light transmission image. This enables the average light transmission value for the land area to be calculated.

Sample Preparation: To obtain a specimen, tape the absorbent article to a rigid flat surface in a planar configuration. Any leg elastics may be cut to facilitate laying the article flat. A rectilinear steel frame (100 mm square, 1.5 mm thick with an opening 60 mm square) is used to mount the specimen. Take the steel frame and place double-sided adhesive tape on the bottom surface surrounding the interior opening. Remove the release paper of the tape, and adhere the steel frame to the apertured layer of the article. Align the frame so that it is parallel and perpendicular to the machine direction (MD) and cross direction (CD) of the apertured layer. Using a razor blade excise the apertured layer from the underlying layers of the article around the outer perimeter of the frame. Carefully remove the specimen such that its longitudinal and lateral extension is maintained to avoid distortion of the apertures. A cryogenic spray (such as Cyto-Freeze, Control Company, Houston TX) can be used to remove the specimen from the underlying layers if necessary. Five replicates obtained from five substantially similar articles are prepared for analysis. If the aperture layer of interest is too small to accommodate the steel frame, reduce the frame dimensions accordingly to accomplish the goals of removal of the specimen without distortion of the apertures while leaving an opening of sufficient size to allow for scanning a significant portion of the apertured layer. An apertured substrate raw material is prepared for testing by extending or activating it under the same process conditions, and to the same extent, as it would be for use on the absorbent article, and then in its extended state adhering it to the steel frame as described above for testing. Condition the samples at about 23° C.±2 C.° and about 50%±2% relative humidity for 2 hours prior to testing.

Light Transmission Image

The light transmission measurement is based on the CIE L*a*b* color system (CIELAB). A flatbed scanner capable of scanning a minimum of 24 bit color at 800 dpi and has manual control of color management (a suitable scanner is an Epson Perfection V750 Pro from Epson America Inc., Long Beach CA or equivalent) is used to acquire images. The scanner is interfaced with a computer running color management software (suitable color management software is MonacoEZColor available from X-Rite Grand Rapids, MI or equivalent). The scanner is calibrated against a color transparency target and corresponding reference file compliant with ANSI method IT8.7/1-1993 using the color management software to construct a calibrated color profile. The resulting calibrated scanner profile is used to color correct an image from a test specimen within an image analysis program that supports sampling in CIE L*a*b* (a suitable program is Photoshop S4 available from Adobe Systems Inc., San Jose, CA or equivalent). All testing is performed in a conditioned room maintained at about 23±2° C. and about 50±2% relative humidity.

Turn on the scanner for 30 minutes prior to calibration. Deselect any automatic color correction or color management options that may be included in the scanner software. If the automatic color management cannot be disabled, the scanner is not appropriate for this application. Place the IT8 target face down onto the scanner glass, close the scanner lid, acquire an image at 200 dpi and 24 bit color and remove the IT8 target. Open the image file on the computer with the color management software. Follow the recommended steps within the color management software to create and export a calibrated color profile. These steps may include, ensuring that the scanned image is oriented and cropped correctly. The calibrated color profile must be compatible with the image analysis program. The color management software uses the acquired image to compare with the included reference file to create and export the calibrated color profile. After the profile is created the scan resolution (dpi) for test specimens can be changed, but all other settings must be kept constant while imaging specimens.

Open the scanner lid and place the specimen flat against the scanner glass with the outward facing surface facing the glass. Acquire and import a scan of the specimen region within the interior of the frame into the image analysis software at 24 bit color and at 800 dpi in transparency mode. If necessary, crop image to a rectangular field of view circumscribing the apertured region. Transparency mode illuminates the specimen from one side with the sensor capturing the image from the opposite side. Assign the calibrated color profile to the image and change the color space mode to L*a*b* Color corresponding to the CIE L*a*b* standard. This produces a color corrected image for analysis. Save this color corrected image in an uncompressed format, such as a TIFF file.

Land Area Mask

The boundaries of the apertured areas and land area are identified by thresholding the L* channel image to generate a binary image, separating apertured areas from the surrounding land area. This binary image will then be used as a mask on the corresponding light transmission image to measure the average Light Transmission Value of only the land area.

To do this, first open the color corrected light transmission image in the image analysis software. To generate the land area mask, first separate the L*, a* and b* channels, and select only the L* channel for analysis. The L* channel represents the "Lightness" of the image and has values that range from 0-100. Threshold the L* channel image at a value of 90 to generate a binary image.

By thresholding at the level described above, a binary mask image is produced with the discrete aperture areas assigned one value, and the surrounding land area assigned a different value. For example, the discrete aperture areas could appear black, and the surrounding land area could appear white. Save this binary mask image in an uncompressed format, such as a TIFF file.

Analysis of Light Transmission Image

Open both the color corrected light transmission image and the corresponding binary mask image in the image analysis software. To analyze the specimen light transmission image, first separate the L*, a* and b* channels, and select only the L* channel for analysis. Register the light transmission image and the binary mask image to each other. Use the binary mask to exclude the apertures from the light transmission image, and calculate an average L* value (Light Transmission Value) for the remaining surrounding land area. Record this value as the Land Area Light Transmission Value to the nearest 0.1 units. In like fashion, repeat this procedure on all of the replicate specimens. Calculate and report the average of the five individual Land Area Light Transmission Values to the nearest 0.1 units.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 108). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patent, patent publication, or patent application, is hereby incorporated by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, those of skill in the art will recognize that various other changes and modifications can be made without departing from the spirit and scope of the invention. It is therefore intended to cover in the appended claims all such changes and modifications that are within the scope of the present disclosure.

What is claimed is:

1. An absorbent article comprising:
    a liquid permeable topsheet comprising:
        a patterned apertured nonwoven material comprising:
            a plurality of land areas in the patterned apertured nonwoven material; and
            a plurality of apertures defined in the patterned apertured nonwoven material, wherein at least some land areas of the plurality of land areas surround at least some apertures of the plurality of apertures, and wherein the plurality of apertures each define an aperture area;

wherein the plurality of apertures are non-homogeneous in a repeat unit such that at least two apertures of the plurality of apertures have a different size or a different shape;

wherein the patterned apertured nonwoven material has an Effective Open Area of about 3% to about 30%, according to an Aperture Test;

wherein the patterned apertured nonwoven material comprises a nonwoven layer, and wherein the plurality of apertures are formed through the nonwoven layer;

wherein a wearer-facing surface of the patterned apertured nonwoven material is hydrophobic, and wherein a garment-facing surface of the patterned apertured nonwoven web is hydrophilic;

wherein the plurality of apertures each comprise a perimeter;

wherein at least one land area of the plurality of land areas is present intermediate a first group of apertures and a second group of apertures;

a liquid impermeable backsheet; and an absorbent core at least partially intermediate the topsheet and the backsheet.

2. The absorbent article of claim 1, wherein the patterned apertured nonwoven material has a plurality of Interaperture Distances, according to the Aperture Test, wherein the Interaperture Distances have a distribution having a median and a mean, and wherein the mean is different than the median.

3. The absorbent article of claim 2, wherein the mean is about 4% to about 25% different than the median.

4. The absorbent article of claim 1, wherein the first group of apertures forms a shape, and wherein the second group of apertures at least partially surrounds the shape.

5. The absorbent article of claim 1, wherein a fiber of the patterned apertured nonwoven material extends into at least one of the apertures.

6. The absorbent article of claim 1, wherein at least some apertures of the plurality of apertures have an Aspect Ratio greater than 2, according to the Aperture Test.

7. The absorbent article of claim 1, wherein the Effective Open Area is about 5% to about 20%.

8. An absorbent article comprising:

a liquid permeable topsheet comprising:
a patterned apertured nonwoven material comprising:
a plurality of land areas in the patterned apertured nonwoven material; and
a plurality of apertures defined in the patterned apertured nonwoven material, wherein at least some land areas of the plurality of land areas surround at least some apertures of the plurality of apertures, and wherein the plurality of apertures each define an aperture area;
wherein the plurality of apertures are non-homogeneous in a repeat unit
such that at least two apertures of the plurality of apertures have a different size or a different shape;
wherein at least some land areas of the plurality of land areas have a width of at least 5 mm, as measured between adjacent apertures;
wherein at least some apertures of the plurality of apertures have an Effective Aperture Area of about 0.3 mm² to about 15 mm², according to an Aperture Test;

wherein the patterned apertured nonwoven material has an Effective Open Area of about 5% to about 30%, according to the Aperture Test;

wherein the patterned apertured nonwoven material comprises a nonwoven layer, and wherein the plurality of apertures are formed through the nonwoven layer;

wherein a wearer-facing surface of the patterned apertured nonwoven material is hydrophobic, and wherein a garment-facing surface of the patterned apertured nonwoven web is hydrophilic;

wherein the plurality of apertures each comprise a perimeter;

wherein a first group of apertures of the plurality of apertures forms a shape;

wherein a second group of apertures of the plurality of apertures at least partially surrounds the shape; and wherein at least one land area of the plurality of land areas is present intermediate the first group of apertures and the second group of apertures;

a liquid impermeable backsheet; and an absorbent core at least partially intermediate the topsheet and the backsheet.

9. The absorbent article of claim 8, wherein the width of the at least some land areas of the plurality of land areas is at least 10 mm.

10. The absorbent article of claim 8, wherein at least some apertures of the plurality of apertures have an Aspect Ratio greater than 2, according to the Aperture Test, and wherein a fiber of the patterned apertured nonwoven material extends into at least one of the apertures.

11. The absorbent article of claim 8, wherein the patterned apertured nonwoven material has a plurality of Interaperture Distances, according to the Aperture Test, wherein the Interaperture Distances have a distribution having a median and a mean, and wherein the mean is different than the median.

12. The absorbent article of claim 8, wherein the Effective Open Area is about 5% to about 20%.

13. The absorbent article of claim 8, wherein the absorbent article is a taped diaper.

14. The absorbent article of claim 8, wherein the plurality of apertures indicates a correct orientation of the absorbent article on a wearer.

15. An absorbent article comprising:

a liquid permeable topsheet comprising:
a patterned apertured nonwoven material comprising:
a plurality of land areas in the patterned apertured nonwoven material;
and a plurality of apertures defined in the patterned apertured nonwoven
material, wherein at least some land areas of the plurality of land areas surround at least some apertures of the plurality of apertures, and wherein the plurality of apertures each define an aperture area;
wherein the plurality of apertures are non-homogeneous in a repeat unit such that at least three apertures of the plurality of apertures have a different size or a different shape;
wherein a wearer-facing surface of the patterned apertured nonwoven material is hydrophobic, and wherein a garment-facing surface of the patterned apertured nonwoven material is hydrophilic;

wherein at least some land areas of the plurality of land areas have a width of at least 5 mm, as measured between adjacent apertures;

wherein at least some apertures of the plurality of apertures have an Effective Aperture Area of about 0.3 mm² to about 15 mm², according to an Aperture Test;

wherein the patterned apertured nonwoven material has an Effective Open Area of about 3% to about 30%, according to the Aperture Test;

wherein at least one land area of the plurality of land areas is present intermediate a first group of apertures and a second group of apertures;

a liquid impermeable backsheet; and an absorbent core at least partially intermediate the topsheet and the backsheet.

16. The absorbent article of claim 15, wherein the patterned apertured nonwoven material has a plurality of Interaperture Distances, according to the Aperture Test, wherein the Interaperture Distances have a distribution having a median and a mean, and wherein the mean is different than the median.

17. The absorbent article of claim 15, wherein the first group of apertures forms a shape, and wherein the second group of apertures at least partially surrounds the shape.

18. The absorbent article of claim 15, wherein at least some apertures have an Aspect Ratio greater than 2, according to the Aperture Test.

19. The absorbent article of claim 15, wherein the absorbent article is a taped diaper, and wherein a fiber of the patterned apertured nonwoven material extends into at least one of the apertures.

20. The absorbent article of claim 15, wherein the absorbent article is a sanitary napkin.

* * * * *